United States Patent
Ludevid Múgica et al.

(10) Patent No.: US 9,637,751 B2
(45) Date of Patent: May 2, 2017

(54) RECOMBINANT PROTEIN BODY-INDUCING POLYPEPTIDES

(75) Inventors: Maria Dolores Ludevid Múgica, Sant Just Desvern (ES); Maria Immaculada Llop Tous, St. Feliu de Llobregat (ES); Pablo Marzábal Luna, Barcelona (ES); Minu Joseph, Terrassa (ES); Blanca Llompart Royo, Barcelona (ES); Margarita Torrent Quetglas, Barcelona (ES); Miriam Bastida Virgili, Molins de Rei (ES)

(73) Assignee: ERA BIOTECH, S.A., Barcelona (ES)

( * ) Notice: Subject to any disclaimer, the term of this patent is extended or adjusted under 35 U.S.C. 154(b) by 839 days.

(21) Appl. No.: 13/149,813

(22) Filed: May 31, 2011

(65) Prior Publication Data

US 2011/0305718 A1   Dec. 15, 2011

Related U.S. Application Data

(60) Provisional application No. 61/349,655, filed on May 28, 2010.

(30) Foreign Application Priority Data

Aug. 13, 2010  (EP) .................................. 10382231

(51) Int. Cl.
| | |
|---|---|
| *C12N 15/67* | (2006.01) |
| *C12N 15/10* | (2006.01) |
| *C12N 15/62* | (2006.01) |
| *C12N 15/82* | (2006.01) |
| *C07K 14/415* | (2006.01) |

(52) U.S. Cl.
CPC ........ *C12N 15/8221* (2013.01); *C07K 14/415* (2013.01); *C12N 15/8216* (2013.01); *C12N 15/8257* (2013.01)

(58) Field of Classification Search
None
See application file for complete search history.

(56) References Cited

U.S. PATENT DOCUMENTS

| | | | |
|---|---|---|---|
| 4,215,040 A | 7/1980 | Hager | |
| 4,882,145 A | 11/1989 | Thornton et al. | |
| 4,886,782 A | 12/1989 | Good et al. | |
| 5,215,912 A | 6/1993 | Hoffman | |
| 5,478,726 A | 12/1995 | Shinnick et al. | |
| 5,589,616 A | 12/1996 | Hoffman | |
| 5,639,854 A | 6/1997 | Sia et al. | |
| 5,948,682 A | 9/1999 | Moloney | |
| 5,990,384 A | 11/1999 | Bagga et al. | |
| 6,642,437 B1 | 11/2003 | Lemaux et al. | |
| 6,942,866 B2 | 9/2005 | Birkett | |
| 7,329,498 B2 | 2/2008 | Harding et al. | |
| 7,575,898 B2 | 8/2009 | Ludevid Mugica et al. | |
| 2004/0005660 A1* | 1/2004 | Ludevid Mugica et al. | 435/69.1 |
| 2006/0121573 A1 | 6/2006 | Torrent et al. | |
| 2006/0123509 A1 | 6/2006 | Torrent et al. | |
| 2006/0182763 A1 | 8/2006 | Kim et al. | |
| 2007/0243198 A1* | 10/2007 | Heifetz et al. | 424/184.1 |
| 2011/0262478 A1 | 10/2011 | Rybicki et al. | |

FOREIGN PATENT DOCUMENTS

| | | |
|---|---|---|
| EP | 0 399 001 B1 | 7/1994 |
| EP | 2 418 284 A1 | 2/2012 |
| WO | WO 96/21029 A1 | 7/1996 |
| WO | WO 00/40738 A1 | 7/2000 |
| WO | WO 02/086077 A2 | 10/2002 |
| WO | WO 03/072731 A2 | 9/2003 |
| WO | WO 2004/003207 A1 | 1/2004 |
| WO | WO 2005/113775 A1 | 12/2005 |
| WO | WO 2006/056483 A1 | 6/2006 |
| WO | WO 2006/056484 A1 | 6/2006 |
| WO | WO 2007/096192 A2 | 8/2007 |
| WO | WO 2011/147995 A1 | 12/2011 |

OTHER PUBLICATIONS

Llop-Tous et al (J. Biol.C hem. 2010, 285(46): 35633-35644;).*
Ackerman, A.L. and Cresswell, P., "Cellular mechanisms governing cross-presentation of exogenous antigens," *Nature Immunology* 5(7):678-684, Nature America Inc., United States (2004).
Alexander, J., et al., "Development of High Potency Universal DR-Restricted Helper Epitopes by Modification of High Affinity DR-Blocking Peptides," *Immunity* 1:751-761, Cell Press, United States (1994).
Altschuler, Y., et al., "The N- and C-Terminal Regions Regulate the Transport of Wheat γ-Gliadin through the Endoplasmic Reticulum in Xenopus Oocytes," *The Plant Cell* 5:443-450, American Society of Plant Physiologists, United States (1993).
Arcalis, E., et al., "Unexpected Deposition Patterns of Recombinant Proteins in Post-Endoplasmic Reticulum Compartments of Wheat Endosperm," *Plant Physiology* 136:3457-3466, American Society of Plant Biologists, United States (2004).

(Continued)

*Primary Examiner* — David T Fox
*Assistant Examiner* — Stephen Uyeno
(74) *Attorney, Agent, or Firm* — Tristan A. Fuierer; Moore & Van Allen, PLLC

(57) ABSTRACT

Polypeptide sequences for inducing recombinant protein bodies are described. The sequences comprise a polyproline II (PPII) structure and/or a proline-rich sequence between two cysteine residues on either end. Recombinant protein bodies are useful for protein production because they allow for simple and efficient purification of high quantities of recombinant protein. In addition, other methods of using recombinant protein bodies, for example, in vaccination and food products, are also described.

27 Claims, 21 Drawing Sheets

(56) References Cited

OTHER PUBLICATIONS

Figure 8:
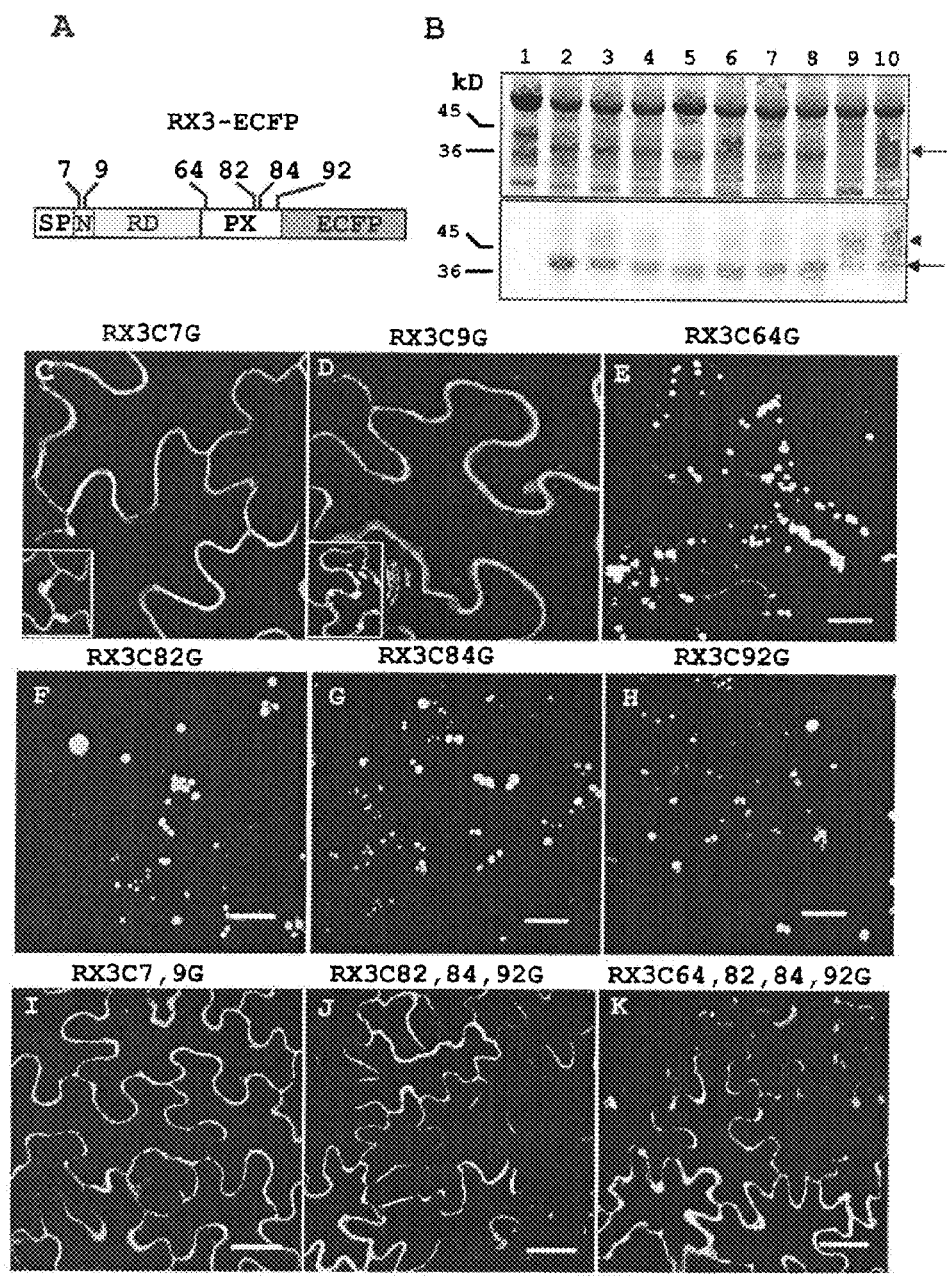

Bagga, S., et al., "Accumulation of 15-Kilodalton Zein in Novel Protein Bodies in Transgenic Tobacco," *Plant Physiol.* 107:13-23, American Society of Plant Physiologists, United States (1995).

Bagga, S., et al., "Coexpression of the Maize δ-Zein and β-Zein Genes Results in Stable Accumulation of δ-Zein in Endoplasmic Reticulum-Derived Protein Bodies Formed by δ-Zein," *The Plant Cell* 9:1683-1696, American Society of Plant Physiologists, United States (1997).

Bicudo, T.C., et al., "γ-Zein Secondary Structure in Solution by Circular Dichroism," *Biopolymers* 89(3):175-178, Wiley Periodicals, Inc., United States (2007).

Blander, J.M. and Medzhitov, R., "On regulation of phagosome maturation and antigen presentation," *Nature Immunology* 7(10):1029-1035, Nature America Inc., United States (2006).

Bochicchio, B. and Tamburro, A.M., "Polyproline II Structure in Proteins: Identification by Chiroptical Spectroscopies, Stability, and Functions," *CHIRALITY* 14:782-792, Wiley-Liss, Inc., United States (2002).

Bockenstedt, L.K., et al., "Identification of a *Borrelia burgdorferi* OspA T Cell Epitope That Promotes Anti-OspA IgG in Mice," *The Journal of Immunology* 15(12):5496-5502, The American Association of Immunologists, United States (1996).

Boes, M., et al., "T-cell engagement of dendritic cells rapidly rearranges MHC class II transport," *Nature* 418:983-988, Nature Publishing Group, England (2002).

Bosch, F.X., et al., "Prevalence of Human Papillomavirus in Cervical Cancer: a Worldwide Perspective," *Journal of the National Cancer Institute* 87(11):796-802, Oxford University Press, England (1995).

Boyer, J.D., et al., "DNA Vaccination as Anti-Human Immunodeficiency Virus Immunotherapy in Infected Chimpanzees," *The Journal of Infectious Diseases* 176:1501-1509, The University of Chicago, United States (1997).

Brett, S.J., et al., "Human T Cell Recognition of Influenza a Nucleoprotein: Specificity and Genetic Restriction of Immunodominant T Helper Cell Epitopes," *The Journal of Immunology* 147(3):984-991, The American Association of Immunologists, United States (1991).

Brown, L.E., et al., "Conservation of Determinants for Class II-Restricted T Cells within Site E of Influenza Virus Hemagglutinin and Factors Influencing Their Expression," Journal of Virology 67(5):2887-2893, American Society for Microbiology, United States (1993).

Brumeanu, T.-D., et al., "Engineering of doubly antigenized immunoglobulins expressing T and B viral epitopes," *Immunotechnology* 2:85-95, Elsevier Science B.V., Netherlands (1996).

Bukrinsky, M.I., et al., "A nuclear localization signal within HIV-1 matrix protein that governs infection of non-dividing cells," *Nature* 365:666-669, Nature Publishing Group, England (1993).

Burgers, W.A., et al., "Construction, Characterization, and Immunogenicity of a Multigene Modified Vaccinia Ankara (MVA) Vaccine Based on HIV Type 1 Subtype C," *AIDS Research and Human Retroviruses* 24(2):195-206, Mary Ann Liebert, Inc. United States (2008).

Calarota, S., et al., "Cellular cytotoxic response induced by DNA vaccination in HIV-1-infected patients," *The Lancet* 351:1320-1325, Lancet Publishing Group, England (1998).

Caldwell, J.W., et al., "Theoretical ππ Absorption, Circular Dichroic, and Linear Dichroic Spectra of Collagen Triple Helices," *Biopolymers* 23:1891-1904, John Wiley & Sons, Inc., United States (1984).

Calvo-Calle, J.M., et al., "Binding of Malaria T Cell Epitopes to DR and DQ Molecules In Vitro Correlates with Immunogenicity In Vivo: Identification of a Universal T Cell Epitope in the *Plasmodium falciparum* Circumsporozoite Protein," *The Journal of Immunology* 159:1362-1373, The American Association of Immunologists, United States (1997).

Casimiro, D.R., et al., "Vaccine-Induced Immunity in Baboons by Using DNA and Replication-Incompetent Adenovirus Type 5 Vectors Expressing a Human Immunodeficiency Virus Type 1 gag Gene," *Journal of Virology* 77(13):7663-7668, American Society for Microbiology, United States (2003).

Chege, G.K., et al., "HIV-1 subtype C Pr55$^{gag}$ virus-like particle vaccine efficiently boosts baboons primed with a matched DNA vaccine," *Journal of General Virology* 89:2214-2227, SGM, England (2008).

Cherpelis, S., et al., "DNA-immunization with a V2 deleted HIV-1 envelope elicits protective antibodies in macaques," *Immunology Letters* 79:47-55, Elsevier Science B.V, Netherlands (2001).

Coleman, C.E., et al., "The Maize γ-Zein Sequesters α-Zein and Stabilizes Its Accumulation in Protein Bodies of Transgenic Tobacco Endosperm," *The Plant Cell* 8:2335-2345, American Society of Plant Physiologists, United States (1996).

Conrad, U. and Fiedler, U., "Compartment-specific accumulation of recombinant immunoglobulins in plant cells: an essential tool for antibody production and immunomodulation of physiological functions and pathogen activity," *Plant Molecular Biology* 38:101-109, Kluwer Academic Publishers, Netherlands, (1998).

Dalcol, I., et al, "Convergent Synthesis of Repeating Peptides (Val-X-Leu-Pro-Pro-Pro)$_8$ Adopting a Polyproline II Conformation," *J. Org. Chem.* 61(20):6775-6782, American Chemical Society, United States (1996).

Dela Cruz, C.S., et al., "Creating HIV-1 reverse transcriptase cytotoxic T lymphocyte target structures by HLA-A2 heavy chain modifications," *International Immunology* 12(9):1293-1302, The Japanese Society for Immunology, Japan (2000).

Deml, L., et al., "Recombinant Human Immunodeficiency Pr55$^{gag}$ Virus-like Particles Presenting Chimeric Envelope Glycoproteins Induce Cytotoxic T-Cells and Neutralizing Antibodies," *Virology* 235:26-39, Academic Press, United States (1997).

Deml, L., et al., "Virus-like Particles: A Novel Tool for the Induction and Monitoring of Both T-Helper and Cytotoxic T-Lymphocyte Activity," *Methods in Molecular Medicine* 94:133-157, Humana Press Inc., United States (2004).

Doan, L.X., et al., "Virus-like particles as HIV-1 vaccines," *Rev. Med. Virol.* 15:75-88, John Wiley & Sons, Ltd., United States (2004).

Doan, T., et al., "Peripheral Tolerance to Human Papillomavirus E7 Oncoprotein Occurs by Cross-Tolerization, Is Largely Th-2-independent, and Is Broken by Dendritic Cell Immunization," *Cancer Research* 60:2810-2815, American Association for Cancer Research, United States (2000).

Dorfman, T., et al., "Functional Domains of the Capsid Protein of Human Immunodeficiency Virus Type 1," *Journal of Virology* 68(12):8180-8187, American Society for Microbiology, United States (1994).

Drakakaki, G., et al., "The Intracellular Fate of a Recombinant Protein Is Tissue Dependent," *Plant Physiology* 141:578-586, American Society of Plant Biologists, United States (2006).

Dyson, N., et al., "The Human Papilloma Virus-16 E7 Oncoprotein Is Able to Bind to the Retinoblastoma Gene Product," *Science* 243:934-937, American Association for the Advancement of Science, United States (1989).

Edmonds, C. and Vousden, K.H., "A Point Mutational Analysis of Human Papillomavirus Type 16 E7 Protein," *Journal of Virology* 63(6):2650-2656, American Society for Microbiology, United States (1989).

Eisenberg, D., et al., "Analysis of Membrane and Surface Protein Sequences with the Hydrophobic Moment Plot," *J. Mol. Biol.* 179:125-142, Academic Press Inc. (London) Ltd., England (1984).

Estcourt, M.J., et al., "DNA vaccines against human immunodeficiency virus type 1," *Immunological Reviews* 199:144-155, Blackwell Munksgaard, England (2004).

Evangelista, R.L., et al., "Process and Economic Evaluation of the Extraction and Purification of Recombinant β-Glucuronidase from Transgenic Corn," *Biotechnol. Prog.* 14:607-614, American Chemical Society and American Institute of Chemical Engineers, United States (1998).

Galili, G., et al., "Assembly and transport of seed storage proteins," *Trends in Cell Biology* 3:437-443, Elsevier Science Publishers Ltd, England (1993).

(56) References Cited

OTHER PUBLICATIONS

Gatta, G., et al., "Survival of European Women with Gynaecological Tumours, During the Period 1978-1989," *Eur J Cancer* 34(14):2218-2225, Elsevier Science Ltd, England (1998).

Geli, M.I., et al., "Two Structural Domains Mediate Two Sequential Events in γ-Zein Targeting: Protein Endoplasmic Reticulum Retention and Protein Body Formation," *The Plant Cell* 6:1911-1922, American Society of Plant Physiologists, United States (1994).

Halsey, R.J., et al., "Chimaeric HIV-1 subtype C Gag molecules with large in-frame C-terminal polypeptide fusions form virus-like particles," *Virus Research* 133:259-268, Elsevier B.V., Netherlands (2008).

Hennegan, K., et al., "Improvement of human lysozyme expression in transgenic rice grain by combining wheat (*Triticum aestivum*) puroindoline b and rice (*Oryza sativa*) Gt 1 promoters and signal peptides," *Transgenic Research* 14:583-592, Springer, Germany (2005).

Herman, E.M. and Larkins, B.A., "Protein Storage Bodies and Vacuoles," *The Plant Cell* 11:601-613, American Society of Plant Physiologists, United States (1999).

Horn, M.E., et al., "Plant molecular farming: systems and products," *Plant Cell Rep* 22:711-720, Springer-Verlag, Germany (2004).

Hurkman, W.J., et al., "Subcellular Compartmentalization of Maize Storage Proteins in *Xenopus* Oocytes Injected with Zein Messenger RNAs," *The Journal of Cell Biology* 89:292-299, The Rockefeller University Press, United States (1981).

Jaffray, A., et al., "Human immunodeficiency virus type 1 subtype C Gag virus-like particle boost substantially improves the immune response to a subtype C gag DNA vaccine in mice," *Journal of General Virology* 85:409-413, SGM, England (2004).

Jutras, I. and Desjardins, M., "Phagocytosis: At the Crossroads of Innate and Adaptive Immunity," *Annu. Rev. Cell Dev. Biol.* 21:511-527, Annual Reviews, United States (2005).

Kahn, S.J. and Wleklinski, M., "The Surface Glycoproteins of *Trypanosoma cruzi* Encode a Superfamily of Variant T Cell Epitopes," *The Journal of Immunology* 159:4444-4451, American Association of Immunologists, United States (1997).

Kaufmann, S.H.E. and Schaible, U.E., "Antigen presentation and recognition in bacterial infections," *Current Opinion in Immunology* 17:79-87, Elsevier Ltd., England (2005).

Kelly, M.A., et al., "Host-Guest Study of Left-Handed Polyproline II Helix Formation," *Biochemistry* 40(48):14376-14383, American Chemical Society, United States (2001).

Kent, S.B.H. et al., "Precise Location of a Continuous Epitope in the Pre-S-gene-coded Envelope Proteins of Hepatitis-B Virus," *Vaccines* 86:365-369, Cold Spring Harbor Laboratory, United States (1986).

Kim, C.S., et al., "Zein Protein Interactions, Rather Than the Asymmetric Distribution of Zein mRNAs on Endoplasmic Reticulum Membranes, Influence Protein Body Formation in Maize Endosperm," *The Plant Cell* 14:655-672, American Society of Plant Biologists, United States (2002).

Von Knebel Doeberitz, M., et al., "Reversible Repression of Papillomavirus Oncogene Expression in Cervical Carcinoma Cells: Consequences for the Phenotype and E6-p53 and E7-pRB Interactions," *Journal of Virology* 68(5):2811-2821, American Society for Microbiology, United States (1994).

Knighton, D.R. et al., "Structure of a Peptide Inhibitor Bound to the Catalytic Subunit of Cyclic Adenosine Monophosphate-Dependent Protein Kinase," *Science* 253:414-420, American Association for the Advancement of Science, United States (1991).

Kogan, M.J., et al., "Exploring the Interaction of the Surfactant N-Terminal Domain of γ-Zein with Soybean Phosphatidylcholine Liposomes," *Biopolymers* 73:258-268, Wiley Periodicals, Inc., United States (2003).

Kogan, M.J., et al., "Self-assembly of the Amphipathic Helix (VHLPPP)$_8$. A Mechanism for Zein Protein Body Formation," *J. Mol. Biol.* 312:907-913, Academic Press, United States (2001).

Kogan, M.J., et al., "Supramolecular Properties of the Proline-Rich γ-Zein N-Terminal Domain," *Biophysical Journal* 83:1194-1204, Biophysical Society, United States (2002).

Lau, A.H. and Thomson, A.W., "Dendritic cells and immune regulation in the liver," *Gut* 52:307-314, British Medical Association, England (2003).

Letvin, N.L., et al., "Potent, protective anti-HIV immune responses generated by bimodal HIV envelope DNA plus protein vaccination," *Proc. Natl. Acad. Sci.* 94:9378-9383, The National Academy of Sciences, United States (1997).

Leung, L., "Immunogenicity of HIV-1 Env and Gag in baboons using a DNA prime/protein boost regimen," *AIDS* 18(7):991-1001, Lippincott Williams & Wilkins, England (2004).

Lim, W.A., et al, "Structural determinants of peptide-binding orientation and of sequence specificity in SH3 domains," *Nature* 372:375-379, Nature Publishing Group, England (1994).

Ludevid, M.D., et al., "Subcellular localization of glutelin-2 in maize (*Zea mays* L.) endosperm," *Plant Molecular Biology* 3:227-234, Martinus Nijhoff/Dr W. Junk Publishers, Netherlands (1984).

Ma, J.K.-C., et al., "Generation and Assembly of Secretory Antibodies in Plants," *Science* 268:716-719, American Association for the Advancement of Science, United States (1995).

Ma, K., et al., "Polyproline II Helix Is•a Key Structural Motif of the Elastic PEVK Segment of Titin," *Biochemistry* 40:3427-3438, American Chemical Society, United States (2001).

Mainieri, D., et al., "Zeolin. A New Recombinant Storage Protein Constructed Using Maize γ-Zein and Bean Phaseolin," *Plant Physiology* 136:3447-3456, American Society of Plant Biologists, United States (2004).

Matsushima, R., et al., "A novel ER-derived compartment, the ER body, selectively accumulates a β-glucosidase with an ER-retention signal in *Arabidopsis*," *The Plant Journal* 33:493-502, Blackwell Publishing Ltd, England (2003).

Menkhaus, T.J., et al., "Considerations for the Recovery of Recombinant Proteins from Plants," *Biotechnol. Prog.* 20:1001-1014, American Chemical Society and American Institute of Chemical Engineers, United States (2004).

Mergener, K., et al., "Analysis of HIV Particle Formation Using Transient Expression of Subviral Constructs in Mammalian Cells," *Virology* 186:25-39, Academic Press, Inc., United States (1992).

Michel, N., et al., "Enhanced Immunogenicity of HPV 16 E7 Fusion Proteins in DNA Vaccination," *Virology* 294:47-59, Elsevier Science, United States (2002).

Milich, D.R., et al., "An Immune Response to the Pre-S1 Region Can Bypass Nonresponse to the Pre-S2 and S Regions of HBsAg," *Vaccines* 87:50-55, Cold Spring Harbor Laboratory, United States (1987).

Montefiori, D.C., et al., "Neutralizing Antibodies Associated with Viremia Control in a Subset of Individuals after Treatment of Acute Human Immunodeficiency Virus Type 1 Infection," *Journal of Virology* 75(21):10200-10207, American Society for Microbiology, United States (2001).

Münger, K., et al., "Interactions of HPV E6 and E7 Oncoproteins with Tumour Suppressor Gene Products," *Cancer Surveys* 12:197-217, Imperial Cancer Research Fund, England (1992).

Muñoz, N., et al., "Epidemiologic Classification of Human Papillomavirus Types Associated with Cervical Cancer," *N Engl J Med* 348(6):518-527, Massachusetts Medical Society, United States (2003).

Neurath, A.R., et al., "Immune Response to Hepatitis-B Virus Determinants Coded by the Pre-S Gene," *Vaccines* 85:185-189, Cold Spring Harbor Laboratory, United States (1986).

Novitsky, V., et al., "Magnitude and Frequency of Cytotoxic T-Lymphocyte Responses: Identification of Immunodominant Regions of Human Immunodeficiency Virus Type 1 Subtype C," *Journal of Virology* 76(20):10155-10168, American Society for Microbiology, United States (2002).

Öhlschläger, P., et al., "An improved rearranged Human Papillomavirus Type 16 E7 DNA vaccine candidate (HPV-I6 E7SH) induces an E7 wildtype-specific T cell response," *Vaccine* 24:2880-2893, Elsevier Ltd., United States (2006).

(56) References Cited

OTHER PUBLICATIONS

Ohta, N., et al., "Epitope Analysis of Human T-Cell Response to MSP-1 of *Plasmodium falciparum* in Malaria-Nonexposed Individuals," *Int Arch Allergy Immunol* 114:15-22, S. Karger AG, Basel, Switzerland (1997).

Okita, T.W. and Rogers, J.C., "Compartmentation of Proteins in the Endomembrane System of Plant Cells," *Annu. Rev. Plant Physiol. Plant Mol. Biol.* 47:327-350, Annual Reviews Inc., United States (1996).

Osen, W., at al., "A DNA vaccine based on a shuffled E7 oncogene of the human papillomavirus type 16 (HPV 16) induces E7-specific cytotoxic T cells but lacks transforming activity," *Vaccine* 19:4276-4286, Elsevier Science Ltd., England (2001).

Pal, R., et al, "Immunization of rhesus macaques with a polyvalent DNA prime/protein boost human immunodeficiency virus type 1 vaccine elicits protective antibody response against simian human immunodeficiency virus of R5 phenotype," *Virology* 348:341-353, Elsevier Inc., United States (2006).

Paliard, X., et al., "Priming of Strong, Broad, and Long-Lived HIV Type 1 p55*gag*-Specific CD8$^+$ Cytotoxic T Cells after Administration of a Virus-Like Particle Vaccine in Rhesus Macaques," *AIDS Research and Human Retroviruses* 16(3):273-282, Mary Ann Liebert, Inc., United States (2000).

Petruccelli, S., et al., "A KDEL-tagged monoclonal antibody is efficiently retained in the endoplasmic reticulum in leaves, but is both partially secreted and sorted to protein storage vacuoles in seeds," *Plant Biotechnology* 4: 511-527, Blackwell Publishing Ltd., England (2006).

Pompa, A. and Vitale, A., "Retention of a Bean Phaseolin/Maize γ-Zein Fusion in the Endoplasmic Reticulum Depends on Disulfide Bond Formation," *The Plant Cell* 18:2608-2621, American Society of Plant Biologists, United States (2006).

Rabanal, F., et al., "CD of Proline-Rich Polypeptides: Application to the Study of the Repetitive Domain of Maize Glutelin-2," *Biopolymers* 33:1019-1028, John Wiley & Sons, Inc., United States (1993).

Rafalski, J.A., et al., "Developmentally regulated plant genes: the nucleotide sequence of a wheat gliadin genomic clone," *The EMBO Journal* 3(6):1409-1415, IRL Press Limited, Oxford, England (1984).

Randall, J., et al., "A modified 10 kD zein protein produces two morphologically distinct protein bodies in transgenic tobacco," *Plant Science* 150:21-28, Elsevier Science Ireland Ltd., Ireland (2000).

Renzoni, D.A., et al., "Structural and Thermodynamic Characterization of the Interaction of the SH3 Domain from Fyn with the Proline-Rich Binding Site on the p85 Subunit of P13-Kinase," *Biochemistry* 35:15646-15653, American Chemical Society, United States (1996).

Richter, L.Z., et al., "Production of hepatitis B surface antigen in transgenic plants for oral immunization," *Nature Biotechnology* 18:1167-1171, Nature Publishing Company, United States (2000).

Robinson, H.L., "DNA vaccines: Basic mechanism and immune responses (Review)," *International Journal of Molecular Medicine* 4:549-555, Spandidos, Greece (1999).

Van Rooijen, G.J.H. and Moloney, M.M., "Plant Seed Oil-bodies as Carriers for Foreign Proteins," *Bio/Technology* 13:72-77, Nature Pub. Co., United States (1995).

Rosenberg, N., et al., "Wheat (*Triticum aestivum* L.) γ-Gliadin Accumulates in Dense Protein Bodies within the Endoplasmic Reticulum of Yeast," *Plant Physiol.* 102:61-69, American Society of Plant Biologists, United States (1993).

Rucker, A.L., et al., "Host-Guest Scale of Left-Handed Polyproline II Helix Formation," *Proteins: Structure, Function and Genetics* 52:68-75, Wiley-Liss, Inc., United States (2003).

Sakuragi, S., et al., "HIV type I Gag virus-like particle budding from spheroplasts of *Saccharomyces cerevisiae*," *PNAS* 99(12):7956-7961, National Academy of Sciences, United States (2002).

Sanderfoot, A.A. and Raikhel, N.V., "The Specificity of Vesicle Trafficking: Coat Proteins and SNAREs," *The Plant Cell* 11:629-641, American Society of Plant Physiologists, United States (1999).

Saron, M.F., at al., "Anti-viral protection conferred by recombinant adenylate cyclase toxins from *Bordetella pertussis* carrying a CD8$^+$ T cell epitope from lymphocytic choriomeningitis virus," *Proc. Natl. Acad. Sci.* 94:3314-3319, The National Academy of Sciences of the USA, United States (1997).

Scheerlinck, J-P. Y. and Greenwood, D.L.V., "Particulate delivery systems for animal vaccines," *Methods* 40:118-124, Elsevier Inc., United States (2006).

Shewry, P.R. and Halford, N. G., "Cereal seed storage proteins: structures, properties and role in grain utilization," *Journal of Experimental Botany* 53(370):947-958, Society for Experimental Biology, England (2002).

Shewry, P.R. and Tatham, A.S., "The prolamin storage proteins of cereal seeds: structure and evolution," *Biochem.* 1 267:1-12, Portland Press, Great Britain (1990).

Shewry, P.R., et al., "Seed Storage Proteins: Structures and Biosynthesis," *The Plant Cell* 7:945-956, American Society of Plant Physiologists, United States (1995).

Shi, W., et al., "Human Papillomavirus Type 16 E7 DNA Vaccine: Mutation in the Open Reading Frame of E7 Enhances Specific Cytotoxic T-Lymphocyte Induction and Antitumor Activity," *Journal of Virology* 9(73):7877-7881, American Society for Microbiology, United States (1999).

Shi, Z., et al., "Polyproline II propensities from GGXGG peptides reveal an anticorrelation with β-sheet scales," *PNAS* 102(50):17964-17968, National Academy of Sciences, United States (2005).

Šmahel., M., et al., "Modified HPV16 E7 Genes as DNA Vaccine against E7-Containing Oncogenic Cells," *Virology* 281:231-238, Academic Press, United States (2001).

Smyth, E., et al., "Solution Structure of Native Proteins With Irregular Folds From Raman Optical Activity," *Biopolymers* 58:138-151, John Wiley & Sons, Inc., United States (2001).

Spencer, D.I.R., et al., "Structure/ Activity Studies of the Anti-MUC1 Monoclonal Antibody C595 and Synthetic MUC1 Mucin-Core-Related Peptides and Glycopeptides," *Biospectroscopy* 5:79-91, John Wiley & Sons, Inc., United States (1999).

Staffileno, L.K., et al., "Cloning of the Amino Terminal Nucleotides of the Antigen I/II of *Streptococcus sobrinus* and the Immune Responses to the Corresponding Synthetic Peptides," *Archs oral Biol.* 35:47s-52s, Pergamon Press plc, Great Britain (1990).

Sugiyama, T., et al., "The Nucleotide Sequence of a Wheat γ-Gliadin Genomic Clone," *Plant Science* 44:205-209, Elsevier Scientific Publishers Ireland Ltd., Ireland (1986).

Suh, Y.S., et al., "Reduction of viral loads by multigenic DNA priming and adenovirus boosting in the SIVmac-macaque model," *Vaccine* 24:1811-1820, Elsevier Ltd., England (2006).

Tackaberry, E.S., et al., "Development of pharmaceuticals in plant expression systems: cloning, expression and immunological reactivity of human cytomegalovirus glycoprotein B (UL55) in seeds of transgenic tobacco," *Vaccine* 17:3020-3029, Elsevier Science Ltd., Netherlands (1999).

Torrent, M., et al., "In maize, glutelin-2 and low molecular weight zeins are synthesized by membranebound polyribosomes and translocated into microsomal membranes," *Plant Molecular Biology* 7:393-403, Martinus Nijhoff Publishers, Netherlands (1986).

Torrent, M., et al., "Lysine-rich modified γ-zeins accumulate in protein bodies of transiently transformed maize endosperms," *Plant Molecular Biology* 34:139-149, Kluwer Academic Publishers, Belgium (1997).

Torrent, M., et al., "Role of Structural domains for maize γ-zein retention in *Xenopus* oocytes," *Planta* 192:512-518, Springer-Verlag, Germany (1994).

Twyman, R.M., et al., "Molecular farming in plants: host system and expressions technology," *TRENDS in Biotechnology* 21(12):570-578, Elsevier Ltd., England (2003).

Velders, M.P., et al., "Defined Flanking Spacers and Enhanced Proteolysis Is Essential for Eradication of Established Tumors by an

(56) References Cited

OTHER PUBLICATIONS

Epitope String DNA Vaccine," *The Journal of Immunology* 166(9):5366-5373, The American Association of Immunologists, United States (2001).
Vergne., I., et al., "Phagosomal pH Determination by Dual Fluorescence Flow Cytometry," *Analytical Biochemistry* 255:127-132, Academic Press, United States (1998).
De Villiers, E-M., et al., "Classification of papillomaviruses," *Virology* 324:17-27, Elsevier Inc., United States (2004).
Wagner, R., et al., "Construction, Expression, and Immunogenicity of Chimeric of HIV-1 Virus-like Particles," *Virology* 220:128-140, Academic Press, Inc., United States (1996).
Wagner, R., et al., "Induction of a MHC Class 1-Restricted, CD8 Positive Cytolytic T-Cell Response by Chimeric HIV-1 Virus-Like Particles in Vivo: Implications on HIV Vaccine Development," *Behring Inst. Mitt.* 95:23-34, Marburg/Lahn: Behringwerke AG, Germany (1994).
Walboomers, J.M.M., et al., "Human Papillovirus Is a Necessary Cause of Invasive Cervical Cancer Worldwide," *J. Pathol.* 189:12-19, John Wiley & Sons, Ltd., United States (1999).
Watanabe, S., et al., "Mutational Analysis of Human Papillomavirus Type 16 E7 Functions," *Journal of Virology* 64(1):207-214, American Society for Microbiology, United States (1990).
Wright, K.E., et al., "Sorting of glycoprotein B from human cytomegalovirus to protein storage vesicles in seeds of transgenic tobacco," *Transgenic Research* 10:177-181, Kluwer Academic Researchers, Netherlands (2001).
Yang, C., et al., "Induction of protective antibodies in *Saimiri* monkeys by immunization with a multiple antigen construct (MAC) containing the *Plasmodium vivax* circumsporozoite protein repeat region and a universal T helper epitope of tetanus toxin," *Vaccine* 15(4):377-386, Elsevier Science Ltd., Great Britain (1997).
Yang, D., et al., "Expression and localization of human lysozyme in the endosperm of transgenic rice," *Planta* 216:597-603, Springer-Verlag, Germany (2003).
Yasutomi, Y., et al., "Simian Immunodeficiency Virus-Specific Cytotoxic T-Lymphocyte Induction through DNA Vaccination of Rhesus Monkeys," *Journal of Virology* 70(1):678-681, American Society for Microbiology, United States (1996).
Zhong, W., et al., "Plasmid DNA and protein vaccination of mice to the outer surface protein A of *Borrelia burgdorferi* leads to induction of T helper cells with specificity for a major epitope and augmentation of protective IgG antibodies in vivo," *Eur. J. Immunol.* 26:2749-2757, VCH Verlagsgesellschaft mbH, Weinheim, Germany (1996).
Syme, C.D., et al., "A Raman optical activity study of rheomorphism in caseins, synucleins and tau: New insight into the structure and behavior of natively unfolded proteins," *Eur. J. Biochem.* 269:148-156, FEBS, England (2002).
International Search Report for International Application No. PCT/EP2009/063223, European Patent Office, The Hague, Netherlands, mailed on Jun. 11, 2010.
International Search Report for International Application No. PCT/EP2011/058864, European Patent Office, The Hague, Netherlands, mailed on Nov. 15, 2011.
Alvarez, I., et al., "Lysine-rich γ-zeins are secreted in transgenic *Arabidopsis* plants," *Planta* 205:420-427, Springer-Verlag, Germany (1998).

Cameron-Mills, V., "The Structure and Composition of Protein Bodies Purified From Barley Endosperm by Silica Sol Density Gradients," *Carlsberg Res. Commun.* 45:557-576, Springer-Verlag, Germany (1980).
EMS-McClung, S.C., et al., "Mutational analysis of the maize gamma zein C-terminal cysteine residues," *Plant Science* 162:131-141, Elsevier Science. Ireland Ltd., Ireland (2002).
Richard, G., et al, "Transport and deposition of cereal prolamine," *Plant Physiol. Biochem.* 34(2):237-243, Gauthier-Villars, France (1996).
Miflin, B.J., et al., "The Development of Protein Bodies in the Storage Tissues of Seeds: Subcellular Separations of Homogenates of Barley, Maize, and Wheat Endosperms and of Pea Cotyledons," *Journal of Experimental Botany* 32(126):199-219, Oxford University Press, England (1981).
Philip, R., et al., "Localization of β-glucuronidase in protein bodies of transgenic tobacco seed by fusion to an amino terminal sequence of the soybean lectin gene," *Plant Science* 137:191-204, Elsevier Science Ireland Ltd., Ireland (1998).
Sojikul, P., et al., "A plant signal peptide-hepatitis B surface antigen fusion protein with enhanced stability and immunogenicity expressed in plant cells," *PNAS* 100(5):2209-2214, National Academy of Sciences, United States (2003).
Takagi, H., et al., "A rice-based edible vaccine expressing multiple T cell epitopes induces oral tolerance for inhibition of Th2-mediated IgE responses," *PNAS* 102(48):17525-17530, National Academy of Sciences, United States (2003).
Baccanari, D., et al., "Purification and Properties of *Escherichia coli* Dihydrofolate Reductase," *Biochemistry* 14(24):5267-5273, American Chemical Society, United States (1975).
Barteri, M., et al., "Low frequency ultrasound induces aggregation of porcine fumarase by free radicals production," *Biophysical Chemistry* 111:35-42, Elsevier B.V., Netherlands (2004).
Castellanos, I.J., et al., "Encapsulation-induced aggregation and loss in activity of γ-chymotrypsin and their prevention," *Journal of Controlled Release* 81:307-319, Elsevier Science B.V., Netherlands (2002).
Esen, A., et al., "Tandem repeats in the N-terminal sequence of a proline-rich protein from corn endosperm," *Nature* 296(5858):678-679, Macmillan Journals Ltd., England (1982).
Llop-Tous, I., et al., "The Expression of a Xylanase Targeted to ER-Protein Bodies Provides a Simple,Strategy to Produce Active Insoluble Enzyme Polymers in Tobacco Plants," *PLoS ONE* 6(4):e19474, 11 pages, Public Library of Science, United States (Apr. 2011).
Llop-Tous, I., et al., "Relevant Elements of a Maize γ-Zein Domain Involved in Protein Body Biogenesis," *The Journal of Biological Chemistry* 285(46):35633-35644, The American Society for Biochemistry and Molecular Biology, Inc., United States (Sep. 2010).
Torrent, M., et al., "Eukaryotic protein production in designed storage organelles," *BMC Biology* 7(5), 14 pages, BioMed Central Ltd., England (2009).
Tsumoto, K., et al., "Solubilization of active green fluorescent protein from insoluble. particles by guanidine and arginine," *Biochemical and Biophysical Research Communications* 312:1383-1386, Elsevier Inc., United States (2003).
Zupan, A.L., et al., "High expression of green fluorescent protein in *Pichia pastoris* leads to formation of fluorescent particles," *Journal of Biotechnology* 109:115-122, Elsevier B.V., Netherlands (2004).

\* cited by examiner

Figure 1
A
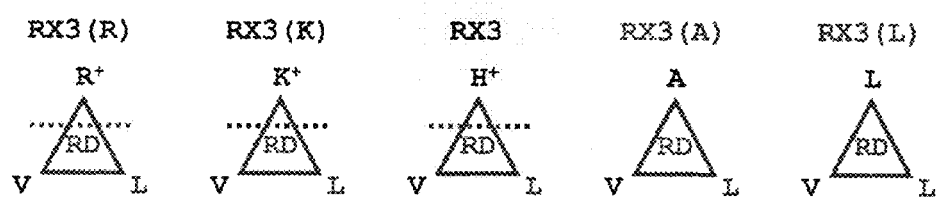
B
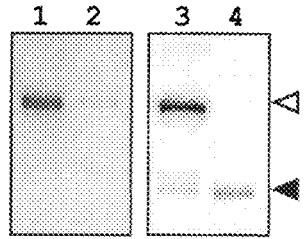
1. RX3-Gfp
2. RX3(R)-Gfp
3. RX3-ECFP
4. RX3(K)-ECFP
C
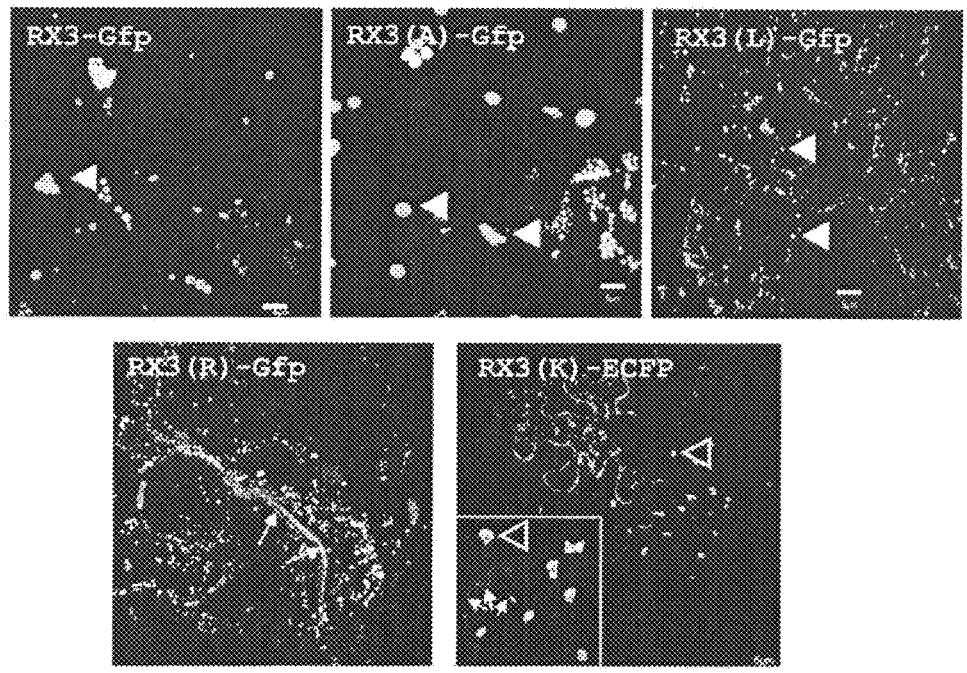

Figure 2
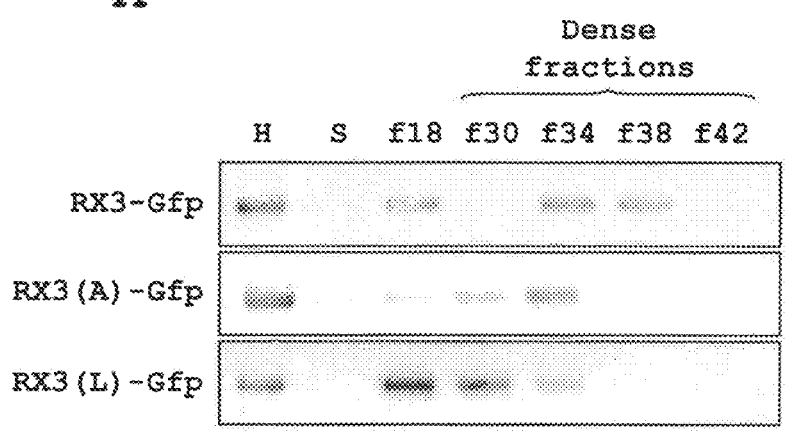
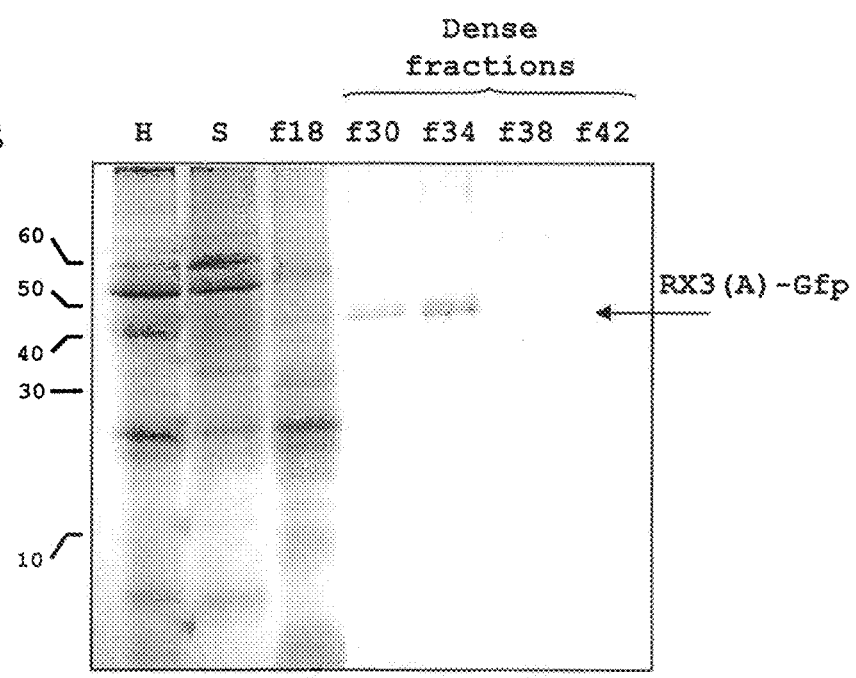

Figure 3
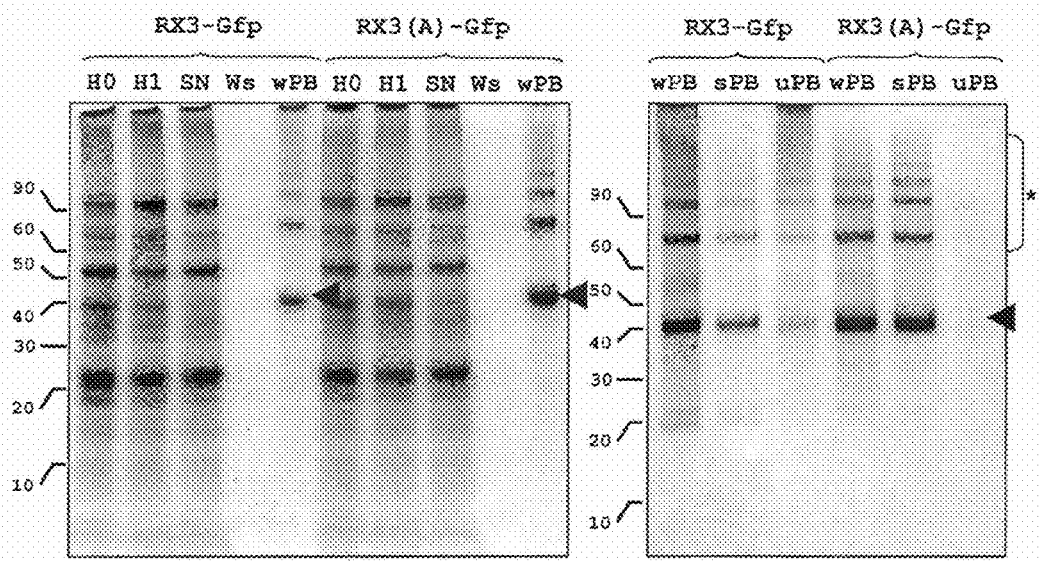
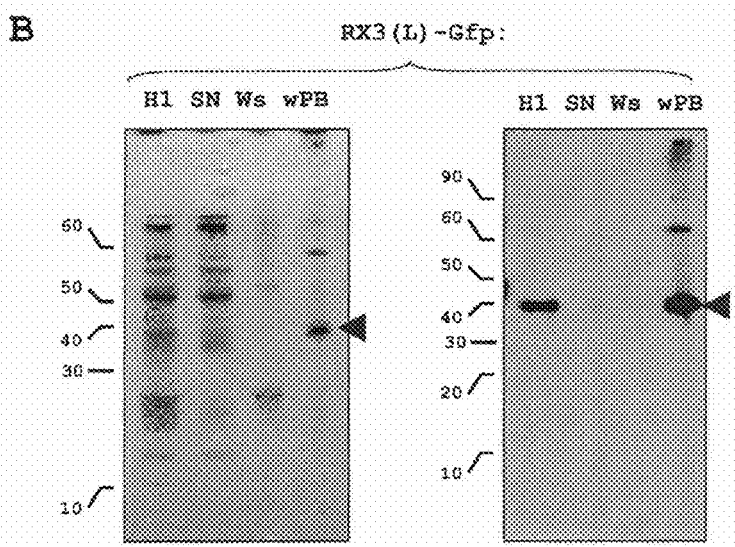

Figure 4
A
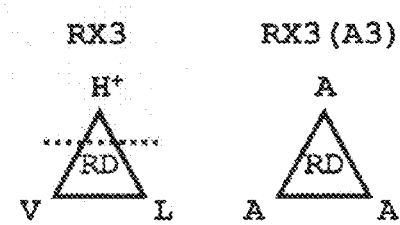
B
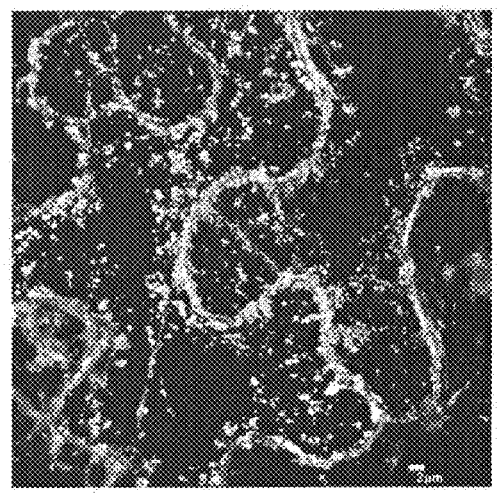
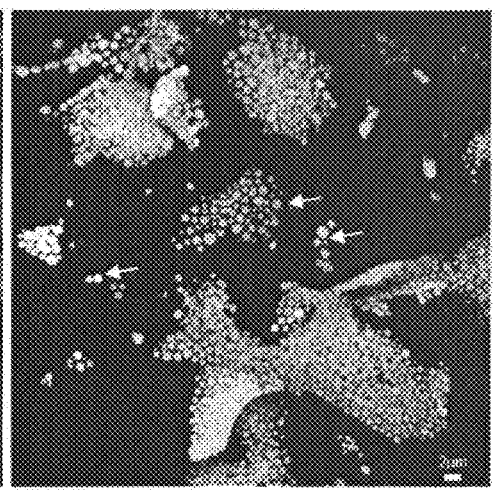

Figure 5
A
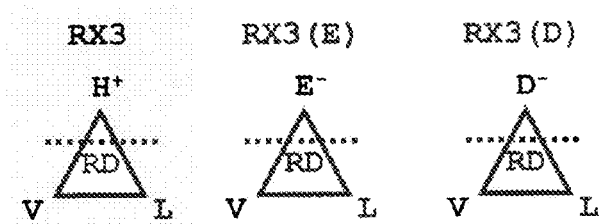
B
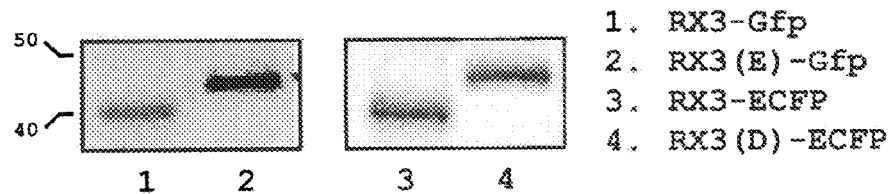
1. RX3-Gfp
2. RX3(E)-Gfp
3. RX3-ECFP
4. RX3(D)-ECFP
C
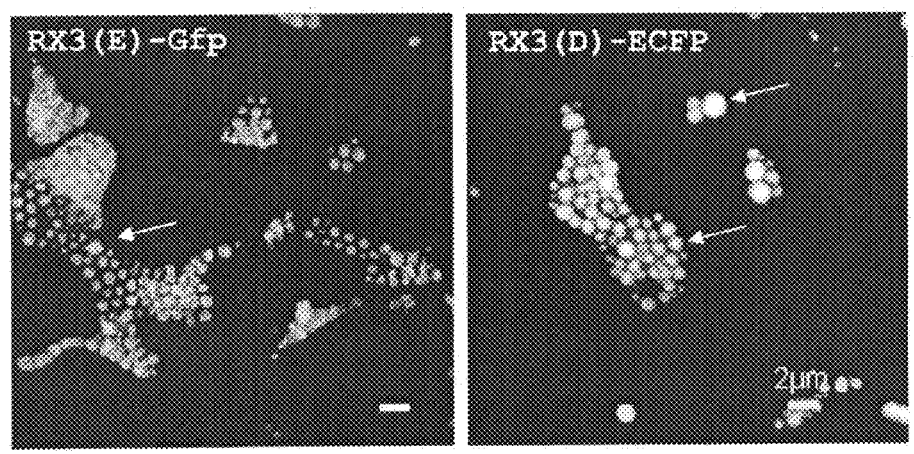

Figure 6
A
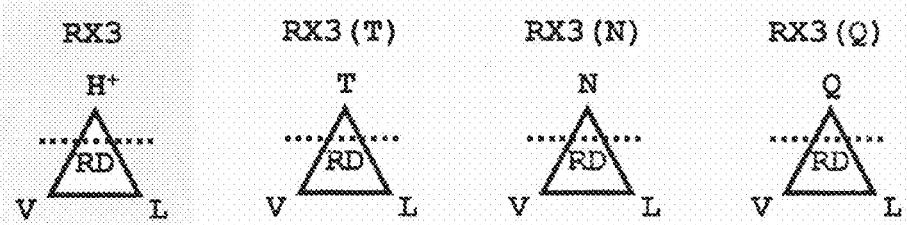
B
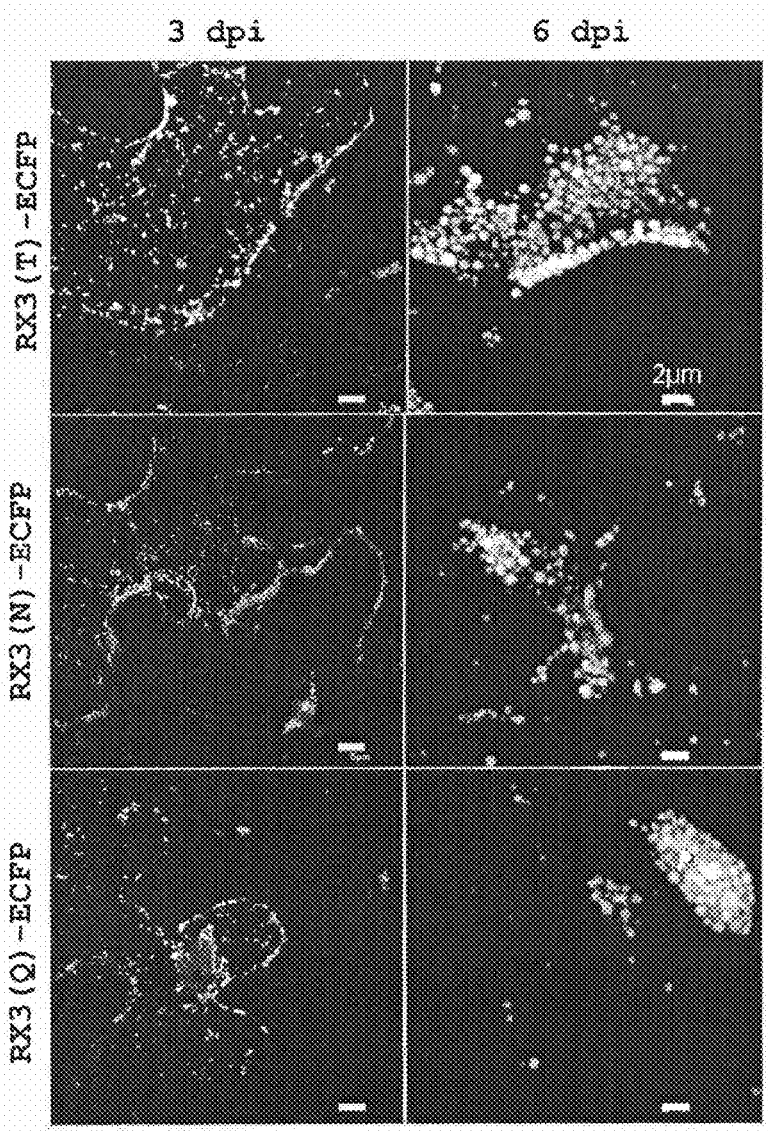

Figure 7
A
RX3: SP-THTSGGCGQ PPPPVHLPPP VHLPPPVHLP PPVHLPPPVH LPPPVHLPPP
PP: SP-THTSGGCGQ PPPPPPPPPP PPPPPPPPPP PPPPPPPPPP PPPPPPPPPP
PA: SP-THTSGGCGQ PPPPAPAPPP APAPPPAPAP PPAPAPPPAP APPPAPAPPP
VHVPPPVHLP PPPHYPTQP PPPQPHPQPH PPPQQPHPS PPQ
PPPPPPHLP PPPPPPPPP PPPPPPPPP PPPPPPPP PPP
APAPPPAHLP PPPAPPALA PAPAPAPPPA PAPPAPAPP PAP
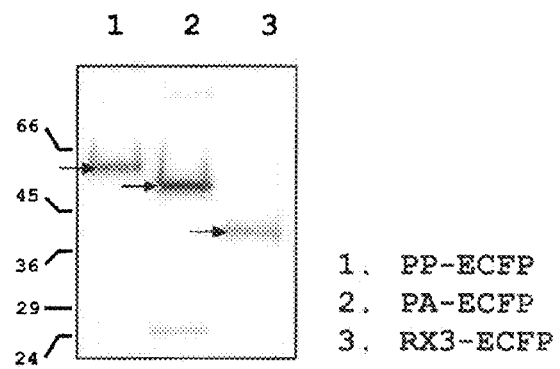
1. PP-ECFP
2. PA-ECFP
3. RX3-ECFP
C
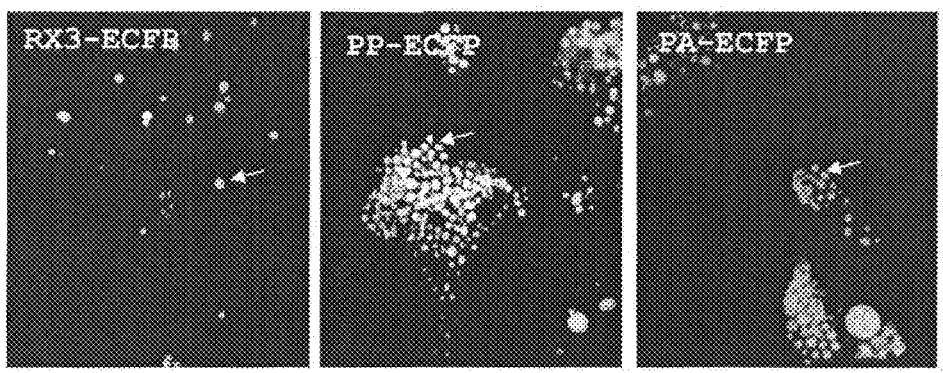

Figure 9
A
```
PP:  SP-THTSGGCGCQ PPPPPPPPPP PPPPPPPPPP PPPPPPPPPP PPPPPPPPPP
PP2: SP-THPPPPCPPC PPPPPPPPPP PPPPPPPPPP PPPPPPPPPP PPPPPPPPPP
     PPPPPPPHLP PPPCPPPPPP PPPPPPPPPP PCPCPPPPPP PCP
     PPPPPPPHLP PPPCPPPPPP PPPPPPPPPP PCPPCPPPPP CPP
```
B
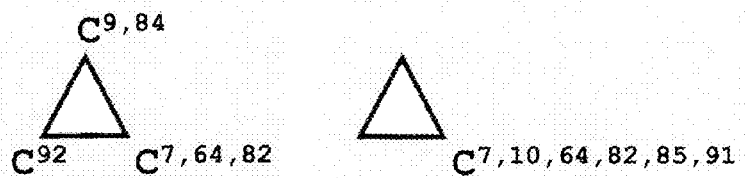
C
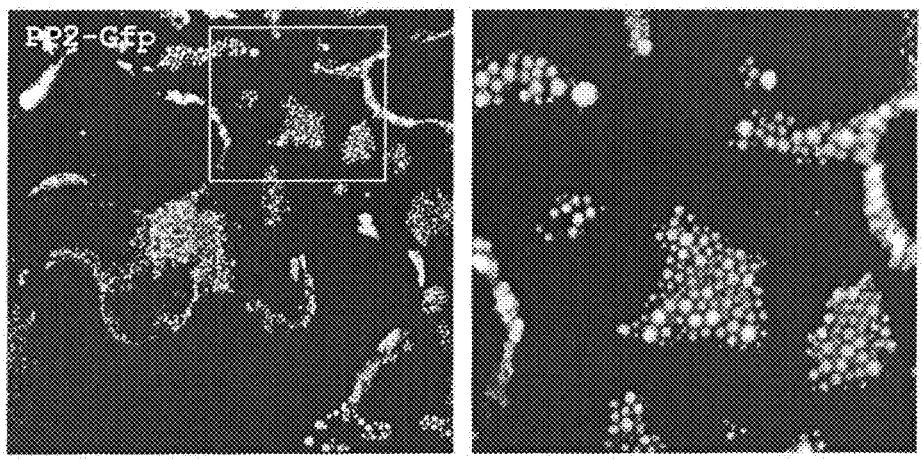

Figure 10
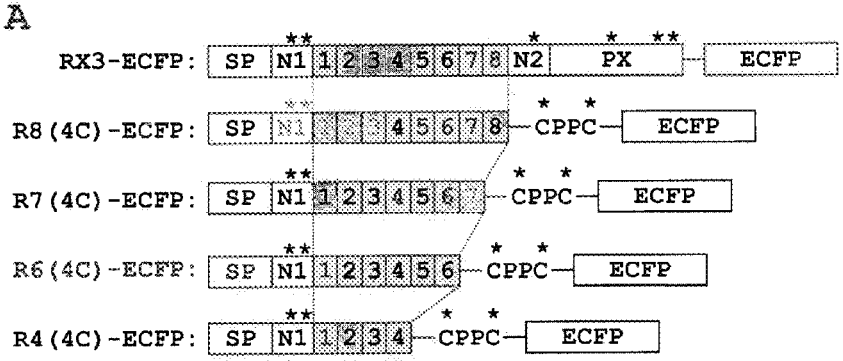
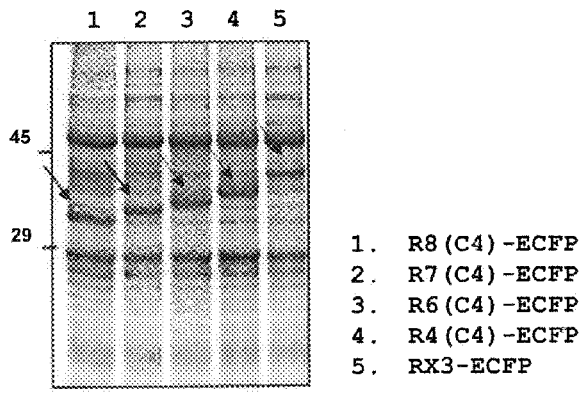
1. R8(C4)-ECFP
2. R7(C4)-ECFP
3. R6(C4)-ECFP
4. R4(C4)-ECFP
5. RX3-ECFP
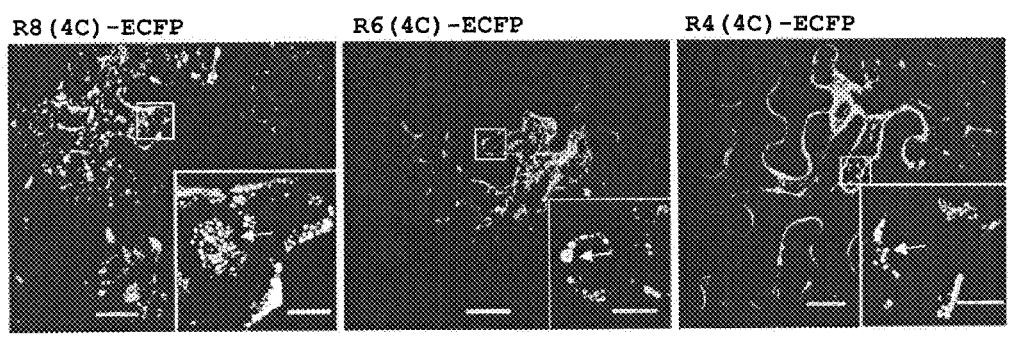

Figure 12
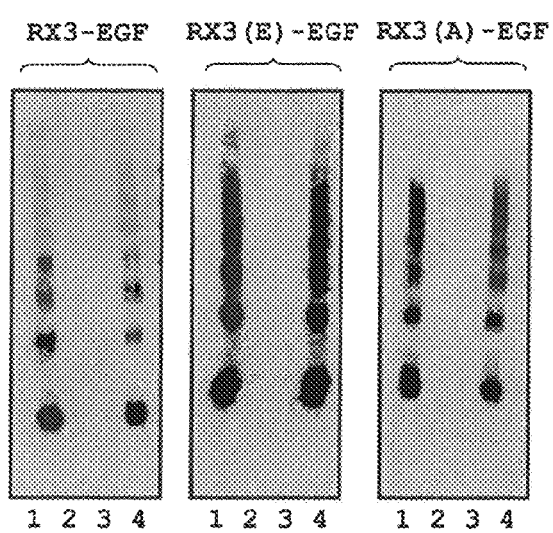
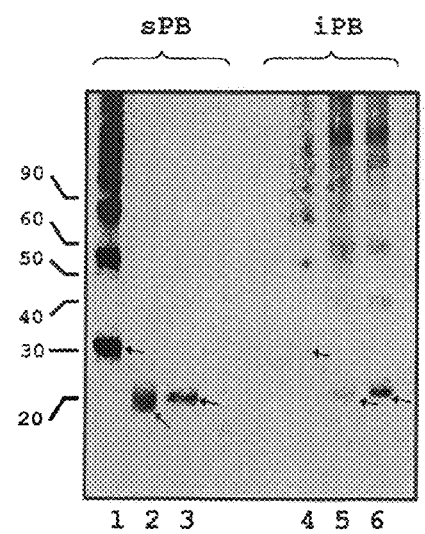
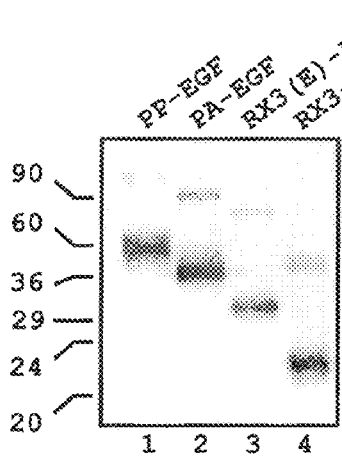
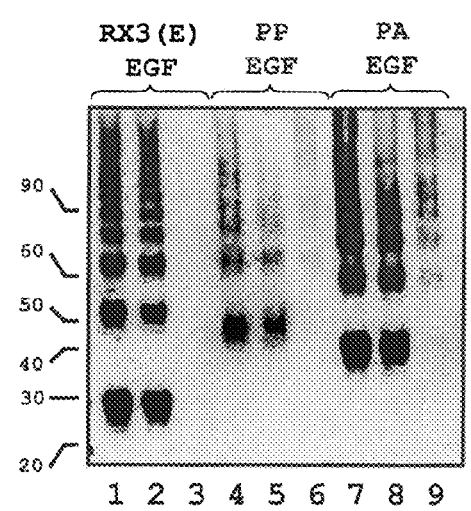

Figure 14
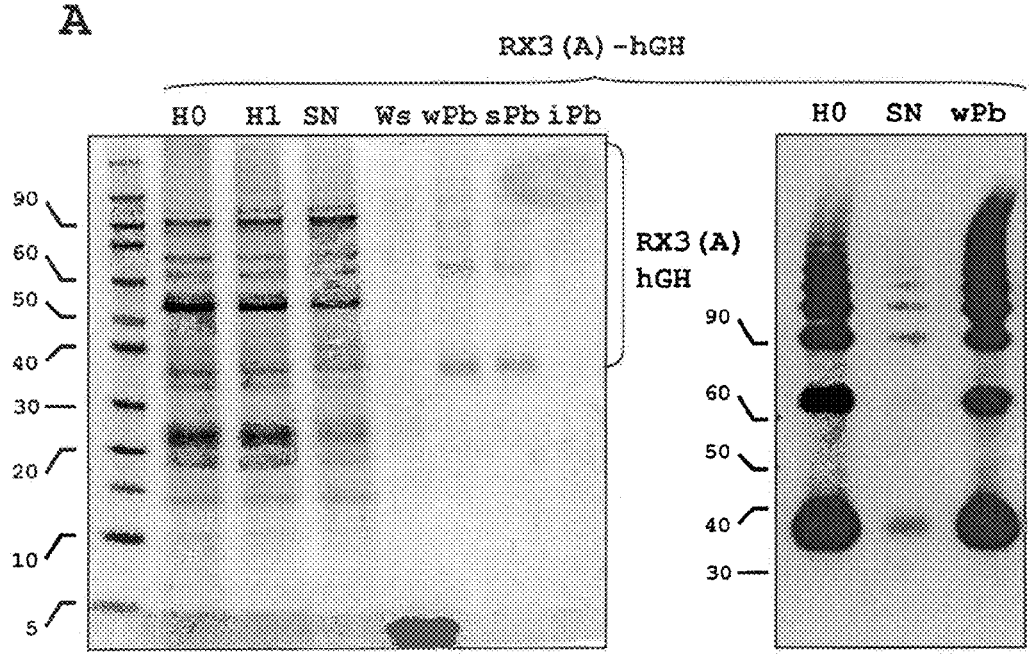
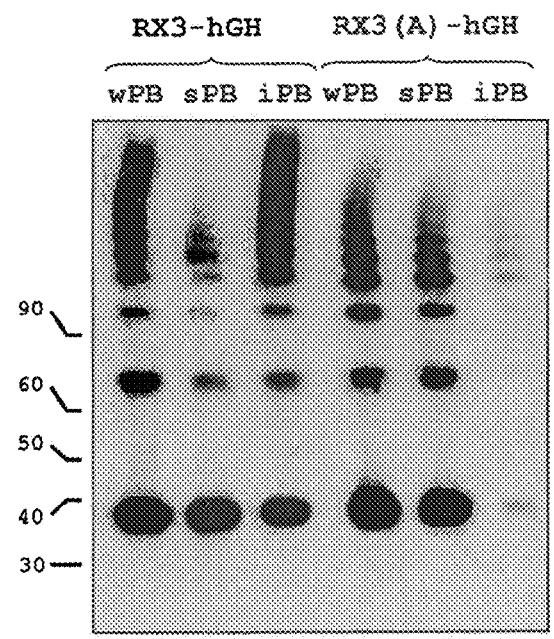

Figure 15a

|  | PBIS | Linker | CS | POI |
|---|---|---|---|---|
| RX3-mcherry: | RX3 | (Gly)x5 |  | mcherry |
| RX3(A)-mcherry: | RX3(A) | (Gly)x5 |  | mcherry |
| RX3(E)-mcherry: | RX3(E) | (Gly)x5 |  | mcherry |
| RX3-hGH: | RX3 | (Gly)x5 | EK | hGH |
| RX3(A)-hGH: | RX3(A) | (Gly)x5 | EK | hGH |
| RX3-EGF: | RX3 | (Gly)x5 | FXa | EGF |
| RX3(A)-EGF: | RX3(A) | (Gly)x5 | FXa | EGF |
| RX3(E)-EGF: | RX3(E) | (Gly)x5 | FXa | EGF |
| PP-EGF: | PP | (Gly)x5 | FXa | EGF |
| PA-EGF: | PP | (Gly)x5 | FXa | EGF |
| RX3-Gfp: | RX3 | (Gly)x5 |  | Gfp |
| RX3(A)-Gfp: | RX3(A) | (Gly)x5 |  | Gfp |
| RX3(L)-Gfp: | RX3(L) | (Gly)x5 |  | Gfp |
| RX3(R)-Gfp: | RX3(R) | (Gly)x5 |  | Gfp |
| RX3(E)-Gfp: | RX3(E) | (Gly)x5 |  | Gfp |
| RX3dir-Gfp: | RX3dir |  |  | Gfp |
| RX3(A)-Xyl: | RX3(A) | (Gly)x5 | EK | Xyl |
| RX3(L)-Xyl: | RX3(L) | (Gly)x5 | EK | Xyl |
| RX3(E)-Xyl: | RX3(E) | (Gly)x5 | EK | Xyl |
| RX3-Xyl: | RX3 | (Gly)x5 | EK | Xyl |
| PP-Xyl: | PP | (Gly)x5 | EK | Xyl |
| PA-Xyl: | PA | (Gly)x5 | EK | Xyl |
| Z(Adh)fusion prot: | PBIS(Adh) | (Gly)x5 |  | Gfp |
| Z(Col)fusion prot: | PBIS(Col) | (Gly)x5 |  | Gfp |

|  | POI | CS | Linker | PBIS |
|---|---|---|---|---|
| EK-RX3: | EKp |  | (Gly)x5 | RX3 |
| DsRED-I-RX3: | DsRED | I | (Gly)x5 | RX3 |
| hGH-I-RX3: | hGH | I | (Gly)x5 | RX3 |
| ECFP-RX3: | ECFP |  | (Gly)x5 | RX3 |
| ECFP-iRX3: | ECFP |  | (Gly)x5 | iRX3 |

Figure 15b

| | PBIS | Linker | POI |
|---:|:---:|:---:|:---:|
| RX3-ECFP: | RX3 | (Gly)x5 | ECFP |
| RX3(K)-ECFP: | RX3(K) | (Gly)x5 | ECFP |
| RX3(A3)-ECFP: | RX3(A3) | (Gly)x5 | ECFP |
| RX3(T)-ECFP: | RX3(T) | (Gly)x5 | ECFP |
| RX3(N)-ECFP: | RX3(N) | (Gly)x5 | ECFP |
| RX3(Q)-ECFP: | RX3(Q) | (Gly)x5 | ECFP |
| RX3(D)-ECFP: | RX3(D) | (Gly)x5 | ECFP |
| PP-ECFP: | PP | (Gly)x5 | ECFP |
| PA-ECFP: | PA | (Gly)x5 | ECFP |
| NPP-ECFP: | NPP | (Gly)x5 | ECFP |
| NPA-ECFP: | NPA | (Gly)x5 | ECFP |
| R8(C4)-ECFP: | R8(C4) | (Gly)x5 | ECFP |
| R7(C4)-ECFP: | R7(C4) | (Gly)x5 | ECFP |
| R6(C4)-ECFP: | R6(C4) | (Gly)x5 | ECFP |
| R4(C4)-ECFP: | R4(C4) | (Gly)x5 | ECFP |
| RX3C7G-ECFP: | RX3C7G | (Gly)x5 | ECFP |
| RX3C9G-ECFP: | RX3C9G | (Gly)x5 | ECFP |
| RX3C64G-ECFP: | RX3C64G | (Gly)x5 | ECFP |
| RX3C82G-ECFP: | RX3C82G | (Gly)x5 | ECFP |
| RX3C84G-ECFP: | RX3C84G | (Gly)x5 | ECFP |
| RX3C92G-ECFP: | RX3C92G | (Gly)x5 | ECFP |
| RX3C7,9G-ECFP: | RX3C7,9G | (Gly)x5 | ECFP |
| RX3C82,84,92G-ECFP: | RX3C82,84,92G | (Gly)x5 | ECFP |
| RX3C64,82,84,92G-ECFP: | RX3C64,82,84,92G | (Gly)x5 | ECFP |
| RX3(PR10)-ECFP: | RX3(PR10) | (Gly)x5 | ECFP |
| PP2-ECFP: | PP2 | (Gly)x5 | ECFP |
| RX3C64,82,84,92G-ECFP: | RX3C64,82,84,92G | (Gly)x5 | ECFP |
| iRX3-ECFP: | iRX3 | (Gly)x5 | ECFP |

Figure 17

A

```
  Z(Adh)  : THTSGGCGCQ  PPTPPTYETEKPLEPAPVEPSYEAEPTPPTRAPDQAEP
  Z(Adh)Px: THTSGGCGCQ  PPTPPTYETEKPLEPAPVEPSYEAEPTPPTRAPDQAEP
  Z(Col)  : THTSGGCGCQ  PGPMGPRGPPGPAGAPGPQGFQGNPGEPGEPGVSGPMG
  Z(Col)Px: THTSGGCGCQ  PGPMGPRGPPGPAGAPGPQGFQGNPGEPGEPGVSGPMG

Z(Adh)  : NKPTPPTP-  VHLPPPCPPC
  Z(Adh)Px: NKPTPPTP-  VHLPPPPCHYPTQPPRPQPHPQPHPCPCQQPHPSPCQ
  Z(Col)  : PRGPPGPPP  VHLPPPCPPC
  Z(Col)Px: PRGPPGPPP  VHLPPPPCHYPTQPPRPQPHPQPHPCPCQQPHPSPCQ
```

B

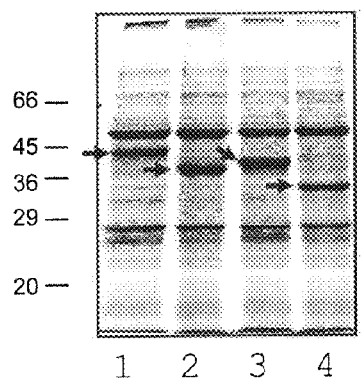

1  2  3  4

C

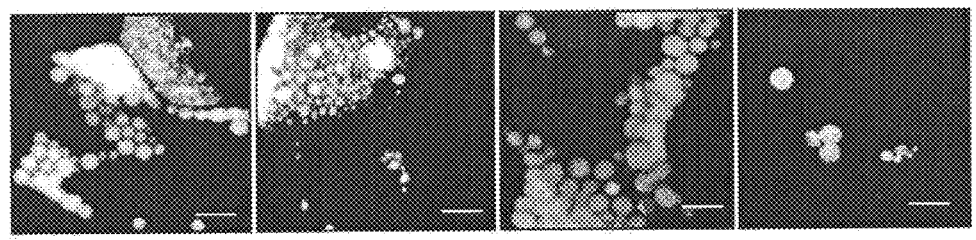

Figure 18
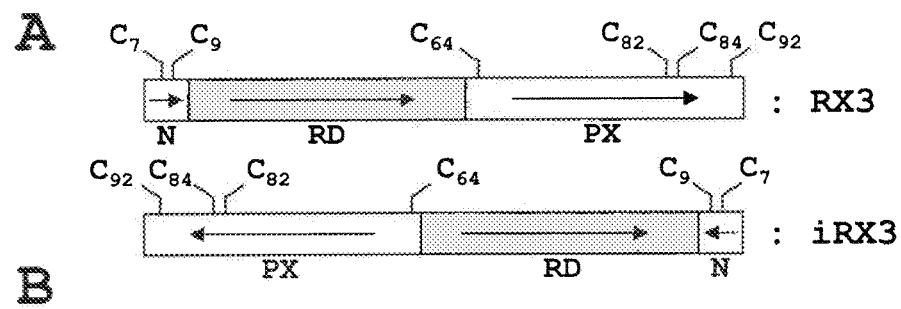
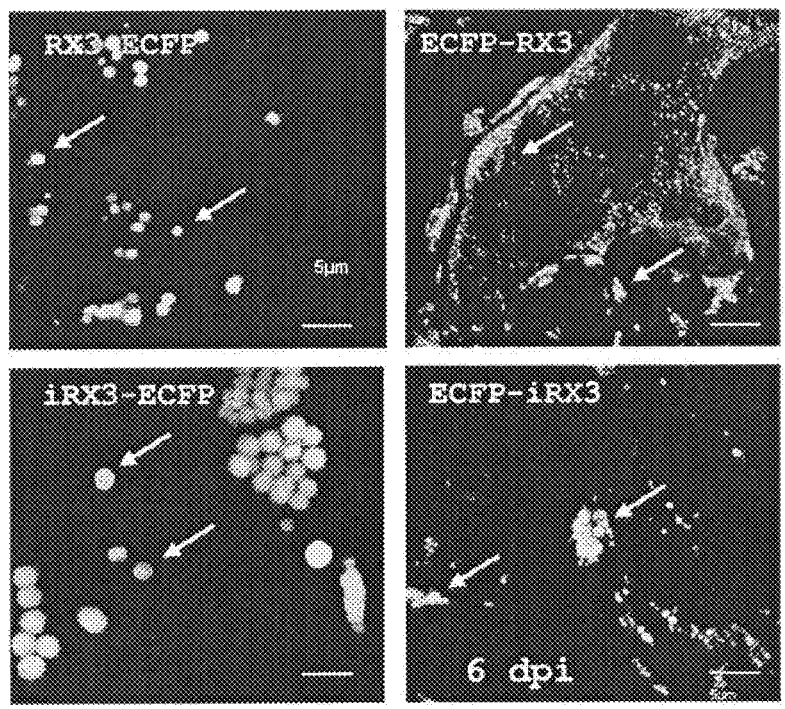
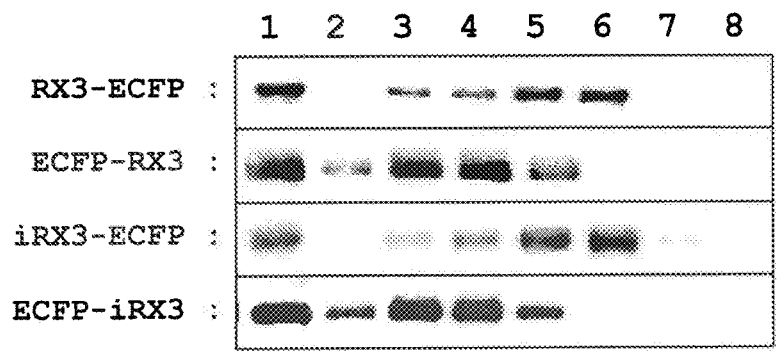

Figure 19
A
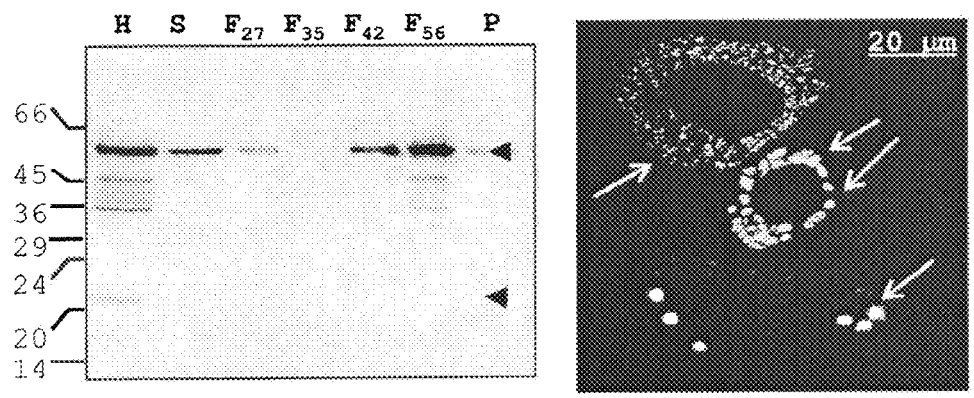
B
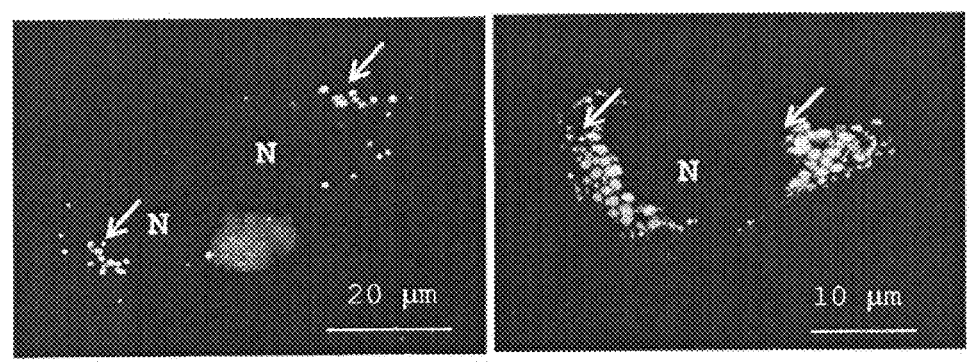
C
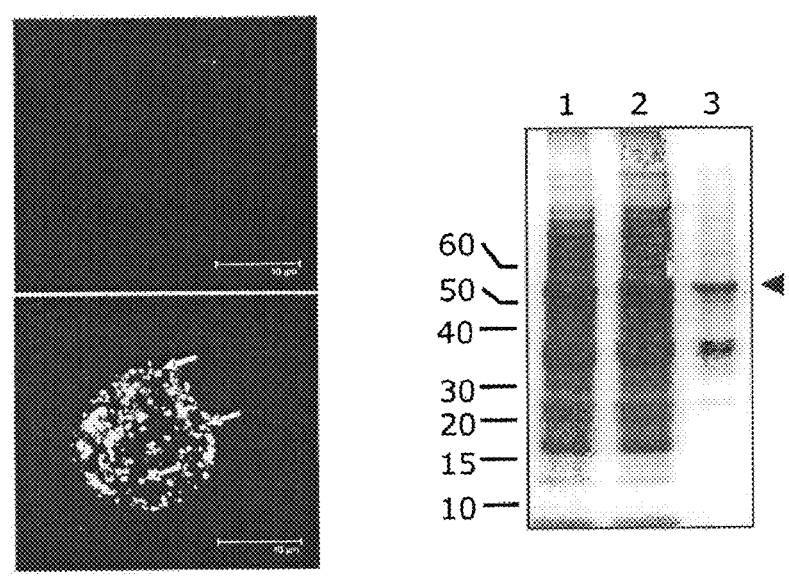

US 9,637,751 B2

RECOMBINANT PROTEIN BODY-INDUCING POLYPEPTIDES

CROSS-REFERENCE TO RELATED APPLICATIONS

This application claims the benefit of U.S. Provisional Application No. 61/349,655, which was filed on May 28, 2010, and European Application No. EP 10 38 2231.8, each of which is herein incorporated by reference in its entirety.

REFERENCE TO A SEQUENCE LISTING SUBMITTED ELECTRONICALLY VIA EFS-WEB

The content of the electronically submitted sequence listing (Name: substitute sequencelisting.ascii.txt, Size: 174, 772 bytes; and Date of Creation: Aug. 8, 2011) is herein incorporated by reference in its entirety.

FIELD OF THE INVENTION

The present invention contemplates peptides that are able to induce the formation of a recombinant protein body-like assembly (RPBLA) in a eukaryotic cell. In addition, heterologous polypeptides that are fused to sequences that mediate the induction of recombinant protein body-like assembly (RPBLA) formation, are stably expressed and accumulated in host systems.

BACKGROUND

Several decades ago, prolamins were described as very specialized storage proteins involved in the formation of natural protein bodies (PB) in the endosperm of cereals. Sherry et al., 1990, *Biochem. J.* 267:1-12. Nevertheless, to this day, little is known about the requirements for the formation of this type of organelle.

The endosperm is a specialized plant tissue that appears to have a greater tendency to sort proteins into PBs than other tissues and cell types. This is true even when the proteins are not fused to prolamins. For example, recombinant phytase protein, which is secreted from rice leaf cells, is retained in PBs when it is expressed in the endosperm. Drakakaki et al., 2006, *Plant Physiology*, 141, 578-586. Similarly, the major glycoprotein (gB) of human cytomegalovirus (Wright et al., 2001, *Transgenic Research* 10: 177-181) and lysozyme (Yang et al., 2003, *Planta* 216: 597-603) also accumulate in PBs in dicot and monocot plant endosperms even when they are not fused to prolamins. Interestingly, even when lysozyme was fused to a non-prolamin related signal peptide and expressed under the control of a non-prolamin promoter (puroindoline b) it accumulated in PBs in rice endosperm. Hennegan et al., 2005, *Transgenic Research* 14:583-592. These data suggest that accumulation of proteins in PBs could require the specialized storage environment of the endosperm.

The hightened propensity for proteins to be sorted in endosperm is also demonstrated by experiments using KDEL-(SEQ ID NO:162) tagged recombinant proteins. The KDEL tag is also known as an "ER retention signal" because it helps maintain proteins in the endoplasmic reticulum (ER). Thus, when human serum albumin is fused to the KDEL tag, it localizes to the ER lumen in leaf cells. However, when expressed in the endosperm, KDEL-tagged human serum albumin was deposited in prolamin aggregates within vacuoles. In addition, a KDEL-tagged monoclonal antibody, which is efficiently retained in the endoplasmic reticulum in leaves, was partially secreted and partially sorted to protein storage vacuoles in seeds. Petruccelli et al, 2006, Plant *Biotechnol J.* 4:511-27.

Therefore, protein transport within cereal endosperm cells is affected by the endosperm-specific environment, including the abundance of endoplasmic reticulum (ER)-derived and vacuolar protein bodies. Accordingly, proteins that are sorted to PBs in the endosperm may not be sorted there in other cells or tissues, and sequences and structures that are sufficient to induce formation of PBs in the endosperm may not necessarily be sufficient for formation of PBs in other cells or tissues.

Furthermore, the specific sequences and structures that are sufficient to induce formation of PBs have not been identified. In fact, when all of the proteins involved in PB formation are compared, no clear homology in terms of sequence, structure, or physical and chemical characteristics is evident.

Gamma zein is a major constituent of protein bodies in maize. Ludevid et al., 1984, *Plant Mol. Biol.* 3: 227-234. The N-terminal domain of gamma zein contains a Pro-X region (P-X) and a highly repetitive sequence $(PPPVHL)_6(PPPVHV)(PPPVHL)$ (repeat domain; "RD") (SEQ ID NO:158) necessary for sorting gamma zein in the ER (Geli, et al. *Plant Cell* 6:1911 (1994)) and for the formation of protein bodies. See also U.S. Published Application No. 2007/0243198. A circular dichroism study of a synthetic peptides series of the sequences (VHLPPP)×3 (SEQ ID NO:159), (VHLPPP)×5 (SEQ ID NO:160), and (VHLPPP)×8 (SEQ ID NO:161) in water at pH 5, showed that these peptides adopt a polyproline II (PPII) helix (Rabanal, *Biopolymers* 33: 1019-28 (1993)). Gamma zein also contains several cysteines that were shown to be required for the formation of stable PBs. Pompa, *Plant Cell* 18: 2608-2621 (2006).

The PPII helix of the RD of gamma zein has a marked amphipathic character. Previous studies have suggested that the amphipathic nature of the PPII helix was important for the formation of stable PBs, and the surfactant properties of the amphipathic PPII helix (VHLPPP)×8 (SEQ ID NO:161) have been demonstrated by several approaches. Kogan et al., 2001, *J. Mol. Biol.* 312: 907-913003; Kogan et al., 2002, *Biophysical J* 83: 1194-1204. For example, it was shown that the synthetic octamer peptide (VHLPPP)×8 (SEQ ID NO:161) was able to lower the surface tension of water, due largely to the adsorption of the amphiphile to the air-water interface with the hydrophobic moiety oriented away from the aqueous phase. Ludevid et al., 1984, *Plant Mol. Biol.* 3: 227-234. It was also demonstrated that this amphipathic peptide interacts with soybean phosphatidylcholine liposomes and assembles to form extended domains over the membrane, increasing its stability and permeability. Kogan et al., 2004, *Biopolymers*, 73: 258-268. The spontaneous amphipathic assembly of (VHLPPP)×8 (SEQ ID NO:161) on the membrane suggests a mechanism of gamma-zein deposition inside maize protein bodies. Based on the amphipathic characteristics of gamma-zein RD, it has been proposed that this protein interacts with the inner face of the ER membrane inducing an internal coat that could be a key element in the mechanism of PB induction (Ludevid, 1984). This coating may then be covalently stabilized via intramolecular disulfide cross-linking involving cysteine residues that flank the repetitive sequence of gamma zein.

While some of the features of the gamma-zein protein have been characterized, it was not previously understood which of these features or combination of features was relevant for protein body formation. Furthermore, other protein body-inducing sequences contain little or no structural or sequence similarity to gamma-zein. As described in more detail below, a minimum polypeptide capable of inducing protein bodies has been identified. Furthermore, recombinant protein body-inducing sequences with improved properties, such as an increased ability to form recombinant protein body-like assemblies (RPBLAs) and an ability to form RPBLAs with improved characteristics, have been identified.

BRIEF SUMMARY OF THE INVENTION

Novel recombinant protein body-inducing sequences (PBIS), fusion proteins and recombinant protein body-like assemblies (RPBLAs) comprising these PBIS, and methods of their use are described herein.

The recombinant PBIS can comprises a sequence that directs the PBIS to the endoplasmic reticulum (ER) and a polyproline II (PPII) structure that is at least 30 amino acids in length and has an N-terminus and a C-terminus. The PPII structure can be located between at least two cysteines at the N-terminus and at least two cystines at the C-terminus, and no more than 10% of the amino acids in the PPII structure can be lysine or arginine. The PPII structure does not contain the sequence (PPPVHL)$_6$ (SEQ ID NO:115).

In addition, the recombinant PBIS can comprises a sequence that directs the PBIS to the endoplasmic reticulum (ER) and a proline-rich sequence that is at least 30 amino acids in length and has an N-terminus and a C-terminus. The proline-rich sequence can be located between at least two cysteines at the N-terminus and at least two cystines at the C-terminus, and no more than 10% of the amino acids in the proline-rich sequence can be lysine or arginine. The proline-rich sequence does not contain the sequence (PPPVHL)$_6$ (SEQ ID NO:115).

In some embodiments at least about 30% of the amino acids in the PPII structure or the proline-rich sequence are proline. In some embodiments at least about 40% of the amino acids in the PPII structure or the proline-rich sequence are proline. In some embodiments, at least about 50% of the amino acids in the PPII structure or the proline-rich sequence are proline.

In some embodiments, no more than about 95% of the amino acids in the PPII structure or the proline-rich sequence are proline. In some embodiments, no more than about 75% of the amino acids in the PPII structure or the proline-rich sequence are proline. In still further embodiments, no more than about 50% of the amino acids in the PPII structure or the proline-rich sequence are proline.

In other embodiments, the PPII structure or the proline-rich sequence comprises at least five proline-rich repeats. In further embodiments, each of the proline-rich repeats is independently selected from the group consisting of: (i) PPPXXX (SEQ ID NO:116); (ii) PPXX (SEQ ID NO:117); (iii) PX; (iv) PPPXX (SEQ ID NO:118); (v) PPPX (SEQ ID NO:119); (vi) PPX; and (vii) PPPXPX (SEQ ID NO:120). In still further embodiments, each of the at least five proline-rich repeats is PPPXXX (SEQ ID NO:116).

The PPII structure or the proline-rich sequence can be non-amphipathic. For example, the PPII structure or the proline-rich sequence can be amphipathic and negatively charged. The PPII structure or the proline-rich sequence can also be amphipathic and non-charged.

Furthermore, the non-amphipathic sequence can consist essentially of amino acids selected from the group consisting of (i) proline, (ii) valine, (iii) leucine, and (iv) alanine The non-amphipathic sequence can comprise a sequence selected from the group consisting of (i) PPPVAL (SEQ ID NO:121); (ii) PPPVLL (SEQ ID NO:122); and (iii) PPPAAA (SEQ ID NO:123).

The amphipathic and negatively charged sequence can consists essentially of amino acids selected from the group consisting of (i) proline, (ii) valine, (iii) leucine, (iv) aspartic acid; and (v) glutamic acid. The amphipathic and negatively charged sequence can comprise a sequence selected from the group consisting of (i) PPPVDL (SEQ ID NO:124); and (ii) PPPVEL (SEQ ID NO:125).

The amphipathic and non-charged sequence can consist essentially of amino acids selected from the group consisting of (i) proline, (ii) valine, (iii) leucine, (iv) threonine (v) asparagine; and (vi) glutamine. The amphipathic and non-charged sequence can comprise a sequence selected from the group consisting of (i) PPPVTL (SEQ ID NO:126); (ii) PPPVNL (SEQ ID NO:127); and (iii) PPPVQL (SEQ ID NO:128).

Some recombinant PBIS described herein contain a proline rich sequence in which the proline rich sequence consists essentially of amino acids selected from the group consisting of (i) proline; (ii) negatively charged amino acids; (iii) amino acids with polar uncharged side chains; and (iv) amino acids with hydrophobic side chains. In other embodiments, the proline rich sequence consists essentially of amino acids selected from the group consisting of (i) proline; and (ii) alanine. In still other embodiments, the proline-rich sequence comprises the sequence PPPAPA (SEQ ID NO:129).

In some embodiments, the PPII structure or the proline-rich sequence is at least 36 amino acids in length. In some embodiments, the PPII structure or the proline-rich sequence is at least 42 amino acids in length. In still other embodiments, the PPII structure or the proline-rich sequence is at least 48 amino acids in length. In further embodiments, the PPII structure or the proline-rich sequence is no more than 96 amino acids in length.

The PPII structure or the proline-rich sequence can be located between at least two cysteines at the N-terminus and at least three cystines at the C-terminus. In some embodiments, the PPII structure or the proline-rich sequence is located between at least two cysteines at the N-terminus and at least four cystines at the C-terminus.

In some embodiments, no more than about 5% of the amino acids in the PPII structure or the proline-rich sequence are lysine or arginine. In still other embodiments, the PPII structure or the proline-rich sequence does not comprise lysine or arginine.

In other embodiments, no more than about 15% of the amino acids in PPII structure are histidine. In still other embodiments, no more than about 10% of the amino acids in the PPII structure or the proline-rich sequence are histidine.

The recombinant PBIS can comprise a first domain which is a PPII structure or a proline-rich sequence and a second domain which is a proline-rich sequence. In some embodiments, the second domain which is a proline-rich sequence is located between the first domain and the two C-terminal cysteines. In some particular embodiments, the second domain which is a proline-rich sequence is from about 5 to about 25 amino acids in length.

In some recombinant PBIS described herein, a PPII structure comprises a proline-rich sequence.

In some recombinant PBIS described herein, the recombinant PBIS does not contain a globular cysteine. In other embodiments, the recombinant PBIS comprises a sequence that directs the PBIS to the endoplasmic reticulum that is the gamma zein signal peptide.

The recombinant PBIS described herein can be capable of forming a recombinant protein body like assembly (RPBLA) when expressed in a cell. In some embodiments, the cell is a tobacco plant cell. In some particular embodiments, the recombinant PBIS is capable of forming a RPBLA when expressed at about 0.5 grams/Kg of tobacco leaves fresh weight.

The RPBLA can be about 0.3 to about 3 micrometers. The RPBLA can have a density of about 1.1 to about 1.4 g/mL.

In some embodiments, the recombinant PBIS has reduced allergenicity.

Fusion protein comprising a recombinant PBIS and a heterologous protein are also described herein. In some embodiments, the fusion protein further comprises a cleavage site between the recombinant PBIS and the heterologous protein. The cleavage site can be cleavable by enzymatic means or is cleavable by chemical means.

Nucleic acid molecules comprising a sequence that encodes a recombinant PBIS or a fusion protein comprising a recombinant PBIS are also described herein. The nucleic acid molecule further comprises a multiple cloning site in some embodiments, and the sequence that encodes the recombinant PBIS can be 5' to the multiple cloning site or the sequence that encodes the recombinant PBIS can be 3' to the multiple cloning site. In some embodiments, the nucleic acid molecule further comprising a promoter. The can be functional in tobacco. The promoter can be functional in a mammalian cell.

Vectors containing the nucleic acid molecules are also described.

Furthermore, host cells comprising recombinant PBIS or fusion proteins thereof are described. Host cells comprising nucleic acids endocing a recombinant PBIS or vectors comprising such nucleic acids are also described. The host cell can be a tobacco plant cell. The host cell can also be a mammalian cell.

Food products comprising the recombinant PBIS or a fusion protein thereof are also provided.

BRIEF DESCRIPTION OF THE DRAWINGS/FIGURES

FIG. 1. (A) Schematic representation of the repeat domain (RD) from different variants of RX3 peptides fused to a reporter fluorescent protein and transformed by agroinfiltration in tobacco leaves. The relative position of the non-proline amino acids along the PPII helix is represented by a triangle. A dashed line separating the hydrophobic side (bottom) from the hydrophilic side (top) is shown in variants with an amphipathic helix. The wild type RX3 repeat domain is shown in the center (grey box). Fully hydrophobic variants where the histidine residues have been replaced by alanine or leucine (RX3(A) and RX3(L), respectively) are shown on the right. The amphipathic positively charged variants where the histidine residues have been replaced by arginine or lysine (RX3(R) and RX3(K), respectively) are shown on the left. (B) Western blot analysis of equivalent amounts of tobacco leaf homogenates expressing RX3-GFP, RX3(R)-GFP, RX3-ECFP, and RX3(K)-ECFP, probed with an anti-GFP antibody. The white head arrow marks the fusion proteins, and the black head arrow marks a partially degraded fluorescent protein. (C) Confocal microscopy images of tobacco leaf cells expressing the wild type RX3 peptide fused to GFP (RX3-GFP), or several variants of RX3 peptide in which the histidine residues from the repetitive domain were mutated to alanine, leucine, arginine or lysine (RX3(A)-GFP, RX3(L)-GFP, RX3(R)-GFP and RX3(K)-ECFP, respectively). Arrows mark the fluorescence corresponding to secreted protein. White arrow heads mark ER derived RPBLAs, and black arrow heads mark chloroplasts. Bars correspond to 5 micrometers.

FIG. 2. (A) Photographs of step density gradient results for several fusion proteins (RX3-GFP, RX3(A)-GFP and RX3(L)-GFP) expressed in tobacco leaves and analyzed by Western blot using an anti-GFP antibody. (B). Coomassie blue staining showing the enrichment in RX3(A)-GFP after a step density gradient. The different fractions of the density gradient ((H) homogenate, (S) supernatant, (f) interface above the corresponding Optiprep™ cushion) are indicated.

FIG. 3. (A) RPBLA recovery by centrifugation at low speed. The left panel shows SDS-PAGE silver staining after isolation of RX3-GFP and RX3(A)-GFP RPBLAs expressed in tobacco leaves. The right panel shows SDS-PAGE silver staining of RX3-GFP and RX3(A)-GFP RPBLAs washed in mild conditions (50 mM borate pH10, 10 mM bME). (B) Coomassie blue staining (left) and Western blot (right; anti GFP antibody) show the recovery by low speed centrifugation of RPBLAs induced in tobacco plants by the expression of RX3(L)-GFP. (H0) Pre-clarified homogenate, (H1) Clarified homogenate by filtration, (SN) Supernatant after RPBLAs recover by centrifugation, (Ws) Washing-step supernatant, (wPB) RPBLAs recovered by centrifugation after washing step, (sPB) solubilized fusion protein from wPB and (iPB) insoluble fraction after the solubilization step. Arrow heads indicate the corresponding monomeric fusion proteins. The asterisk indicates the multimeric forms of the fusion protein.

FIG. 4. (A) Schematic representation of the repeat domain (RD) from RX3(A3) as described in FIG. 1. (B) Confocal microscopy images of tobacco leaf cells 3 and 6 days post infiltration (dpi) with the RX3(A3)-ECFP expressing vector. RPBLAs are indicated with arrows. Bars correspond to 2 micrometers.

FIG. 5. (A) Schematic representation of the repeat domain from amphipathic negatively charged variants of RX3 peptides (RX3(E) and RX3(D)) as described for FIG. 1. (B) Anti-GFP Western blot on equivalent amounts of homogenates from tobacco leaves expressing RX3-GFP, RX3(E)-GFP, RX3-ECFP, and RX3(D)-ECFP. (C) Confocal microscopy images of tobacco leaf cells expressing RX3(E)-GFP (left), and RX3(D)-ECFP (right). The RPBLAs are indicated with arrows. Bars correspond to 2 micrometers.

FIG. 6. (A) Schematic representation of the repeat domain from polar non charged variants of RX3 peptides (RX3(T), RX3(N), and RX3(Q)) as described for FIG. 1. (B) Images of RPBLAs induced by the expression of these assembler peptides fused to ECFP at 3 and 6 days post agroinfiltration (dpi). The bars shown in 3 and 6 dpi images correspond to 5 and 2 micrometers, respectively.

FIG. 7. (A) Sequence alignment of the mature RX3 (SEQ ID NO:131), PP (SEQ ID NO:132), and PA (SEQ ID NO:133) assembler peptides. Identity between the three peptides is indicated in bold, and cysteine residues are indicated by grey boxes. SP indicates signal peptide. (B) Anti-GFP Western blot of equivalent amounts of homogenates of tobacco leaves expressing PP-ECFP, PA-ECFP and RX3-ECFP. Arrows mark the fusion proteins. (C) Confocal microscopy images of tobacco leaf cells expressing RX3-ECFP, PP-ECFP, and PA-ECFP. RPBLAs are indicated by arrows.

FIG. 8. (A) Diagram showing the positions of the cysteine residues in the RX3 assembler peptide fused to ECFP. (B) SDS-PAGE/coomassie blue staining (upper panel) and anti-GFP immunoblot (lower panel) showing total protein analysis of tobacco leaves: untransformed tobacco (lane1); RX3-ECFP expressing tobacco (lane2); RX3 Cys7 expressing tobacco (lane 3); RX3 Cys9 expressing tobacco (lane 4); RX3 Cys64 expressing tobacco (lanes); RX3 Cys82 expressing tobacco (lane6); RX3 Cys84 expressing tobacco (lane7); RX3 Cys92 expressing tobacco (lane8); RX3 Cys7-Cys9 expressing tobacco (lane9); and RX3 Cys82-Cys84-Cys92 expressing tobacco (lane10). Arrows indicate the electrophoretic bands of RX3-ECFP and RX3-ECFP Cys mutants, and the arrowhead indicates an additional immunoreactive band. (C-K) Confocal images showing the fluorescence pattern of epidermal cells transformed with RX3-Cys mutants fused to ECFP. Bars in C—H correspond to 10 μm. Bars in I-K correspond to 20 μm.

FIG. 9. (A) Sequence alignment of mature PP (SEQ ID NO:132) and PP2 (SEQ ID NO:130). Identity between the two peptides is indicated in bold, and the cysteine residues are indicated by grey boxes. SP indicates signal peptide. (B) Schematic representation of the PPII helix from PP and PP2. Cysteine residues are indicated. (C) Confocal microscopy images of tobacco leaf cells expressing PP2-GFP. The left panel is a magnification of the right panel.

FIG. 10. (A) Schematic representation of versions of the RX3 peptide fused to ECFP presenting a progressive reduction in the number of units in the RD. The units are shown in numbered grey boxes, and cysteine residues are indicated by asterisks. The sequence CPPC corresponds to SEQ ID NO:134. SP indicates signal peptide from gamma zein. PX indicates pro-X domain. N1 and N2 indicate non-repetitive sequences. (B) SDS-PAGE gel stained by Coomassie blue showing the protein pattern of equivalent amount of homogenates from tobacco leaves expressing RX3-, R8(4C)-, R7(4C)-, R6(4C)- and R4(4C)-ECFP fusion proteins (arrows). (C) Confocal microscopy images of tobacco leaf cells expressing R8(4C)-, R6(4C)- and R4(4C)-ECFP. Arrows in insets mark RPBLAs. Bars correspond to 20 micrometers in full image and 5 micrometers in insets.

Figure 11:
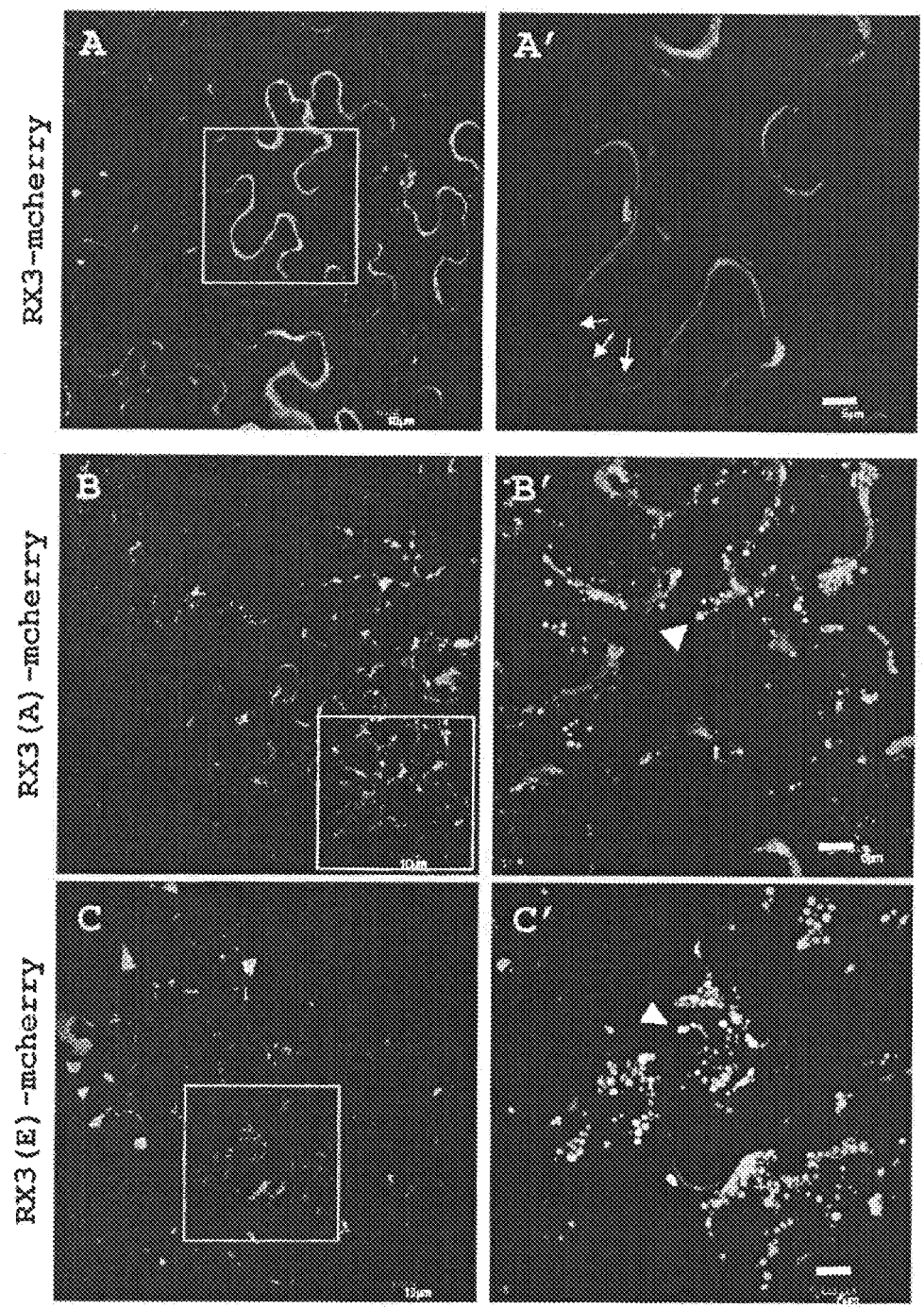

FIG. 11. (A, B, and C) Confocal microscopy images of tobacco leaf cells expressing mCherry fluorescent protein fused to RX3, RX3(A) and RX3(E) peptides (A, B and C, respectively). (A', B' and C') Higher magnification of the images in A, B, and C to highlight RPBLAs (arrow heads). The arrows show secreted RX3-mCherry. Bars correspond to 5 micrometers.

FIG. 12. (A) Western blot comparing the recovery by low speed centrifugation of RPBLAs induced by the expression of RX3-, RX3(E)- and RX3(A)-EGF. The clarified homogenate (lane 1), the supernatant after RPBLA recovery by centrifugation (lane 2), washing-step supernatant (lane 3), and the RPBLAs recovered by centrifugation after washing step (lane 4) are shown. (B) Western blot showing the solubilized RX3(E)-EGF (lane 1), RX3(A)-EGF (lane 2), and RX3-EGF (lane 3) after incubation in mild conditions. The unsolubilized fraction of the corresponding fusion protein was recovered by centrifugation at 16000×g for 10' and is shown in lanes 4, 5 and 6, respectively. (C) Western blot analysis of equivalent amounts of homogenates from tobacco leaves expressing PP-, PA-, RX3(E)- and RX3-EGF. (D) Western blots showing the solubilized RX3(E)-EGF (lane 2), PP-EGF (lane 5), and PA-EGF (lane 8) fusion proteins from the corresponding RPBLAs isolated by low speed centrifugation (lanes 1, 4 and 7, respectively). The remaining unsolubilized fusion protein is shown in lanes 3, 6, and 9.

Figure 13:
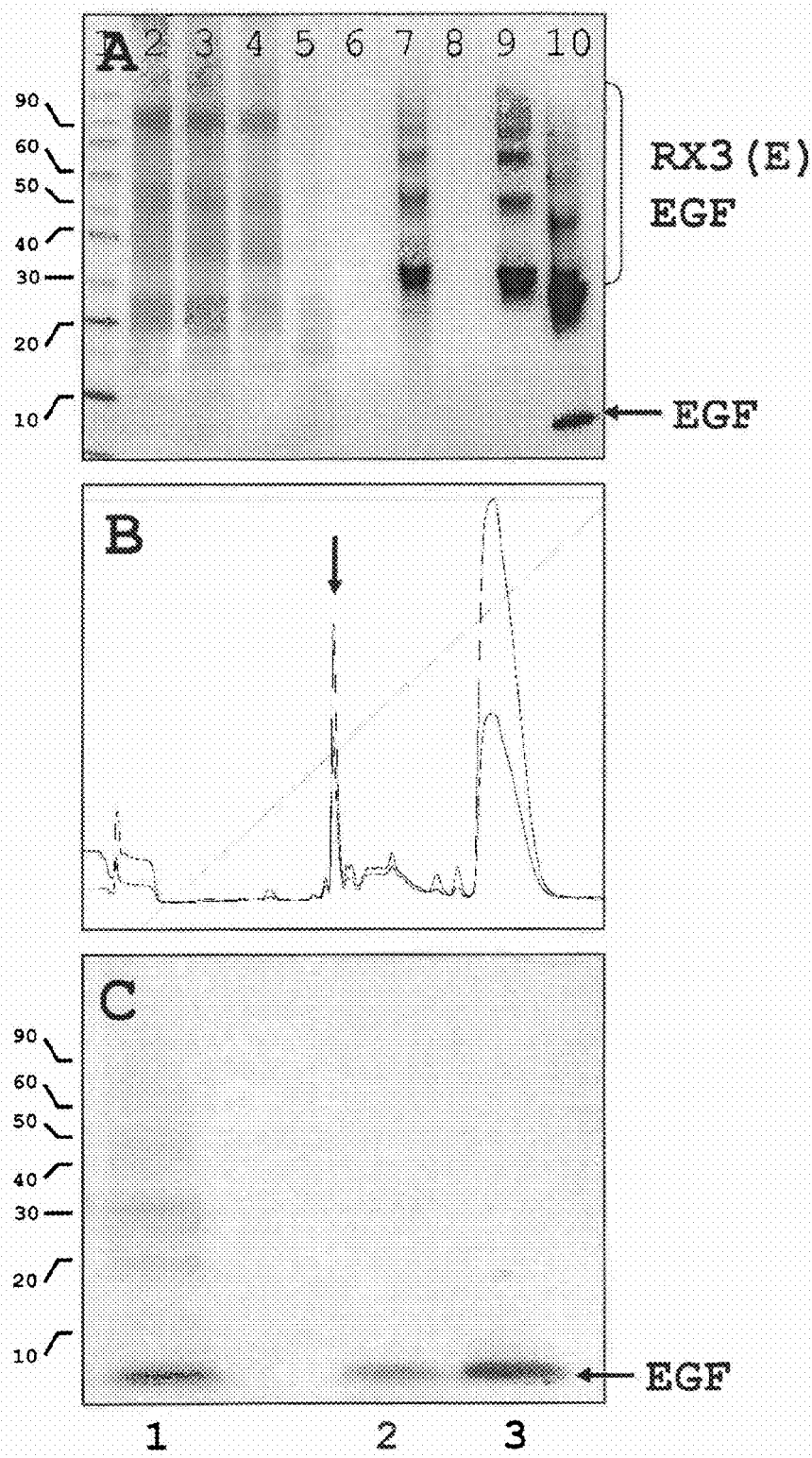

FIG. 13. (A) SDS-PAGE silver staining of the RX3(E)-EGF downstream process from RPBLAs isolation by low speed centrifugation to fusion protein cleavage by FXa digestion: molecular marker (lane 1); pre-clarified homogenate (lane 2); clarified homogenate by filtration (lane 3); supernatant after RPBLAs recover by centrifugation (lane 4); washing-step supernatant (lane 5,6); RPBLAs recovered by centrifugation after washing step (lane 7); insoluble fraction after the solubilization step (lane 8); solubilized fusion protein from wPB (lane 9); and cleaved RX3(E)-EGF fusion protein (lane 10). (B) Chromatogram of the EGF purification by reverse phase FPLC. Arrow indicates the EGF peak which corresponds to 30% of acetonitrile. (C) Coomassie blue staining showing the RF-FPLC input (lane 1) and the two fractions (lanes 2-3) containing pure EGF and corresponding to the peak indicated by an arrow in (B).

FIG. 14. (A) SDS-PAGE Coomassie blue staining (left) and Western blot (right) show isolated RX3(A)-hGH RPBLAs. (B) Anti-hGH Western blot showing the solubilization efficiency of RX3-hGH and RX3(A)-hGH. (H0) pre-clarified homogenate; (H1) clarified homogenate by filtration; (SN) supernatant after RPBLAs recover by centrifugation; (Ws) washing-step supernatant; (wPB) RPBLAs recovered by centrifugation after washing step; (sPB) solubilized fusion protein from wPB; and (iPB) insoluble fraction after the solubilization step.

FIG. 15. (A and B) Schematic representation of the fusion proteins indicating the protein body inducing sequence (PBIS), the 5 glycine linker ((Gly)×5) (SEQ ID NO:180), the cleavage site (CS), and the protein of interest (POI). CS are the enterokinase cleavage site (EK), the FXa cleavage site (FXa), and Intein MxeGyrA from new England Biolabs (I). POI are mcherry, human growth hormone (hGH), epidermal growth factor (EGF), enhanced cyan fluorescent protein (ECFP), Enterokinase protease (EKp), Xylanase (Xyl) and green fluorescent protein (GFP). Zera(Adh) fusion proteins are the fusion proteins based on the following PBIS derived from an adhesin fragment forming a PPII helix (PBIS(Adh)): Z(Adh), Z(Adh2), Z(Adh)Px and Z(Adh2)Px. Zera(Col) fusion proteins are the fusion proteins based on the following PBIS derived from a Collagen fragment forming a PPII helix (PBIS(Col)): Z(Col), Z(Col 2), Z(Col) Px and Z(Col 2)Px.

Figure 16:
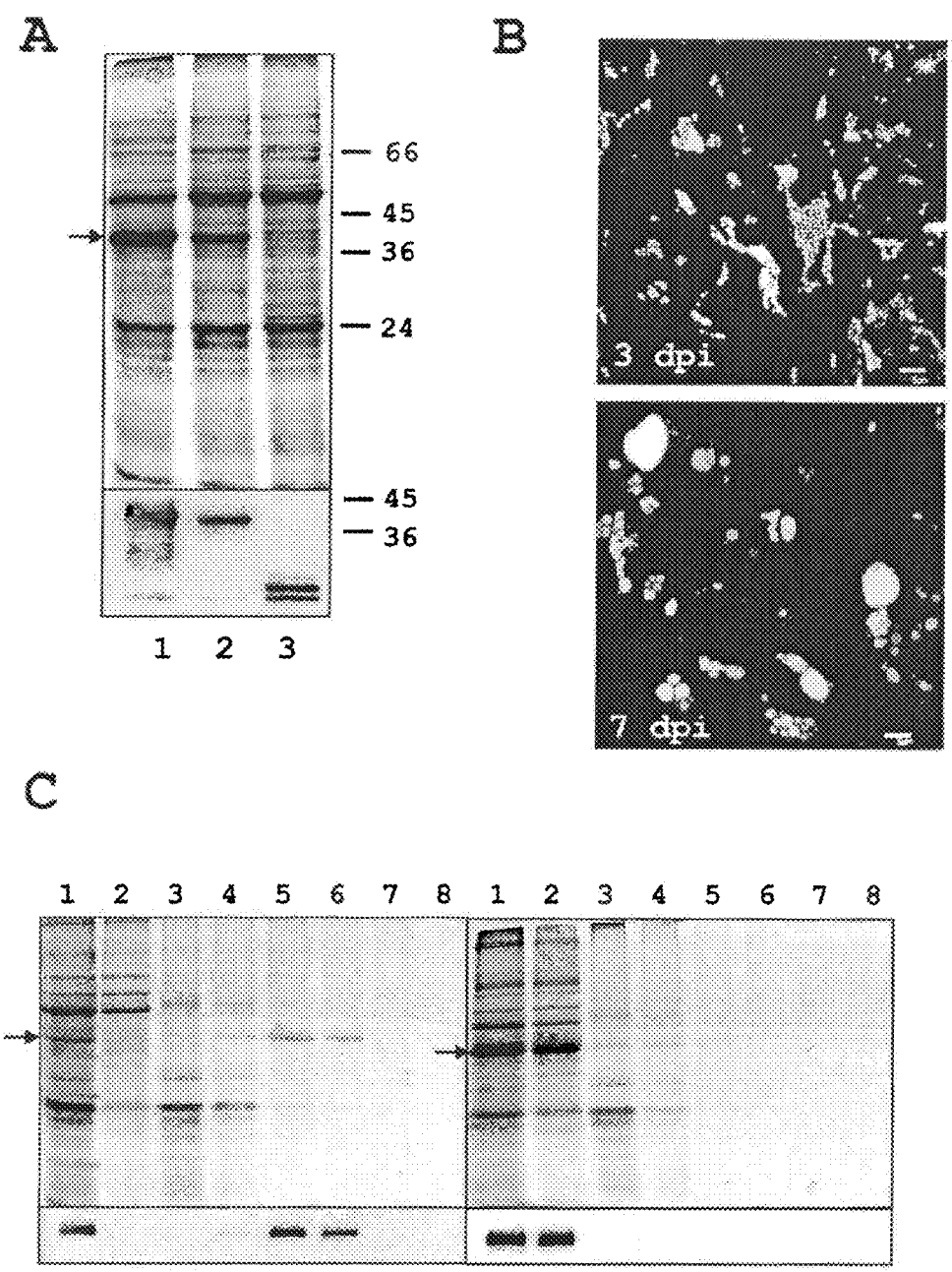

FIG. 16. (A) The upper panel shows Coomassie blue staining of 20 micrograms of total protein from pre-clarified homogenates of tobacco leaves expressing RX3Δ Cys$_{64,82,84,92}$-ECFP-KDEL (lane 1), RX3-ECFP (lane 2), and SP-ECFP-KDEL (lane 3). The bottom panel shows a Western blot of the same homogenates by means of an anti-GFP antibody. The arrow indicates the fusion proteins. (B) Confocal microscopy images of tobacco leaves expressing RX3ΔCys$_{64,82,84,92}$-ECFP-KDEL, three and seven days after infiltration (dpi). White bars correspond to 5 micrometers. (C) Density determination of RX3-ECFP (left) and RX3ΔCys$_{64,82,84,92}$-ECFP-KDEL (right) by step-density gradient. Equivalent amounts of the recovered fractions were analyzed by Coomassie blue staining (upper panels) and Western blot using anti-GFP antibody (lower panels). The lanes show: (1) sample loaded on the Optiprep™ density gradient, (2) supernatant recovered from above the 18% Optiprep™ cushion, (3) fraction between 18-30%, (4) fraction between 30-34%, (5) fraction between 34-38%, (6) fraction between 38-42%, (7) fraction between 42-46%, and (8) fraction recovered in the pellet.

Figure 17:
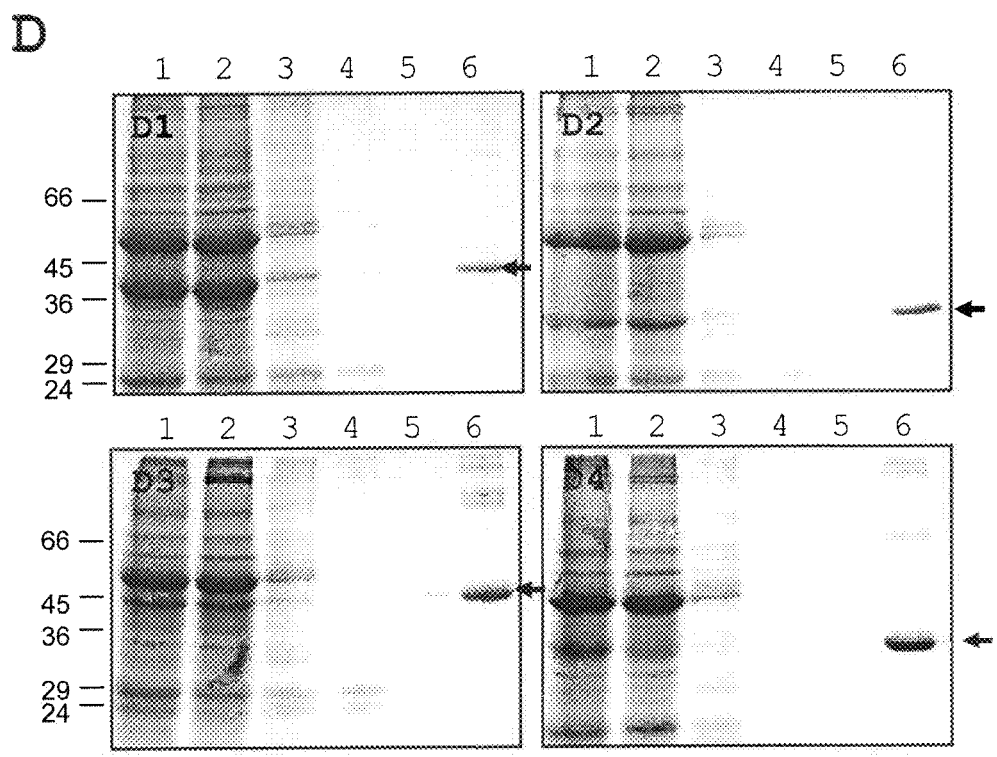

FIG. 17. (A) Sequence alignment of Z(Adh) (SEQ ID NO:152), Z(Adh)Px (SEQ ID NO:153), Z(Col) (SEQ ID NO:154), and Z(Col)Px (SEQ ID NO:155) assembler peptides. The signal peptide (from 27 KDa gamma zein in all cases) is not shown. The underlined amino acids (Adh—SEQ ID NO:156; Col—SEQ ID NO:157) correspond to the protein fragments from adhesin or collagen genes. The black bar indicates the fragments with a high propensity to adopt a PPII structure. (B) Coomassie blue staining of pre-clarified homogenates coming from equivalent amounts (20 micrograms of total protein) of tobacco leaves expressing Z(Adh) Px-GFP, Z(Col)Px-GFP, Z(Adh)-GFP and Z(Col)-GFP (lanes 1 to 4, respectively). Arrows mark the fusion proteins. (C) From left to right, confocal microscopy images of tobacco leaves expressing Z(Adh)-GFP, Z(Col)-GFP, Z(Adh)Px-GFP, and Z(Col)Px-GFP. White bars correspond to 5 micrometers. (D) Downstream process of RPBLAs recovery by means of low speed centrifugation at 1500×g analyzed by Coomassie blue staining. The pre-clarified homogenate (lane 1) was centrifuged at 1500×g and supernatant (lane 2) was discarded. After three rounds of washing steps (lanes 3-5), the pellet corresponding to the RPBLAs fraction (lane 6) was obtained. The process performed over equivalent amounts of tobacco leaves expressing Z(Adh)-GFP (D1), Z(Col)-GFP (D2), Z(Adh)Px-GFP (D3) and Z(Col)Px-GFP (D4) is shown.

FIG. 18. (A) Schematic representation of the mature assembler peptides: (i) RX3 and (ii) inverted RX3 (iRX3). The orientation of the different domains: (N)N-terminal fragment, (RD, in grey) repetitive domain and (PX) Pro-X domain is indicated by arrows. The position of the cysteine residues is also shown. (B) Confocal microscopy images of tobacco leaf cells expressing RX3-ECFP, ECFP-RX3, iRX3-ECFP and ECFP-iRX3. The RPBLAs are indicated with arrows. Bars correspond to 5 micrometers. (C) RPLBAs density determination of tobacco plants expressing RX3-ECFP, ECFP-RX3, iRX3-ECFP or ECFP-iRX3. The homogenate (lane 1) was loaded on top of a multi-step Optiprep density gradient, and the following fractions were collected after centrifugation at 80,000×g: (lane 2) Supernatant, (lane 3) interphase above 1,117 g/cm$^3$ cushion, (lane 4) interphase above 1.175 g/cm$^3$ cushion, (lane 5) interphase above 1.21 g/cm$^3$ cushion, (lane 6) interphase above 1.233 g/cm$^3$ cushion, (lane 7) interphase above 1.26 g/cm$^3$ cushion, and (lane 8) pellet at the bottom of the tube. Equivalent volumetric amounts of each fraction were analysed by Western blot by means of anti-RX3 antibody.

FIG. 19. (A) Accumulation of hGH-iRX3 in RPBLAs in CHO cells. The left panel shows the determination of the RPBLAs density induced by hGH-iRX3 expression in CHO cells. The homogenate (H) was loaded in a multi-step sucrose density gradient, and the following fractions were collected after centrifugation at 80.000×g: (S) Supernatant, (F27) interphase above 27% sucrose cushion, (F35) interphase above 35% sucrose cushion, (F42) interphase above 42% sucrose cushion, (F56) interphase above 56% sucrose cushion and (P) pellet at the bottom of the tube. The molecular markers are indicated on the left in kDa, and the expected position of the hGH-iRX3 fusion protein and hGH are indicated on the right by arrowheads. The antibody used in the Western blot corresponds to anti-hGH. The right panel shows immunohistochemistry of hGH-iRX3 fusion protein in mammalian CHO cells. Confocal microscopy images of CHO cells expressing hGH-iRX3 that were incubated with an anti-hGH antibody show the accumulation of the fusion protein in intracellular RPBLAs (arrows). (B) Immunohistochemistry of EK-RX3 and DsRED-iRX3 fusion proteins in mammalian CHO cells. The left panel shows confocal microscopy images of CHO cells expressing EK-RX3 incubated with an antibody anti-RX3 (aR8). The right panel shows that the RPBLAs can be observed directly by the intrinsic florescence of DsRED-iRX3. The intracellular RPBLAs containing the DsRED-iRX3 fusion protein are shown by arrows. N corresponds to the cellular nucleus. (C) Induction of RPBLAs by the expression of hGH-iRX3 in Sf9 insect cells. The left panel shows confocal microscopy images of insect cells expressing hGH-iRX3 and incubated with an anti-hGH antibody. The upper image corresponds to non-infected Sf9 cells showing background labelling. The lower image shows an Sf9 cell expressing the hGH-iRX3 fusion protein in RPBLAs (arrows). The right panel shows the RPBLAs recovery by low speed centrifugation. A pre-clarified homogenate of Sf9 insect cells expressing hGH-I-RX3 (lane1) was centrifuged at 5000×g. The supernatant (lane 2) was discarded and the corresponding pellet containing the RPBLAs (lane 3) was obtained after several washing steps. The arrow head indicates the position of the hGH-I-RX3 fusion protein.

DETAILED DESCRIPTION OF THE INVENTION

The following provides a description of recombinant protein body-inducing sequences (PBIS) that are useful for the formation of recombinant protein body-like assemblies (RPBLAs). The recombinant PBIS can be fused to proteins of interest, and RPBLAs formed by the expression of the fusion proteins in cells can be used to simply and efficiently purify high quantities of the protein of interest. In addition, RPBLAs can be used in therapeutics such as vaccinations.

The section headings used herein are for organizational purposes only and are not to be construed as in any way limiting the subject matter described.

I. Definitions

Unless otherwise expressly defined, the terms used herein are to be understood according to their ordinary meaning in the art. Terms used in the singular or referred to as "a" or "an" also include the plural and vice versa, unless otherwise specified or indicated by context. Standard techniques and procedures are generally performed according to conventional methods in the art and various general references (see generally, Sambrook et al. Molecular Cloning: A Laboratory Manual, 2nd ed. (1989) Cold Spring Harbor Laboratory Press, Cold Spring Harbor, N.Y., which is incorporated herein by reference), which are provided throughout this document.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature. The two polypeptides may be operably attached directly by a peptide bond or may be linked indirectly through a linker described herein or otherwise known in the art.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. An "expression vector" is a vector that is capable of directing the expression of genes to which it is operably associated.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The terms "operably associated" and "operably linked" refer to the association of two molecules so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation. Two molecules are "operably linked" whether they are attached directly (e.g., a fusion protein) or indirectly (e.g., via a linker).

As used herein, the term "expression" refers to the transcription of RNA (e.g., mRNA) from a nucleic acid template and/or the translation of mRNA into a polypeptide. The term "increased expression" is intended to include an alteration in gene expression at the level of increased mRNA production and/or at the level of polypeptide expression, generally resulting in an increased amount of a gene product or protein. In some instances, "increased expression" is used interchangeably with the term "overexpression" or "overexpressed.".

A "selectable marker" is a gene, the expression of which creates a detectable phenotype and which facilitates detection of host cells that contain a plasmid having the selectable marker. Non-limiting examples of selectable markers include drug resistance genes and nutritional markers. For example, the selectable marker can be a gene that confers resistance to an antibiotic selected from the group consisting of: ampicillin, kanamycin, erythromycin, chloramphenicol, gentamycin, kasugamycin, rifampicin, spectinomycin, D-Cycloserine, nalidixic acid, streptomycin, or tetracycline. Other non-limiting examples of selection markers include adenosine deaminase, aminoglycoside phosphotransferase, dihydrofolate reductase, hygromycin-B-phosphotransferase, thymidine kinase, and xanthine-guanine phosphoribosyl-transferase. A single plasmid can comprise one or more selectable markers.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, a recombinant protein body-inducing sequence (PBIS) is a polypeptide that is capable of mediating the formation of a recombinant protein body-like assembly (RPBLA) outside of the endosperm.

A polyproline II (PPII) structure is a type of helical secondary protein structure. Particular features of exemplary PPII structures have been described, for example, by Eisenberg et al., *J. Mol. Biol.* 179: 125-142 (1984), Bicudo et at (2008, *Biopolymers,* 89:175-178) Fernández-Carneado, *J. Mol. Biol.* 372: 708-22 (2004); Bochicchio and Tamburro, *Chirality* 14:782-92 (2002); Knighton et al. *Science* 253: 414-420 (1991); and Caldwell et al. *Biopolymers* 10:1891-1904 (1984), each of which is herein incorporated by reference in its entirety.

II. Recombinant Protein Body-Inducing Sequences (PBIS)

Protein body-inducing sequences (PBIS) are polypeptides that mediate the formation of protein bodies, which are described in more detail below. A naturally occurring PBIS has been identified in the maize protein gamma-zein and is described in more detail in U.S. Pat. No. 7,575,898, U.S. Published Application No. 2006/0121573, U.S. Published Application No. 2006/0123509, and U.S. Published Application No. 2007/0243198, each of which is incorporated herein by reference in its entirety.

Recombinant PBIS are non-naturally occurring proteins or protein fragments that mediate the formation of recombinant protein body-like assemblies (RPBLAs). Improved properties have been identified in recombinant PBIS and are described herein. In some embodiments, the recombinant PBIS is an isolated recombinant PBIS, e.g., a recombinant PBIS isolated from an RPBLA expressed in a recombinant host cell. Exemplary recombinant PBIS that do not contain the gamma zein sequences are described herein. Thus in some embodiments, the recombinant PBIS does not contain the gamma zein Pro-X (P—X) region, and in some embodiments, the recombinant PBIS does not contain the gamma zein highly repetitive sequence (PPPVHL)$_6$(PPPVHV)(PPPVHL) (repeat domain; RD) (SEQ ID NO:158). In some embodiments the recombinant PBIS does not contain either the gamma zein P-X region or the gamma zein RD domain. In some embodiments, the recombinant PBIS does not contain the KDEL sequence. In some embodiments, the recombinant PBIS comprises a sequence that can induce RPBLA formation in the absence of a KDEL sequence.

In some embodiments, the recombinant PBIS assemble to mediate the formation of recombinant protein body-like assemblies (RPBLAs).

In some embodiments, the recombinant PBIS comprises a polyproline II (PPII) structure. In some embodiments, the recombinant PBIS comprises a proline-rich sequence.

The PPII structure or the proline-rich sequence can be at least 30 amino acids in length. The recombinat PBIS can comprise at least two cysteines upstream from the amino terminus (N-terminus) of the PPII structure or the proline-rich sequence. The recombinant PBIS can comprise at least two cysteines downstream from the carboxy terminus (C-terminus) of the PPII structure or the proline-rich sequence. In addition, the recombinant PBIS can comprise at least two cysteines upstream from the amino terminus of the PPII structure or the proline-rich sequence and at least two cysteines downstream from the carboxy terminus of the PPII structure or the proline-rich sequence.

In some embodiments, the recombinant PBIS comprises a PPII structure between at least two cysteines upstream from the N-terminus and at least two cysteines downstream from the C terminus and further comprises an additional cysteine and a proline-rich sequence between the PPII structure and the two C-terminal cysteines.

In some embodiments, the recombinant PBIS comprises a first proline-rich sequence between at least two cysteines upstream from the N-terminus and at least two cysteines downstream from the C terminus and further comprises an additional cysteine and an second proline-rich sequence between the first proline-rich sequence and the two C-terminal cysteines.

The recombinant PBIS can also comprise a sequence that localizes the recombinant PBIS to the endoplasmic reticulum (ER).

In some embodiments, no more than about 10% of the amino acids in the PPII structure or the proline-rich sequence are lysine or arginine. In some embodiments, no more than about 9%, about 8%, about 7%, about 6%, about 5%, about 4%, about 3%, about 2% or about 1% of the amino acids in the PPII structure or the proline-rich sequence are lysine or arginine. In some embodiments, the PPII structure or the proline-rich sequence does not contain lysine. In some embodiments, the PPII structure or the proline-rich sequence does not contain arginine. In some embodiments, the PPII structure or the proline-rich sequence does not contain lysine or arginine.

In some embodiments, no more than about 15% of the amino acids in the PPII structure or the proline-rich sequence are histidine. In some embodiments, no more than about 14%, about 13%, about 12%, about 11%, about 10%, about 9%, about 8%, about 7%, about 6%, about 5%, about 4%, about 3%, about 2% or about 1% of the amino acids in the PPII structure or the proline-rich sequence are histidine. In some embodiments, the PPII structure or the proline-rich sequence does not contain a histidine.

In some embodiments, the PPII structure or the proline-rich sequence does not contain the sequence (PPPVHL)$_6$ (SEQ ID NO:115). In some embodiments, the PPII structure or the proline-rich sequence does not contain the sequence PPPVHL (SEQ ID NO:136).

In some embodiments, the recombinant PBIS is capable of mediating the formation of an RPBLA when it is expressed at a particular minimum concentration. Thus, in some embodiments, the recombinant PBIS is capable of mediating the formation of an RPBLA when it is expressed at about 0.5 grams/kilogram of tobacco leaves fresh weight.

The ability of a recombinant sequence to function as a PBIS can be tested according to methods described herein or other methods known in the art.

In some embodiments, the recombinant PBIS is less allergenic than a wild-type PBIS, for example, the PBIS of maize gamma-zein.

Allergenicity can be determined according to methods described herein or other methods known in the art. For example, amino acid sequence homology has been used to asses allergenic potential. Sequence homology comparisons can be used to determine the extent to which a newly expressed or identified protein is similar in structure to a known allergen. This information can predict whether that protein has allergenic potential. These comparisons can be conducted using various algorithms such as FASTA or BLASTP to predict overall structural similarities. IgE cross-reactivity between the newly expressed or identified protein and a known allergen can be considered a possibility when there is more than 35 percent identity in a segment of 80 or more amino acids (Food and Agriculture Organization of the United Nations (FAO) and the World Health Organization (WHO) (2001)). Other scientifically justified criteria can also be used to predict IgE cross-reactivity.

In some embodiments, the allergenicity of a recombinant PBIS is determined using the Allergen Online Database (version 10.0, January 2010; http://www.allergenonline.com) developed by the Food Allergy Research and Resource Program. Thus, in some embodiments, the recombinant PBIS contains fewer hits with more than 35% identity to allergenic peptides than the PBIS of maize gamma-zein using the Allergen Online Database.

In some embodiments, the recombinant PBIS contains no more than 9 hits with at least 35% identity to a known allergenic peptide. In some embodiments, the recombinant PBIS contains no more than 8 hits with at least 35% identity to a known allergenic peptide. In some embodiments, the recombinant PBIS contains no more than 7 hits with at least 35% identity to a known allergenic peptide. In some embodiments, the recombinant PBIS contains no more than 6 hits with at least 35% identity to a known allergenic peptide. In some embodiments, the recombinant PBIS contains no more than 5 hits with at least 35% identity to a known allergenic peptide. In some embodiments, the recombinant PBIS contains no more than 4 hits with at least 35% identity to a known allergenic peptide. In some embodiments, the recombinant PBIS contains no more than 3 hits with at least 35% identity to a known allergenic peptide. In some embodiments, the recombinant PBIS contains no more than 2 hits with at least 35% identity to a known allergenic peptide. In some embodiments, the recombinant PBIS contains no more than 1 hit with at least 35% identity to a known allergenic peptide. In some embodiments, the recombinant PBIS does not contain any hits with at least 35% identity to a known allergenic peptide.

In some embodiments, the recombinant PBIS contains no more than 9 hits with at least 30% identity to a known allergenic peptide. In some embodiments, the recombinant PBIS contains no more than 8 hits with at least 30% identity to a known allergenic peptide. In some embodiments, the recombinant PBIS contains no more than 7 hits with at least 30% identity to a known allergenic peptide. In some embodiments, the recombinant PBIS contains no more than 6 hits with at least 30% identity to a known allergenic peptide. In some embodiments, the recombinant PBIS contains no more than 5 hits with at least 30% identity to a known allergenic peptide. In some embodiments, the recombinant PBIS contains no more than 4 hits with at least 30% identity to a known allergenic peptide. In some embodiments, the recombinant PBIS contains no more than 3 hits with at least 30% identity to a known allergenic peptide. In some embodiments, the recombinant PBIS contains no more than 2 hits with at least 30% identity to a known allergenic peptide. In some embodiments, the recombinant PBIS contains no more than 1 hit with at least 30% identity to a known allergenic peptide. In some embodiments, the recombinant PBIS does not contain any hits with at least 30% identity to a known allergenic peptide.

Several techniques have been developed in order to determine the allergenic response developed after the administration of an allergen. For instance, the presence of IgE, an immunoglobulin associated with allergenicity, can been determined by ELISA assays and by ELISA competitive tests. Kim et al., Yonsei Medical Journal 47: 505-12 (2006); Fritsché, Toxicology letters 140-141:303-309 (2003), both of which are which is herein incorporated by reference in their entirety. In some embodiments, the recombinant PBIS generates a decreased IgE antibody response in vivo compared to the PBIS of maize gamma-zein. In some embodiments, the recombinant PBIS generates a decreased response in an allergy skin prick test compared to the PBIS of maize gamma-zein.

Additionally, resistance to pepsin digestion has been observed in several food allergens. Thus, a correlation exists between resistance to digestion by pepsin and allergenic potential. The method outlined in The United States Pharmacopoeia (1995) was used in the establishment of the correlation. Astwood et al. Nat Biotechnol 14:1269-73 (1996), which is herein incorporated by reference in its entirety. Therefore, the resistance of a protein to degradation in the presence of pepsin under appropriate conditions indicates that a protein can have allergenic potential. In some embodiments, the recombinant PBIS is less resistant to protein degradation in the presence of pepsin than the PBIS of maize gamma-zein.

Further analysis can be conducted to determine the likelihood of the newly expressed or identified protein's allergenic potential. Ex vivo procedures have also been described as the testing for allergenicity using cells or tissue culture. Evaluation of Allergenicity of Genetically Modified Foods: Report of Joint FAO/WHO Expert Consultation on Allergenicity of Foods Derived from Biotechnology; Food and Agriculture Organization of the United Nations (FAO); Rome Italy (2001). One of these techniques is based on the fact that the IgE-mediated mast cell triggering capacity of allergenic epitopes can be measured using a functional in vitro assay. Based on peritoneal rat mast cells passively sensitized with specific rat IgE and labeled with 3H-serotonin, cells are triggered for mediator release with standard dilutions of the allergen. Fritsché, Toxicology letters 140-141:303-309 (2003). Thus, in some embodiments, the recombinant PBIS generates decreased mediator release compared to the PBIS of maize gamma-zein.

The IgE dependent allergic reaction is composed of two phases. The first phase is an inducing step, where the immune system of the host is sensitized by the allergen. As a result, specific IgE anti-allergen antibodies are produced, and the antibodies are then fixed by mast cells in target organs. The second phase is a triggering phase mediated by the allergen binding to these IgE antibodies and stimulating mediator (histamine) release from mast cells. For evaluating allergenicity of antigens, either or both phases can be examined by appropriate in vivo tests, essentially as described in Fritsché, Toxicology letters 140-141:303-309 (2003), which is herein incorporated by reference in its entirety. Thus, for example, in some embodiments, the recombinant PBIS generates a decreased IgE antibody production compared to the PBIS of maize gamma-zein. In some embodiments, the recombinant PBIS generates a decreased mediator release from mast cells compared to the PBIS of maize gamma-zein.

III. Polyproline II Structures and Proline-Rich Sequences

As described above, the recombinant PBIS used herein can comprise a polyproline type II (PPII) structure. A PPII helix is a secondary protein structure. PPII structures can have a left-handed helical structure with an overall shape resembling a triangular prism. The PPII structure can be quite extended and some PPII structures have been found to have a helical pitch of 9.3 Å/turn, 3 residues per turn, and (1) and ψ angles centered around −75° and 145°, respectively.

The PPII structure has been described in the literature (see, e.g., Eisenberg D, et al. *J. Mol. Biol.* 179:125-142 (1984), which is herein incorporated by reference in its entirety). Proteins and peptides with PPII structures have been identified and presented in the literature. Such proteins and peptides, include, for example, poly-glutamate and poly-aspartate (Rucker, A., et al., *Proteins: Structure, Function, and Bioinformatics* 53: 68-75 (2003)), poly-GGXGG (X is not glycine) (Shi, Z., et al., *PNAS* 102:17964-17968 (2005)), mucin (Di, S., et al., *Biospectroscopy* 5:79-91 (1999)), titin (Ma, K., et al., *Biochemistry* 27: 3427-38 (2001)), Bowman-Birk protease inhibitor (Smyth, E., et al., *Biopolymers* 58:138-51 (2001)), protein kinase inhibitor (Knighton, D. R., et al., *Science* 253: 414-420 (1991)), p85 subunit of P13 kinase (Renzoni, D. A., et al., *Biochemistry* 35: 15646-53 (1996)), alpha-synuclein, human tau-46, casein milk proteins (Syme, C. D., et al., *Eur J Biochem* 269:148-56 (2002)), and the ligand-acceptor complex of SH-3-5 (Try-Kinase) (Lim, W. A., et al., *Nature* 372: 375-9 (1994)).

Proline residues are greatly favored in PPII helices. Glycine and tyrosine are generally disfavored, but are found in some PPII structures such as collagen. Conformational analysis of synthetic peptides of repetitive sequences where histidine of gamma zein was substituted by Ala, Glu, and Lys indicates that all of these peptides adopted a PPII type structure. Therefore, the PPII conformation is adopted independently of both the sign of charge on the charged amino acid (Lys or Glu) and the residue being charged or uncharged (Ala). Dalcol, *J. Org. Chem.* 61: 6775-6782 (1996). The length of the repetitive sequence, acidic pH, and high peptide concentrations increased PPII content. At pH 3.0 there is more PPII content that at pH 7, except when histidine was substituted by glutamic acid. In this case, destabilization of PPII is probably due to the protonation of carboxyl groups of glutamic acid at pH 3 and the subsequent side chain-side-chain interactions by hydrogen bonding (Dalcol, 1996).

The PPII structure is a dynamic feature of a protein. Bicudo et at (2008, *Biopolymers,* 89:175-178) analyzed the secondary structure of gamma zein purified from maize PBs by circular dichroism when solubilized in water, SDS and 2-propanol, with and without reducing agent. The PPII conformation was only 1% in SDS, 4% in propanol and about 7% in water. Taking into account that the RD represents 22% of the whole gamma-zein sequence, these results indicate that at least 30% of this domain will adopt a PPII structure in water. Fernández-Carneado, *J. Mol. Biol.* 372: 708-22 (2004); Bicudo, 2007. Furthermore, the extent of PPII can be greatly increased by the zein-zein interactions that lead protein assembly and PBs formation. Therefore polypeptides are considered to have PPII structure if they have a propensity to form the PPII structure.

Methods of determining whether a sequence forms a PPII structure are also known. For example, spectroscopies based on optical activity, such as circular dichroism (CD), vibrational circular dichrosim (VCD), and Raman optical activity (ROA) can be used. See, e.g., Bochicchio and Tamburro, *Chirality* 14:782-92 (2002), which is herein incorporated by reference in its entirety. In silico methods can also be used. In addition, PPII structure in crystallized proteins can be determined by X-ray diffraction. Knighton et al. *Science* 253: 414-420 (1991); Caldwell et al. *Biopolymers* 10:1891-1904 (1984). CD is very sensitive to secondary structure. Thus, in some embodiments, the method of determining PPII structure is CD. The CD spectra of a peptide from about 30 to about 100 amino acids in length can be determined at about pH 7 and about 5° C. The presence of PPII structure can be characterized by a CD pattern with a minimum at about $\lambda=202$ nm and a maximum at about $\lambda=228$ nm. The percentage of PPII structure in a sample peptide can be determined by the ratio of the $[\theta max]_M$ (the molar elipticity at the maximum around $\lambda=228$ nm) magnitudes of the sample peptide compared to a $H-(Pro)_n$—OH reference peptide. It can be considered that the reference peptide, which has a similar length to the sample peptide, has 100% PPII structure. A more detailed description of the CD spectra-based method to determine the PPII structure is found in Dalcol et al. *Org. Chem.* 61: 6675-6782 (1996), which is hereby incorporated by reference in its entirety.

For example, a poly-proline peptide $(H-(Pro)_n$—OH) can be considered as the reference, and can be considered to form 100% PPII helix. In some embodiments, the $[\theta max]_M$ of the PPII structure is at least about 25%, at least about 30%, at least about 40%, at least about 50%, at least about 55%, at least about 60%, at least about 65%, at least about 70%, at least about 75%, at least about 80%, at least about 85%, at least about 90%, at least about 95%, or 100% of the $[\theta max]_M$ of the reference polypeptide $((H-(Pro)_n$—OH).

As described above, the recombinant PBIS can comprise a proline-rich sequence. In some embodiments, the PPII structure comprises a proline-rich sequence. In some embodiments, the recombinant PBIS comprises a PPII structure and a proline-rich sequence that does not have a propensity to form a PPII helix. In some embodiments, a proline-rich sequence is capable of forming a PPII structure.

An amphipathic molecule is a molecule that has a region with significantly higher hydrophobic character compared to the rest of the molecule, which is hydrophobic in comparison with that region. The hydrophobic or the hydrophilic character of a molecule or a region thereof has an important effect on its behavior with regard to the surrounding media. Hydrophobic surfaces tend to avoid interaction with aqueous media, while hydrophilic surfaces are stabilized by aqueous media. Since a protein is a three-dimensional structure, only some of its amino acid residues are exposed to the media. As a consequence, only the amino acids located at the surface, hence exposed to the media, should be considered in determining if a protein or protein region is hydrophobic, hydrophilic, or amphipathic in character.

As mentioned herein, the PPII structure is an extended left-handed helix with three amino acids per turn. Each single turn can be represented as a triangle (e.g., FIG. 1A) with each one of the 3 amino acids in a turn placed at one of the triangle's vertexes in a clock-wise order. As a result, the stacking of consecutive triangles (turns) of the PPII structure will generate a triangle prism representing the structure of the protein or protein region. In a PPII helix, the amino acids that are placed at the edges of the triangle prism are exposed to the media and all should be considered in hydrophobic/hydrophilic determinations. A PPII structure can be considered amphipathic when one of the edges of the triangle prism has a significantly different hydrophobic character with regard to the other two edges considered independently.

The hydrophobic/hydrophilic character of an amino acid is determined by the nature of its side chain. The Kyte-Doolittle hydrophobicity scale (Kyte J., Doolittle R. F., *J. Mol. Biol.* 157:105-132 (1982)) is derived from the physicochemical properties of the amino acid side chains, and it is commonly used and well accepted. The amino acids will be classified in three groups based on Kyte-Doolittle values: (i) amino acids ranging from 4.5 to 1.8, which will be considered as non-polar or hydrophobic (I, V, L F C, M and A), (ii) amino acids ranging from $-0.4$ to $-1.6$, which will be considered as partially polar or partially hydrophilic (G, S, T, W, Y and P), and (iii) amino acids ranging from $-3.2$ to $-4.5$, which will be considered as polar or hydrophilic (R, H, D, E, N, Q and K). The amino acids from the polar group include amino acids that are positively charged (R, H, and K), negatively charged (D and E), and non-charged (Q and N). In order to simplify the calculation of the hydrophobicity of a PPII helix, a consensus polarity value that takes this classification into account has been assigned: (i) 0 for non polar amino acids, (ii) 0.5 for partially polar amino acids, and (iii) 1 for polar amino acids.

The amphipathic character of a PPII structure can be calculated taking into account the amino acid classification described herein in the context of the spatial amino acid distribution in the triangular prism. The percentage of the hydrophilic amino acids can be calculated for each edge (edge 1: i, i+4, i+7 . . . ; edge 2: i+1, i+5, i+8 . . . ; edge 3: i+2, i+6, i+9 . . . ), and the PPII structure can be considered amphipathic when the difference of the percentage of one of the edges is at least about 35 with regard to the two other two edges considered independently.

Thus, since every third residue in the PPII structure is aligned along one side of the helix, if the hydrophobicity of residues along one side of the helix is different from the hydrophobicity of residues along another side of the helix, the PPII helix will be amphipathic. The PPII helix of the RD of gamma zein has a marked amphipathic character. With 3.0 residues per turn, the valine and leucine residues of gamma zein are aligned on the same side of the helix (edges 1 and 2, respectively), whereas the polar histidine residues, which are charged, are aligned on the opposite side (edge 3). This amphipathicity is clearly pointed out by the calculation mentioned above, wherein, the percentage of hydrophilic amino acids is 29.4, 29.4, and 78.1 on edges 1, 2, and 3, respectively. By way of further example, the table below provides additional information about exemplary recombinant PBIS sequences described herein.

In some embodiments, the PPII structure or the proline rich sequence comprises the sequence $(GXY)_n$, wherein n is at least 5, at least 6, at least 7, at least 8, at least 9, at least 10, at least 12, at least 14, at least 16, at least 18, or at least 20. In some embodiments, the sequence comprising $(GXY)_n$ comprises at least about 20%, about 30%, about 40%, about 50%, about 60%, or about 65% prolines.

In some embodiments, the PPII structure or the proline-rich sequence comprises a proline-rich repeat. As described, a proline-rich repeat is a sequence that comprises at least two copies of a sequence that contains proline. The repeat can be

| PPII groups | PBIS | residues* | % Proline | % identity** | Edges polarity*** | Diff in edge polarity**** | net charge |
|---|---|---|---|---|---|---|---|
| Amphypatic positivelly charged | RX3 | 11-63 | 54.7 | 100 | (29.4/29.4/78.1) | (0/48.7/48.7) | +8 |
| | RX3(K) | 11-63 | 54.7 | 84.9 | (29.4/29.4/78.1) | (0/48.7/48.7) | +8 |
| | RX3(R) | 11-63 | 54.7 | 84.9 | (29.4/29.4/78.1) | (0/48.7/48.7) | +8 |
| Amphypatic negativelly | RX3(D) | 11-63 | 54.7 | 84.9 | (29.4/29.4/78.1) | (0/48.7/48.7) | −8 |
| | RX3(E) | 11-63 | 54.7 | 84.9 | (29.4/29.4/78.1) | (0/48.7/48.7) | −8 |
| Amphypatic non charged | RX3(N) | 11-63 | 54.7 | 84.9 | (29.4/29.4/78.1) | (0/48.7/48.7) | 0 |
| | RX3(Q) | 11-63 | 54.7 | 84.9 | (29.4/29.4/78.1) | (0/48.7/48.7) | 0 |
| Non-Amphypatic | RX3(A) | 11-63 | 54.7 | 86.8 | (29.4/29.4/34.4) | (0/5/5) | +1 |
| | RX3(A)2 | 11-63 | 54.7 | 84.9 | (29.4/29.4/28.1) | (0/1.3/1.3) | 0 |
| | RX3(A3) | 11-63 | 54.7 | 54.7 | (29.4/29.4/28.1) | (0/1.3/1.3) | 0 |
| | RX3(L) | 11-63 | 54.7 | 84.9 | (29.4/29.4/28.1) | (0/1.3/1.3) | 0 |
| | RX3(V) | 11-63 | 54.7 | 84.9 | (29.4/29.4/28.1) | (0/1.3/1.3) | 0 |
| | RX3(T) | 11-63 | 54.7 | 84.9 | (29.4/29.4/53.1) | (0/23.7/23.7) | 0 |
| | PP | 11-63 | 96.2 | 58.5 | (50/52.9/56.3) | (0/1.3/1.3) | +1 |
| | PP3 | 11-63 | 100 | 54.7 | (50/50/50) | (0/0/0) | 0 |
| | PA | 11-63 | 66 | 58.5 | (29.4/29.4/56.7) | (0/27.3/27.3) | +1 |
| | PA2 | 11-63 | 67.9 | 54.7 | (29.4/29.4/53.1) | (0/23.7/23.7) | 0 |
| | Z(Col) | 11-63 | 39.6 | 38.6 | (52.9/52.9/56.3) | (0/3.4/3.4) | +1 |
| | Z(Col2) | 11-56 | 36.9 | 27.8 | (50/50/50) | (0/0/0) | 0 |
| | Z(Adh) | 11-63 | 39.6 | 35.8 | (64.7/61.8/50) | (2.9/14.7/11.8) | −5 |
| | Z(Adh2) | 11-56 | 39.6 | 27.8 | (68.8/65.6/46.7) | (4.4/22.1/18.9) | −6 |

*Residues indicates the amino acids used in this analysis: relative position determined with regard to the N-terminus of the mature protein.
**The % identity indicates the percent of amino acids that are identical to gamma zein RX3.
***Edges polarity indicates the percentage of polar amino acids on edges 1, 2, and 3 of the triangular prism representation of the PPII structure.
****Diff in edge polarity indicates the difference in the percentage of poalr amino acids among the edges of the triangular prism representation of the PPII structure (edge 1 v edge 2, edge 1 v edge 3, and edge 2 v edge 3).

In some embodiments, the PPII structure or the proline-rich sequence is non-amphipathic. In some embodiments, the PPII structure or the proline-rich sequence is amphipathic and negatively charged. In some embodiments, the PPII structure or the proline-rich sequence is amphipathic and non-charged. In some embodiments, the PPII structure or the proline-rich sequence is not amphipathic and negatively charged.

In some embodiments, the percentage of prolines along the length of the PPII structure or the proline-rich sequence is consistent. Thus, for example, in some embodiments, 10-amino acid windows across the length of the PPII structure or the proline-rich sequence differ in proline percentage by no more about 50%, about 45%, about 35%, about 30%, about 25%, about 20%, about 15%, about 10%, or about 5%.

In some embodiments, the proline amino acids present in the PPII structure or the proline-rich sequence can be hydroxylated rendering hydroxyproline (e.g., (2S,4R)-4-Hydroxyproline, or L-hydroxyproline ($C_5H_9O_3N$)). This is a common post-translational modification of proline that differs only by the presence of a hydroxyl (OH) group attached to the gamma carbon atom of proline. Hydroxyproline is present in proline-rich sequences such as in collagen. For instance, in the canonical GXY triad (where X and Y are independently any amino acid), a proline occupying the Y position can be hydroxylated. Hydroxyprolines do not not interfere with the PPII helix formation.

In some embodiments, the PPII structure or the proline-rich sequence comprises a collagen-related sequence. Thus, at least two amino acids in length (e.g., PX), at least three amino acids in length (e.g., PPX, PXP, XPP, or PXX), at least four amino acids in length (e.g., PPPX (SEQ ID NO:119), PPXX (SEQ ID NO:117), PXXX (SEQ ID NO:137), PPXP (SEQ ID NO:138), PXPP (SEQ ID NO:139)), at least five amino acids in length (e.g., PPPXX (SEQ ID NO:140)), at least six amino acids in length (e.g., PPPXXX (SEQ ID NO:116) or PPPXPX (SEQ ID NO:141)), at least seven amino acids in length, at least eight amino acids in length, at least nine amino acids in length, or at least ten amino acids in length. The repeats listed here are provided only by way of example.

The proline-rich repeat can comprise at least two copies, at least three copies, at least four copies, at least five copies, at least six copies, at least seven copies, at least eight copies, at least nine copies, or at least ten copies of a sequence that contains proline. The proline-rich repeat can contain all copies of the same repeat (i.e. a homomeric proline-rich repeat) or can contain a combination of proline-rich repeats (i.e. a heteromeric proline-rich repeat). By way of example, the sequence PPPAAAPPPAAAPPPAAA (SEQ ID NO:142) is a homomeric proline-rich repeat that contains three copies of the same PPPAAA (SEQ ID NO:123) repeat, and the sequence PPPAAAPPPAAAPPAPPPPPAPPP (SEQ ID NO:143) is a heteromeric proline-rich repeat that contains two copies of one sequence, PPPAAA (SEQ ID NO:123), and two copies of a different sequence, PPAPPP (SEQ ID NO:144).

In some embodiments, the PPII structure or the proline-rich sequence comprises at least 2, at least 3, at least 4, at least 5, at least 6, at least 7, at least 8, at least 9, at least 10, at least 11, at least 12, at least 13, at least 14, or at least 15 PX repeats. In some embodiments, at least 2, at least 3, at least 4, at least 5, at least 6, at least 7, at least 8, at least 9, at least 10, at least 11, at least 12, at least 13, at least 14, or at least 15 of the PX repeats are consecutive repeats. In some embodiments, at least 2, at least 3, at least 4, at least 5, at least 6, at least 7, at least 8, at least 9, at least 10, at least 11, at least 12, at least 13, at least 14, or at least 15 of the PX repeats are homomeric. In some embodiments, at least 2, at least 3, at least 4, at least 5, at least 6, at least 7, at least 8, at least 9, at least 10, at least 11, at least 12, at least 13, at least 14, or at least 15 of the PX repeats are heteromeric.

In some embodiments, the PPII structure or the proline-rich sequence comprises at least 2, at least 3, at least 4, at least 5, at least 6, at least 7, at least 8, at least 9, at least 10, at least 11, at least 12, at least 13, at least 14, or at least 15 3-amino acid repeats (e.g., PPX, PXP, XPP, or PXX). In some embodiments, at least 2, at least 3, at least 4, at least 5, at least 6, at least 7, at least 8, at least 9, at least 10, at least 11, at least 12, at least 13, at least 14, or at least 15 of the 3-amino acid repeats are consecutive repeats. In some embodiments, at least 2, at least 3, at least 4, at least 5, at least 6, at least 7, at least 8, at least 9, at least 10, at least 11, at least 12, at least 13, at least 14, or at least 15 of the 3-amino acid repeats are homomeric. In some embodiments, at least 2, at least 3, at least 4, at least 5, at least 6, at least 7, at least 8, at least 9, at least 10, at least 11, at least 12, at least 13, at least 14, or at least 15 of the 3-amino acid repeats are heteromeric.

In some embodiments, the PPII structure or the proline-rich sequence comprises at least 2, at least 3, at least 4, at least 5, at least 6, at least 7, at least 8, at least 9, at least 10, at least 11, at least 12, at least 13, at least 14, or at least 15 4-amino acid repeats (e.g., PPPX (SEQ ID NO:119), PPXX (SEQ ID NO:117), PXXX (SEQ ID NO:137), PPXP (SEQ ID NO:138), PXPP (SEQ ID NO:139)). In some embodiments, at least 2, at least 3, at least 4, at least 5, at least 6, at least 7, at least 8, at least 9, at least 10, at least 11, at least 12, at least 13, at least 14, or at least 15 of the 4-amino acid repeats are consecutive repeats. In some embodiments, at least 2, at least 3, at least 4, at least 5, at least 6, at least 7, at least 8, at least 9, at least 10, at least 11, at least 12, at least 13, at least 14, or at least 15 of the 4-amino acid repeats are homomeric. In some embodiments, at least 2, at least 3, at least 4, at least 5, at least 6, at least 7, at least 8, at least 9, at least 10, at least 11, at least 12, at least 13, at least 14, or at least 15 of the 4-amino acid repeats are heteromeric.

In some embodiments, the PPII structure or the proline-rich sequence comprises at least 2, at least 3, at least 4, at least 5, at least 6, at least 7, at least 8, at least 9, at least 10, at least 11, at least 12, at least 13, at least 14, or at least 15 5-amino acid repeats (e.g., PPPXX (SEQ ID NO:140)). In some embodiments, at least 2, at least 3, at least 4, at least 5, at least 6, at least 7, at least 8, at least 9, at least 10, at least 11, at least 12, at least 13, at least 14, or at least 15 of the 5-amino acid repeats are consecutive repeats. In some embodiments, at least 2, at least 3, at least 4, at least 5, at least 6, at least 7, at least 8, at least 9, at least 10, at least 11, at least 12, at least 13, at least 14, or at least 15 of the 3-amino acid repeats 5-amino acid repeats are homomeric. In some embodiments, at least 2, at least 3, at least 4, at least 5, at least 6, at least 7, at least 8, at least 9, at least 10, at least 11, at least 12, at least 13, at least 14, or at least 15 of the 5-amino acid repeats are heteromeric.

In some embodiments, the PPII structure or the proline-rich sequence comprises at least 2, at least 3, at least 4, at least 5, at least 6, at least 7, at least 8, at least 9, at least 10, at least 11, at least 12, at least 13, at least 14, or at least 15 6-amino acid repeats (e.g., PPPXXX (SEQ ID NO:116) or PPPXPX (SEQ ID NO:141)). In some embodiments, at least 2, at least 3, at least 4, at least 5, at least 6, at least 7, at least 8, at least 9, at least 10, at least 11, at least 12, at least 13, at least 14, or at least 15 of the 6-amino acid repeats are consecutive repeats. In some embodiments, at least 2, at least 3, at least 4, at least 5, at least 6, at least 7, at least 8, at least 9, at least 10, at least 11, at least 12, at least 13, at least 14, or at least 15 of the 6-amino acid repeats are homomeric. In some embodiments, at least 2, at least 3, at least 4, at least 5, at least 6, at least 7, at least 8, at least 9, at least 10, at least 11, at least 12, at least 13, at least 14, or at least 15 of the 6-amino acid repeats are heteromeric.

In some embodiments, the PPII structure or the proline-rich sequence consists essentially of amino acids selected from the group consisting of (i) proline, (ii) valine, (iii) leucine, and (iv) alanine. In some embodiments, the PPII structure or the proline-rich sequence consists essentially of amino acids selected from the group consisting of (i) proline, (ii) valine, (iii) leucine, (iv) aspartic acid; and (v) glutamine. In some embodiments, the PPII structure or the proline-rich sequence consist essentially of amino acids selected from the group consisting of (i) proline, (ii) valine, (iii) leucine, (iv) threonine; (v) asparagine; and (vi) glutamine. In some embodiments, the PPII structure or the proline-rich sequence consists essentially of amino acids selected from the group consisting of (i) proline, (ii) negatively charged amino acids (i.e., D and E), (iii) amino acids with polar uncharged side chains (i.e., N, and Q), (iv) amino acids with partially polar uncharged side chains (i.e., S, T, W, Y, and G) or with amino acids with partially polar uncharged side chains selected from the group consisting of S, T, and G, or (v) amino acids with hydrophobic side chains (i.e., A, I, L, M, F, and V) or with a hydrophobic side chain selected from the group consisting of A, I, L, M, and V. In some embodiments, the PPII structure or the proline-rich sequence consists essentially of amino acids selected from the group consisting of (i) proline; and (ii) alanine. In some embodiments, the PPII structure or the proline-rich sequence does not contain a cysteine.

The PPII structure or the proline-rich sequence can comprise a sequence selected from the group consisting of (i) PPPVAL (SEQ ID NO:121); (ii) PPPVLL (SEQ ID NO:122); and (iii) PPPAAA (SEQ ID NO:123). The PPII structure or the proline-rich sequence can comprise a sequence selected from the group consisting of (i) PPPVDL (SEQ ID NO:124); and (ii) PPPVEL (SEQ ID NO:125). The PPII structure or the proline-rich sequence can comprise a sequence selected from the group consisting of (i) PPPVTL (SEQ ID NO:126); (ii) PPPVNL (SEQ ID NO:127); and (iii) PPPVQL (SEQ ID NO:128). The PPII structure or the proline-rich sequence can comprise the sequence PPPAPA (SEQ ID NO:129). The PPII structure or the proline-rich sequence can comprise the sequence PPPVSL (SEQ ID NO:181). In some embodiments, the PPII structure of the proline-rich sequence comprises at least one, at least two, at least three, at least four, at least five, at least six, at least seven, at least eight, at least nine, or at least ten consecutive repeats of one of the aforementioned repeats. In some embodiments, the PPII structure of the proline-rich sequence comprises at least one, at least two, at least three, at least four, at least five, at least six, at least seven, at least eight, at least nine, or at least ten consecutive repeats of a combination of the aforementioned repeats. In some embodiments, the PPII structure of the proline-rich sequence comprises at least one, at least two, at least three, at least four, at least five, at least six, at least seven, at least eight, at least nine, or at least ten repeats of one of the aforementioned repeats. In some embodiments, the PPII structure of the proline-rich sequence comprises at least one, at least two, at least three, at least four, at least five, at least six, at least seven, at least eight, at least nine, or at least ten repeats of a combination of the aforementioned repeats.

In some embodiments, at least about 40% of the amino acids in the PPII structure or the proline-rich sequence are proline. In some embodiments, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the amino acids in the PPII structure or the proline-rich sequence are proline.

In some embodiments, no more than about 99%, about 98%, about 97%, about 96%, about 95%, about 90%, about 85%, about 80%, about 75%, about 70%, about 65%, about 60%, about 55%, about 50%, about 45%, or about 40% of the amino acids in the PPII structure or proline-rich sequence are proline.

In some embodiments, the PPII structure or the proline-rich sequence is at least 30 amino acids in length. In some embodiments, the PPII structure or the proline-rich sequence is at least 32, at least 34, at least 36, at least 38, at least 40, at least 42, at least 44, at least 46, at least 48, or at least 56 amino acids in length.

In some embodiments, the PPII structure or the proline-rich sequence is no more than 100, no more than 98, no more than 96, no more than 94, no more than 92, no more than 90, no more than 88, no more than 86, no more than 84, no more than 82, no more than 80, no more than 78, no more than 76, no more than 74, no more than 72, no more than 70, no more than 68, no more than 66, no more than 64, no more than 62, no more than 60, no more than 58, no more than 56, no more than 54, or no more than 52 amino acids in length.

In some embodiments, the PPII structure or the proline-rich sequence is from about 36 to about 100 amino acids, from about 36 to about 90, from about 36 to about 80, or from about 36 to about 70 amino acids in length. In some embodiments, the PPII structure or the proline-rich sequence is from about 42 to about 100 amino acids, from about 42 to about 90, from about 42 to about 80, or from about 42 to about 70 amino acids in length. In some embodiments, the PPII structure or the proline-rich sequence is from about 48 to about 100 amino acids, from about 48 to about 90, from about 48 to about 80, or from about 48 to about 48 amino acids in length.

In some embodiments, a recombinant PBIS comprises a PPII structure and a proline-rich sequence. The proline-rich sequence can be N-terminal or C-terminal to the PPII structure. The proline-rich sequence can be fused directly to the N- or C-terminal of the PPII structure or can be fused indirectly, i.e., through an amino acid linker.

In some embodiments, a recombinant PBIS comprises a proline-rich sequence and a second proline-rich sequence. The second proline-rich sequence can be N-terminal or C-terminal to the proline-rich sequence. The second proline-rich sequence can be fused directly to the N- or C-terminal of the proline-rich sequence or can be fused indirectly, i.e., through an amino acid linker.

In some embodiments, the proline-rich sequence fused (directly or indirectly) to a PPII structure or a second proline-rich sequence fused (directly or indirectly) to a proline-rich sequence comprises the Pro-X region of gamma-zein. In some embodiments, the proline-rich sequence fused (directly or indirectly) to a PPII structure or a second proline-rich sequence fused (directly or indirectly) to a proline-rich sequence comprises at least 3, at least 4, at least 5, at least 6, at least 7, at least 8, at least 9, or at least 10 PX repeats. The PX repeats can be consecutive or can be separated by additional amino acids. In some embodiments, the proline-rich sequence fused (directly or indirectly) to a PPII structure or a second proline-rich sequence fused (directly or indirectly) to a proline-rich sequence comprises the sequence CHYPYQPPRPQPHPQPHP (SEQ ID NO:182).

In some embodiments, the proline-rich sequence fused (directly or indirectly) to a PPII structure or a second proline-rich sequence fused (directly or indirectly) to a proline-rich sequence comprises at least about 10 amino acids, at least about 15 amino acids, at least about 20 amino acids, at least about 30 amino acids, at least about 40 amino acids, at least about 50 amino acids, at least about 75 amino acids, or at least about 100 amino acids.

In some embodiments, the proline-rich sequence fused (directly or indirectly) to a PPII structure or a second proline-rich sequence fused (directly or indirectly) to a proline-rich sequence comprises no more than about 200 amino acids, about 150 amino acids, about 100 amino acids, or about 50 amino acids.

In some embodiments, the proline-rich sequence fused (directly or indirectly) to a PPII structure or a second proline-rich sequence fused (directly or indirectly) to a proline-rich sequence comprises about 10 to about 20 amino acids, about 10 to about 30 amino acids, about 10 to about 40 amino acids, about 15 to about 50 amino acids, about 15 to about 30 amino acids, about 15 to about 40 amino acids, or about 15 to about 50 amino acids.

IV. Cysteine Residues

As described above, the recombinant PBIS can comprise a PPII structure, a polyproline-rich sequence or both a PPII structure and a proline-rich sequence between at least two cysteines at the N-terminus and at least two cysteines at the C-terminus. The cysteines at the N- and C-termini can be linked directly to the N- and C-termini or can be linked indirectly, e.g., via additional amino acids. In some embodiments, the recombinant PBIS comprises at least three cysteines, or at least four cysteines downstream of the C-terminus. In some embodiments, the recombinant PBIS comprises at least three cysteines, or at least four cysteines upstream of the N-terminus.

Unless otherwise stated, the position of cysteine residues are relative to the N- or C-termini of a PPII structure, a proline-rich sequence or both a PPII structure and a proline-rich sequence.

In some embodiments, the recombinant PBIS comprises multiple PPII structures and/or proline-rich sequences separated by an additional cysteine. By way of example only, the recombinant PBIS can comprise, from N-terminus to C-terminus: two cysteine residues, a PPII structure, a cysteine residue, a proline-rich sequence, and two cysteine residues. Additional amino acids can also be present between any or all of the recited regions. In some embodiments, a cysteine is separated from the PPII structure, a proline-rich sequence, or both a PPII structure and a proline-rich sequence by no more than about 20 amino acids, about 15 amino acids, about 10 amino acids, or about 5 amino acids. In another example, the recombinant PBIS can comprise, from N-terminus to C-terminus: two cysteine residues, a first proline-rich sequence, a cysteine residue, a second proline-rich sequence, and two cysteine residues.

In some embodiments, the at least two cysteines upstream of the N-terminus are separated by one amino acid (i.e., CXC), by two amino acids (i.e., COX (SEQ ID NO:145)), by three amino acids, by four amino acids, by five amino acids, by six amino acids, by seven amino acids, by eight amino acids, by nine amino acids, by ten amino acids, by eleven amino acids, by twelve amino acids, by thirteen amino acids, by fourteen amino acids, or by fifteen amino acids. In some embodiments, the at least two cysteines upstream from the N-terminus are two consecutive amino acids that are not separated by any amino acids. In some embodiments, the at least two cysteines upstream of the N-terminus are separated by one to ten amino acids or by one to eight amino acids. In some embodiments, the at least two cysteines upstream of the N-terminus are separated by two to ten amino acids or by two to eight amino acids. In some embodiments, the at least two cysteines upstream of the N-terminus are separated by three to ten amino acids or by three to eight amino acids. In some embodiments, the at least two cysteines upstream of the N-terminus are separated by four to ten amino acids or by four to eight amino acids.

In some embodiments, the at least two cysteines downstream of the C-terminus are separated by one amino acid, by two amino acids, by three amino acids, by four amino acids, by five amino acids, by six amino acids, by seven amino acids, by eight amino acids, by nine amino acids, or by ten amino acids. In some embodiments, the at least two cysteines downstream from the C-terminus are two consecutive amino acids that are not separated by any amino acids.

In some embodiments, the at least two cysteines at the N-terminus are not in a globular domain. In some embodiments, the at least two cysteines at the C-terminus are not in a globular domain. In some embodiments, the recombinant PBIS does not contain a cysteine in a globular domain.

IV. Signaling Peptide

As described above, the recombinant PBIS can comprise a signal that directs the recombinant PBIS to a particular location in the cell. For example, the recombinant PBIS can be directed into the lumen of the endoplasmic reticulum (ER) via a signal peptide.

The signal can be any domain that directs the recombinant PBIS to the ER. By way of example only, an ER-signaling domain can be an ER-signaling peptide derived from a zein protein such as gamma-zein or alpha-zein, a gliadin protein such as alpha-gliadin or gamma-gliadin, or the pathogenesis-related protein of PR10 class 25.

The characteristics of the signal peptides responsible for directing the protein to the ER have been extensively studied (von Heijne et al., 2001 *Biochim. Biophys. Acta* 1541:114-119). The signal peptides do not share homology at a primary structure, but have a common tripartite structure: a central hydrophobic h-region and hydrophilic N- and C-terminal flanking regions. These similarities, and the fact that proteins are translocated through the ER membrane using apparently common pathways, permits interchange of the signal peptides between different proteins or even from different organisms belonging to different phyla. See, Martoglio et al., 1998 *Trends Cell Biol.* 8:410-415.

The signal peptide can be cleaved once the recombinant PBIS has reached the appropriate cellular location, e.g., the ER. In most eukaryotes, the signal peptide is cleaved co-translationally. Hence, the large majority of the protein found in the endomembrane compartment (e.g., the ER, Golgi, vacuoles) is the mature protein, i.e., the protein without the signal peptide. As a consequence, the mature protein is capable of inducing the formation of RPBLAs.

V. PBIS Fusion Proteins

As described herein, the recombinant PBIS can be fused to any product of interest. The product of interest can, for example, be a protein or peptide. The recombinant PBIS can be fused to the N or the C terminus to a protein or peptide of interest. In addition, the recombinant PBIS can be fused directly to the protein or peptide of interest or can be fused indirectly, e.g., via a spacer, to the protein or peptide of interest. In some embodiments, the fusion protein is an isolated fusion protein, e.g., a fusion protein isolated from a recombinant host cell expressing an RPBLA.

One skilled in the art will appreciate that the choice of protein or peptide that can be produced using the invention as described is large and varied. They may be, for instance, industrial enzymes, antigens, cytokines, receptors, agonist nutraceutical proteins, value-added products, pharmaceutically active proteins, etc. The proteins of interest include, but are not limited to, 16ESH, CTB, Gb, Les, TB, PAP, Cap, E2, NP, Her, Glucosa oxidase, Glucose Isomerase, Peroxidase, Alternative oxidase, GOOX, Beta-Galactosidase, Glucose amilase, lipase, versatile lipase, cloroperoxidase, Xylose isomerase, Mn peroxidase, Catalase, formate dehydrogenase, Alcohol dehydrogenase, alphalantitrypsine, defensine, human growth hormone, GM-CSF, EGF, and hepatocyte growth factor. One skilled in the art will appreciate that this list is by no means exhaustive.

Thus, the recombinant PBIS can be fused to, for example, an enzyme, a hormone, such as calcitonin, erythropoietin, thrombopoietin, human growth hormone, epidermal growth factor, and the like, an interferon, or a cytokine. Other examples of proteins or peptides of interest include any protein having therapeutic, nutraceutical, agricultural, or industrial use. For example, in some embodiments, the recombinant PBIS can be fused to peptides enriched in essential amino acids. Illustrative activities of other such proteins include (a) light capture and emission as are provided by green fluorescent protein (GFP), enhanced cyan fluorescent protein (ECFP), red fluorescent protein (DsRed) and the like; (b) enzymatic activity that can be associated with primary and secondary intracellular signaling and metabolic pathways, exemplified by enterokinase, beta-glucuronidase (GUS), phytase, carbonic anhydrase, and industrial enzymes (hydrolases, glycosidases, cellulases, oxidoreductases, and the like); (c) protein-protein, protein-receptor, and protein-ligand interaction such as, for example antibodies (mabs such as IgG, IgM, IgA, etc.) and fragments thereof, hormones (calcitonin, human growth hormone (hGH), epidermal growth factor (EGF) and the like), protease inhibitors, antibiotics, antimicrobials, HIV entry inhibitors (Ryser et al., 2005 *Drug Discov Today.* 10:1085-1094), collagen, human lactoferrin, and cytokines; (d) protein and peptide antigens for vaccines (human immunodeficiency virus, HIV; hepatitis B pre-surface, surface and core antigens, Foot and Mouth Disease Virus (FMDV) structural polyprotein gene P1 (Dus Santos et al., 2005 *Vaccine.* 23:1838-1843), T cell stimulating peptides of U.S. Pat. No. 4,882,145, gastroenteritis corona virus, human papilloma virus, and the like); (e) protein-non protein interactions such as, phytohaemagglutinin (PHA), the Ricin Toxin subunit B (RTB), and other lectins.

As described herein, the protein of interest can maintain its functional activity when expressed as a fusion to the recombinant PBIS, or when purified from an RPBLA. Assays for the bioactivity of such expressed polypeptides are well known in the art and are available in one or more publications. For example, ECFP activity can be measured by quantifying the fluorescence emitted at a 470-530 nm wavelength when the protein has been excited at 458 nm. See Richards et al., 2003 *Plant Cell Rep.* 22:117-121. The enzymatic activity of enterokinase (EK), for example, can be measured with two different approaches. The activity can be determined by analyzing the cleavage of a fusion protein containing the enterokinase specific cleavage site by Western blot, as discussed in the Invitrogen Life Technologies catalog (E180-01 and E180-02), and also by quantifying the EK activity using fluorogenic peptide substrate for EK (Sigma G-5261, CAS® RN 70023-02-8); enzyme activity is measured by an increase of fluorescence (excitation at 337 nm, emission at 420 nm) caused by the release of β-naphthylamine from the peptide over time. See LaVallie et al., 1993 *J. Biol. Chem.* 268:23311-23317. The activity of the enzyme beta-glucuronidase (GUS) can be measured by the conversion of the substrate MUG (4-methyl umbelliferyl glucuronide) to the product MU. This product can be quantified by measuring the fluorescence with excitation at 365 nm, emission at 455 nm on a spectrofluorimeter. See, Pai-Hsiang et al., 2001 *J. Plant Physiol.* 158:247-254; and Jefferson et al., 1987 *EMBO J.* 6:3901-3907. Phytase assays are carried out by the quantification of inorganic ortho phosphates liberated from the AAM reagent consisting of acetone, 5.0 N sulfuric acid, and 10 mM ammonium molybdate. See Ullah et al., 1999 *Biochem. Biophys. Res. Commun.* 264:201-206.

Similar assays are available for other biological proteins. The RTB activity assays can be performed by measuring the binding of RTB to asialofetuin, lactose and galactose, as described in Reed et al., 2005 *Plant Cell Rep.* 24:15-24. EGF is a growth factor involved in fibroblast proliferation. EGF activity can be assayed by the quantification of the induction of DNA synthesis measured by incorporation of the pyrimidine analog 5-bromo-2'-deoxyuridine (BrdU), instead of thymidine, into the DNA of proliferating cells using the cell proliferation ELISA kit. Oliver, et al., 2004 *Am. J. Physiol. Cell Physiol.* 286:1118-1129; Catalog no. 1647229, Roche Diagnostics, Mannheim, Germany.

It is noted that light capture and emission constitutes a separate and special type of "biological activity" that is luminescent activity. These proteins are useful, for example, as reporter molecules in many types of assays or screens used in the analysis or discovery of biologically important molecules, and their luminescent activity requires the presence of correct secondary and tertiary protein structure.

In some embodiments, the recombinant PBIS fusion protein comprises a spacer amino acid sequence. The spacer amino acid sequence can be an amino acid sequence cleavable by enzymatic or chemical means or not cleavable. By "not cleavable" it is meant that cleavage of the spacer does not occur without destruction of some or all of the biologically active polypeptide.

The spacer can be placed between the recombinant PBIS and biologically active polypeptide. An illustrative spacer is an amino acid sequence that is cleavable by a protease such as an enterokinase, Arg-C endoprotease, Glu-C endoprotease, Lys-C endoprotease, Factor Xa, SUMO proteases (Tauseef et al., 2005 *Protein Expr. Purif.* 43:1-9) and the like. The spacer can also correspond to an auto-cleavable sequence such as the FMDV viral auto-processing 2A sequence, protein introns (inteins) such as the Ssp DNAb intein and the like, as are commercially available from New England Biolabs and others. The use of an intein linker can be advantageous because such sequences can be selectively induced to cause protein splicing and thereby eliminate themselves from an expressed, recovered, protein. Inteins are particularly interesting since they do not require large protein enzymes to reach their target site in order to cleave the recombinant PBIS from the protein of interest. This property may be particularly useful for direct isolation of proteins of interest from intact RPBLAs. Alternatively, a spacer can be an amino acid sequence that is specifically cleavable by a chemical reagent, such as, for example, cyanogen bromide that cleaves at methionine residues.

VII. Nucleic Acids Encoding Recombinant PBIS and Recombinant PBIS Fusion Proteins Polynucleotides that encode a recombinant PBIS are also described herein. Similarly, polynucleotides that encode a fusion protein comprising a recombinant PBIS are also described. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain embodiments, the polynucleotides are isolated. In certain embodiments, the polynucleotides are substantially pure.

Such polynucleotides can, for example, be incorporated in an expression vector for producing a recombinant PBIS or a fusion protein comprising a recombinant PBIS in a cell. Expression vectors are replicable DNA constructs which have synthetic or cDNA-derived DNA fragments encoding a recombinant PBIS or a fusion protein comprising a recombinant PBIS, operatively linked to suitable transcriptional or translational regulatory elements. The transcriptional or translational regulatory elements can be derived from, for example, mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Esherichia coli, including pCR 1, pBR322, pMB9 and their derivatives, wider host range plasmids, such as M13 and filamentous single-stranded DNA phages.

In some embodiments, the vector comprising a polynucleotide that encodes a recombinant PBIS further comprises a multiple cloning site. A multiple cloning site is a polynucleotide sequence comprising one or more unique restriction sites. Non-limiting examples of the restriction sites include EcoRI, SadI, KpnI, SmaI, XmaI, BamHI, XbaI, HincII, PstI, SphI, HindIII, AvaI, or any combination thereof.

Multiple cloning sites can be used in vectors comprising a polynucleotide encoding a recombinant PBIS to simplify the insertion of a polynucleotide encoding a protein or peptide of interest into the vector such that the vector can be used to express a fusion protein comprising the recombinant PBIS and the protein or peptide of interest. In some embodiments, the polynucleotide that encodes the recombinant PBIS is 5' to the multiple cloning site. In some embodiments, the polynucleotide that encodes the recombinant PBIS is 3' to the multiple cloning site.

The vectors can comprise at least one promoter. The promoter can be any sequence that is suitable for driving expression of a recombinant PBIS or fusion protein comprising a recombinant PBIS. In one particular embodiment, the promoter drives expression in tobacco leaves.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

A recombinant nucleic acid molecule such as a DNA molecule, comprising a gene vector or construct containing one or more regulatory sequences (control elements) such as a promoter suitable for driving the expression of the gene in a compatible eukaryotic host cell organism operatively linked to an exogenous nucleic acid segment (e.g., a DNA segment or sequence) that defines a gene that encodes a contemplated fusion protein, as discussed above, is also contemplated. More particularly, also contemplated is a recombinant DNA molecule that comprises a gene vector comprising a promoter for driving the expression of the fusion protein in host organism cells operatively linked to a DNA segment that defines a gene encodes a protein body-inducing sequence (PBIS) linked to a polypeptide of interest. That recombinant DNA molecule, upon suitable transfection and expression in a host eukaryotic cell, provides a contemplated fusion protein as RPBLAs.

As is well known in the art, so long as the required nucleic acid, illustratively DNA sequence, is present, (including start and stop signals), additional base pairs can usually be present at either end of the DNA segment and that segment can still be utilized to express the protein. This, of course, presumes the absence in the segment of an operatively linked DNA sequence that represses expression, expresses a further product that consumes the fusion protein desired to be expressed, expresses a product that consumes a wanted reaction product produced by that desired fusion protein, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known.

A DNA segment that encodes a fusion protein can be synthesized by chemical techniques, for example, the phosphotriester method of Matteucci et al., 1981 J. Am. Chem. Soc., 103:3185. Of course, by chemically synthesizing the coding sequence, any desired modifications can be made simply by substituting the appropriate bases for those encoding the native amino acid residue sequence.

DNA segments containing a gene encoding the fusion protein can also be obtained from recombinant DNA molecules (plasmid vectors) containing that gene.

A vector that directs the expression of a fusion protein gene in a host cell is referred to herein as an "expression vector". An expression vector contains expression control elements including the promoter. The fusion protein-coding gene is operatively linked to the expression vector to permit the promoter sequence to direct RNA polymerase binding and expression of the fusion protein-encoding gene. Useful in expressing the polypeptide coding gene are promoters that are inducible, viral, synthetic, constitutive as described by Paszkowski et al., 1989 EMBO J., 3:2719 and Odell et al., 1985 Nature, 313:810, as well as temporally regulated, spatially regulated, and spatiotemporally regulated as given in Chua et al., 1989 Science, 244:174-181.

Expression vectors compatible with eukaryotic cells, such as those compatible with cells of mammals, algae or insects and the like, are contemplated herein. Such expression vectors can also be used to form the recombinant DNA molecules of the present invention. Eukaryotic cell expression vectors are well known in the art and are available from several commercial sources. Normally, such vectors contain one or more convenient restriction sites for insertion of the desired DNA segment and promoter sequences. Optionally, such vectors contain a selectable marker specific for use in eukaryotic cells.

The choice of which expression vector and ultimately to which promoter a fusion protein-encoding gene is operatively linked depends directly on the functional properties desired, e.g., the location and timing of protein expression, and the host cell to be transformed. These are well known limitations inherent in the art of constructing recombinant DNA molecules. However, a vector useful in practicing the present invention can direct the replication, and preferably also the expression (for an expression vector) of the fusion protein gene included in the DNA segment to which it is operatively linked.

Typical vectors useful for expression of genes in cells from higher plants and mammals are well known in the art and include plant vectors derived from the tumor-inducing (Ti) plasmid of *Agrobacterium tumefaciens* described by Rogers et al. (1987) *Meth. in Enzymol.*, 153:253-277 and mammalian expression vectors pKSV-10, above, and pCI-neo (Promega Corp., #E1841, Madison, Wis.). However, several other expression vector systems are known to function in plants including pCaMVCN transfer control vector described by Fromm et al. (1985) *Proc. Natl. Acad. Sci. USA*, 82:58-24. Plasmid pCaMVCN (available from Pharmacia, Piscataway, N.J.) includes the cauliflower mosaic virus CaMV $^{35}$S promoter.

In some embodiments, isolated RPBLAs or isolated fusion proteins comprising recombinant PBIS comprise an active protein of interest. In some embodiments, the specific activity of the protein of interest in the fusion protein or the RPBLA is at least equal to the specific activity of the same protein of interest fused to RX3 and expressed in RPBLA in the same host cell. In some embodiments, the specific activity of the protein of interest in the fusion protein or the RPBLA is at least about twice, three times, four times, five times, six times, seven times, eight times, nine times, ten times, or twenty times higher than the specific activity of the same protein of interest fused to RX3 and expressed in RPBLA in the same host cell.

VIII. Recombinant Protein Body-Like Assemblies (RPBLAs), Host Cells, and Methods of Making Recombinant Protein Body-Like Assemblies (RPBLAs)

Natural protein bodies have been described in the endosperm of cereals. They are induced by the expression of prolamins and glutelins. Protein bodies are organelles that are highly enriched in assembled proteins (e.g., prolamins, glutelins) and surrounded by a membrane, which can be derived from the ER or the vacuole. Most protein bodies are round-shaped (generally spherical) structures, with diameters of about 0.5 to about 3.0 microns Recombinant protein body-like assemblies (RPBLAs) can be formed by the expression of a recombinant PBIS in a cell. Similar to natural protein bodies, which are organelles that are highly enriched in PBIS, RPBLAs are recombinant organelles that are highly enriched in recombinant PBIS. The assembled PBIS or recombinant PBIS in the organelles are surrounded by a membrane. In cells, RPBLAs are typically found in the cytoplasm of the cell and therefore are surrounded by an additional membrane (plasma membrane), these membranes (plasma membrane and/or organelle membrane) can be removed during or after the process of RPBLA recovery, and the organelle is still considered an RPBLA. In some embodiments, the RPBLAs are isolated RPBLAs.

When expressed in animal cells, RPBLAs are generally spherical in shape, have diameters of about 0.5 to about 3 microns and have a surrounding membrane. RPBLAs expressed in plant cells are also usually generally spherical, have diameters of about 0.5 to about 2 microns, and are surrounded by a membrane. However, RPBLAs can sometimes be amorphous in shape and of non-uniform size.

In some embodiments, the RPBLAs are at least about 0.3, at least about 0.4, or at least about 0.5 micrometers. In some embodiments, the RPBLAs are about 3 micrometers or smaller, about 2.5 micrometers or smaller, or about 2 micrometers or smaller. In some embodiments, the RPBLAs are from about 0.3 to about 3.0 micrometers, from about 0.3 to about 2.5 micrometers, or from about 0.3 to about 2 micrometers. In some embodiments, the RPBLAs are from about 0.5 to about 3.0 micrometers, from about 0.5 to about 2.5 micrometers, or from about 0.5 to about 2 micrometers.

In some embodiments, the RPBLAs have a predetermined density that can differ among different fusion proteins, but is predictable across hosts for a particular fusion protein being prepared. That predetermined density of the RPBLAs is typically greater than that of substantially all of the endogenous host cell proteins present in the homogenate, and is typically about 1.1 to about 1.4 g/ml. The high density of RPBLAs is due to the general ability of the recombinant fusion proteins to self-assemble and accumulate into ordered aggregates associated with membranes.

In some embodiments, an RPBLA has a density of at least about 1.1 g/ml. In some embodiments, the RPBLA has a density of from about 1.1 to about 1.4 g/ml, from about 1.1 to about 1.35 g/ml, or from about 1.1 to about 1.3 g/ml. In some embodiments, the RPBLA has a density of from about 1.15 to about 1.4 g/ml, from about 1.15 to about 1.35 g/ml, or from about 1.15 to about 1.3 g/ml. In some embodiments, the RPBLA has a density that is no more than about 1.4 g/ml.

By way of example, the table below provides the diameter and density of representative RPBLAs obtained from transiently transfected tobacco plants agroinfiltrated with the listed constructs. The sizes in the table are approximate and can vary slightly depending on the specific conditions of the analysis (dpi, plant age, growth conditions, etc)

| Fusion protein | Diamter (μm) | Density (g/mL) |
|---|---|---|
| RX3-ECFP | 1 < d < 2 | 1.21-1.26 |
| RX3(E)-ECFP | 1 < d < 5 | 1.166-1.185 |
| RX3(D)-ECFP | 1 < d < 2 | nd |
| RX3(Q)-ECFP | 0.5 < d < 2 | around 1.17 |
| RX3(N)-ECFP | 0.5 < d < 1 | nd |
| RX3(T)-ECFP | 0.5 < d < 1 | nd |
| RX3(A)-ECFP | 1 < d < 2 | 1.194-1.204 |
| RX3(A3)-ECFP | 1 < d < 2 | around 1.17 |
| RX3(L)-ECFP | around 0.5 | 1.160-1.204 |
| PA-ECFP | 0.5 < d < 1 | 1.175-1.204 |
| PP-ECFP | 0.5 < d < 1 | 1.175-1.204 |
| ECFP-iRX3 | 0.5 < d < 1 | 1.11-1.17 |
| iRX3-ECFP | 1 < d < 3 | 1.21-1.23 |

The contemplated RPBLAs can be characterized by their densities as noted above, and their size and shape. The step-cushion iodixanol (Optiprep®) density gradient described in the examples and materials and methods is a useful method to determine the density of given RPBLAs. Other complementary or suitable methods that can be used to determine the density of RPBLAs include step-cushion density gradients that are based on other density-providing solutes such as sucrose, glycerol, and Percoll.

In some embodiments, the RPBLAs are produced in a eukaryotic cell. For example, RPBLAs can be produced in plants, animals, insects or fungi. Suitable host cells for production of RBPLAs include, by way of example, higher plants (e.g., tomato, tobacco, *arabidopsis*, alfalfa), mammalian cells (e.g., CHO, cos and 293T cells), filamentous fungi (e.g., *Tricoderma resei* and *Aspergillus* sp.), and insect cells. See also U.S. Pat. No. 7,575,898 and U.S. Published Application No. 2006/0121573, which are herein incorporated by reference and describe other exemplary host cells that can be used to produce an RPBLA as described herein. In some embodiments, an RPBLA is expressed in a tobacco plant cell.

In still other embodiments, the host cell is a higher eukaryotic cell. Higher eukaryotic cells include established cell lines of mammalian origin. Various mammalian cell culture systems are advantageously employed to express RPBLAs because proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Baculovirus systems for production of heterologous proteins in insect cells are reviewed by Luckow and Summers, *Bio/Technology* 6:47 (1988).

RPBLAs can also be produced in different tissues such a leaves, grains, roots and cotyledons. In some embodiments, an RPBLA is expressed in a tobacco leaf cell.

As described in more detail below, an RPBLA can be produced by culturing a host cell comprising a polynucleotide encoding a recombinant PBIS or a fusion protein comprising a recombinant PBIS under suitable conditions for RPBLA formation. For example, an RPBLA can be produced in a plant host cell by transforming a plant host cell with a polynucleotide comprising a sequence that encodes a recombinant PBIS or a fusion protein comprising a recombinant PBIS, generating transformed plants from the host cell, and growing the plants under conditions that are suitable for RPBLA formation.

Certain conditions that are suitable for RPBLA formation are described in the examples below. Other conditions that are suitable for RPBLA formation can be determined by those of skill in the art by expressing recombinant PBIS as described herein and assessing the ability of such known recombinant PBIS to form an RPBLA under the tested conditions.

IX. Purification of RPBLAs and Fusion Proteins Comprising Recombinant PBIS

The recombinant PBIS or fusion proteins comprising the recombinant PBIS can also be purified according to any suitable method. Standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column.

Isolated proteins can be physically characterized using known techniques such as proteolysis, nuclear magnetic resonance and x-ray crystallography.

Fusion proteins can be prepared according to a method that comprises transforming a eukaryotic host cell system such as an animal, animal cell culture, plant or plant cell culture, fungus culture, insect cell culture or algae culture with a nucleic acid (DNA or RNA) sequence comprising (i) a first nucleic acid encoding a recombinant PBIS that is operatively linked to (ii) a second nucleic acid sequence encoding a polypeptide product of interest that is biologically active. The use of indirect means of introducing DNA, such as via viral transduction or infection, is also contemplated, and shall be used interchangeably with direct DNA delivery methods such as transfection.

The transformed host cell or entity is maintained for a time period and under culture conditions suitable for expression of the fusion protein and assembly of the expressed fusion protein into RPBLAs. Upon expression, the resulting fusion protein accumulates in the transformed host-system as RPBLAs. The fusion protein can then be recovered from the host cells or the host cells containing the fusion protein can be used as desired, as for an animal food containing an added nutrient or supplement. The fusion protein can be isolated as part of the RPBLAs or free from the RPBLAs.

Culture conditions suitable for expression of the fusion protein are typically different for each type of host entity or host cell. However, those conditions are known by skilled workers and are readily determined. Similarly, the duration of maintenance can differ with the host cells and with the amount of fusion protein desired to be prepared. Again, those conditions are well known and can readily be determined in specific situations. Additionally, specific culture conditions can be obtained from the citations and examples herein.

In another particular embodiment, a fusion protein is prepared according to a method that comprises transforming the host cell system such as an animal, animal cell culture, plant, plant cell culture, fungus or algae with a nucleic acid sequence comprising, in addition to the nucleic acid sequences (i) and (ii) previously mentioned, and in frame nucleic acid sequence (iii) that codes for a spacer amino acid sequence. The spacer amino acid sequence can be an amino acid sequence cleavable by enzymatic or chemical means or not cleavable, as noted before. In one particular embodiment, the nucleic acid sequence (iii) is placed between said nucleic acid sequences (i) and (ii), e.g., the 3' end of the third nucleic acid sequence (iii) is linked to the 5' end of the second nucleic acid sequence (ii). In another embodiment, the 5' end of the third nucleic acid sequence (iii) is linked to the 3' end of the second nucleic acid sequence (ii).

An insect cell system can also be used to express a contemplated fusion protein. For example, in one such system *Autographa californica* nuclear polyhedrosis virus (AcNPV) or baculovirus is used as a vector to express foreign genes in *Spodoptera frugiperda* cells or in *Trichoplusia larvae*. The sequences encoding a fusion protein can be cloned into a non-essential region of the virus, such as the polyhedrin gene, and placed under control of the polyhedrin promoter. Successful insertion of a fusion protein sequence renders the polyhedrin gene inactive and produces recombinant virus lacking coat protein. The recombinant viruses can then be used to infect, for example, *S. Frugiperda* cells or *Trichoplusia larvae* in which the fusion protein can be expressed, for example as described in Engelhard et al. (1994) *Proc. Natl. Acad. Sci.*, USA, 91:3224-3227; and V. Luckow, "Insect Cell Expression Technology", pages 183-218, in Protein Engineering: Principles and Practice, J. L. Cleland et al. eds., Wiley-Liss, Inc, 1996). Heterologous genes placed under the control of the polyhedrin promoter of the *Autographa californica* nuclear polyhedrosis virus (AcNPV) are often expressed at high levels during the late stages of infection.

Recombinant baculoviruses containing the fusion protein gene are constructed using the baculovirus shuttle vector system (Luckow et al., 1993 *J. Virol.*, 67:4566-4579], sold commercially as the Bac-To-Bac™ baculovirus expression system (Life Technologies). Stocks of recombinant viruses are prepared and expression of the recombinant protein is monitored by standard protocols (O'Reilly et al., Baculovirus Expression Vectors: A Laboratory Manual, W.H. Freeman and Company, New York, 1992; and King et al., The Baculovirus Expression System: A Laboratory Guide, Chapman & Hall, London, 1992). Use of baculovirus or other delivery vectors in mammalian cells, such as the 'BacMam' system described by T. Kost and coworkers (see, for example Merrihew et al., 2004 *Methods Mol. Biol.* 246:355-365), or other such systems as are known to those skilled in the art are also contemplated in the instant invention.

Plant expression systems typically provide systemic or constitutive expression of an inserted transgene. Systemic expression can be useful where most or all of a plant is used as the source of RPBLAs and their fusion proteins. However, it can be more efficacious to express RPBLAs and their fusion protein contents in a plant storage organ such as a root, seed or fruit from which the particles can be more readily isolated or ingested.

One manner of achieving storage organ expression is to use a promoter that expresses its controlled gene in one or more preselected or predetermined non-photosynthetic plant organs. Expression in one or more preselected storage organs with little or no expression in other organs such as roots, seed or fruit versus leaves or stems is referred to herein as enhanced or preferential expression. Expression in substantially only one storage organ and substantially no expression in other storage organs is referred to as organ-specific expression; i.e., a ratio of expression products in a storage organ relative to another of about 100:1 or greater indicates organ specificity. Storage organ-specific promoters are thus members of the class of storage organ-enhanced promoters.

Exemplary plant storage organs include the roots of carrots, taro or manioc, potato tubers, and the meat of fruit such as red guava, passion fruit, mango, papaya, tomato, avocado, cherry, tangerine, mandarin, palm, melons such cantaloupe and watermelons and other fleshy fruits such as squash, cucumbers, mangos, apricots, peaches, as well as the seeds of maize (corn), soybeans, rice, oil seed rape and the like.

Transfection of plant cells using *Agrobacterium tumefaciens* is typically best carried out on dicotyledonous plants. Monocots are usually most readily transformed by so-called direct gene transfer of protoplasts. Direct gene transfer is usually carried out by electroporation, by polyethyleneglycol-mediated transfer or bombardment of cells by microprojectiles carrying the needed DNA. These methods of transfection are well-known in the art and need not be further discussed herein. Methods of regenerating whole plants from transfected cells and protoplasts are also well-known, as are techniques for obtaining a desired protein from plant tissues. See, also, U.S. Pat. Nos. 5,618,988 and 5,679,880 and the citations therein.

A transgenic plant formed using *Agrobacterium* transformation, electroporation or other methods typically contains a single gene on one chromosome. A transgenic plant can also be homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced chimer particle accumulation relative to a control (native, non-transgenic) or an independent segregant transgenic plant. A homozygous transgenic plant exhibits enhanced chimer particle accumulation as compared to both a native, non-transgenic plant and an independent segregant transgenic plant.

The expressed RPBLAs and their fusion proteins can be obtained from the expressing host cells by usual means utilized in biochemical or biological recovery. Because the RPBLAs are dense relative to the other proteins present in the host cells, the RPBLAs are particularly amenable to being collected by centrifugation of a cellular homogenate.

Thus, regions of different density are formed in the homogenate to provide a region that contains a relatively enhanced concentration of the RPBLAs and a region that contains a relatively depleted concentration of the RPBLAs. The RPBLAs-depleted region is separated from the region of relatively enhanced concentration of RPBLAs, thereby purifying said fusion protein. The region of relatively enhanced concentration of RPBLAs can thereafter be collected or can be treated with one or more reagents or subjected to one or more procedures prior to isolation of the RPBLAs or the fusion protein therein. In some embodiments, the collected RPBLAs are used as is, without the need to isolate the fusion protein, as where the RPBLAs are used as an oral vaccine. The fusion protein containing the biologically active polypeptide can be obtained from the collected RPBLAs by dissolution of the surrounding membrane in an aqueous buffer containing a detergent and a reducing agent as discussed previously. Illustrative reducing agents include 2-mercaptoethanol, thioglycolic acid and thioglycolate salts, dithiothreitol (DTT), sulfite or bisulfite ions, followed by usual protein isolation methods. Sodium dodecyl sulfate (SDS) is an exemplary detergent, and other ionic (deoxycholate, N-Lauroylsarcosine, and the like), non-ionic (Tween® 20, Nonidet® P-40, octyl glucoside and the like) and zwitterionic (CHAPS, Zwittergent™ 3-X serie and the like) surfactants can be used. A minimal amount of surfactant that dissolves or disperses the fusion protein is utilized.

XI. Uses of RPBLAs

As described herein, the formation of RPBLAs allows fusion proteins comprising a recombinant PBIS to be purified using very simple techniques. Therefore, fusion proteins comprising a recombinant PBIS and a protein of interest can be easily expressed and purified. In some embodiments, the protein of interest is a therapeutic protein. As such, a therapeutic can be formulated by purifying a fusion protein comprising a recombinant PBIS and a protein of interest and optionally removing the recombinant PBIS using methods described herein or known in the art. The isolated protein of interest can then be formulated for pharmaceutical use according to known techniques.

Thus, in some embodiments, the fusion protein or protein of interest obtained by the methods described herein is formulated into a "pharmaceutically acceptable" form. "Pharmaceutically acceptable" refers to a bioproduct that is, within the scope of sound medical judgment, suitable for contact with the tissues of human beings and animals without excessive toxicity or other complications commensurate with a reasonable benefit/risk ratio.

Fusion protein or protein of interest obtained by the methods described herein can be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

A specific dosage and treatment regimen for any particular patient will depend upon a variety of factors, including the particular protein, peptide or therapeutic compound used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Furthermore, the RPBLAs can be used therapeutically themselves. For example, the use of RPBLAs in vaccines and inocula has been previously described in U.S. Published Application No. 2007/0243198, which is herein incorporated by reference in its entirety.

RPBLAs can be used as the immunogen of an inoculum or vaccine in a human patient or other suitable animal host such as a chimpanzee, mouse, rat, horse, sheep, bovine, dog, cat or the like. An inoculum can induce a B cell or T cell response (stimulation) such as production of antibodies that immunoreact with the immunogenic epitope or antigenic determinant, or T cell activation to such an epitope, whereas a vaccine provides protection against the entity from which the immunogen has been derived via one or both of a B cell or T cell response. An inoculum can induce a TH1 response, such as cytokines that promote inflammation (e.g., interferon gamma). An inoculum can induce a TH2 response, such as cytokines with anti-inflammatory effects (e.g., interleukin 4, 5, and/or 13).

The RPBLAs of a contemplated vaccine or inoculum can act upon antigen presenting cells (APCs) such as dendritic cells and monocytes/macrophages that engulf the RPBLAs and process their contents. In acting upon those cell types, the RPBLAs can improve the antigen delivery to antigen-presenting cells. Those RPBLAs can also improve the antigen processing and presentation to antigen-presenting cells.

Thus, a vaccine or inoculum can be produced by dissolving or dispersing an immunogenic effective amount of recombinant protein body-like assemblies (RPBLAs) in a pharmaceutically acceptable diluent. The RPBLAs can contain a recombinant fusion protein that itself comprises two sequences linked together: one sequence is a recombinant PBIS, and the other is a biologically active polypeptide to which an immunological response is to be induced by said vaccine or inoculum.

T cell activation can be measured by a variety of techniques. In usual practice, a host animal is inoculated with a contemplated RPBLA vaccine or inoculum, and peripheral mononuclear blood cells (PMBC) are thereafter collected. Those PMBC are then cultured in vitro in the presence of the biologically active polypeptide (T cell immunogen) for a period of about three to five days. The cultured PMBC are then assayed for proliferation or secretion of a cytokine such as IL-2, GM-CSF of IFN-gamma. Assays for T cell activation are well known in the art. See, for example, U.S. Pat. No. 5,478,726 and the art cited therein.

A contemplated inoculum or vaccine comprises an immunogenically effective amount of RPBLAs that are dissolved or dispersed in a pharmaceutically acceptable diluent composition that typically also contains water. When administered to a host animal in which an immunological response to the biologically active polypeptide is to be induced by the vaccine or inoculum, such as a host animal in need of immunization or in which antibodies are desired to be induced, such as a mammal (e.g., a mouse, dog, goat, sheep, horse, bovine, monkey, ape, or human) or bird (e.g., a chicken, turkey, duck or goose), an inoculum induces antibodies that immunoreact with one or more antigenic determinants of the target biologically active polypeptide.

The amount of RPBLA immunogen utilized in each immunization is referred to as an immunogenically effective amount and can vary widely, depending inter alia, upon the RPBLA immunogen, patient immunized, and the presence of an adjuvant in the vaccine. Immunogenically effective amounts for a (i) vaccine and an (ii) inoculum provide the (i) protection or (ii) antibody or T cell activity, respectively, discussed hereinbefore.

Vaccines or inocula typically contain a RPBLA immunogen concentration of about 1 microgram to about 1 milligram per inoculation (unit dose), and preferably about 10 micrograms to about 50 micrograms per unit dose. The term "unit dose" as it pertains to a vaccine or inoculum of the present invention refers to physically discrete units suitable as unitary dosages for animals, each unit containing a predetermined quantity of active material calculated to individually or collectively produce the desired immunogenic effect in association with the required diluent; i.e., carrier, or vehicle.

Vaccines or inocula are typically prepared from a recovered RPBLA immunogen by dispersing the immunogen, in particulate form, in a physiologically tolerable (acceptable) diluent vehicle such as water, saline, phosphate-buffered saline (PBS), acetate-buffered saline (ABS), Ringer's solution, or the like to form an aqueous composition. The diluent vehicle can also include oleaginous materials such as peanut oil, squalane, or squalene as is discussed hereinafter.

The preparation of inocula and vaccines that contain proteinaceous materials as active ingredients is also well understood in the art. Typically, such inocula or vaccines are prepared as parenterals, either as liquid solutions or suspensions; solid forms suitable for solution in, or suspension in, liquid prior to injection can also be prepared. The preparation can also be emulsified, which is particularly preferred.

The immunogenically active RPBLAs are often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents that enhance the immunogenic effectiveness of the composition.

RPBLAs can also be used in order to increase nutritional value of food products. For example, fusions proteins comprising a recombinant PBIS and a protein or peptide with nutritional value (e.g., peptides enriched in essential amino acids) and can be expressed in a food product. Such fusion proteins, can, in some embodiments, include a recombinant PBIS that is less allergenic than a wild-type PBIS. Certain recombinant PBIS described herein have a lower predicted allergenicity when compared to the zein PBIS (RX3). Moreover, based on this observation, the authors of the present invention have also developed new recombinant PBIS that show a reduced predicted allergenicity, hereinafter referred to RX3-LA1 and RX3-LA2. Thus, in some embodiments, the recombinant PBIS is less allergenic than a wild-type PBIS, for example, the PBIS of maize gamma-zein.

Therefore, in another aspect, foods, food supplements, cosmetic preparations, and nutritional formulations containing the RPBLAs described herein or materials derived from host cells or organisms comprising said RPBLAs are also provided. The RPBLAs may be formed by the PBIS as such or by fusion proteins comprising the RPBLAs. In one embodiment, the RPBLA forming part of the foodstuff is formed by the assembly of a fusion protein comprising a PBIS selected from the group of PA, RX3(A3), R8(4C), RX3-LA1, RX3-LA2 and a combination thereof.

The term "foodstuff" as used herein, refers to a substance or composition which is suitable for human and/or animal consumption. The term "foodstuff" as used herein can mean a foodstuff in a form which is ready for consumption. Alternatively or in addition, however, the term foodstuff as used herein can mean one or more food materials that are used in the preparation of a foodstuff. By way of example only, the term foodstuff encompasses both baked goods produced from dough as well as the dough used in the preparation of said baked goods.

The foodstuff according to the present invention can be derived from the whole or part of recombinant organisms expressing RPBLAs. For example, the foodstuff can be derived from the endosperm of a plant expressing the RPBLA. Food products and food supplements containing the propagating material of the invention, or parts thereof, may include cereal-based foods, for example breakfast cereals, flours, and foods containing these flours for example breads, breadcrumb, batter, cakes, pastries, biscuits, bakery goods and pasta. Moreover, foods and food supplements containing the propagating material of vegetables, or parts thereof, for example tubers and yams are also provided. The food product can be, for example, selected from (a) a babyfood or formulae; (b) a bakery product (for example a bread, yeasted goods, or a cake); (c) a bakery supply product (for example, a custard, or a bakery filling or topping); (d) a batter; (e) a breading; (f) a cereal; (g) a confectionary; (h) a flavor or beverage emulsion; (i) a fruit filling; (j) a gravy, soup, sauce, or food thickener; (k) a meal or meal component; (l) a meat product; (m) a pet food; (n) a pharmaceutical or nutraceutical; (o) a potato or yam product; (p) a dairy product (for example a dessert or yogurt); (q) a salad dressing; (r) a snack or cracker; (s) a spread; and (t) a pasta product (for example a noodle).

Having now generally described the invention, the same will be more readily understood through reference to the following examples which are provided by way of illustration, and are not intended to be limiting, unless specified.

EXAMPLES

Materials and Methods

Plasmid Construction for Plant Transformation.

All the plasmids constructs were constructed by cloning a DNA fragment coding for a fusion protein shown in FIGS. 15a and 15b (SEQ ID NO:XX) by SalI/BamHI digestion into the pC2300 vector (AF234315) opened by the same restriction enzymes.

Plant material.

Tobacco (*Nicotiana benthamiana*) plants were grown in an in vitro growth chamber at 24-26° C. with a 16 hour photoperiod. Adult plants were grown in greenhouse between 18-28° C. Humidity was maintained between 55 and 65% with average photoperiod of 16 hours.

Plantlets for agroinfiltration (Vaquero et al., 1999 Proc. Natl. Acad. Sci., USA 96(20):11128-11133; Kapila et al., 1997 Plant Sci. 122:101-108) were grown from seeds for 4-6 weeks in the in vitro conditions described above.

Tobacco Agroinfiltration by Vacuum.

*A. tumefaciens* strain EHA 105 containing a desired construct was grown on LB medium (Triptone 10 g/l, yeast extract 5 g/l, NaCl 10 g/l) supplemented with kanamycin (50 mg/l) and rifampicine (100 mg/l) at 28° C. with shaking (250 rpm) overnight (about 18 hours). *Agrobacteria* were then inoculated in 30 ml of LB also supplemented with kanamycin (50 mg/l) and rifampicin (100 mg/l). After overnight (about 18 hours) culture at 28° C., agrobacterial cells were collected by centrifugation for 10 minutes at 3,000×g and resuspended in 10 ml of liquid MS medium with MES (Sigma Chemical) 4.9 g/l and sucrose 30 g/l at pH 5.8. The bacterial culture was adjusted to a final OD600 of 0.1 for agroinfiltration. Then, the cell culture was supplemented with acetosyringone to a final concentration of 0.2 mM and incubated for 90 minutes at 28° C. (Torrent, M., Llop-Tous, I., and Ludevid, M.D. (2009) In Recombinant Proteins from plants. Methods in Molecular Biology. Vol 483. Ed by Gomord V and Faye L, Springer Verlag, Humana Press, Heidelberg; pp 193-208; Voinnet, O., Rivas, S., Mestre, P., and Baulcombe, D. (2003) Plant J. 33, 949-956). Individual *Agrobacterium* cultures carrying the RX3 constructs and the HC-Pro silencing suppressor constructs (Goytia et al., 2006) were mixed together. The plants were totally covered with the suspension, and vacuum was applied (100 KPa) for 5-6 seconds. The suspension was removed, and plants were maintained in the greenhouse. Plant material was recovered and total protein extraction was analyzed by immunoblot using an appropriate antibody.

Tobacco Agroinfiltration by Syringe.

*Agrobacterium tumefaciens* strain EHA 105 was grown at 28° C. in L-broth supplemented with 50 µg mL$^{-1}$ kanamycin and 50 µg mL$^{-1}$ rifampycin to stationary phase. Bacteria were sedimented by centrifugation at 5000 g for 15 minutes at room temperature and resuspended in 10 mM MES buffer pH 5.6, 10 mM MgCl2 and 200 µM acetosyringone to a final OD600 of 0.2. Cells were left in this medium for 3 h at room temperature. Individual *Agrobacterium* cultures carrying the RX3 constructs and the HC-Pro silencing suppressor constructs (Goytia et al., 2006) were mixed together and infiltrated into the abaxial face of leaves of 2 4-week-old *Nicotiana benthamiana* plants.

Protein Extraction and Total Protein or Immunoblot Analysis.

Total soluble proteins (TSPs) from transformed leaves were extracted in 100 mM Tris-HCl buffer pH 7.5 containing 100 mM NaCl, 0.5% SDS and 200 mM DTT during 1 hour at RT. The resulting extracts were centrifuged at 10,000×g for 30 min at 4° C., and TSPs were separated on SDS-polyacrylamide gels. The proteins were detected by staining with Coomassie blue or silver staining or by immunoblot using the anti-R8 antiserum (Torrent, M., Llompart, B., Lasserre-Ramassamy, S., Llop-Tous, I., Bastida, M., Marzábal, P., Westerholm-Pavinen, A., Saloheimo, M., Heifetz, P. B., and Ludevid, M. D. (2009) BMC Biology 7, 5), an anti-GFP, or an anti-hGH raised in rabbits injected with a recombinant GFP or hGH protein expressed and purified from *E. Coli* cells, and a commercial anti-EGF (Abcam).

Subcellular Fractionation and RPBLAs Density Determination.

Agroinfiltrated tobacco leaf tissues were ground in a mortar at 0° C. in the HB homogenization buffer (Tris 10 mM pH 8.0, 0.25 M sucrose and protease inhibitors). The homogenate was filtered through two layers of Miracloth (22-24 micrometers, Calbiochem) to remove tissue debris before being centrifuged at 50×g for 5 minutes at 4° C. The resulting clarified homogenates from the various tissues were loaded onto multistep Iodixanol (Optiprep, Sigma) density based gradients (preferred steps for density calculations: 1.11, 1.17, 1.19, 1.21, 1.23 and 1.25 g/cm$^3$) buffered with the HB buffer. The gradients were centrifuged at 4° C. for 2 hours at 80,000×g in a Beckman SW40 Ti rotor. Equivalent aliquots of supernatant, interphase fractions, and pellet were analyzed by SDS-PAGE and immunoblot by using specific antibodies.

As indicated above, this technique is a suitable technique to determine the density of RPBLAs. The following table provides a detailed ratio between the % of iodixanol (w/v) in the given cushion and the corresponding density:

TABLE 1

Percent Iodixanol at Various Densities.

| Percent Iodixanol (w/v) | Density (g/mL) |
|---|---|
| 8 | 1.069 |
| 10 | 1.079 |
| 12 | 1.088 |
| 14 | 1.098 |
| 16 | 1.107 |
| 18 | 1.117 |
| 20 | 1.127 |
| 22 | 1.136 |
| 24 | 1.146 |
| 26 | 1.156 |
| 28 | 1.165 |
| 30 | 1.175 |
| 32 | 1.185 |
| 34 | 1.194 |
| 36 | 1.204 |
| 38 | 1.214 |
| 40 | 1.223 |
| 42 | 1.233 |
| 44 | 1.243 |
| 46 | 1.252 |
| 48 | 1.262 |
| 50 | 1.272 |

Immunocytochemistry and Imaging: Confocal Microscopy.

Sections of leaf tobacco tissues transformed with fluorescent-derived sequences were mounted in water for direct confocal observation. Micrographs were obtained by using the confocal laser scanning microscope Leica TCS SP (Heidelberg, Germany). Green fluorescent images were collected after 515 nm excitation using a 530-630 nm emission window. Cyan fluorescent images were collected at 458 nm excitation and an emission window of 470-530 nm. Green fluorescent protein images were collected at 488 nm excitation with the Argon ion laser by using an emission window set at 495-535 nm. Red fluorescent images were collected after 543 nm excitation with a HeNe laser and emission window 550-600. Optical sections were 0.5 µm thick. Digital images and projections were recorded by using the confocal microscope software. Images presented in the microscopy figures are representative of at least five independent experiments.

RPBLAs Number and Size Determination by Confocal Microscopy.

The distribution by size (in relative percent) of PBs along time was determined by measuring the apparent diameters of around 500 PBs per time point (2, 4, 7, and 10 dpi). Three independent transformed plants were analyzed per time point, and software Olympus fluoview v. 1.6a was used to measure the fluorescent PBs observed under the FV1000 Olympus confocal microscope. For PB number determination, confocal projections corresponding to $10^5$ µm$^3$ (70×70×20) of transformed tissue were used. Forty confocal images from 8 independent transformed plants were analyzed per time point. The results were statistically analyzed by One-way Analysis of Variance (ANOVA) and the Bonferroni Multiple Comparisons Test ($p<0.05$ was considered significantly different).

RPBLAs Isolation at Low Speed Centrifugation.

Around 1 gram of agroinfiltrated tobacco leaf tissues was ground in a mortar at 0° C. in 5 mL of PBP3 homogenization buffer (Tris 100 mM pH 8.0, 50 mM KCl, 6 mM MgCl$_2$, 10 mM EDTA and 0.5 M NaCl). The homogenate (H0) was filtered through one layer of Miracloth (22-24 micrometers, Calbiochem). The resulting clarified homogenates from pre-clarified homogenates (H1) were centrifuged at low speed (1,500×g) for 10 minutes, and the resulting pellet and supernatant (SN) were analyzed. The low speed centrifugation pellet was resuspended by gentle sonication (Cycle 50%, output control 3, 10 seconds, Brandson sonifier 250) in 3-5 mL of wash buffer (0.5% Triton® X-100) and finally incubated for 15-60 minutes at room temperature. After a second low speed centrifugation, equivalent amounts of the resulting pellet (wPB) and the supernatant (Ws) were analyzed.

EGF Purification

A wPB fraction from 80 grams (fresh weight) of Zera(E)-EGF agroinfiltred tobacco plant leaves was solubilized as indicated above and cleaved with 30 microliters of FXa (Quiagen) in the presence of 2 mM CaCl$_2$ at 37° C. The reaction was stopped after 3 hours by adding 50 mM EDTA. The sample was then diluted 5 fold in Buffer A. The EGF was purified by means of a 3 mL Resource reverse phase column from Amersham. The acetonitrile gradient was performed with 20 column volumes with Buffer A (10 mM acetate pH4, 2 mM bME and 5% acetonitrile) and Buffer B (10 mM acetate pH4, 2 mM bME and 75% acetonitrile). Pure EGF was recovered in two fraction at around 40% of acetonitrile and was dialysed against 50 mM Tris pH8, 2 mM bME and 100 mM NaCl overnight at 4° C. in a 3.5 kDA dialysis membrane.

EGF Activity Assay

Human epithelial carcinoma cell line cells (A431), which overexpress EGF receptor, were seeded in plates (P-35) at 0.5×10$^5$ cells/plate. Cells were incubated for 48 hours in growth medium (MEM×1, 2 mM glutamine, 1% of non-essential amino acids) and 10% FBS (Fetal bovine serum). Afterwards they were starved overnight in growth medium without FBS. Then, the standard EGF (from 0 to 100 ng EGF/mL) from Promega and the corresponding samples (solubilyzed RX3(E)-EGF and EGF) were added at the same range of concentrations, and the cells were incubated for 9 minutes. Then, the cells were washed twice with cold PBS and frozen in liquid N$_2$ to stop cell metabolism. In order to analyze the phosphorylation of the EGF receptor, the cells were scrapped and equivalent amounts of total protein were analysed by PathScan® Phospho-EGF Receptor (Tyr1068) sandwich ELISA kit essentially as described by the manufacturer.

Example 1

Accumulation of RX3-GFP, RX3(R)-GFP, RX3(K)-ECFP, RX3(A)-GFP and RX3(L)-GFP in RPBLAs of Transformed Tobacco Plants It has been described that the amphipathicity of the repeat domain of RX3 is essential in self-assembly and RPBLAs formation (Ludevid et al., Plant Mol. Biol. (1984) 3:277-234; Kogan et al., J. Mol. Biol. (2001) 312:907-913). In order to characterize the importance of the amphipathicity on the capacity of RPBLAs induction, a set of RX3 tags fused to a reporter fluorescent protein (GFP or ECFP) were analyzed (FIG. 1A): the native RX3 with histidines (PPPVHL)$_6$(PPPVHV)(PPPVHL) (SEQ ID NO:158) [RX3], two RX3 variants with an enhanced amphipathic character obtained by the substitution of the histidines by arginine (PPPVRL)×8 (SEQ ID NO:146) [RX3(R)] and lysine (PPPVKL)×8 (SEQ ID NO:147) [RX3(K)], and two RX3 variants with a fully hydrophobic RD where histidines were replaced by alanine (PPPVAL)×8 (SEQ ID NO:148) [RX3 (A)] and leucine and (PPPVLL)×8 (SEQ ID NO:149) [RX3 (L)].

As expected, tobacco plants transformed with RX3-GFP accumulated a large number of round-shaped fluorescent RPBLAs of about 1 micrometer diameter inside the cell. Surprisingly, in spite of the absence of an amphipathic RD, the fusion proteins RX3(A)-GFP and RX3(L)-GFP were also retained inside the endoplasmic reticulum (ER) of the cell and formed RPBLAs (FIG. 1C).

The RX3(A)-GFP fusion protein accumulated in large RPBLAs, which were slightly bigger than the RPBLAs obtained from the expression of RX3-GFP. The RX3(L)-GFP RPBLAs measured about 0.5 micrometers. No fluorescence was observed at the surface of the cell, indicating that the protein accumulated efficiently in RPBLAs and was not secreted. These studies also indicate that RX3 tags with a fully hydrophobic RD are able to assemble and induce the formation of RPBLAs in plants.

Based on the surprising results obtained with the RX3 tags containing hydrophobic RD, it was decided to further characterize the importance of RD amphipathicity of RX3 tags by analyzing the accumulation of amphipathic RX3 in which all of the histidines were replaced by arginines [RX3(R)] or lysines [RX3(K)]. Arginine and lysine have a high pKa (12 and 10.5, respectively) compared to histidine. Thus, these substitutions result in an RD with a higher positive net charge at the endoplasmic reticulum pH value, an increased net positive charge and an increased amphipathicity of the RD. Suprisingly, confocal microscopy analysis showed very low fluorescence using these constructs. When the same conditions used for the other RX3 variants were applied to RX3(R)-GFP and RX3(K)-ECFP, no significant signal was observed. Similarly, low accumulation of RX3(R)-GFP and RX3(K)-ECFP fusion proteins was observed by Western blot using an anti-GFP antibody. As shown in FIG. 1B, RX3(R)-GFP accumulated poorly compared to RX3-GFP, and no RX3(K)-ECFP fusion protein was observed. Interestingly, in the homogenates expressing RX3(K)-ECFP, only a higher mobility band that was immunoreactive with anti-GFP antibody was observed. This band probably corresponds to partially degraded ECFP (FIG. 1B, lane 4, black arrowhead). Long-exposed images of a tobacco leaf agroinfiltrated with pRX3(R)-GFP or pRX3(K)-ECFP, showed that the protein is not efficiently retained in ER derived RPBLAs. The expression of RX3(R)-GFP resulted in the secretion of the majority of the fusion protein, and only a few and very small RPBLAs accumulated inside the cell (FIG. 1C). Regarding RX3(K)-ECFP the results were even more surprising, because no RPBLAs were observed, and the fluorescence was associated to the chloroplasts and secretion (FIG. 1C, inbox). Based on this experiment and the fact that most of the fusion protein seems to be degraded, it is possible that the fluorescence associated with chloroplasts is due to the partially degraded ECFP. It is unlikely that RX3(K)-ECFP is sorted to this organelle.

Cumulatively, these results indicate that, contrary to what it has been suggested in the literature, the amphipathicity of RX3 is not a key element necessary for protein assembly and RPBLAs induction. Moreover, the enhancement of the amphipathicity of the RD by the substitution of histidine with arginine or lysines significantly reduces the capacity of these peptides to induce the formation of RPBLAs.

Example 2

Density Characterization of RPBLAs Induced by RX3-GFP, RX3(A)-GFP, and RX3(L)-GFP in Tobacco Plants One characteristic of RPBLAs is their high density, which can be determined by step-density gradients (Torrent, BMC Biology 2009, 7:5). In the present study, Optiprep™ gradients were carried out by loading filtered plant homogenates under the following Optiprep™ step cushions:

| Optiprep ™ % | Density (g/mL) |
| --- | --- |
| 18 | 1.117 |
| 30 | 1.175 |
| 34 | 1.194 |
| 38 | 1.214 |
| 42 | 1.233 |
| 46 | 1.252 |

Microsomes (ER, Golgi, etc.) sediment in fraction f18, the interphase above the low density cushion with 18% of Optiprep™. Typically, RPBLAs are denser than microsomes and are recovered from fractions denser than 26-28% of Optiprep™.

As shown in FIG. 2, when the homogenate of a tobacco plant expressing the fusion protein RX3-GFP was ultracentrifuged in the given step density gradient, as expected, most of the protein was recovered in the dense fractions f34 and f38. This result demonstrates that the fusion protein assembles tightly inside the ER and forms dense RPBLAs. Some RX3-GFP is also observed in the low density fraction f18 corresponding to microsomes, but this probably represents newly synthesized fusion protein that is not yet fully assembled in dense structures.

As mentioned above, two of the constructs analyzed had a fully hydrophobic RD (RX3(A)-GFP and RX3(L)-GFP), and both induced the formation of RPBLAs inside the cell. When RX3(A)-GFP was analyzed by density gradient, most of the fusion protein accumulated in dense fractions (f30 and f34), confirming that RX3(A)-GFP accumulates in dense RPBLAs. Similar results were obtained when clarified homogenates from tobacco leaves transformed with RX3 (L)-GFP were analyzed. In that case, even though the RPBLAs were less dense than the ones induced by the expression of RX3(A)-GFP, a significant fraction of them were recovered in dense fractions (FIG. 2B; f30 and f34).

These data show that, in spite of the absence of an amphipathic RD, RX3(A)-GFP and to some extent RX3(L)-GFP, are able to self assemble efficiently in RPBLAs that are dense enough to be isolated from most of the cellular contaminants. The analysis by Coomassie blue staining of equivalent volumes of the fractions recovered from a density gradient loaded with RX3(A)-GFP homogenate is shown in FIG. 2B. It can be seen that while most of the cellular contaminants are recovered in fractions S and f18, f30 and f34 contained a very pure fraction of RX3(A)-GFP.

Example 3

Downstream Procedure for RPBLAs Isolation from Tobacco Plants by Low Speed Centrifugation Density gradient centrifugation is an analytical procedure appropriate for RPBLAs density determination, but it is not suitable for purifying these organelles at large scale. A downstream process based on a simple centrifugation at a low speed and some washing steps of the sediment recovered (see experimental procedures) has been developed that permits the recovery of a clean RPBLA fraction.

This simple downstream process was applied to tobacco plants transformed with RX3-GFP and RX3(A)-GFP, and equivalent amounts of the different steps of the process were analyzed by western and SDS-PAGE stained by Coomassie blue. As shown in FIG. 3A, almost all of the fusion protein present in the corresponding homogenates (H0) was recovered in the RPBLAs fraction (wPB). The yield in both cases was similar and very high as no fusion protein is lost in the supernatant (SN) and washing step (Ws). This observation was confirmed by Western blot. The fact that more RX3(A)-GFP fusion protein is recovered than RX3-GFP (FIG. 3A, compare wPB fractions) from the same amount of biomass processed does not reflect a better recovery yield, but a higher accumulation rate of RX3(A)-GFP in the tobacco leaves. The efficient recovery is a quite surprising result given that RX3(A)-GFP RPBLAs are less dense than RX3-GFP.

The enrichment achieved in the process is also very high. Most of the contaminants present in the homogenate (H0) are removed along the process, and the fraction corresponding to the washed RPBLAs (wPB) contained almost exclusively the fusion protein. Several bands are observed in wPB fraction, but they correspond to several oligomerization states of the same fusion protein and not to protein impurities.

The downstream recovery of RPBLAs of RX3(L)-GFP was adapted by centrifuging the corresponding homogenate at a higher speed (4,000-5,000×g) in order to recover more efficiently the small and less dense organelles containing this fusion protein (FIG. 2). Surprisingly, even for RX3(L)-GFP, the yield was very efficient and most of the fusion protein was recovered in the RPBLAs fraction (wPB), as can be observed in FIG. 3B (right panel). The fact that a higher speed is needed to recover RX3(L)-GFP containing RPBLAs does not significantly affect the enrichment of the process as was demonstrated by SDS-PAGE gels stained by Coomassie blue (FIG. 3B, left panel). These results confirm that RX3 tags with a fully hydrophobic RD are suitable for protein production and purification through RPBLAs isolation.

Example 4

Solubilization of RX3 Fusion Proteins

Solubilization of RX3-based fusion proteins from the RPBLAs fraction is one of the key steps in RPBLA downstream processing. The RPBLAs fractions recovered by low speed centrifugation essentially as shown in Example 3 were used to compare the solubility of RX3-GFP and RX3(A)-GFP. The substitution of histidines of the RD with alanines was expected to decrease the solubility of the fusion proteins in aqueous solution because the total polarity of the protein is reduced, but surprisingly, RX3(A)-GFP was much more soluble in each of the conditions tested.

As an example, in FIG. 3A solubilized (sPB) fractions are compared to unsolubilized (uPB) fractions after incubating the cleaned RPBLAs fraction (wPB) for 4 hours in mild buffer (50 mM Tris pH 8, 5 mM TCEP and 10 mM 2bME). Just after the solubilization step, the sample was centrifuged at 16,000 g for 10 minutes and the sPB was recovered as the supernatant. The uPB was recovered as the pellet.

As expected, RX3-GFP was only partially solubilized. Most of the fusion protein in the monomeric form is solubilized at the given conditions (FIG. 3A, compare sPB vs uPBs, arrowhead), but a large amount of the tightly aggregated multimeric forms of the fusion proteins remains in the unsolubilized fraction (FIG. 3A, asterisk). In contrast, in the same solubilizing conditions practically all of the RX3(A)-GFP protein was solubilized, independently of the aggregation form. This surprising result, allowing a very high yield in recovering the fusion protein from the washed RPBLAs was confirmed with a broad spectrum of fully hydrophobic assembler peptides fused to several proteins as shown below.

Example 5

Accumulation of RX3(A3)-ECFP in RPBLAs of Transformed Tobacco Plants

In previous experiments all the new RX3 variants consisted of single mutations of the histidines present in the RD, so the role of the valine and leucine residues before and after the histidines was still not analyzed. In order to do that, all the valine, histidine, and leucine residues present along the RD were replaced by alanines, in a new RX3 non-amphipathic variant (RX3(A3)) (FIG. 4A). Tobacco leaves were transformed with a vector expressing RX3(A3) peptide fused to ECFP, and the RPBLAs formation was analyzed by confocal microscopy at 3 and 6 days post infiltration (dpi). Even in the first days after infiltration (3 dpi), the presence of a large number of small RPBLAs was observed, indicating that the RX3(A3) variant was very efficient. This observation was confirmed at 6 dpi by the presence of a huge number of large RPBLAs organized in clusters (FIG. 4B) demonstrating that this new assembler peptide is unexpectedly more efficient than the wild type RX3.

The analysis of RX3(A3)-ECFP expression in plants indicates that the valine and leucine residues present in the RD are not necessary for protein assembly and RPBLA formation. A clear consequence of this conclusion is that the valines, histidines and leucines present in the RD can be substituted by any other hydrophobic amino acid, provided that the RD structure is not unfolded. The next experiments demonstrate that these residues can be also substituted by polar non-charged and negatively charged amino acids.

Example 6

Accumulation of RX3(E)-GFP and RX3(D)-ECFP in RPBLAs of Transformed Tobacco Plants As mentioned above, the replacement of the histidine residues from the RD by lysine or arginine increases the net charge and consequently the amphipathicity of this domain. Surprisingly, it also dramatically reduces the efficiency of the assembler peptide in terms of RPBLAs formation and in total protein accumulation. Based on these results, the substitution of histidines by aspartic and glutamic acid was also expected to result in a reduction in the accumulation in RPBLAs, because the addition of these residues also increases the net charge of the RD, hence its amphipathicity. However, as shown in FIG. 5B, Western blot of total protein extracts from tobacco plants transformed with RX3(E)-GFP, RX3(D)-ECFP and the corresponding controls (RX3-GFP and RX3-ECFP, respectively) indicated that the fusion proteins having acidic amino acids accumulated slightly better than the controls. The lower mobility of RX3(E)-GFP and RX3(D)-ECFP can be explained by their higher content in acidic amino acids, as has been reported previously for other proteins.

Furthermore, tobacco plants transformed with RX3(E)-GFP and RX3(D)-ECFP induced the formation of a large number of big round-shaped fluorescent RPBLAs organized in clusters (FIG. 5C). In fact, big RPBLAs from 1 to 2 micrometers are frequently present in most of the transformed cells. Interestingly, the mean size of these RPBLAs was significantly larger than those induced by the expression of the GFP or ECFP fused to RX3.

Example 7

Accumulation of RX3(T)-ECFP, RX3(N)-ECFP, and RX3(Q)-ECFP in RPBLAs of Tobacco Plants The results above demonstrate that substitution of histidine by hydrophobic or acidic amino acids enhanced the capacity of the assembler peptide to induce the RPBLAs. In addition, the negative effect of increasing the positive charge of the RD by substituting the histidines by basic amino acids was observed. However, the effect of polar non-charged amino acids on the functionality of the assembler peptide was still unknown. Therefore, three new constructs were created in which all the histidines of the RD were replaced by threonine, asparagine and glutamine residues and fused to ECFP(RX3(T)-ECFP, RX3(N)-ECFP, and RX3(Q)-ECFP, respectively). The addition of these amino acids results in an RD that is amphipathic, but without net charge (FIG. 6A).

Tobacco leaves expressing all these constructs were analyzed by confocal microscopy at 3 and 6 days post infiltration (dpi). At 3 dpi, a large number of small RPBLAs was observed, indicating that all these RX3 variants were very efficient. This observation was confirmed at 6 dpi by the presence of many large RPBLAs organized in clusters (FIG. 4B).

These results demonstrate that the expression in plants of RX3 variants having polar non charged amino results in RPBLAs formation.

Example 8

Accumulation of PP-ECFP and PA-ECFP in RPBLAs of Transformed Tobacco Plants

The two main domains of RX3 (RD and PX) are both proline rich sequences, which typically adopt a PPII structure. The study of a synthetic RD by circular dichroism confirmed the presence of PPII helix in this domain in aqueous solution (Dalcol, J. Org. Chem., 1996, 61 (20), pp 6775-6782). Proteins having PPII domains are abundant in plants and in other organisms. However, they do not generally have the capacity to induce the formation of RPBLAs. For instance, collagen (Caldwell J W, Applequist J. Theoretical absorption, circular dichroic, and linear dichroic spectra of collagen triple helices. Biopolymers 1984; 10:1891-1904), alpha-casein milk proteins (Syme C D, Blanch E W, Holt C, Ross J, Goedert M, Hecht L, Barron L D. A Raman optical activity study of rheomorphism in caseins, synucleins) tau (Eur J Biochem 2002; 269:148-156.), and PKA (Knighton D R, Zheng J, Ten Eyck L F, Xoung N, Taylor S S, Sowadski I M. Structure of a peptide inhibitor bound to the catalytic subunit of cyclic adenosine monophosphate-dependent protein kinase. Science 1991; 253:414-420.) are examples of proteins having PPII helixes but not having the capacity to induce RPBLAs. As a result, it was expected that other elements in RX3, in addition to the PPII structure sequence, would be necessary to induce the formation of RPBLAs.

In order to identify such elements along the RX3 sequence, the RD and the PX domains were substituted by a proline based sequence non homologous to RX3. The PPII structure was maintained and the number and relative position of the cysteine residues were not modified (PP; FIG. 7A). Additionally, a similar, but more hydrophobic, peptide was synthesized in which RD and PX domains were replaced by the heptapeptide PPPAPA (SEQ ID NO:129) repeated all along the sequence (PA; FIG. 7A). These two peptides have essentially the same PPII structure as RX3, but do not share primary homology other than the high proline content and the number and position of the cysteines.

The analysis of tobacco leaves over-expressing RX3-ECFP, PP-ECFP or PA-ECFP by Western blot showed that surprisingly the two synthetic peptides fused to ECFP accumulated with higher efficiency than the natural RX3 (FIG. 7B; compare lanes 1 and 2 versus 3). PP-ECFP, and to a lesser extent PA-ECFP, presented lower mobility in the SDS-PAGE gel than RX3-ECFP, even though all three fusion proteins have the same number of amino acids. This indicates that PP and PA present a PPII extended helix that is more stable than RX3, even in the Western blot conditions. As a consequence, the assembly of these synthetic peptides would be favored, and the protein would show increased accumulation, as was determined by Western blot. This hypothesis was confirmed by the observation of tobacco leaves in the confocal microscope six days after the transformation with vectors expressing RX3-, PP- and PA-ECFP fusion proteins. FIG. 7C displays confocal images of leaves transformed with PP-ECFP and PA-ECFP, which presented a larger number of RPBLAs compared to leaves expressing RX3-ECFP. Moreover, the average size of RPBLAs induced by PP- and PA-ECFP expression was two-folds larger than the average size of RX3-ECFP RPBLAs.

Comparison of the sequence of these 3 protein body-inducing sequences (FIG. 7A), reveals that the sole region of homology among them is the first ten amino acids after the signal peptide (THTSGGCGCQ) (SEQ ID NO:150). In order to confirm that this sequence does not play a specific role in the protein assembly, the sequence was replaced by a synthetic proline based sequence (THPPPPCPCP) (SEQ ID NO:151). The proline-based sequence maintained the positions of the cysteines in the context of PA-ECFP constructs. This construct (NPA-ECFP) was as efficient in RPBLAs induction as PA-ECFP.

Additionally, the signal peptide of gamma-zein from RX3 was also replaced by the PR10 signal peptide, also known as PR-S (Vervoerd, 1995). The resulting construct was fused to GFP(RX3(PR10)-GFP). The signal peptide is unlikely to influence RPBLA formation since it is cleaved cotranslationally at the entrance of the protein to the ER, and as expected the accumulation rate and the induction of RPBLAs was completely independent of the signal peptide used.

The fact PP, PA, NPP and NPA peptides share no primary sequence homology with RX3 indicates that unexpectedly, the capacity to assemble and induce RPBLAs is not dependent on the sequence of RX3, but on the three dimensional structure of it. The extended PPII helix present in RX3, PP, PA peptides, and their variants, is a key feature responsible of the RPBLAs induction.

As a result of cloning procedures, PP and PA peptides include part of the last repeat of the RX3 repeat domain. In order to demonstrate that the last RX3 repeat is not required to form RPBLAs, a new set of constructs lacking this repeat is created: PP3 (SEQ ID NO:171) and PA2 (SEQ ID NO:172). The new constructs maintain the capacity to induce RPBLAs.

Example 9

Determination of the Cysteine Residues of RX3 Involved in the Induction or Stabilization of RPBLAs in Transformed Tobacco Plants The work presented here provides key insights into specific traits of RX3 that enable its multimerization and RPBLAs formation. A relevant but not unique trait is the presence of cysteine residues which could participate in the inter-disulfide bonds between RX3 molecules.

Point mutations of each of the six cysteines was used as a straight-forward way to determine the role of disulfide bonds in RX3 polymerization. Over expression of RX3-ECFP devoid of C7 or C9 (RX3C7G-ECFP and RX3C9G-ECFP) clearly disturbed the multimerization process of fusion protein: both mutants were highly secreted (FIG. 8C-D). In fact, in cell-by-cell image analysis of epidermal cells transformed with individual C7 or C9 mutants, fusion proteins were mainly secreted and only a few highly fluorescent single cells displayed fluorescent RPBLA-like spots. This observation indicates that high expression rates of the recombinant protein in the ER results in an increase of aggregation efficiency, indicating that a higher critical protein concentration is needed for protein aggregation as compared to wild type RX3 (FIG. 8C-D, inboxes). As expected, when both cysteine residues were mutated at the same time (FIG. 8I; RX3C7,9G-ECFP) no accumulation of RPBLAs was observed. These results demonstrate that the presence of two cysteine residues near the N-terminal end of the RX3 domain is necessary to retain the protein in the ER to induce the formation of RPBLAs. However, the multiple mutant RX3C64,82,84,92G-ECFP, which maintains exclusively the first two cysteines, demonstrated that C7 and C9 are not sufficient to retain the fusion protein in the ER and allow it form RPBLAs (FIG. 8K). Thus, some of the other cysteines present in the RX3 peptide play a role in its proper protein assembly.

The mutation of the cysteine residue localized in the middle of the RX3 domain (C64) did not have a significant effect on the oligomerization process and proteins accumulated in RPBLAs (FIG. 8E; RX3C64G-ECFP). Moreover, individual mutations of the three cysteine residues located at the C-terminal end of RX3 (C82, C84 or C92) did not have a significant effect on the capacity to accumulate in RPBLAs (FIG. 8F-H; RX3C82G-ECFP, RX3C84G-ECFP or RX3C92G-ECFP respectively). The normal aggregation capacities of these single mutants indicates that none of these residues is required by itself to induce and stabilize RPBLAs. However, since the multiple C-terminal Cys mutant (FIG. 8J; RX3C82,84,92G-ECFP) was unable to progress with RPBLAs biogenesis, it is evident that RX3 also requires at least two cysteine residues near the C-terminal end to form RPBLAs.

In addition, protein concentration is known to be a key parameter that controls the aggregation of self-assembling peptides (Wetzel, R. (1999) In Methods in Enzymology, vol. 309, Academic Press, San Diego, Calif.). However, the expression of RX3-ECFP and RX3 Cys mutants was clearly visualized in SDS-PAGE Coomassie blue staining gels, and no significant differences in protein levels were observed between those proteins which formed RPBLAs and those which were secreted and did not aggregate (FIG. 8B). Hence differences in protein multimerization of the RX3 mutants tested are related to differences in their intrinsic properties that affect aggregation capacities. Modifications of RX3 sequence could either impair aggregation capacity or raise the protein concentration threshold needed for oligomerization.

The determination of the minimal number of cysteines required for an assembler peptide to allow efficient induction of RPBLAs is critical. First of all, cysteine residues in an assembler peptide can negatively affect the proper folding of the protein of interest, hence its activity, mainly when this protein also contains cysteine residues. However, the presence of cysteines in the assembler peptide assures the cross-linking of the fusion protein by disulphide bonds formation. This cross-linking results in the stabilization and robustness of the RPBLAs. These characteristics are desirable because they allow for easy isolation of this organelle. Furthermore, any industrial application in which the RPBLAs organelle is used will depend on cross-linking by disulphide bond formation. Notably, the isolation of organelles formed, for example by the addition of a KDEL sequence at the C-terminus of the protein, will be more difficult due to their reduced stability.

Example 10

The Orientation of Cysteine Residues do not Affect the Capacity of PP Peptide to Accumulate in RPBLAs in Transformed Tobacco Plants The importance of cysteine residues in protein assembly and RPBLAs induction was demonstrated by single and multiple mutations of these residues in Example 9. However the influence of the orientation of these residues remained to be explored. In order to do that, a new assembler peptide (PP2) was synthesized. PP2 is homologous to PP except for the position of some of the cysteine residues (FIG. 9A; C9→10, C84→85 and C92→91).

Highly-rich proline peptides form a PPII helix that is characterized by having three amino acids per turn (Brochicchio, 2002), as shown in FIG. 9B. In nature RX3, cysteine residues are oriented towards each of the three sides of the helix. It was hypothesized that this orientation could be important to promote the assembly and stabilization in all three dimensions that allows natural and RPBLAs to form into the usual big (up to 3 micrometers) round-shape organelles full of proteins assembled and stabilized by disulfide bridges. Thus, PP2 was designed so that all the cysteine residues are oriented towards the same side of the helix. Unexpectedly, PP2 fused to GFP was able to accumulate as much as PP-GFP and even more surprisingly, to induce the formation of large RPBLAs (FIG. 9C)

Example 11

Accumulation of R8(4C)-ECFP, R7(4C)-ECFP, R6(4C)-ECFP, and R4(4C)-ECFP in RPBLAs of Transformed Tobacco Plants The minimal length of the PPII required for RPBLAs biogenesis was also determined. In order to do so, a minimal RX3-ECFP derived protein, R8(4C)-ECFP, was created by deleting the PX sequence of RX3 and adding an additional minimal sequence. Thus, R8(4C)-ECFP lacks C82, C84, and C92, but contains an additional new cysteine residue linked to C64 by two prolines to reinforce interchain disulfide bridges (FIG. 10A). The distribution pattern of R8(C4)-ECFP protein when expressed in *N. benthamiana* leaves accumulated in evident spherical fluorescent spots that, at high magnification, appeared to be small RPBLAs (FIG.

10C). Whereas RPBLAs induced by RX3-ECFP reached a diameter average of 1.4 μm at 4 dpi and increased progressively to reach up to 2 μm at 7 dpi, fluorescent spots induced by R8(C4)-ECFP rarely reached diameters of 1 μm at 7 dpi (see table below). Therefore, as suggested previously, the pair of cysteines at each side of the PPII helix (RD in the context of R8(C4)) are sufficient to nucleate protein aggregates which will evolve to RPBLAs. The observation that RX3-ECFP has a stronger tendency to form large RPBLAs than R8(C4)-ECFP may be due to the fact that RX3-ECFP oligomers have more probabilities of growing by increasing the inter-chain cross-linking by virtue of its six cysteine residues.

Therefore, the extent to which polymerization is related to the length of the PPII was also examined. These experiments were performed by progressively shortening the RD. Three more constructs were generated from R8(C4)-ECFP. The repeat domain was shortened to 7, 6 and 4 PPPVHL (SEQ ID NO:136) units (FIG. 10A). As shown in FIG. 10C, over-expressed proteins containing six or four repeat units (R6(C4)-ECFP and R4(C4)-ECFP, respectively) were still able to form small aggregates but secretion increases with shortening of the repeat domain (FIG. 10B inset). R7(C4)-EGF produced similar results as R8(C4)-EGF.

Coomassie blue stain analysis of total proteins extracted from leaves over-expressing RX3-truncated proteins (FIG. 10B) showed that the concentration of recombinant proteins was similar in all cases. This indicates that each of the fusion proteins is stable and that the lower aggregation efficiency in some mutants was not related to protein expression levels. In addition, achieving good protein expression levels does not necessarily result in the formation of RPBLAs. These results indicate that there is a critical size that favors optimal RX3 peptide interactions and determines the efficiency of PBs formation.

TABLE 2

RPBLAs size after 4 and 7 days from plant transformation.

| Fusion protein | Size Range (μm) | |
| --- | --- | --- |
| | 4 dpi | 7 dpi |
| RX3-ECFP | 1.1-1.85 | 1.1-1.85 |
| R8(4C)-ECFP | 0.4-0.7 | 0.9-1.3 |
| R7(4C)-ECFP | 0.4-0.75 | 0.78-1.3 |
| R6(4C)-ECFP | 0.3-0.6 | 1-1.4 |
| R4(4C)-ECFP | 0.2-0.4 | 0.75-1 |

Based on the significant increase in fusion protein secretion of R4(C4)-ECFP compared to the other constructs, R4(C4) marks the minimal length of an efficient assembler peptide. These results indicate that peptides longer than 24 amino acids (length of the R4(C4) repeat domain) adopting a PPII helix and flanked by one pair of cysteine residues at each end are sufficient to be retained in the ER and to induce the formation of RPBLAs. Peptides that are 36 amino acids (length of the R6(4C) repeat domain) or longer adopting a PPII helix and flanked by one pair of cysteine residues at each end are sufficient to induce the formation of RPBLAs that are at least about 0.3 lam in size at 4 dpi.

Example 12

Accumulation of RX3(A)-mCherry RX3(E)-mCherry in RPBLAs of Transformed Tobacco Plants The fluorescent protein mCherry is highly soluble and reluctant to accumulate in RPBLAs when fused to RX3. Confocal microscopic analysis of tobacco leaves transformed with a vector expressing RX3-mCherry showed a clear secretion pattern, as shown in FIG. 11A where most of the red fluorescence observed was localized to the periphery of the cell. Interestingly, when tobacco leaves were transformed with RX3(A)-mCherry, most of the fluorescence was observed inside the cell, indicating that the fusion protein was retained efficiently within the cell.

Moreover, a clear particulate pattern was observed (FIGS. 11B and 11B'), indicating that the fusion protein accumulated in RPBLAs. The size of these recombinant protein bodies (about 1 micrometer in diameter) matches with RPBLAs characterized previously in plants transformed with several fusion proteins (see, U.S. Pat. No. 7,575,898; and US Patent Publications No. 20060123509, No. 20060121573, and No. 20070243198).

This result was unexpected for at least two reasons. First, the efficiency of RPBLA formation was increased when mCherry was fused to RX3(A) compared to the unmodified prolamin derived RX3 that contains the naturally occurring repeat domain. Additionally, it was described that the amphipathicity of the repeat domain of RX3 is important for protein body formation (Kogan, 2002), and RX3(A) was mutated in order to have a fully hydrophobic repeat domain (see Example 1).

As indicated above, the high solubility of mCherry could be one of the major factors reducing the capacity of fusion of mCherry with natural RX3 to form RPBLAs. In order to determine if the higher performance of RX3(A) is due to the simple increase in the hydrophobic content of the RD (substitution of histidines (positively charged amino acids) to hydrophobic alanines), a fusion of mCherry to RX3(E) was expressed. As shown in FIG. 11C, RX3(E)-mCherry was efficiently retained in the cell, and in addition, it accumulated in RPBLAs that are even bigger than those induced by the expression of RX3(A)-mCherry.

The fact that RX3(E), having an amphipathic charged RD, is also able to induce the formation of RPBLAs when fused to mCherry, indicates that the increase in the performance of RX3(A) compared to RX3 is not due to an unspecific increase of the hydrophobic character of the peptide, but is due to the increase of the assembly capacity and therefore, protein body-inducing capacity of these two synthetic RX3 derived peptides.

Example 13

Accumulation of EGF fused to RX3, RX3(A), RX3(E), PP and PA Assembler Peptides in Transformed Tobacco Plants The production and purification of the epidermal growth factor (EGF) fused to RX3 in tobacco agroinfiltrated plants have been reported previously (WO2006056484). The process of RPBLAs isolation by low speed centrifugation, the solubilization, and the cleavage of the RX3-EGF fusion protein and the subsequent purification of EGF by reverse phase (RF) FPLC have been developed in WO2007096192. In order to test the efficacy of the new assembler peptides, EGF was fused to RX3(A) and RX3(E) and an equivalent downstream process was performed. The RPBLAs induced by the expression of RX3(A)-EGF and RX3(E)-EGF were as efficiently recovered by low speed centrifugation as the control RPBLAs induced by the expression of RX3-EGF (FIG. 12A). In all three cases, almost all of the fusion protein was recovered in the wPB fraction (FIG. 12A, lane 4) with only insignificant losses in the supernatant (FIG. 12A, lane 2) and the washing step (FIG. 12A, lane 3). From these results, it is apparent that almost all the fusion protein is tightly assembled in the RPBLAs organelles and is easily recovered in the wPBs fraction.

A key point in the downstream is the solubilization of the fusion protein from the RPBLAs. After RX3-EGF RPBLAs solubilization in mild conditions (50 mM borate buffer at pH10 and 10 mM of bME at 25° C. for 4 hours), only a low percentage of the fusion protein was solubilized. In fact, only 50% of the RX3-EGF monomer was solubilized (FIG. 12B; compare lane 3 (sPBs) to lane 6 (iPBs)). Surprisingly, the solubilization of RPBLAs containing RX3(A)-EGF or RX3(E)-EGF was much more efficient. Almost all of the monomeric form of RX3(A)-EGF was solubilized, and almost no RX3(A)-EGF seems to remain insoluble in the conditions used (FIG. 12B; compare lane 1 (sPBs) to lane 4 (iPBs)).

The effects of PP-EGF and PA-EGF on downstream processing were also examined. FIG. 12C shows that these two fusion proteins accumulate at the same level as RX3-EGF and RX3(E)-EGF in tobacco agroinfiltrated leaves. In addition, after RPBLAs recovery by low speed centrifugation, PP-EGF and PA-EGF were solubilized very efficiently, similar to RX3(E)-EGF, in the mild conditions described above (FIG. 12D). As mentioned before, the differences in electrophoretic mobility between all these fusion proteins is not related to a difference in protein size, but due to slight differences in protein conformation even under SDS-PAGE conditions.

Unexpectedly, the new assembler peptides RX3(A), RX3(E), PP, and PA all greatly increase the solubility of the fusion proteins without affecting their capacity to assemble and induce the formation of RPBLAs. This striking result is of major importance in the RPBLAs downstream processing because it dramatically increases the total yield of the process (at least two-fold for RX3(A) and more than ten-fold for RX3(E), PP and PA).

In order to assess the conformation of the EGF produced by means of these new assembler peptides, the activity of the solubilized RX3(E)-EGF, as well as the EGF cleaved by FXa from this fusion protein and purified by RF-FPLC, was tested. FIG. 13A shows a silver stained gel with all the downstream steps from the non-clarified homogenate to the cleavage step. After cleavage with the site-specific protease FXa, the liberated EGF was purified as described in the material and methods by RF-FPLC. The EGF protein was recovered at 30% of acetonitrile in only two fractions corresponding to the sharp peak indicated by an arrow in FIG. 13B. The purity of a mix of the two fractions recovered (FIG. 13C) was estimated at more than 92% by HPLC. The EGF activity was measured in vitro by the analysis of the EGF receptor phosphorylation of A431 cells incubated with increasing amounts of RX3(E)-EGF and EGF. As a negative control these cells were incubated in parallel with RX3. Three independent experiments demonstrated that RX3(E)-EGF and EGF were 50% and 100% active, respectively, compared to a commercial EGF from Promega (GS02A).

Example 14

Accumulation of hGH Fused to RX3 and RX3(A) Assembler Peptides in Transformed Tobacco Plants Human growth hormone was chosen as an additional example to check the capacity of the RX3 variants to increase the downstream process. Tobacco plants expressing the RX3(A)-hGH fusion protein were homogenized, and the RPBLAs induced were isolated by low speed centrifugation. As shown in FIG. 14A (left panel), a highly pure fraction of RPBLAs (wPB) was obtained from the homogenate (H0). The fusion protein RX3(A)-hGH in its different oligomeric forms is the only protein observed in this fraction when it was analyzed by Coomassie staining Interestingly, when the yield of the process was analyzed by Western blot, most of the fusion protein accumulated in stable tightly assembled RPBLAs, which can be recuperated by centrifugation, and only a small amount of it is lost in the corresponding supernatant (FIG. 14A, left panel).

Once RPBLAs containing RX3(A)-hGH were obtained by this simple centrifugation method, they were incubated for 3 hours in mild solubilization buffer (50 mM borate pH10, 10 mM beta-mercaptoethanol (bME) at room temperature). As a reference, equivalent amounts of RPBLAs containing RX3-hGH were incubated in the same conditions and analyzed in parallel by Western blot using anti-hGH antibodies. Surprisingly, the RX3(A)-hGH fusion protein was much more soluble than RX3-hGH, even though the high yield in RPBLAs recovery indicates that the organelles induced by the expression of either one of these two fusion proteins are both stable and tightly assembled. The increase in water solubility is surprising given the fact that replacing the RX3 histidine residues with alanines in RX3(a) increases the hydrophobicity of the assembler peptide (Eisenberg, 1984)).

Example 15

Dependence of Cys Residues in Dense RPBLA Biogenesis in Transformed Tobacco Plants As mentioned above, one of the essential elements of PBIS in dense RPBLAs formation is the presence of at least 2 cysteine residues at each end of a polyproline type II domain. Nevertheless, there are other assembler peptides (e.g., hydrophobin, ELP) that are retained in the ER and accumulate in vesicle-like structures when fused to a KDEL sequence, even in the absence of disulfide bridge formation. The presence of a KDEL at the C-terminal end of certain assembler proteins is sufficient to retain the molecule in the ER, and the assembler capacity of the protein leads to the formation of vesicle structures.

In order to determine if the addition of an ER retention sequence at the end of the RX3 assembler peptide could substitute for the necessity of the Cys residues, the RX3 variant RX3$\Delta$Cys$_{64,82,84,92}$-ECFP, which was not able to induce RPBLAs and was secreted as shown in example 9, was fused to an ECFP having a KDEL (RX3$\Delta$Cys$_{64,82,84,92}$-ECFP-KDEL).

The analysis of tobacco leaves over-expressing RX3-ECFP and RX3$\Delta$Cys$_{64,82,84,92}$-ECFP-KDEL by Coomasie staining and Western blot (FIG. 16A) showed that the two RX3 based fusion proteins accumulated at similar levels. In order to determine whether RX3$\Delta$Cys$_{64,82,84,92}$-ECFP-KDEL accumulates in RPBLAs, leaves expressing this fusion protein were analysed by confocal microscopy at 3 and 7 days post infiltration (dpi). As observed previously in RX3-ECFP expressing tobacco leaves, around 1 micrometer round shape vesicles induced by the expression of RX3$\Delta$Cys$_{64,82,84,92}$-ECFP-KDEL were observed even only 3 dpi (FIG. 16B). This observation demonstrates that the KDEL sequence attached to the C-terminal end of ECFP allows an efficient retention of the fusion protein inside the cell. Additionally, it also shows that the assembler capacity of the RX3 based peptide allows the auto-assembly and induction of vesicle structures. These vesicle structures keep growing after 3 dpi, and, interestingly, at 7 dpi irregular big vesicle structures, some over 5 micrometers were observed (FIG. 16B). RPBLAs of this size were not observed in tobacco leaves over-expressing the control RX3-ECFP fusion protein, suggesting that the mechanism of auto-assembly of RX3-ECFP into RPBLAs is not the same as the mechanisms of assembly of RX3ΔCys$_{64,82,84,92}$-ECFP-KDEL vesicles.

A technical approach to indirectly characterize the tightness of the fusion protein assembly inside vesicle structures is the determination of the density of the vesicle structures by step-cushion Optiprep™ gradients. Therefore, vesicle structures induced by RX3ΔCys$_{64,82,84,92}$-ECFP-KDEL (or RX3-ECFP) expression in tobacco plants were carried out by loading filtered plant homogenates on top of the following Optiprep™ step cushions:

TABLE 3

Correspondence table of Optiprep concentration (%) and density (g/mL)

| % Optiprep ™ | Density (g/mL) |
|---|---|
| 18 | 1.117 |
| 30 | 1.175 |
| 34 | 1.194 |
| 38 | 1.214 |
| 42 | 1.233 |
| 46 | 1.252 |

As exemplified by RX3-ECFP gradient, dense RPBLAs are recovered from fractions having densities around 1.2 g/mL (FIG. 16C, left, lanes 5 and 6), which are free of most of the endogenous proteins. In fact, the density and toughness of RPBLAs is of great interest in RPBLAs isolation as has already been described in U.S. Published Application No. 2006/0123509. When RX3ΔCys$_{64,82,84,92}$-ECFP-KDEL vesicle structures were analysed by the same means, surprisingly almost all the fusion protein was recovered in the supernatant fraction (FIG. 16C, right). This result clearly demonstrates that RX3ΔCys$_{64,82,84,92}$-ECFP-KDEL fusion proteins accumulate in vesicle-like structures that can not be considered true RPBLAs. Intracellular organelles derived from the ER or the Golgi apparatus, for example, typically sediment between 18 and 30% of Optiprep cushions, but during the process of tissue homogenization a large proportion of the soluble proteins present in the lumen of the microsomes is liberated and will be recovered in the supernatant. Therefore, it can be concluded that RX3Δ Cys$_{64,82,84,92}$-ECFP-KDEL fusion protein is retained in the ER, but does not assemble or assembles only weakly, and dense RPBLAs are not formed.

Example 16

Accumulation of Z(Adh)-GFP, Z(Adh)Px-Gfp, Z(Col)-Gfp, Z(Col)Px-Gfp in RPBLAs of Transformed Tobacco Plants It has been demonstrated that PBIS with low sequence homology to RX3 are able to generate RPBLAs. PP and PA share less than 60% of identity to the RX3 sequence between C9 and C64 residues. On the other hand, it is important to point out that PP and PA sequences have a high percent of prolines (96.2 and 67.9 percent, respectively); significantly higher than the wild type RX3 (54.7%). The RPBLA-induction capacity of other protein sequences adopting a PPII structure was assessed. The sequences met the following criteria: (i) less than 40% to RX3 and (ii) less than 40% proline content. A fragment of human collagen COL2A1 comprising amino acids 135 to 179 (AccN: CAA34683), and the 884 to 927 fragment from the Surface adhesin AgI/II (*Streptococcus mutans* strain NG8; GeneBank: GQ456171. AccN: ACV69919) were selected. As shown in FIG. 17A, such sequences were used to substitute the RD on R8(C4) (Z(Adh) and Z(Col)) or on the RX3 (Z(Adh)Px and Z(Col) Px) assembler peptides.

These assembler peptides fused to GFP accumulated at high levels in tobacco leaves and were represented as a major band in pre-clarified homogenates from these leaves stained by Coomassie (FIG. 17B). Z(Adh)-Gfp and Z(Adh) Px-Gfp, with a predicted MW of 37.7 kDa and 34.6 kDa respectively, have a lower mobility in SDS-PAGE gel. This shift in migration, also observed in most of the assembler peptides adopting a PPII structure described above (such as PP, RX3(E), etc), can be attributed to the strong stability of this secondary structure.

The analysis by confocal microscopy of tobacco plants expressing Z(Adh)-GFP, Z(Adh)Px-GFP, Z(Col)-GFP and Z(Col)Px-GFP showed that these fusion proteins accumulated inside the cell in round-shaped fluorescent RPBLAs of about 1 micrometer of diameter. In spite of the low percentage of homology to RX3 and the low content in prolines, the fusion proteins were also retained inside the endoplasmic reticulum (ER), and their assembly efficiently induced the formation of RPBLAs (FIG. 17C).

Unlike the vesicle-like structures produced by ELP, hydrophobin or RX3ΔCys$_{64,82,84,92}$-ECFP-KDEL, an important feature of RPBLAs is the tight packing of the protein inside the dense organelles. This feature allows RPBLA isolation by centrifugation. Therefore, the observation that Z(Adh)-GFP, Z(Adh)Px-GFP, Z(Col)-GFP and Z(Col)Px-GFP are recovered in the pellet (RPBLAs fraction) after centrifugation at 1500×g (FIG. 17D), demonstrates that these fusion proteins induce the formation of dense RPBLAs. The presence of the Px domain, hence the increase of the number of cys residues (from 4 to 6) and also the enlargement of the assembler peptide by a proline rich sequence, resulted in a significant increase of the tightness of the assembly and a higher efficiency recovery of RPBLAs (compare Z(Adh)-GFP versus Z(Adh)Px-GFP and Z(Col)-GFP versus Z(Col)Px-GFP in FIG. 17). Density gradient and FRAP experiments support this data.

As can be observed from Z(Adh)-GFP, Z(Adh)Px-GFP, Z(Col)-GFP and Z(Col)Px-GFP sequence comparison (FIG. 17A), the last repeat of the RX3 domain was maintained in all of the constructs tested for cloning reasons. In order to demonstrate that the Adh and Col PPII structures do not need the repeat of the RX3 domain in order to form RPBLAs, another set of constructs lacking this repeat (Z(Adh2)-GFP; Z(Adh2)Px-GFP, Z(Co12)-GFP and Z(Co12)Px-GFP) was tested. The constructs lacking the repeat all maintained the capacity to induce RPBLAs.

Example 17

Determination of Xylanase Activity on RPBLAs Induced by the Expression of RX3-Xyl, RX3(L)-Xyl, RX3(E)-Xyl, RX3(A)-Xyl PP-Xyl and PA-Xyl in Transformed Tobacco Plants As described previously (WO2007/096192A1), the RPBLAs induced by the expression of wild-type RX3 fusion proteins have the ability of maintaining the activity of the protein of interest (POI) fused to such PBIS.

In order to determine how the assembler peptides described herein affect the activity of proteins fused to them, non-amphipathic (PP, PA, RX3(A) and RX3(L)) and negatively charged amphipathic (RX3(E)) assembler peptides were studied. The xylanase enzyme (DQ465452) was chosen as the reporter POI and was fused through a linker comprising 5 glycines to all these assembler peptides as well as to the wild-type RX3 as a reference.

Tobacco leaves over-expressing PP-Xyl, PA-Xyl, RX3 (E)-Xyl, RX3(L)-Xyl, RX3(A)-Xyl and RX3-Xyl were harvested 6 days post agroinfiltration, avoiding necrotic tissue in order to diminish inconsistency and variability. Downstream processing by low-speed centrifugation was carried out for each construct, and the enriched RPBLAs fraction was analyzed in SDS-PAGE by Coomassie blue staining. In all cases, the RPBLAs fraction was highly enriched in the fusion protein, which was the most abundant protein in the fraction. The protein content was determined by EZQ Protein Quantitation Kit (Invitrogen, Molecular Probes), and the xylanase activity associated with each sample was quantified with a synthetic substrate (DiFMUX2), measuring the corresponding fluorescent product every 2 minutes (wavelength: excitation 360/40 nm, emission 460/40 nm.

Unexpectedly, among all the samples analyzed, the RPBLAs fraction having the lowest specific activity (11.7 nmols/(minute*microgram of protein)) corresponded to the RX3-Xyl fusion protein. Taking this fusion protein as the reference, RX3(A)-Xyl showed almost double the specific activity; RX3(E)-Xyl and RX3(L)-Xyl showed about a 3-fold increase; and PP-Xyl and PA-Xyl had specific activities above 7-fold higher than the reference (see table 4). The activity was measured using the same amount of fusion protein, so the increased specific activity of these assembler peptides compared to RX3 could be related to different RPBLAs properties. This observation is of great importance taking into account that a high specific activity is a useful attribute in enzyme applications.

TABLE 4

Specific activity of RPBLAs induced by the expression of different assembler peptides.

|  | nmols/min/µg prot | Std. Dev | FOLD | Std. Dev. Rel |
|---|---|---|---|---|
| RX3-Xyl | 11.7 | 0.63 | 1.0 | 0.05 |
| PA-Xyl | 84.7 | 0.57 | 7.3 | 0.05 |
| PP-Xyl | 84.4 | 4.51 | 7.2 | 0.50 |
| RX3 (A)-Xyl | 21 | 0.5 | 1.8 | 0.05 |
| RX3 (E)-Xyl | 33.5 | 2.89 | 2.9 | 0.25 |
| RX3 (L)-Xyl | 41.2 | 4.00 | 3.5 | 0.34 |

Example 18

Independence of the Orientation of the RX3 Repeat Domain with Regard to the Cysteine Residues in its Capacity to Induce RPBLAs in Tobacco Plants The repetitive domain (RD) from wild type RX3 is flanked by 2 and 4 cysteine residues located at the N-terminal and C-terminal, respectively. This asymmetric distribution could be of some importance regarding the assembly capacity and/or the efficiency in RPBLAs induction. In order to test this, a new construct was generated (iRX3) such that the flanking regions of the RD, were swapped and cloned in the inverted orientation (FIG. 18A). When tobacco leaves were agroinfiltrated with a construct coding for the inverted RX3 assembler peptide fused to ECFP (iRX3-ECFP), big round-shape RPBLAs were observed. Surprisingly, the size of RPBLAs induced was significantly bigger than the corresponding RPBLAs obtained by the expression of the RX3-ECFP fusion protein used as a reference (FIG. 18B). The mean size of RX3-ECFP and iRX3-ECFP was about 1 and 2.5 micrometers, respectively.

High density and tightness in RPBLAs allows for efficient isolation by centrifugation from the rest of cellular organelles and soluble proteins (US Published Application No. 2006/0123509), so the density of iRX3-ECFP RPBLAs was determined by a multi-step Optiprep density gradient. A comparison of the RPBLAs distribution along the density gradient induced by the expression of iRX3-ECFP and RX3-ECFP showed no significant differences. In both cases, the majority of the RPBLAs formed 6 days after agroinfiltration and were recovered from high density fractions ranging from 1.175 to 1.26 g/cm$^3$ (FIG. 18C; lanes 4 to 7). The fractions are also are free from most of the endogenous cellular proteins.

The importance of the relative position of the assembler peptide (RX3 and iRX3) with regard to the protein of interest (ECFP) was also analyzed. Two additional constructs were generated by cloning the RX3 or the iRX3 assembler peptide at the C-terminal end of the ECFP (FIG. 18; ECFP-RX3 and ECFP-iRX3). Tobacco leaves expressing these fusion proteins were able to induce RPBLAs, although smaller in size than the corresponding N-terminal fusion proteins (RX3-ECFP and iRX3-ECFP). In FIG. 18B, the confocal images show that ECFP-RX3 and ECFP-iRX3 induce a large number of small RPBLAs, most of them around 0.5 micrometers. Interestingly, in spite of the reduced size, some RPBLAs where recovered in the dense fractions 1.175 and 1.21 g/cm$^3$ (FIG. 18C, lanes 4 and 5), which are free from most of the cellular contaminants. The presence of some fusion protein in the fractions with lower density (FIG. 18C, lanes 2 and 3) may represent the fusion protein which has not assembled into full RPBLAs, probably due to slower assembly kinetics. It can also be concluded that RPBLAs induced by the expression of fusion proteins having the assembler peptide linked at the C-terminal end of the protein of interest can be isolated by centrifugation.

Example 19

Accumulation in RPBLAs of hGH-I-RX3, DsRED-I-RX3 and EK-RX3 in CHO Cells

In order to demonstrate that the recombinant PBIS fused at the C-terminal end of the POI can induce the formation of RPBLAs in CHO cells, three constructs were generated expressing the following fusion proteins: (i) hGH-I-RX3, (ii) EK-RX3, and (iii) DsRED-I-RX3 (see FIG. 19). In all three cases, after CHO cell transfection, the observation of the characteristic pattern of intracellular spots demonstrated that the corresponding fusion proteins were retained inside the cells in RPBLAs (FIGS. 19A and B). The heterogeneity of RPBLAs sizes, which can be clearly observed in FIG. 19A, can be associated with different stages of RPBLAs formation or to differences in the transfection efficiency and the resulting differences in fusion protein expression levels.

A technical approach to indirectly characterize the tightness of the fusion protein assembly inside a protein body is the determination of the RPBLAs density by step-cushion sucrose gradients. Therefore, RPBLAs induced by the expression of hGH-I-RX3 in CHO cells were loaded on top of the following sucrose step-cushions gradient:

TABLE 5

Sucrose concentration (%) and density (g/mL)

| % Sucrose | Density (g/mL) |
|---|---|
| 20 | 1.08 |
| 27 | 1.12 |
| 35 | 1.16 |
| 42 | 1.2 |
| 56 | 1.28 |

The analysis of equivalent volumes of the different fractions recovered from the density gradient by Western blot showed that the majority of the fusion protein loaded (FIG. 19A, lane H) was recovered in dense fractions (FIG. 19A, lane F42 and F56). A small amount of fusion protein not assembled was also observed in S and F27 fractions, probably due to slower assembly kinetics. As high dense RPBLAs are typically recovered from fractions having densities around 1.2 g/mL, it can be concluded that RPBLAs can be induced by fusion proteins having the RX3 domain at the C-terminal end of the protein.

Example 20

Accumulation in RPBLAs of hGH-I-RX3 in SF9 Insect Cells

A demonstration that fusion proteins having the RX3 assembler peptide at the C-terminal end of the protein are able to induce RPBLAs in insect cells was performed with hGH-I-RX3. Insect cells infected with a pBacPAK8 recombinant virus expressing hGH-I-RX3 showed the immunofluorescence pattern characteristic of RPBLAs accumulation (FIG. 19C). The spots distributed uniformly along the cell correspond to RPBLAs and demonstrated that the fusion protein was efficiently retained in the ER. When SF9 cells expressing hGH-I-RX3 were homogenated and centrifuged at low speed (3000×g), a large proportion of the fusion protein was recovered in the RPBLAs fraction (FIG. 19C, right panel, lane 3). As observed in N-terminal RX3 fusion proteins (US Publication No. 2006/0123509), the tight assembly in dense organelles (RPBLAs) induced by RX3: RX3 interactions allows an efficient recovery of a fraction highly enriched in RPBLAs.

Example 21

Accumulation of RPBLAs in Mammalian Cells

Sequences encoding the following proteins are fused to sequences encoding xylanase and cloned into the vector pcDNA 3.1 (Invitrogen) for expression in mammalian cells: RX3, RX3(A), RX3(L), RX3(A3), RX3(E), RX3(D), RX3(T), RX3(N), RX3(Q), PP, PA, RX3C64G, RX3C82G, RX3C84G, RX3C92G, PP2, R8(C4), R7(C4), R6(C4), R4(C4), Z(Adh), Z(Adh)Px, Z(Col), Z(Col)Px, and iRX3. The resulting vectors are introduced into 293T, Cos1, and CHO cells using the lipofectamine based transfection method (Invitrogen).

Western blots of transfected cells show accumulation of all of the fusion proteins. In addition, localization of the fusion proteins by immunocytochemistry indicates that the fusion proteins accumulate in spherical RPBLAs having diameters of about 0.5 to about 3 microns. The density of the RPBLAs is determined by loading on sucrose step-cushions and is about 1.1 to about 1.4 g/mL. The RPBLAs are purified using low speed centrifugation (less than about 5000×g), and the recovered RPBLAs are at least about 95% pure. RPBLAs are solubilized by incubating in mild buffer (50 mM Tris pH 8, 5 mM TCEP and 10 mM 2bME) for about 4 hours and then centrifugation at about 16,000 g for about 10 minutes. High yields of protein in the solubilized portion are recovered. The xylanase activity is measured using a synthetic substrate (DiFMUX2) and high activity levels are observed.

Example 22

Accumulation of RPBLAs in Insect Cells

Sequences encoding the following proteins are fused to sequences encoding xylanase and cloned into the pFastBAck baculoviral expression vector system (Invitrogen): RX3, RX3(A), RX3(L), RX3(A3), RX3(E), RX3(D), RX3(T), RX3(N), RX3(Q), PP, PA, RX3C64G, RX3C82G, RX3C84G, RX3C92G, PP2, R8(C4), R7(C4), R6(C4), R4(C4), Z(Adh), Z(Adh)Px, Z(Col), Z(Col)Px, and iRX3. Recombinant virus is produced using the BaculoGold Transfection Kit (PharMingen, San Diego, Calif., USA). Sf9 cells were allowed to attach to the bottom of culture dishes and after 15 minutes to 1 hour incubation, viral stock is added to the cultures which are maintained at 27° C. in humidified air for about 30 to about 36 hours.

Western blots of infected cells show accumulation of all of the fusion proteins. In addition, localization of the fusion proteins by immunocytochemistry indicates that the fusion proteins accumulate in spherical RPBLAs having diameters of about 0.5 to about 3 microns. The density of the RPBLAs is determined by loading on sucrose step-cushions and is about 1.1 to about 1.4 g/mL. The RPBLAs are purified using low speed centrifugation (less than about 5000×g), and the recovered RPBLAs are at least about 95% pure. RPBLAs are solubilized by incubating in mild buffer (50 mM Tris pH 8, 5 mM TCEP and 10 mM 2bME) for about 4 hours and then centrifugation at about 16,000 g for about 10 minutes. High yields of protein in the solubilized portion are recovered. The xylanase activity is measured using a synthetic substrate (DiFMUX2) and high activity levels are observed.

Example 23

Accumulation of RPBLAs in Filamentous Fungi Cells

Sequences encoding the following proteins are fused to sequences encoding xylanase and cloned into Trichoderma reesei expression vectors: RX3, RX3(A), RX3(L), RX3 (A3), RX3(E), RX3(D), RX3(T), RX3(N), RX3(Q), PP, PA, RX3C64G, RX3C82G, RX3C84G, RX3C92G, PP2, R8(C4), R7(C4), R6(C4), R4(C4), Z(Adh), Z(Adh)Px, Z(Col), Z(Col)Px, and iRX3. The expression vectors are introduced into the *T. reesei* strain RutC-30 (Montenecourt B S and Eveleigh D E, *Adv Chem Ser* 181:289-301 (1979)) essentially as described in Penttilä M, et al., *Gene* 61:155-164 (1987)).

Transformants are selected on plates containing 125 μg/ml of hygromycin B. The transformants are streaked on selective medium containing lactose for induced expression and are screened by fluorescence microscopy. Mycelia from the transformants producing the highest amounts of the fusion proteins are harvested by filtration.

Western blots of transformed mycelia cells show accumulation of all of the fusion proteins. In addition, localization of the fusion proteins by immunocytochemistry indicates that the fusion proteins accumulate in spherical RPBLAs having diameters of about 0.5 to about 3 microns. The density of the RPBLAs is determined by loading on Optiprep step-cushions and is about 1.1 to about 1.4 g/mL. The RPBLAs are purified using low speed centrifugation (less than about 5000×g), and the recovered RPBLAs are at least about 95% pure. RPBLAs are solubilized by incubating in mild buffer (50 mM Tris pH 8, 5 mM TCEP and 10 mM 2bME) for about 4 hours and then centrifugation at about 16,000 g for about 10 minutes. High yields of protein in the solubilized portion are recovered. The xylanase activity is measured using a synthetic substrate (DiFMUX2) and high activity levels are observed.

Example 24

Construction of Non-Allergenic PBIS

Prolamin proteins and peptides derived from prolamins can be allergenic. Interestingly, when the putative allergenicity of the RX3 peptide was analysed by the AllergenOnline Database (version 10.0, January 2010; http://www.allergenonline.com), developed by the Food Allergy Research and Resource Program (FARRP), 10 hits with more than 35% identity to allergenic peptides were found. This result suggests that wild-type RX3 has an allergenic potential. Low allergenic or non-allergenic versions of this peptide are useful in several applications (e.g, nutrition). Therefore, the same analysis was performed with the different variants of RX3 peptides described in this application, and the results demonstrated that PA and RX3(A3), are significantly less allergenic than the wild type RX3. The sequence analysis of PA and RX3(A3) in the AllergenOnline Database, showed only three and two hits with more than 35% of identity to allergenic peptides, respectively.

Based on these observations, several new non-allergenic versions of the RX3 assembler peptide are synthesized: RX3(LA1) (SEQ ID NO:163) and RX3(LA2) (SEQ ID NO:164). These two peptides have no hits with more than 35% of identity to allergenic peptides, indicating that they are not allergenic. Fusion proteins of RX3(LA1) and RX3 (LA2) to GFP and ECFP are expressed in tobacco leaves, and their capacity to form RPBLAs is demonstrated using the techniques described herein.

Noteably, R8(4C) has no hits with more than 35% identify to allergenic peptides, indicating that it is not allergenic at all. This result indicates that the allergenicity of RX3 is mainly due to the amino acid sequence in the Pro-X domain. In order to avoid putative allergenic effects in the assembler peptides, several non-allergenic R8(4C) variants are synthesized and tested for RPBLA induction in tobacco plants.

\* \* \*

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A recombinant protein body-inducing polypeptide sequence (PBIS) comprising a polyproline II (PPII) structure that is at least 36 amino acids in length and has an N-terminus and a C-terminus wherein
   (i) the PPII structure is located between at least two cysteines at the N-terminus and at least two cysteines at the C-terminus;
   (ii) no more than 10% of the amino acids in the PPII structure are lysine or arginine;
   (iii) the PPII structure does not contain the sequence (PPPVHL)$_6$ showing the sequence set forth in SEQ ID NO:115; and
   (iv) the PPII structure is selected from the group consisting of a non-amphipathic PPII structure, an amphipathic and negatively charged PPII structure, and an amphipathic and non-charged PPII structure, wherein the non-amphipathic PPII structure, is selected from the group consisting of a sequence comprising at least 6 repeats of the sequence set forth in SEQ ID NO: 121, a sequence comprising at least 6 repeats of the sequence set forth in SEQ ID NO: 122, a sequence comprising at least 6 repeats of the sequence set forth in SEQ ID NO: 123, a sequence comprising at least 6 repeats of the sequence set forth in SEQ ID NO: 120 wherein the X residues are proline, and a sequence comprising at least 6 repeats of the sequence set forth in SEQ ID NO: 129; wherein the amphipathic and negatively charged PPII structure is selected from the group consisting of a sequence comprising at least 6 repeats of the sequence set forth in SEQ ID NO: 124 and a sequence comprising at least 6 repeats of the sequence set forth in SEQ ID NO: 125; and wherein the non-charged PPII structure is selected from the group consisting of a sequence comprising at least 6 repeats of the sequence set forth in SEQ ID NO: 126, a sequence comprising at least 6 repeats of the sequence set forth in SEQ ID NO: 127, and a sequence comprising at least 6 repeats of the sequence set forth in SEQ ID NO: 128.

2. The recombinant PBIS of claim 1 wherein at least 40% of the amino acids in the PPII structure are proline.

3. The recombinant PBIS of claim 1 wherein no more than 98% of the amino acids in the PPII structure are proline.

4. The recombinant PBIS of claim 1, wherein no more than 5% of the amino acids in the PPII structure are lysine or arginine.

5. The recombinant PBIS of claim 1, wherein no more than 15% of the amino acids in the PPII structure are histidine.

6. The recombinant PBIS of claim 1, wherein the PBIS further comprises a cysteine and a proline-rich sequence between the PPII structure and the two C-terminal cysteines or between the PPII structure and the two N-terminal cysteines.

7. A recombinant protein body-inducing polypeptide sequence (PBIS) comprising a proline-rich sequence that is at least 36 amino acids in length and has an N-terminus and a C-terminus, wherein;
  (i) the proline-rich sequence is located between at least two cysteines at the N-terminus and at least two cysteines at the C-terminus;
  (ii) no more than 10% of the amino acids in the proline-rich sequence are lysine or arginine;
  (iii) the proline-rich sequence does not contain the sequence (PPPVHL)$_6$ showing the sequence set forth in SEQ ID NO:115,
  (iv) the proline-rich sequence comprises at least 40% of proline residues and wherein the proline-rich sequence is selected from the group consisting of a non-amphipathic proline-rich sequence, an amphipathic and negatively charged proline-rich sequence, and an amphipathic and non-charged proline-rich sequence, wherein the non-amphipathic proline-rich sequence is selected from the group consisting of a sequence comprising at least 6 repeats of the sequence set forth in SEQ ID NO: 121, a sequence comprising at least 6 repeats of the sequence set forth in SEQ ID NO: 122, a sequence comprising at least 6 repeats of the sequence set forth in SEQ ID NO: 123, a sequence comprising at least 6 repeats of the sequence set forth in SEQ ID NO: 120 wherein the X residues are proline, and a sequence comprising at least 6 repeats of the sequence set forth in SEQ ID NO: 129; wherein the amphipathic and negatively charged proline-rich sequence is selected from the group consisting of a sequence comprising at least 6 repeats of the sequence set forth in SEQ ID NO: 124 and a sequence comprising at least 6 repeats of the sequence set forth in SEQ ID NO: 125; and wherein the non-charged proline-rich sequence is selected from the group consisting of a sequence comprising at least 6 repeats of the sequence set forth in SEQ ID NO: 126, a sequence comprising at least 6 repeats of the sequence set forth in SEQ ID NO: 127, and a sequence comprising at least 6 repeats of the sequence set forth in SEQ ID NO: 128.

8. The recombinant PBIS of claim 7, wherein the PBIS further comprises a cysteine and PPII structure between the proline-rich sequence and the two C-terminal cysteines or between the proline-rich sequence and the two N-terminal cysteines.

9. The recombinant PBIS of claim 7, wherein the PBIS further comprises a cysteine and a second proline-rich sequence between the proline-rich sequence and the two C-terminal cysteines or between the proline-rich sequence and the two N-terminal cysteines.

10. The recombinant PBIS of claim 1, wherein the non amphipathic PPII structure is selected from the group consisting of RX3(A) showing the sequence set forth in SEQ ID NO:89; RX3(L) showing the sequence set forth in SEQ ID NO:86; RX3(A3) showing the sequence set forth in SEQ ID NO:71; PP showing the sequence set forth in SEQ ID NO: 132; PA showing the sequence set forth in SEQ ID NO: 133; PA2 showing the sequence set forth in SEQ ID NO: 172; PP2 showing the sequence set forth in SEQ ID NO: 74 and PP3 showing the sequence set forth in SEQ ID NO: 171; wherein the amphipathic and negatively charged PPII structure is selected from the group consisting of RX3(D) showing the sequence set forth in SEQ ID NO:56 and RX3 (E) showing the sequence set forth in SEQ ID NO: 83 and the amphipathic and non-charged PPII structure is selected from the group consisting of RX3(T) showing the sequence set forth in SEQ ID NO:62; RX3(N) showing the sequence set forth in SEQ ID NO: 65 and RX3(Q) showing the sequence set forth in SEQ ID NO: 68.

11. The recombinant PBIS of claim 1, wherein the recombinant PBIS is capable of forming a recombinant protein body like assembly (RPBLA) when expressed in a eukaryotic cell.

12. The recombinant PBIS of claim 1, further comprising a sequence that directs the PBIS to the endoplasmic reticulum (ER).

13. A fusion protein comprising the recombinant PBIS of claim 1 and a heterologous protein.

14. The fusion protein of claim 13, further comprising a cleavage site between the recombinant PBIS and the heterologous protein.

15. A nucleic acid molecule comprising a sequence that encodes the recombinant PBIS of claim 1.

16. A vector comprising the nucleic acid of claim 15.

17. A host cell comprising the recombinant PBIS of claim 1.

18. A host cell comprising the nucleic acid of claim 15.

19. A recombinant protein body like assembly (RPBLA) comprising the recombinant PBIS of claim 1.

20. A recombinant PBIS or fusion protein isolated from the RPBLA of claim 19.

21. A method for producing an RPBLA comprising culturing the cell of claim 17 under suitable conditions for RPBLA formation.

22. A method for purifying an RPBLA comprising (i) culturing the cell of claim 17 under suitable conditions for RPBLA formation; and (ii) purifying the recombinant protein body.

23. A method for producing an RPBLA comprising (i) transforming a plant host system with the nucleic acid of claim 15; (ii) generating plants from said transformed plant host system; and (iii) growing said plants under conditions suitable for RPBLA formation.

24. A method for producing an RPBLA comprising (i) transforming a plant host system with the nucleic acid of claim 15; (ii) generating plants from said transformed plant host system; (iii) growing said plants under conditions suitable for RPBLA formation; and (iv) purifying the RPBLA.

25. A method of purifying a fusion protein comprising (i) providing RPBLAs that comprise a membrane-enclosed fusion protein, wherein the fusion protein is the fusion protein of claim 13; (ii) contacting the RPBLAs with an aqueous buffer containing a membrane-disassembling amount of a surfactant; (iii) maintaining the contact for a time period sufficient to disassemble the membrane and at a temperature that does not denature the fusion protein to separate the membrane from the fusion protein; and (iv) collecting the separated fusion protein.

26. A method of purifying a protein comprising (i) providing RPBLAs that comprise a membrane-enclosed fusion protein, wherein the fusion protein is the fusion protein of claim 14; (ii) contacting the RPBLAs with an aqueous buffer containing a membrane-disassembling amount of a surfactant; (iii) maintaining the contact for a time period sufficient to disassemble the membrane and at a temperature that does not denature the fusion protein to separate the membrane from the fusion protein; (iv) collecting the separated fusion protein; and (v) cleaving the cleavage site between the recombinant PBIS and the heterologous protein.

27. A vaccine comprising an immunogenically effective amount of the RPBLA of claim 19.

* * * * *

SEQUENCE LISTING

```
<160> NUMBER OF SEQ ID NOS: 187

<210> SEQ ID NO 1
<211> LENGTH: 1076
<212> TYPE: DNA
<213> ORGANISM: Artificial sequence
<220> FEATURE:
<223> OTHER INFORMATION: RX3-Gfp (SalI-BamHI DNA sequence cloned in
      pC2300)

<400> SEQUENCE: 1
gtcgacccat gagggtgttg ctcgttgccc tcgctctcct ggctctcgct gcgagcgcca      60
cctccacgca tacaagcggc ggctgcggct gccagccacc gccgccggtt catctaccgc     120
cgccggtgca tctgccacct ccggttcacc tgccacctcc ggtgcatctc ccaccgccgg     180
tccacctgcc gccgccggtc cacctgccac cgccggtcca tgtgccgccg ccggttcatc     240
tgccgccgcc accatgccac taccctactc aaccgccccg gcctcagcct catcccagc      300 cacacccatg cccgtgccaa cagccgcatc caagcccgtg ccagaccatg agcagtaaag     360
gagaagaact tttcactgga gttgtcccaa ttcttgttga attagatggt gatgttaatg     420
ggcacaaatt ttctgtcagt ggagagggtg aaggtgatgc aacatacgga aaacttaccc     480
ttaaatttat ttgcactact ggaaaactac ctgttccatg ccaacactt  gtcactactt     540 tctcttatgg tgttcaatgc ttttcaagat acccagatca tatgaagcgg cacgacttct     600
tcaagagcgc catgcctgag ggatacgtgc aggagaggac catcttcttc aaggacgacg     660
ggaactacaa gacacgtgct gaagtcaagt ttgagggaga caccctcgtc aacaggatcg     720
```

```
agcttaaggg aatcgatttc aaggaggacg gaaacatcct cggccacaag ttggaataca      780
actacaactc ccacaacgta tacatcatgg ccgacaagca aaagaacggc atcaaagcca      840
acttcaagac ccgccacaac atcgaagacg gcggcgtgca actcgctgat cattatcaac      900
aaaatactcc aattggcgat ggccctgtcc ttttaccaga caaccattac ctgtccacac      960
aatctgccct ttcgaaagat cccaacgaaa agagagacca catggtcctt cttgagtttg     1020
taacagctgc tgggattaca catggcatgg atgaactata caaataatga ggatcc         1076

<210> SEQ ID NO 2
<211> LENGTH: 336
<212> TYPE: DNA
<213> ORGANISM: Artificial sequence
<220> FEATURE:
<223> OTHER INFORMATION: RX3 DNA

<400> SEQUENCE: 2
atgagggtgt tgctcgttgc cctcgctctc ctggctctcg ctgcgagcgc cacctccacg       60
catacaagcg gcggctgcgg ctgccagcca ccgccgccgg ttcatctacc gccgccggtg      120
catctgccac ctccggttca cctgccacct ccggtgcatc tcccaccgcc ggtccacctg      180
ccgccgccgg tccacctgcc accgccggtc catgtgccgc cgccggttca tctgccgccg      240
ccaccatgcc actaccctac tcaaccgccc cggcctcagc ctcatcccca gccacaccca      300
tgcccgtgcc aacagccgca tccaagcccg tgccag                               336

<210> SEQ ID NO 3
<211> LENGTH: 112
<212> TYPE: PRT
<213> ORGANISM: Artificial sequence
<220> FEATURE:
<223> OTHER INFORMATION: RX3 PROTEIN

<400> SEQUENCE: 3

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

<210> SEQ ID NO 4
<211> LENGTH: 1101
<212> TYPE: DNA
<213> ORGANISM: Artificial sequence
<220> FEATURE:
<223> OTHER INFORMATION: RX3DIR-GFP (SalI-BamHI DNA sequence cloned in
      pC2300)

<400> SEQUENCE: 4
gtcgacacca tgagggtgtt gctcgttgcc ctcgctctcc tggctctcgc tgcgagcgcc       60
```

```
acctccacgc atacaagcgg cggctgcggc tgccagccac cgccgccggt tcatctaccg    120
ccgccggtgc atctgccacc tccggttcac ctgccacctc cggtgcatct cccaccgccg    180
gtccacctgc cgccgccggt ccacctgcca ccgccggtcc atgtgccgcc gccggttcat    240
ctgccgccgc caccatgcca ctaccctact caaccgcccc ggcctcagcc tcatccccag    300
ccacacccat gcccgtgcca acagccgcat ccaagcccgt gccaaaggcg cgccggtgga    360
ggcggaggta ccatgagcag taaaggagaa gaacttttca ctggagttgt cccaattctt    420
gttgaattag atggtgatgt taatgggcac aaattttctg tcagtggaga gggtgaaggt    480
gatgcaacat acggaaaact tacccttaaa tttatttgca ctactggaaa actacctgtt    540
ccatggccaa cacttgtcac tactttctct tatggtgttc aatgcttttc aagataccca    600
gatcatatga agcggcacga cttcttcaag agcgccatgc ctgagggata cgtgcaggag    660
aggaccatct tcttcaagga cgacgggaac tacaagacac gtgctgaagt caagtttgag    720
ggagacaccc tcgtcaacag gatcgagctt aagggaatcg atttcaagga ggacggaaac    780
atcctcggcc acaagttgga atacaactac aactcccaca cgtatacat  catggccgac    840
aagcaaaaga acggcatcaa agccaacttc aagacccgcc acaacatcga agacggcggc    900
gtgcaactcg ctgatcatta tcaacaaaat actccaattg gcgatggccc tgtcctttta    960
ccagacaacc attacctgtc cacacaatct gcccttttcga aagatcccaa cgaaaagaga   1020
gaccacatgg tccttcttga gtttgtaaca gctgctggga ttacacatgg catggatgaa   1080
ctatacaaat aatgaggatc c                                              1101
```

<210> SEQ ID NO 5
<211> LENGTH: 1072
<212> TYPE: DNA
<213> ORGANISM: Artificial sequence
<220> FEATURE:
<223> OTHER INFORMATION: RX3-ECFP (SalI-BamHI DNA sequence cloned in pC2300)

<400> SEQUENCE: 5

```
gcgacccatg agggtgttgc tcgttgccct cgctctcctg gctctcgctg cgagcgccac     60
ctccacgcat acaagcggcg gctgcggctg ccagccaccg ccgccggttc atctaccgcc    120
gccggtgcat ctgccacctc cggttcacct gccacctccg gtgcatctcc caccgccggt    180
ccacctgccg ccgccggtcc acctgccacc gccggtccat gtgccgccgc cggttcatct    240
gccgccgcca ccatgccact accctactca accgccccgg cctcagcctc atccccagcc    300
acacccatgc ccgtgccaac agccgcatcc aagcccgtgc cagaccatgg tgagcaaggg    360
cgaggagctg ttcaccgggg tggtgcccat cctggtcgag ctggacggcg acgtaaacgg    420
ccacaggttc agcgtgtccg gcgagggcga gggcgatgcc acctacggca agctgaccct    480
gaagttcatc tgcaccaccg gcaagctgcc cgtgccctgg cccaccctcg tgaccaccct    540
gacctggggc gtgcagtgct tcagccgcta ccccgaccac atgaagcagc acgacttctt    600
caagtccgcc atgcccgaag gctacgtcca ggagcgtacc atcttcttca aggacgacgg    660
caactacaag acccgcgccg aggtgaagtt cgagggcgac accctggtga accgcatcga    720
gctgaagggc atcgacttca aggaggacgg caacatcctg gggcacaagc tggagtacaa    780
ctacatcagc cacaacgtct atatcaccgc cgacaagcag aagaacggca tcaaggccca    840
cttcaagatc cgccacaaca tcgaggacgg cagcgtgcag ctcgccgacc actaccagca    900
gaacacccc atcggcgacg gccccgtgct gctgcccgac aaccactacc tgagcaccca    960
```

| | |
|---|---|
| gtccgccctg agcaaagacc ccaacgagaa gcgcgatcac atggtcctgc tggagttcgt | 1020 |
| gaccgccgcc gggatcactc tcggcatgga cgagctgtac aagtaaggat cc | 1072 |

<210> SEQ ID NO 6
<211> LENGTH: 1098
<212> TYPE: DNA
<213> ORGANISM: Artificial sequence
<220> FEATURE:
<223> OTHER INFORMATION: RX3C7G-ECFP (SalI-BamHI DNA sequence cloned in pC2300)

<400> SEQUENCE: 6

| | |
|---|---|
| gtcgacacca tgaggttgtc gctcgttgcc ctcgctctcc tggctctcgc tgcgagcgcc | 60 |
| acctccacgc atacaagcgg cggcggcggc tgccagccac cgccgccggt tcatctaccg | 120 |
| ccgccggtgc atctgccacc tccggttcac ctgccacctc cggtgcatct cccaccgccg | 180 |
| gtccacctgc cgccgccggt ccacctgcca ccgccggtcc atgtgccgcc gccggttcat | 240 |
| ctgccgccgc caccatgcca ctaccctact caaccgcccc ggcctcagcc tcatccccag | 300 |
| ccacacccat gcccgtgcca acagccgcat ccaagcccgt gccaaaggcg cgccggtgga | 360 |
| ggcggaggta ccatggtgag caagggcgag gagctgttca ccggggtggt gcccatcctg | 420 |
| gtcgagctgg acggcgacgt aaacggccac aggttcagcg tgtccggcga gggcgagggc | 480 |
| gatgccacct acggcaagct gaccctgaag ttcatctgca ccaccggcaa gctgcccgtg | 540 |
| ccctggccca ccctcgtgac cacccgacc tggggcgtgc agtgcttcag ccgctacccc | 600 |
| gaccacatga gcagcacga cttcttcaag tccgccatgc ccgaaggcta cgtccaggag | 660 |
| cgtaccatct tcttcaagga cgacggcaac tacaagaccc gcgccgaggt gaagttcgag | 720 |
| ggcgacaccc tggtgaaccg catcgagctg aagggcatcg acttcaagga ggacggcaac | 780 |
| atcctgggc acaagctgga gtacaactac atcagccaca cgtctatat caccgccgac | 840 |
| aagcagaaga cggcatcaa ggcccacttc aagatccgcc acaacatcga ggacggcagc | 900 |
| gtgcagctcg ccgaccacta ccagcagaac acccccatcg gcgacggccc cgtgctgctg | 960 |
| cccgacaacc actacctgag cacccagtcc gccctgagca agacccccaa cgagaagcgc | 1020 |
| gatcacatgg tcctgctgga gttcgtgacc gccgccggga tcactctcgg catggacgag | 1080 |
| ctgtacaagt aaggatcc | 1098 |

<210> SEQ ID NO 7
<211> LENGTH: 336
<212> TYPE: DNA
<213> ORGANISM: Artificial sequence
<220> FEATURE:
<223> OTHER INFORMATION: RX3C7G DNA

<400> SEQUENCE: 7

| | |
|---|---|
| atgagggtgt tgctcgttgc cctcgctctc ctggctctcg ctgcgagcgc cacctccacg | 60 |
| catacaagcg gcggctgcgg ctgccagcca ccgccgccgg ttcatctacc gccgccgtg | 120 |
| catctgccac ctccggttca cctgccacct ccggtgcatc tcccaccgcc ggtccacctg | 180 |
| ccgccgccgg tccacctgcc accgccggtc catgtgccgc cgccggttca tctgccgccg | 240 |
| ccaccatgcc actaccctac tcaaccgccc ggcctcagc ctcatcccca gccacaccca | 300 |
| tgcccgtgcc aacagccgca tccaagcccg tgccag | 336 |

<210> SEQ ID NO 8
<211> LENGTH: 112
<212> TYPE: PRT

<213> ORGANISM: Artificial sequence
<220> FEATURE:
<223> OTHER INFORMATION: RX3C7G PROTEIN

<400> SEQUENCE: 8

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Val His Leu Pro Pro Val His Leu
                35                  40                  45

Pro Pro Pro Val His Leu Pro Pro Val His Leu Pro Pro Val
50                  55                          60

His Leu Pro Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Pro His Pro Ser Pro Cys Gln
            100                 105                 110
```

<210> SEQ ID NO 9
<211> LENGTH: 1098
<212> TYPE: DNA
<213> ORGANISM: Artificial sequence
<220> FEATURE:
<223> OTHER INFORMATION: RX3C9G-ECFP (SalI-BamHI DNA sequence cloned in pC230)

<400> SEQUENCE: 9

```
gtcgacacca tgagggtgtt gctcgttgcc ctcgctctcc tggctctcgc tgcgagcgcc      60
acctccacgc atacaagcgg cggctgcggc ggccagccac cgccgccggt tcatctaccg     120
ccgccggtgc atctgccacc tccggttcac ctgccacctc cggtgcatct cccaccgccg     180
gtccacctgc cgccgccggt ccacctgcca ccgctggtcc atgtgccgcc gccggttcat     240
ctgccgccgc caccatgcca ctaccctact caaccgcccc ggcctcagcc tcatccccag     300
ccacacccat gcccgtgcca acagccgcat ccaagcccgt gccaaaggcg cgccggtgga     360
ggcggaggta ccatggtgag caagggcgag gagctgttca ccggggtggt gcccatcctg     420
gtcgagctgg acggcgacgt aaacggccac aggttcagcg tgtccggcga gggcgagggc     480
gatgccacct acggcaagct gaccctgaag ttcatctgca ccaccggcaa gctgcccgtg     540
ccctggccca cctcgtgac cacccctgacc tggggcgtgc agtgcttcag ccgctacccc     600
gaccacatga agcagcacga cttcttcaag tccgccatgc ccgaaggcta cgtccaggag     660
cgtaccatct tcttcaagga cgacggcaac tacaagaccc gcgccgaggt gaagttcgag     720
ggcgacaccc tggtgaaccg catcgagctg aagggcatcg acttcaagga ggacggcaac     780
atcctggggc acaagctgga gtacaactac atcagccaca acgtctatat caccgccgac     840
aagcagaaga acggcatcaa ggccacttc aagatccgcc acaacatcga ggacggcagc     900
gtgcagctcg ccgaccacta ccagcagaac ccccatcg cgacggccc cgtgctgctg     960
cccgacaacc actacctgag cacccagtcc gccctgagca agacccaa cgagaagcgc    1020
gatcacatgg tcctgctgga gttcgtgacc gccgccggga tcactctcgg catggacgag    1080
ctgtacaagt aaggatcc                                                 1098
```

<210> SEQ ID NO 10
<211> LENGTH: 336

```
<212> TYPE: DNA
<213> ORGANISM: Artificial sequence
<220> FEATURE:
<223> OTHER INFORMATION: RX3C9G DNA

<400> SEQUENCE: 10
atgagggtgt tgctcgttgc cctcgctctc ctggctctcg ctgcgagcgc cacctccacg      60
catacaagcg gcggctgcgg cggccagcca ccgccgccgg ttcatctacc gccgccggtg     120
catctgccac ctccggttca cctgccacct ccggtgcatc tcccaccgcc ggtccacctg     180
ccgccgccgg tccacctgcc accgctggtc catgtgccgc cgccggttca tctgccgccg     240
ccaccatgcc actaccctac tcaaccgccc ggcctcagcc tcatccccag ccacaccca     300
tgcccgtgcc aacagccgca tccaagcccg tgccaa                              336

<210> SEQ ID NO 11
<211> LENGTH: 112
<212> TYPE: PRT
<213> ORGANISM: Artificial sequence
<220> FEATURE:
<223> OTHER INFORMATION: RX3C9G PROTEIN

<400> SEQUENCE: 11

Met Arg Val Leu Leu Val Ala Leu Ala Leu Ala Leu Ala Ala Ser
1               5                   10                  15

Ala Thr Ser Thr His Thr Ser Gly Gly Cys Gly Gly Gln Pro Pro
            20                  25                  30

Pro Val His Leu Pro Pro Val His Leu Pro Pro Val His Leu
                35                  40                  45

Pro Pro Pro Val His Leu Pro Pro Val His Leu Pro Pro Val
        50                  55                  60

His Leu Pro Pro Leu Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
                100                 105                 110

<210> SEQ ID NO 12
<211> LENGTH: 1098
<212> TYPE: DNA
<213> ORGANISM: Artificial sequence
<220> FEATURE:
<223> OTHER INFORMATION: RX3C64G -ECFP (SalI-BamHI DNA sequence cloned
      in pC2300)

<400> SEQUENCE: 12
gtcgacacca tgagggtgtt gctcgttgcc ctcgctctcc tggctctcgc tgcgagcgcc      60
acctccacgc atacaagcgg cggctgcggc tgccagccac cgccgccggt tcatctaccg     120
ccgccggtgc atctgccacc tccggttcac ctgccacctc cggtgcatct cccaccgccg     180
gtccacctgc cgccgccggt ccacctgcca ccgccggtcc atgtgccgcc gccggttcat     240
ctgccgccgc caccaggcca ctaccctact caaccgcccc ggcctcagcc tcatccccag     300
ccacacccat gcccgtgcca acagccgcat ccaagcccgt gccaaaggcg cgccggtgga     360
ggcggaggta ccatggtgag caagggcgag gagctgttca ccggggtggt gcccatcctg     420
gtcgagctgg acggcgacgt aaacggccac aggttcagcg tgtccggcga gggcgagggc     480
gatgccacct acggcaagct gaccctgaag ttcatctgca ccaccggcaa gctgcccgtg     540
```

```
cccctggccca ccctcgtgac caccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat caccgccgac    840
aagcagaaga acggcatcaa ggcccacttc aagatccgcc acaacatcga ggacggcagc    900
gtgcagctcg ccgaccacta ccagcagaac ccccatcg gcgacggccc cgtgctgctg      960
cccgacaacc actacctgag cacccagtcc gccctgagca agacccccaa cgagaagcgc   1020
gatcacatgg tcctgctgga gttcgtgacc gccgccggga tcactctcgg catggacgag   1080
ctgtacaagt aaggatcc                                                 1098
```

```
<210> SEQ ID NO 13
<211> LENGTH: 336
<212> TYPE: DNA
<213> ORGANISM: Artificial sequence
<220> FEATURE:
<223> OTHER INFORMATION: RX3C64G -ECFP DNA

<400> SEQUENCE: 13
atgagggtgt tgctcgttgc cctcgctctc ctggctctcg ctgcgagcgc cacctccacg     60
catacaagcg gcggctgcgg ctgccagcca ccgccgccgg ttcatctacc gccgccggtg    120
catctgccac ctccggttca cctgccacct ccggtgcatc tcccaccgcc ggtccacctg    180
ccgccgccgg tccacctgcc accgccggtc catgtgccgc cgccggttca tctgccgccg    240
ccaccaggcc actaccctac tcaaccgccc ggcctcagc ctcatcccca gccacaccca     300
tgcccgtgcc aacagccgca tccaagcccg tgccaa                              336
```

```
<210> SEQ ID NO 14
<211> LENGTH: 112
<212> TYPE: PRT
<213> ORGANISM: Artificial sequence
<220> FEATURE:
<223> OTHER INFORMATION: RX3C64G -ECFP PROTEIN

<400> SEQUENCE: 14

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
                20                  25                  30

Pro Val His Leu Pro Pro Pro Val His Leu Pro Pro Val His Leu
            35                  40                  45

Pro Pro Pro Val His Leu Pro Pro Val His Leu Pro Pro Pro Val
        50                  55                  60

His Leu Pro Pro Pro Val His Val Pro Pro Val His Leu Pro Pro
65                  70                  75                  80

Pro Pro Gly His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110
```

```
<210> SEQ ID NO 15
<211> LENGTH: 1098
<212> TYPE: DNA
<213> ORGANISM: Artificial sequence
<220> FEATURE:
```

<223> OTHER INFORMATION: RX3C82G -ECFP (SalI-BamHI DNA sequence cloned in pC2300)

<400> SEQUENCE: 15

```
gtcgacacca tgagggtgtt gctcgttgcc ctcgctctcc tggctctcgc tgcgagcgcc     60
acctccacgc atacaagcgg cggctgcggc tgccagccac cgccgccggt tcatctaccg    120
ccgccggtgc atctgccacc tccggttcac ctgccacctc cggtgcatct cccaccgccg    180
gtccacctgc cgccgccggt ccacctgcca ccgccggtcc atgtgccgcc gccggttcat    240
ctgccgccgc caccatgcca ctaccctact caaccgcccc ggcctcagcc tcatccccag    300
ccacacccag gcccgtgcca acagccgcat ccaagcccgt gccaaaggcg cgccggtgga    360
ggcggaggta ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgcccgtg    540
ccctggccca cctcgtgac cacccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat caccgccgac    840
aagcagaaga acggcatcaa ggcccacttc aagatccgcc acaacatcga ggacggcagc    900
gtgcagctcg ccgaccacta ccagcagaac ccccccatcg gcgacggccc cgtgctgctg    960
cccgacaacc actacctgag cacccagtcc gccctgagca agaccccaa cgagaagcgc    1020
gatcacatgg tcctgctgga gttcgtgacc gccgccggga tcactctcgg catggacgag    1080
ctgtacaagt aaggatcc                                                 1098
```

<210> SEQ ID NO 16
<211> LENGTH: 336
<212> TYPE: DNA
<213> ORGANISM: Artificial sequence
<220> FEATURE:
<223> OTHER INFORMATION: RX3C82G DNA

<400> SEQUENCE: 16

```
atgagggtgt tgctcgttgc cctcgctctc ctggctctcg ctgcgagcgc cacctccacg     60
catacaagcg gcggctgcgg ctgccagcca ccgccgccgg ttcatctacc gccgccggtg    120
catctgccac ctccggttca cctgccacct ccggtgcatc tcccaccgcc ggtccacctg    180
ccgccgccgg tccacctgcc accgccggtc catgtgccgc cgccggttca tctgccgccg    240
ccaccatgcc actaccctac tcaaccgccc cggcctcagc ctcatcccca gccacaccca    300
ggcccgtgcc aacagccgca tccaagcccg tgccaa                              336
```

<210> SEQ ID NO 17
<211> LENGTH: 112
<212> TYPE: PRT
<213> ORGANISM: Artificial sequence
<220> FEATURE:
<223> OTHER INFORMATION: RX3C82G PROTEIN

<400> SEQUENCE: 17

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
```

```
                    20                  25                  30
Pro Val His Leu Pro Pro Val His Leu Pro Pro Val His Leu
                35                  40                  45
Pro Pro Pro Val His Leu Pro Pro Val His Leu Pro Pro Val
        50                  55                  60
His Leu Pro Pro Pro Val His Val Pro Pro Val His Leu Pro Pro
 65                  70                  75                  80
Pro Pro Cys His Tyr Pro Thr Gln Pro Arg Pro Gln Pro His Pro
                85                  90                  95
Gln Pro His Pro Gly Pro Cys Gln Gln Pro His Pro Ser Pro Cys Gln
                100                 105                 110
```

<210> SEQ ID NO 18
<211> LENGTH: 1098
<212> TYPE: DNA
<213> ORGANISM: Artificial sequence
<220> FEATURE:
<223> OTHER INFORMATION: RX3C84G -ECFP (SalI-BamHI DNA sequence cloned in pC2300)

<400> SEQUENCE: 18

```
gtcgacacca tgagggtgtt gctcgttgcc ctcgctctcc tggctctcgc tgcgagcgcc      60
acctccacgc atacaagcgg cggctgcggc tgccagccac cgccgccggt tcatctaccg     120
ccgccggtgc atctgccacc tccggttcac ctgccacctc cggtgcatct cccaccgccg     180
gtccacctgc cgccgccggt ccacctgcca ccgccggtcc atgtgccgcc gccggttcat     240
ctgccgccgc caccatgcca ctaccctact caaccgcccc ggcctcagcc tcatccccag     300
ccacacccat gcccgggcca acagccgcat ccaagcccgt gccaaaggcg cgccggtgga     360
ggcggaggta ccatggtgag caagggcgag gagctgttca ccggggtggt gcccatcctg     420
gtcgagctgg acggcgacgt aaacggccac aggttcagcg tgtccggcga gggcgagggc     480
gatgccacct acggcaagct gaccctgaag ttcatctgca ccaccggcaa gctgcccgtg     540
ccctggccca ccctcgtgac caccctgacc tggggcgtgc agtgcttcag ccgctacccc     600
gaccacatga agcagcacga cttcttcaag tccgccatgc ccgaaggcta cgtccaggag     660
cgtaccatct tcttcaagga cgacggcaac tacaagaccc gcgccgaggt gaagttcgag     720
ggcgacaccc tggtgaaccg catcgagctg aagggcatcg acttcaagga ggacggcaac     780
atcctgggcg acaagctgga gtacaactac atcagccaca cgtctatat caccgccgac     840
aagcagaaga acggcatcaa ggcccacttc aagatccgcc acaacatcga ggacggcagc     900
gtgcagctcg ccgaccacta ccagcagaac accccatcg gcgacggccc cgtgctgctg     960
cccgacaacc actacctgag cacccagtcc gccctgagca agacccaa cgagaagcgc    1020
gatcacatgg tcctgctgga gttcgtgacc gccgccggga tcactctcgg catggacgag    1080
ctgtacaagt aaggatcc                                                  1098
```

<210> SEQ ID NO 19
<211> LENGTH: 336
<212> TYPE: DNA
<213> ORGANISM: Artificial sequence
<220> FEATURE:
<223> OTHER INFORMATION: RX3C84G DNA

<400> SEQUENCE: 19

```
atgagggtgt tgctcgttgc cctcgctctc tggctctcg ctgcgagcgc cacctccacg      60
catacaagcg gcggctgcgg ctgccagcca ccgccgccgg ttcatctacc gccgccggtg     120
```

```
catctgccac ctccggttca cctgccacct ccggtgcatc tcccaccgcc ggtccacctg      180
ccgccgccgg tccacctgcc accgccggtc catgtgccgc cgccggttca tctgccgccg      240
ccaccatgcc actaccctac tcaaccgccc cggcctcagc ctcatcccca gccacaccca      300
tgcccgggcc aacagccgca tccaagcccg tgccaa                                336
```

<210> SEQ ID NO 20
<211> LENGTH: 112
<212> TYPE: PRT
<213> ORGANISM: Artificial sequence
<220> FEATURE:
<223> OTHER INFORMATION: RX3C84G PROTEIN

<400> SEQUENCE: 20

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
            35                  40                  45

Pro Pro Pro Val His Leu Pro Pro Val His Leu Pro Pro Val
    50                  55                  60

His Leu Pro Pro Pro Val His Val Pro Pro Val His Leu Pro Pro
65                  70                  75                  80

Pro Pro Cys His Tyr Pro Thr Gln Pro Pro Arg Pro Gln His Pro
                85                  90                  95

Gln Pro His Pro Cys Pro Gly Gln Gln Pro His Pro Ser Pro Cys Gln
            100                 105                 110
```

<210> SEQ ID NO 21
<211> LENGTH: 1098
<212> TYPE: DNA
<213> ORGANISM: Artificial sequence
<220> FEATURE:
<223> OTHER INFORMATION: RX3C92G -ECFP (SalI-BamHI DNA sequence cloned
      in pC2300)

<400> SEQUENCE: 21

```
gtcgacacca tgagggtgtt gctcgttgcc ctcgctctcc tggctctcgc tgcgagcgcc      60
acctccacgc atacaagcgg cggctgcggc tgccagccac cgccgccggt tcatctaccg      120
ccgccggtgc atctgccacc tccggttcac ctgccacctc cggtgcatct cccaccgccg      180
gtccacctgc cgccgccggt ccacctgcca ccgccggtcc atgtgccgcc gccggttcat      240
ctgccgccgc caccatgcca ctaccctact caaccgcccc ggcctcagcc tcatccccag      300
ccacacccat gccgtgccaa cagccgcatc caagcccggc caaaggcgcg ccggtggag      360 ggcggaggta ccatggtgag caagggcgag gagctgttca ccggggtggt gcccatcctg      420
gtcgagctgg acggcgacgt aaacggccac aggttcagcg tgtccggcga gggcgagggc      480
gatgccacct acggcaagct gaccctgaag ttcatctgca ccaccggcaa gctgcccgtg      540
ccctggccca cctcgtgac cacccctgacc tggggcgtgc agtgcttcag ccgctacccc      600
gaccacatga agcagcacga cttcttcaag tccgccatgc ccgaaggcta cgtccaggag      660
cgtaccatct tcttcaagga cgacggcaac tacaagaccc gcgccgaggt gaagttcgag      720
ggcgacaccc tggtgaaccg catcgagctg aagggcatcg acttcaagga ggacggcaac      780
atcctggggc acaagctgga gtacaactac atcagccaca acgtctatat caccgccgac      840
```

```
aagcagaaga acggcatcaa ggcccacttc aagatccgcc acaacatcga ggacggcagc    900
gtgcagctcg ccgaccacta ccagcagaac accccccatcg cgacggccc cgtgctgctg   960 cccgacaacc actacctgag cacccagtcc gccctgagca agaccccaa cgagaagcgc   1020 gatcacatgg tcctgctgga gttcgtgacc gccgccggga tcactctcgg catggacgag   1080
ctgtacaagt aaggatcc                                                 1098

<210> SEQ ID NO 22
<211> LENGTH: 336
<212> TYPE: DNA
<213> ORGANISM: Artificial sequence
<220> FEATURE:
<223> OTHER INFORMATION: RX3C92G DNA

<400> SEQUENCE: 22
atgagggtgt tgctcgttgc cctcgctctc ctggctctcg ctgcgagcgc cacctccacg    60
catacaagcg gcggctgcgg ctgccagcca ccgccgccgg ttcatctacc gccgccggtg   120
catctgccac ctccggttca cctgccacct ccggtgcatc tcccaccgcc ggtccacctg   180
ccgccgccgg tccacctgcc accgccggtc catgtgccgc cgccggttca tctgccgccg   240
ccaccatgcc actaccctac tcaaccgccc ggcctcagc ctcatcccca gccacaccca    300
tgcccgtgcc aacagccgca tccaagcccg ggccaa                             336

<210> SEQ ID NO 23
<211> LENGTH: 112
<212> TYPE: PRT
<213> ORGANISM: Artificial sequence
<220> FEATURE:
<223> OTHER INFORMATION: RX3C92G Protein

<400> SEQUENCE: 23

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Gly Gln
            100                 105                 110

<210> SEQ ID NO 24
<211> LENGTH: 1098
<212> TYPE: DNA
<213> ORGANISM: Artificial sequence
<220> FEATURE:
<223> OTHER INFORMATION: RX3C64,82,84,92G -ECFP (SalI-BamHI DNA sequence
      cloned in pC2300)

<400> SEQUENCE: 24
gtcgacacca tgagggtgtt gctcgttgcc ctcgctctcc tggctctcgc tgcgagcgcc    60
acctccacgc atacaagcgg cggctgcggc tgccagccac cgccgccggt tcatctaccg   120
ccgccggtgc atctgccacc tccggttcac ctgccacctc cggtgcatct cccaccgccg   180
```

```
gtccacctgc cgccgccggt ccacctgcca ccgccggtcc atgtgccgcc gccggttcat    240
ctgccgccgc caccaggcca ctaccctact caaccgcccc ggcctcagcc tcatccccag    300
ccacacccag gcccgggcca acagccgcat ccaagcccgg gccaaaggcg cgccggtgga    360
ggcggaggta ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgccgtg     540 ccctggccca ccctcgtgac caccctgacc tggggcgtgc agtgcttcag ccgctacccc    600
gaccacatga gcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca cgtctatat caccgccgac    840 aagcagaaga acggcatcaa ggcccacttc aagatccgcc acaacatcga ggacggcagc    900
gtgcagctcg ccgaccacta ccagcagaac ccccatcg cgacggccc cgtgctgctg       960 cccgacaacc actacctgag cacccagtcc gccctgagca agacccaa cgagaagcgc     1020 gatcacatgg tcctgctgga gttcgtgacc gccgccggga tcactctcgg catggacgag   1080
ctgtacaagt aaggatcc                                                 1098

<210> SEQ ID NO 25
<211> LENGTH: 336
<212> TYPE: DNA
<213> ORGANISM: Artificial sequence
<220> FEATURE:
<223> OTHER INFORMATION: RX3C64,82,84,92G DNA

<400> SEQUENCE: 25
atgagggtgt tgctcgttgc cctcgctctc ctggctctcg ctgcgagcgc cacctccacg     60
catacaagcg gcggctgcgg ctgccagcca ccgccgccgg ttcatctacc gccgccggtg    120
catctgccac ctccggttca cctgccacct ccggtgcatc tcccaccgcc ggtccacctg    180
ccgccgccgg tccacctgcc accgccggtc catgtgccgc cgccggttca tctgccgccg    240
ccaccaggcc actaccctac tcaaccgccc cggcctcagc ctcatcccca gccacaccca    300
ggcccgggcc aacagccgca tccaagcccg ggccaa                              336

<210> SEQ ID NO 26
<211> LENGTH: 112
<212> TYPE: PRT
<213> ORGANISM: Artificial sequence
<220> FEATURE:
<223> OTHER INFORMATION: RX3C64,82,84,92G Protein

<400> SEQUENCE: 26

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
                20                  25                  30

Pro Val His Leu Pro Pro Pro Val His Leu Pro Pro Val His Leu
            35                  40                  45

Pro Pro Pro Val His Leu Pro Pro Val His Leu Pro Pro Val
        50                  55                  60

His Leu Pro Pro Pro Val His Val Pro Pro Val His Leu Pro Pro
65                  70                  75                  80
```

Pro Pro Gly His Tyr Pro Thr Gln Pro Pro Arg Pro Gln Pro His Pro
                85                  90                  95

Gln Pro His Pro Gly Pro Gly Gln Gln Pro His Pro Ser Pro Gly Gln
            100                 105                 110

<210> SEQ ID NO 27
<211> LENGTH: 1098
<212> TYPE: DNA
<213> ORGANISM: Artificial sequence
<220> FEATURE:
<223> OTHER INFORMATION: RX3C82,84,92G -ECFP (SalI-BamHI DNA sequence
      cloned in pC2300)

<400> SEQUENCE: 27

| | |
|---|---|
| gtcgacacca tgagggtgtt gctcgttgcc ctcgctctcc tggctctcgc tgcgagcgcc | 60 |
| acctccacgc atacaagcgg cggctgcggc tgccagccac cgccgccggt tcatctaccg | 120 |
| ccgccggtgc atctgccacc tccggttcac ctgccacctc cggtgcatct cccaccgccg | 180 |
| gtccacctgc cgccgccggt ccacctgcca ccgccggtca tgtgccgcc gccggttcat | 240 |
| ctgccgccgc caccatgcca ctaccctact caaccgcccc ggcctcagcc tcatccccag | 300 |
| ccacacccag gcccgggcca acagccgcat ccaagcccgg ccaaaggcg cgccggtgga | 360 |
| ggcggaggta ccatggtgag caagggcgag gagctgttca ccggggtggt gcccatcctg | 420 |
| gtcgagctgg acggcgacgt aaacggccac aggttcagcg tgtccggcga gggcgagggc | 480 |
| gatgccacct acggcaagct gaccctgaag ttcatctgca ccaccggcaa gctgcccgtg | 540 |
| ccctggccca cctcgtgac cacctgacc tggggcgtgc agtgcttcag ccgctacccc | 600 |
| gaccacatga agcagcacga cttcttcaag tccgccatgc ccgaaggcta cgtccaggag | 660 |
| cgtaccatct tcttcaagga cgacggcaac tacaagaccc gcgccgaggt gaagttcgag | 720 |
| ggcgacaccc tggtgaaccg catcgagctg aagggcatcg acttcaagga ggacggcaac | 780 |
| atcctggggc acaagctgga gtacaactac atcagccaca cgtctatat caccgccgac | 840 |
| aagcagaaga acggcatcaa ggcccacttc aagatccgcc acaacatcga ggacggcagc | 900 |
| gtgcagctcg ccgaccacta ccagcagaac ccccccatcg gcgacggccc cgtgctgctg | 960 |
| cccgacaacc actacctgag cacccagtcc gccctgagca agacccccaa cgagaagcgc | 1020 |
| gatcacatgg tcctgctgga gttcgtgacc gccgccggga tcactctcgg catggacgag | 1080 |
| ctgtacaagt aaggatcc | 1098 |

<210> SEQ ID NO 28
<211> LENGTH: 336
<212> TYPE: DNA
<213> ORGANISM: Artificial sequence
<220> FEATURE:
<223> OTHER INFORMATION: RX3C82,84,92G DNA

<400> SEQUENCE: 28

| | |
|---|---|
| atgagggtgt tgctcgttgc cctcgctctc ctggctctcg ctgcgagcgc cacctccacg | 60 |
| catacaagcg gcggctgcgg ctgccagcca ccgccgccgg ttcatctacc gccgccggtg | 120 |
| catctgccac ctccggttca cctgccacct ccggtgcatc tcccaccgcc ggtccacctg | 180 |
| ccgccgccgg tccacctgcc accgccggtc atgtgccgc gccggttca tctgccgccg | 240 |
| ccaccatgcc actaccctac tcaaccgccc cggcctcagc ctcatcccca gccacaccca | 300 |
| ggcccgggcc aacagccgca tccaagcccg ggccaa | 336 |

<210> SEQ ID NO 29
<211> LENGTH: 112
<212> TYPE: PRT
<213> ORGANISM: Artificial sequence
<220> FEATURE:
<223> OTHER INFORMATION: RX3C82,84,92G Protein

<400> SEQUENCE: 29

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Val His Leu
        35                  40                  45

Pro Pro Pro Val His Leu Pro Pro Val His Leu Pro Pro Val
50                  55                  60

His Leu Pro Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Gly Pro Gly Gln Gln Pro His Pro Ser Pro Gly Gln
            100                 105                 110
```

<210> SEQ ID NO 30
<211> LENGTH: 1098
<212> TYPE: DNA
<213> ORGANISM: Artificial sequence
<220> FEATURE:
<223> OTHER INFORMATION: RX3C7,9G -ECFP (SalI-BamHI DNA sequence cloned in pC2300)

<400> SEQUENCE: 30

```
gtcgacacca tgaggttgtc gctcgttgcc ctcgctctcc tggctctcgc tgcgagcgcc      60
acctccacgc atacaagcgg cggcggcggc ggccagccac cgccgccggt tcatctaccg     120
ccgccggtgc atctgccacc tccggttcac ctgccacctc cggtgcatct cccaccgccg     180
gtccacctgc cgccgccggt ccacctgcca ccgccggtcc atgtgccgcc gccggttcat     240
ctgccgccgc caccatgcca ctaccctact caaccgcccc ggcctcagcc tcatccccag     300
ccacacccat gcccgtgcca acagccgcat ccaagcccgt gccaaaggcg cgccggtgga     360
ggcggaggta ccatggtgag caagggcgag gagctgttca ccggggtggt gcccatcctg     420
gtcgagctgg acggcgacgt aaacggccac aggttcagcg tgtccggcga gggcgagggc     480
gatgccacct acggcaagct gaccctgaag ttcatctgca ccaccggcaa gctgcccgtg     540
ccctggccca ccctcgtgac caccctgacc tggggcgtgc agtgcttcag ccgctacccc     600
gaccacatga agcagcacga cttcttcaag tccgccatgc ccgaaggcta cgtccaggag     660
cgtaccatct tcttcaagga cgacggcaac tacaagaccc gcgccgaggt gaagttcgag     720
ggcgacaccc tggtgaaccg catcgagctg aagggcatcg acttcaagga ggacggcaac     780
atcctgggca caagctgga gtacaactac atcagccaca acgtctatat caccgccgac     840
aagcagaaga acggcatcaa ggcccacttc aagatccgcc acaacatcga ggacggcagc     900
gtgcagctcg ccgaccacta ccagcagaac ccccccatcg gcgacggccc cgtgctgctg     960
cccgacaacc actacctgag cacccagtcc gccctgagca agacccccaa cgagaagcgc    1020
gatcacatgg tcctgctgga gttcgtgacc gccgccggga tcactctcgg catggacgag    1080
ctgtacaagt aaggatcc                                                  1098
```

<210> SEQ ID NO 31
<211> LENGTH: 336
<212> TYPE: DNA
<213> ORGANISM: Artificial sequence
<220> FEATURE:
<223> OTHER INFORMATION: RX3C7,9G DNA

<400> SEQUENCE: 31

```
atgaggttgt cgctcgttgc cctcgctctc ctggctctcg ctgcgagcgc cacctccacg     60
catacaagcg gcggcggcgg cggccagcca ccgccgccgg ttcatctacc gccgccggtg    120
catctgccac ctccggttca cctgccacct ccggtgcatc tcccaccgcc ggtccacctg    180
ccgccgccgg tccacctgcc accgccggtc catgtgccgc cgccggttca tctgccgccg    240
ccaccatgcc actaccctac tcaaccgccc cggcctcagc ctcatcccca gccacaccca    300
tgcccgtgcc aacagccgca tccaagcccg tgccaa                              336
```

<210> SEQ ID NO 32
<211> LENGTH: 112
<212> TYPE: PRT
<213> ORGANISM: Artificial sequence
<220> FEATURE:
<223> OTHER INFORMATION: RX3C7,9G Protein

<400> SEQUENCE: 32

```
Met Arg Leu Ser Leu Val Ala Leu Ala Leu Leu Ala Leu Ala Ala Ser
1               5                  10                  15

Ala Thr Ser Thr His Thr Ser Gly Gly Gly Gly Gln Pro Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110
```

<210> SEQ ID NO 33
<211> LENGTH: 1098
<212> TYPE: DNA
<213> ORGANISM: Artificial sequence
<220> FEATURE:
<223> OTHER INFORMATION: PP -ECFP (SalI-BamHI DNA sequence cloned in pC2300)

<400> SEQUENCE: 33

```
gtcgacacca tgagagttct tttggtggct cttgctcttt tggctcttgc tgcttctgct     60
acttctactc acactagtgg tggttgtggt tgtcaaccac ctcctcctcc accaccgcct    120
ccgcctccac ctccccccac ccacccccg ccaccaccc ctccaccgcc accgccacct    180
ccgccgcctc cccccacc cctcctccg cccctcctc ctcctccccc gccacctcac    240
ctgcccccc ctccctgtcc tccgccgcca ccgcctcccc caccaccacc acctccccca    300
ccgcctccat gtccttgtcc accgccccca cccgccctt gtccaaggcg cgccggaggt    360
ggaggtggaa ccatggtgag caagggcgag gagctgttca ccggggtggt gcccatcctg    420
gtcgagctgg acggcgacgt aaacggccac aggttcagcg tgtccggcga gggcgagggc    480
```

```
gatgccacct acggcaagct gaccctgaag ttcatctgca ccaccggcaa gctgcccgtg    540
ccctggccca ccctcgtgac caccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca cgtctatat caccgccgac    840 aagcagaaga acggcatcaa ggcccacttc aagatccgcc acaacatcga ggacggcagc    900
gtgcagctcg ccgaccacta ccagcagaac cccccatcg cgacggccc cgtgctgctg    960 cccgacaacc actacctgag cacccagtcc gccctgagca agacccccaa cgagaagcgc    1020
gatcacatgg tcctgctgga gttcgtgacc gccgccggga tcactctcgg catggacgag    1080
ctgtacaagt aaggatcc                                                  1098

<210> SEQ ID NO 34
<211> LENGTH: 336
<212> TYPE: DNA
<213> ORGANISM: Artificial sequence
<220> FEATURE:
<223> OTHER INFORMATION: PP DNA

<400> SEQUENCE: 34
atgagagttc ttttggtggc tcttgctctt ttggctcttg ctgcttctgc tacttctact    60
cacactagtg gtggttgtgg ttgtcaacca cctcctcctc caccaccgcc tccgcctcca    120
cctcccccac ctccaccccc gccaccaccc cctccaccgc caccgccacc tccgccgcct    180 cccccccac ccctcctcc gccccctcct cctcctcccc cgccacctca cctgccccca    240 cctcctgtc ctccgccgcc accgcctccc ccaccaccac cacctccccc accgcctcca    300
tgtccttgtc caccgccccc accccgcct tgtcca                              336

<210> SEQ ID NO 35
<211> LENGTH: 112
<212> TYPE: PRT
<213> ORGANISM: Artificial sequence
<220> FEATURE:
<223> OTHER INFORMATION: PP Protein (including 19 aa signal peptide)

<400> SEQUENCE: 35

Met Arg Val Leu Leu Val Ala Leu Ala Leu Leu Ala Leu Ala Ala Ser
1               5                  10                  15

Ala Thr Ser Thr His Thr Ser Gly Gly Cys Gly Cys Gln Pro Pro
            20                  25                  30

Pro Pro Pro Pro Pro Pro Pro Pro Pro Pro Pro Pro Pro Pro Pro
        35                  40                  45

Pro Pro Pro Pro Pro Pro Pro Pro Pro Pro Pro Pro Pro Pro Pro
    50                  55                  60

Pro Pro Pro Pro Pro Pro Pro Pro Pro Pro Pro His Leu Pro Pro
65                  70                  75                  80

Pro Pro Cys Pro Pro Pro Pro Pro Pro Pro Pro Pro Pro Pro Pro
                85                  90                  95

Pro Pro Pro Pro Cys Pro Cys Pro Pro Pro Pro Pro Pro Cys Pro
            100                 105                 110

<210> SEQ ID NO 36
<211> LENGTH: 1098
```

-continued

```
<212> TYPE: DNA
<213> ORGANISM: Artificial sequence
<220> FEATURE:
<223> OTHER INFORMATION: PA -ECFP (SalI-BamHI DNA sequence cloned in
      pC2300)

<400> SEQUENCE: 36
gtcgacacca tgagagttct tttggtggct cttgctcttt tggctcttgc tgcttctgct     60
acttctactc acactagtgg tggttgtggt tgtcaacctc ctcctcctgc tcctgcacct    120
cctccagctc cagctccacc accagcccct gctccacctc ctgcaccagc tcctccgcct    180
gcaccggcac caccaccagc accagcccct ccaccggctc cagcacctcc ccctgctcac    240
ctgccacctc caccttgtcc tccacccgca ccagctccgc ctccagctcc tgccccgcca    300
cccgctccat gtccttgtcc tgcccctgct cctccaccat gtccaaggcg cgccggaggt    360
ggaggtggaa ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgcccgtg    540
ccctggccca ccctcgtgac caccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat caccgccgac    840
aagcagaaga acggcatcaa ggcccacttc aagatccgcc acaacatcga ggacggcagc    900
gtgcagctcg ccgaccacta ccagcagaac cccccatcg gcgacggccc cgtgctgctg    960
cccgacaacc actacctgag cacccagtcc gccctgagca agaccccaa cgagaagcgc   1020 gatcacatgg tcctgctgga gttcgtgacc gccgccggga tcactctcgg catggacgag   1080
ctgtacaagt aaggatcc                                                 1098

<210> SEQ ID NO 37
<211> LENGTH: 336
<212> TYPE: DNA
<213> ORGANISM: Artificial sequence
<220> FEATURE:
<223> OTHER INFORMATION: PA DNA

<400> SEQUENCE: 37
atgagagttc ttttggtggc tcttgctctt ttggctcttg ctgcttctgc tacttctact     60
cacactagtg gtggttgtgg ttgtcaacct cctcctcctg ctcctgcacc tcctccagct    120
ccagctccac caccagcccc tgctccacct cctgcaccag ctcctccgcc tgcaccggca    180
ccaccaccag caccagcccc tccaccggct ccagcacctc ccctgctca cctgccacct    240 ccaccttgtc ctcacccgc accagctccg cctccagctc ctgccccgcc acccgctcca    300
tgtccttgtc ctgcccctgc tcctccacca tgtcca                             336

<210> SEQ ID NO 38
<211> LENGTH: 112
<212> TYPE: PRT
<213> ORGANISM: Artificial sequence
<220> FEATURE:
<223> OTHER INFORMATION: PA Protein

<400> SEQUENCE: 38

Met Arg Val Leu Leu Val Ala Leu Ala Leu Leu Ala Leu Ala Ala Ser
```

```
              1               5                  10                 15
Ala Thr Ser Thr His Thr Ser Gly Gly Cys Gly Cys Gln Pro Pro
             20                  25                 30
Pro Ala Pro Ala Pro Pro Pro Ala Pro Ala Pro Pro Ala Pro Ala
             35                  40                 45
Pro Pro Pro Ala Pro Ala Pro Pro Pro Ala Pro Ala Pro Pro Ala
             50                  55                 60
Pro Ala Pro Pro Pro Ala Pro Ala Pro Pro Ala His Leu Pro Pro
   65                70                   75             80
Pro Pro Cys Pro Pro Pro Ala Pro Ala Pro Pro Ala Pro Ala Pro
                85                 90                 95
Pro Pro Ala Pro Cys Pro Cys Pro Ala Pro Ala Pro Pro Cys Pro
             100                 105                110
```

```
<210> SEQ ID NO 39
<211> LENGTH: 1008
<212> TYPE: DNA
<213> ORGANISM: Artificial sequence
<220> FEATURE:
<223> OTHER INFORMATION: R8(C4)-ECFP (SalI-BamHI DNA sequence cloned
      in pC2300)

<400> SEQUENCE: 39
gtcgacacca tgagggtgtt gctcgttgcc ctcgctctcc tggctctcgc tgcgagcgcc     60
acctccacgc atacaagcgg cggctgcggc tgccagccac cgccgcctgt acatcttcca    120
ccaccagttc atttgcctcc acctgttcac cttcctccac ctgtgcactt gccacctcca    180
gtgcatcttc ctcctccagt tcaccttcca ccaccagtgc atgttccacc acctgttcac    240
ttgccaccac caccatgtcc tccctgtgga ggcggaggta ccatggtgag caagggcgag    300
gagctgttca ccggggtggt gcccatcctg gtcgagctgg acggcgacgt aaacggccac    360
aggttcagcg tgtccggcga gggcgagggc gatgccacct acggcaagct gaccctgaag    420
ttcatctgca ccaccggcaa gctgcccgtg ccctggccca ccctcgtgac cacccctgacc    480 tggggcgtgc agtgcttcag ccgctacccc gaccacatga gcagcacga cttcttcaag    540 tccgccatgc ccgaaggcta cgtccaggag cgtaccatct tcttcaagga cgacggcaac    600
tacaagaccc gcgccgaggt gaagttcgag ggcgacaccc tggtgaaccg catcgagctg    660
aagggcatcg acttcaagga ggacggcaac atcctggggc acaagctgga gtacaactac    720
atcagccaca acgtctatat caccgccgac aagcagaaga acggcatcaa ggcccacttc    780
aagatccgcc acaacatcga ggacggcagc gtgcagctcg ccgaccacta ccagcagaac    840
acccccatcg gcgacggccc cgtgctgctg cccgacaacc actacctgag cacccagtcc    900
gccctgagca agaccccaa cgagaagcgc gatcacatgg tcctgctgga gttcgtgacc    960
gccgccggga tcactctcgg catggacgag ctgtacaagt aaggatcc              1008
```

```
<210> SEQ ID NO 40
<211> LENGTH: 258
<212> TYPE: DNA
<213> ORGANISM: Artificial sequence
<220> FEATURE:
<223> OTHER INFORMATION: R8(C4) DNA

<400> SEQUENCE: 40
atgagggtgt tgctcgttgc cctcgctctc ctggctctcg ctgcgagcgc cacctccacg     60
catacaagcg gcggctgcgg ctgccagcca ccgccgcctg tacatcttcc accaccagtt    120
```

```
catttgcctc cacctgttca ccttcctcca cctgtgcact tgccacctcc agtgcatctt    180
cctcctccag ttcaccttcc accaccagtg catgttccac cacctgttca cttgccacca    240
ccaccatgtc ctccctgt                                                  258
```

<210> SEQ ID NO 41
<211> LENGTH: 86
<212> TYPE: PRT
<213> ORGANISM: Artificial sequence
<220> FEATURE:
<223> OTHER INFORMATION: R8(C4) Protein

<400> SEQUENCE: 41

```
Met Arg Val Leu Leu Val Ala Leu Ala Leu Ala Leu Ala Ala Ser
1               5                   10                  15

Ala Thr Ser Thr His Thr Ser Gly Gly Cys Gly Cys Gln Pro Pro
                20                  25                  30

Pro Val His Leu Pro Pro Val His Leu Pro Pro Val His Leu
                35                  40                  45

Pro Pro Pro Val His Leu Pro Pro Val His Leu Pro Pro Val
        50                  55                  60

His Leu Pro Pro Pro Val His Val Pro Pro Val His Leu Pro Pro
65                  70                  75                  80

Pro Pro Cys Pro Pro Cys
                85
```

<210> SEQ ID NO 42
<211> LENGTH: 987
<212> TYPE: DNA
<213> ORGANISM: Artificial sequence
<220> FEATURE:
<223> OTHER INFORMATION: R7(C4)-ECFP (SalI-BamHI DNA sequence cloned in pC2300)

<400> SEQUENCE: 42

```
gtcgacacca tgagggtgtt gctcgttgcc ctcgctctcc tggctctcgc tgcgagcgcc     60
acctccacgc atacaagcgg cggctgcggc tgccagccac cgccgcctgt acatctaccg    120
ccgccggtgc atctgccacc tccggtgcac ctgccacctc cggtgcatct cccaccgccg    180
gtccacctgc cgccgccggt ccacctgcca ccgccggtcc atgtgccacc accatgtcct    240
ccctgtggag gcggaggtac catggtgagc aagggcgagg agctgttcac cggggtggtg    300
cccatcctgg tcgagctgga cggcgacgta acggccaca ggttcagcgt gtccggcgag    360
ggcgagggcg atgccaccta cggcaagctg accctgaagt tcatctgcac caccggcaag    420
ctgcccgtgc cctggcccac cctcgtgacc accctgacct ggggcgtgca gtgcttcagc    480
cgctaccccg accacatgaa gcagcacgac ttcttcaagt ccgccatgcc cgaaggctac    540
gtccaggagc gtaccatctt cttcaaggac gacggcaact acaagacccg cgccgaggtg    600
aagttcgagg gcgacaccct ggtgaaccgc atcgagctga agggcatcga cttcaaggag    660
gacggcaaca tcctggggca caagctggag tacaactaca tcagccacaa cgtctatatc    720
accgccgaca agcagaagaa cggcatcaag gcccacttca gatccgccaa caacatcgag    780
gacggcagcg tgcagctcgc cgaccactac cagcagaaca cccccatcgg cgacggcccc    840
gtgctgctgc ccgacaacca ctacctgagc acccagtccg ccctgagcaa agaccccaac    900
gagaagcgcg atcacatggt cctgctggag ttcgtgaccg ccgccgggat cactctcggc    960
atggacgagc tgtacaagta aggatcc                                        987
```

<210> SEQ ID NO 43
<211> LENGTH: 237
<212> TYPE: DNA
<213> ORGANISM: Artificial sequence
<220> FEATURE:
<223> OTHER INFORMATION: R7(C4) DNA

<400> SEQUENCE: 43

```
atgagggtgt tgctcgttgc cctcgctctc ctggctctcg ctgcgagcgc cacctccacg      60
catacaagcg gcggctgcgg ctgccagcca ccgccgcctg tacatctacc gccgccggtg     120
catctgccac ctccggtgca cctgccacct ccggtgcatc tcccaccgcc ggtccacctg     180
ccgccgccgg tccacctgcc accgccggtc catgtgccac caccatgtcc tccctgt       237
```

<210> SEQ ID NO 44
<211> LENGTH: 79
<212> TYPE: PRT
<213> ORGANISM: Artificial sequence
<220> FEATURE:
<223> OTHER INFORMATION: R7(C4) Protein

<400> SEQUENCE: 44

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Cys Pro Pro Cys
65                  70                  75
```

<210> SEQ ID NO 45
<211> LENGTH: 969
<212> TYPE: DNA
<213> ORGANISM: Artificial sequence
<220> FEATURE:
<223> OTHER INFORMATION: R6(C4)-ECFP (SalI-BamHI DNA sequence cloned in pC2300)

<400> SEQUENCE: 45

```
gtcgacacca tgagggtgtt gctcgttgcc ctcgctctcc tggctctcgc tgcgagcgcc      60
acctccacgc atacaagcgg cggctgcggc tgccagccac cgccgcctgt acatctaccg     120
ccgccggtgc atctgccacc tccggtgcac ctgccacctc cggtgcatct cccaccgccg     180
gtccacctgc cgccgccggt ccacctgcca ccaccatgtc ctccctgtgg aggcggaggt     240
accatggtga gcaagggcga ggagctgttc accggggtgg tgcccatcct ggtcgagctg     300
gacggcgacg taaacggcca caggttcagc gtgtccggcg agggcgaggg cgatgccacc     360
tacggcaagc tgaccctgaa gttcatctgc accaccggca agctgcccgt gccctggccc     420
accctcgtga ccaccctgac ctggggcgtg cagtgcttca gccgctaccc cgaccacatg     480
aagcagcacg acttcttcaa gtccgccatg cccgaaggct acgtccagga cgtaccatc     540 ttcttcaagg acgacggcaa ctacaagacc cgcgccgagg tgaagttcga gggcgacacc     600
ctggtgaacc gcatcgagct gaagggcatc gacttcaagg aggacggcaa catcctgggg     660
cacaagctgg agtacaacta catcagccac aacgtctata tcaccgccga caagcagaag     720
aacggcatca aggcccactt caagatccgc cacaacatcg aggacggcag cgtgcagctc     780
```

```
gccgaccact accagcagaa caccccatc ggcgacggcc ccgtgctgct gcccgacaac      840
cactacctga gcacccagtc cgccctgagc aaagaccca acgagaagcg cgatcacatg      900
gtcctgctgg agttcgtgac cgccgccggg atcactctcg gcatggacga gctgtacaag      960
taaggatcc                                                              969

<210> SEQ ID NO 46
<211> LENGTH: 219
<212> TYPE: DNA
<213> ORGANISM: Artificial sequence
<220> FEATURE:
<223> OTHER INFORMATION: R6(C4) DNA

<400> SEQUENCE: 46
atgagggtgt tgctcgttgc cctcgctctc ctggctctcg ctgcgagcgc cacctccacg      60
catacaagcg gcggctgcgg ctgccagcca ccgccgcctg tacatctacc gccgccggtg     120
catctgccac ctccggtgca cctgccacct ccggtgcatc tcccaccgcc ggtccacctg     180
ccgccgccgg tccacctgcc accaccatgt cctccctgt                             219

<210> SEQ ID NO 47
<211> LENGTH: 73
<212> TYPE: PRT
<213> ORGANISM: Artificial sequence
<220> FEATURE:
<223> OTHER INFORMATION: R6(C4) Protein

<400> SEQUENCE: 47

Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Cys Pro Pro Cys
65                  70

<210> SEQ ID NO 48
<211> LENGTH: 933
<212> TYPE: DNA
<213> ORGANISM: Artificial sequence
<220> FEATURE:
<223> OTHER INFORMATION: R4(C4)-ECFP (SalI-BamHI DNA sequence cloned in
      pC2300)

<400> SEQUENCE: 48
gtcgacacca tgagggtgtt gctcgttgcc ctcgctctcc tggctctcgc tgcgagcgcc      60
acctccacgc atacaagcgg cggctgcggc tgccagccac cgccgcctgt acatctaccg     120
ccgccggtgc atctgccacc tccggtgcac ctgccaccgc cggtccatgt gccaccacca     180
tgtcctccct gtggaggcgg aggtaccatg gtgagcaagg gcgaggagct gttcaccggg     240
gtggtgccca tcctggtcga gctggacggc gacgtaaacg gccacaggtt cagcgtgtcc     300
ggcgagggcg agggcgatgc cacctacggc aagctgaccc tgaagttcat ctgcaccacc     360
ggcaagctgc ccgtgccctg gcccaccctc gtgaccaccc tgacctgggg cgtgcagtgc     420
ttcagccgct accccgacca catgaagcag cacgacttct tcaagtccgc catgcccgaa     480
```

-continued

```
ggctacgtcc aggagcgtac catcttcttc aaggacgacg gcaactacaa gacccgcgcc    540
gaggtgaagt tcgagggcga caccctggtg aaccgcatcg agctgaaggg catcgacttc    600
aaggaggacg gcaacatcct ggggcacaag ctggagtaca actacatcag ccacaacgtc    660
tatatcaccg ccgacaagca gaagaacggc atcaaggccc acttcaagat ccgccacaac    720
atcgaggacg gcagcgtgca gctcgccgac cactaccagc agaacacccc catcggcgac    780
ggccccgtgc tgctgcccga caaccactac ctgagcaccc agtccgccct gagcaaagac    840
cccaacgaga agcgcgatca catggtcctg ctggagttcg tgaccgccgc cgggatcact    900
ctcggcatgg acgagctgta caagtaagga tcc                                933
```

<210> SEQ ID NO 49
<211> LENGTH: 183
<212> TYPE: DNA
<213> ORGANISM: Artificial sequence
<220> FEATURE:
<223> OTHER INFORMATION: R4(C4) DNA

<400> SEQUENCE: 49

```
atgagggtgt tgctcgttgc cctcgctctc ctggctctcg ctgcgagcgc cacctccacg     60
catacaagcg gcggctgcgg ctgccagcca ccgccgcctg tacatctacc gccgccggtg    120
catctgccac ctccggtgca cctgccaccg ccggtccatg tgccaccacc atgtcctccc    180
tgt                                                                 183
```

<210> SEQ ID NO 50
<211> LENGTH: 61
<212> TYPE: PRT
<213> ORGANISM: Artificial sequence
<220> FEATURE:
<223> OTHER INFORMATION: R4(C4) Protein

<400> SEQUENCE: 50

```
Met Arg Val Leu Leu Val Ala Leu Ala Leu Leu Ala Leu Ala Ala Ser
  1               5                  10                  15

Ala Thr Ser Thr His Thr Ser Gly Gly Cys Gly Cys Gln Pro Pro Pro
             20                  25                  30

Pro Val His Leu Pro Pro Val His Leu Pro Pro Val His Leu
             35                  40              45

Pro Pro Pro Val His Val Pro Pro Pro Cys Pro Pro Cys
    50                  55                  60
```

<210> SEQ ID NO 51
<211> LENGTH: 1115
<212> TYPE: DNA
<213> ORGANISM: Artificial sequence
<220> FEATURE:
<223> OTHER INFORMATION: RX3(PR10)-ECFP (SalI-BamHI DNA sequence cloned
      in pC2300)

<400> SEQUENCE: 51

```
gtcgacccat gaatttcctc aaaagttttcc ccttttatgc cttcctttgt tttggccaat     60
actttgtagc tgttactcat gctactcaca ctagtggtgg atgtggatgt caaccaccac    120
caccggtgca ccttccacca cctgttcatt tgcctccacc agtacacttg ccacctccag    180
tccacttgcc acctccagtg catctcccctc cacctgttca cctcccacca cctgttcacg    240
ttccacctcc tgttcacctg ccaccaccac catgtcatta tccaactcaa ccacctaggc    300
cacaaccaca tccacaacct catccatgtc catgtcaaca gccacatcct tcaccatgtc    360
```

```
aaaggcgcgc cggaggtgga ggtggaacca tggtgagcaa gggcgaggag ctgttcaccg    420
gggtggtgcc catcctggtc gagctggacg gcgacgtaaa cggccacagg ttcagcgtgt    480
ccggcgaggg cgagggcgat gccacctacg gcaagctgac cctgaagttc atctgcacca    540
ccggcaagct gcccgtgccc tggcccaccc tcgtgaccac cctgacctgg ggcgtgcagt    600
gcttcagccg ctaccccgac cacatgaagc agcacgactt cttcaagtcc gccatgcccg    660
aaggctacgt ccaggagcgt accatcttct tcaaggacga cggcaactac aagacccgcg    720
ccgaggtgaa gttcgagggc gacaccctgg tgaaccgcat cgagctgaag ggcatcgact    780
tcaaggagga cggcaacatc ctggggcaca gctggagta caactacatc agccacaacg    840
tctatatcac cgccgacaag cagaagaacg gcatcaaggc ccacttcaag atccgccaca    900
acatcgagga cggcagcgtg cagctcgccg accactacca gcagaacacc cccatcggcg    960
acggccccgt gctgctgccc gacaaccact acctgagcac ccagtccgcc ctgagcaaag   1020
accccaacga gaagcgcgat cacatggtcc tgctggagtt cgtgaccgcc gccgggatca   1080
ctctcggcat ggacgagctg tacaagtaag gatcc                              1115

<210> SEQ ID NO 52
<211> LENGTH: 354
<212> TYPE: DNA
<213> ORGANISM: Artificial sequence
<220> FEATURE:
<223> OTHER INFORMATION: RX3(PR10) DNA

<400> SEQUENCE: 52
atgaatttcc tcaaaagttt cccctttat gccttccttt gttttggcca atactttgta     60
gctgttactc atgctactca cactagtggt ggatgtggat gtcaaccacc accaccggtg    120
caccttccac cacctgttca tttgcctcca ccagtacact tgccacctcc agtccacttg    180
ccacctccag tgcatctccc tccacctgtt cacctccac cacctgttca cgttccacct    240
cctgttcacc tgccaccacc accatgtcat tatccaactc aaccacctag ccacaacca    300 catccacaac ctcatccatg tccatgtcaa cagccacatc cttcaccatg tcaa          354

<210> SEQ ID NO 53
<211> LENGTH: 118
<212> TYPE: PRT
<213> ORGANISM: Artificial sequence
<220> FEATURE:
<223> OTHER INFORMATION: RX3(PR10) Protein

<400> SEQUENCE: 53

Met Asn Phe Leu Lys Ser Phe Pro Phe Tyr Ala Phe Leu Cys Phe Gly
1               5                   10                  15

Gln Tyr Phe Val Ala Val Thr His Ala Thr His Thr Ser Gly Gly Cys
            20                  25                  30

Gly Cys Gln Pro Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Leu Pro Pro Val His Val Pro Pro
65                  70                  75                  80

Pro Val His Leu Pro Pro Pro Cys His Tyr Pro Thr Gln Pro Pro
                85                  90                  95

Arg Pro Gln Pro His Pro Gln Pro His Pro Cys Pro Cys Gln Gln Pro
            100                 105                 110
```

His Pro Ser Pro Cys Gln
          115

<210> SEQ ID NO 54
<211> LENGTH: 1098
<212> TYPE: DNA
<213> ORGANISM: Artificial sequence
<220> FEATURE:
<223> OTHER INFORMATION: RX3(D)-ECFP (SalI/BamHI fragment)

<400> SEQUENCE: 54

```
gtcgacacca tgagagttct tttggtggct cttgctcttt tggctcttgc tgcttctgct      60
acttctactc acactagtgg aggatgtgga tgtcaaccac caccaccagt tgatcttcca     120
cctccagttg atttgcctcc acctgtggat tgccacctc ctgttgattt gcctccacca     180
gttgatctcc caccacctgt ggatcttcca ccaccagtgg atgttccacc tcctgttgat     240
cttccacctc ctccatgtca ttatccaact caaccaccta ggccacaacc acatccacaa     300
cctcatccat gtccatgtca acagccacat ccttcaccat gtcaaaggcg cgccggaggt     360
ggaggtggaa ccatggtgag caagggcgag gagctgttca ccggggtggt gcccatcctg     420
gtcgagctgg acggcgacgt aaacggccac aggttcagcg tgtccggcga gggcgagggc     480
gatgccacct acggcaagct gaccctgaag ttcatctgca ccaccggcaa gctgcccgtg     540
ccctggccca ccctcgtgac caccctgacc tggggcgtgc agtgcttcag ccgctacccc     600
gaccacatga agcagcacga cttcttcaag tccgccatgc ccgaaggcta cgtccaggag     660
cgtaccatct tcttcaagga cgacggcaac tacaagaccc gcgccgaggt gaagttcgag     720
ggcgacaccc tggtgaaccg catcgagctg aagggcatcg acttcaagga ggacggcaac     780
atcctggggc acaagctgga gtacaactac atcagccaca acgtctatat caccgccgac     840
aagcagaaga acggcatcaa ggcccacttc aagatccgcc acaacatcga ggacggcagc     900
gtgcagctcg ccgaccacta ccagcagaac ccccatcg cgacggccc cgtgctgctg     960
cccgacaacc actacctgag cacccagtcc gccctgagca agacccccaa cgagaagcgc    1020
gatcacatgg tcctgctgga gttcgtgacc gccgccggga tcactctcgg catggacgag    1080
ctgtacaagt aaggatcc                                                  1098
```

<210> SEQ ID NO 55
<211> LENGTH: 336
<212> TYPE: DNA
<213> ORGANISM: Artificial sequence
<220> FEATURE:
<223> OTHER INFORMATION: RX3(D) DNA

<400> SEQUENCE: 55

```
atgagagttc ttttggtggc tcttgctctt ttggctcttg ctgcttctgc tacttctact      60
cacactagtg gaggatgtgg atgtcaacca ccaccaccag ttgatcttcc acctccagtt     120
gatttgcctc cacctgtgga tttgccacct cctgttgatt tgcctccacc agttgatctc     180
ccaccacctg tggatcttcc accaccagtg gatgttccac ctcctgttga tcttccacct     240
cctccatgtc attatccaac tcaaccacct aggccacaac cacatccaca acctcatcca     300
tgtccatgtc aacagccaca tccttcacca tgtcaa                               336
```

<210> SEQ ID NO 56
<211> LENGTH: 112
<212> TYPE: PRT
<213> ORGANISM: Artificial sequence
<220> FEATURE:

<223> OTHER INFORMATION: RX3(D) Prot (including 19 aa signal peptide)

<400> SEQUENCE: 56

```
Met Arg Val Leu Leu Val Ala Leu Ala Leu Leu Ala Leu Ala Ala Ser
1               5                   10                  15
Ala Thr Ser Thr His Thr Ser Gly Gly Cys Gly Cys Gln Pro Pro
            20                  25                  30
Pro Val Asp Leu Pro Pro Pro Val Asp Leu Pro Pro Pro Val Asp Leu
                35                  40                  45
Pro Pro Pro Val Asp Leu Pro Pro Val Asp Leu Pro Pro Val
        50                  55                  60
Asp Leu Pro Pro Pro Val Asp Val Pro Pro Val Asp Leu Pro Pro
65                  70                  75                  80
Pro Pro Cys His Tyr Pro Thr Gln Pro Pro Arg Pro Gln Pro His Pro
                85                  90                  95
Gln Pro His Pro Cys Pro Cys Gln Gln Pro His Pro Ser Pro Cys Gln
                100                 105                 110
```

<210> SEQ ID NO 57
<211> LENGTH: 1098
<212> TYPE: DNA
<213> ORGANISM: Artificial sequence
<220> FEATURE:
<223> OTHER INFORMATION: RX3(K)-ECFP (SalI/BamHI fragment)

<400> SEQUENCE: 57

```
gtcgacacca tgagagttct tttggtggct cttgctcttt tggctcttgc tgcttctgct      60
acttctactc acactagtgg aggatgtgga tgtcaaccac caccaccagt taagcttcca     120
cctccagtta agttgcctcc acctgtgaag ttgccacctc tgttaagct ccctccacca     180
gttaagctcc caccacctgt gaagcttcca ccaccagtga aggttccacc tcctgttaag    240
cttccacctc ctccatgtca ttatccaact caaccaccta ggccacaacc acatccacaa    300
cctcatccat gtccatgtca acagccacat ccttcaccat gtcaaaggcg cgccggaggt    360
ggaggtggaa ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgcccgtg    540
ccctggccca cctcgtgac cacctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat cacggccgac    840
aagcagaaga acggcatcaa ggcccacttc aagatccgcc acaacatcga ggacggcagc    900
gtgcagctcg ccgaccacta ccagcagaac ccccatcg cgacggccc cgtgctgctg      960
cccgacaacc actacctgag cacccagtcc gccctgagca agacccccaa cgagaagcgc   1020
gatcacatgg tcctgctgga gttcgtgacc gccgccggga tcactctcgg catggacgag   1080
ctgtacaagt aaggatcc                                                  1098
```

<210> SEQ ID NO 58
<211> LENGTH: 336
<212> TYPE: DNA
<213> ORGANISM: Artificial sequence
<220> FEATURE:

<223> OTHER INFORMATION: RX3(K) DNA

<400> SEQUENCE: 58

```
atgagagttc ttttggtggc tcttgctctt tggctcttg ctgcttctgc tacttctact    60
cacactagtg gaggatgtgg atgtcaacca ccaccaccag ttaagcttcc acctccagtt  120
aagttgcctc cacctgtgaa gttgccacct cctgttaagc tccctccacc agttaagctc  180
ccaccacctg tgaagcttcc accaccagtg aaggttccac ctcctgttaa gcttccacct  240
cctccatgtc attatccaac tcaaccacct aggccacaac acatccaca acctcatcca   300
tgtccatgtc aacagccaca tccttcacca tgtcaa                            336
```

<210> SEQ ID NO 59
<211> LENGTH: 112
<212> TYPE: PRT
<213> ORGANISM: Artificial sequence
<220> FEATURE:
<223> OTHER INFORMATION: RX3(K) Prot

<400> SEQUENCE: 59

```
Met Arg Val Leu Leu Val Ala Leu Ala Leu Leu Ala Leu Ala Ala Ser
1               5                   10                  15
Ala Thr Ser Thr His Thr Ser Gly Gly Cys Gly Cys Gln Pro Pro
            20                  25                  30
Pro Val Lys Leu Pro Pro Pro Val Lys Leu Pro Pro Pro Val Lys Leu
        35                  40                  45
Pro Pro Pro Val Lys Leu Pro Pro Pro Val Lys Leu Pro Pro Val
    50                  55                  60
Lys Leu Pro Pro Pro Val Lys Val Pro Pro Pro Val Lys Leu Pro Pro
65                  70                  75                  80
Pro Pro Cys His Tyr Pro Thr Gln Pro Pro Arg Pro Gln Pro His Pro
                85                  90                  95
Gln Pro His Pro Cys Pro Cys Gln Gln Pro His Pro Ser Pro Cys Gln
            100                 105                 110
```

<210> SEQ ID NO 60
<211> LENGTH: 1098
<212> TYPE: DNA
<213> ORGANISM: Artificial sequence
<220> FEATURE:
<223> OTHER INFORMATION: RX3(T)-ECFP (SalI/BamHI fragment)

<400> SEQUENCE: 60

```
gtcgacacca tgagagttct tttggtggct cttgctcttt ggctcttgc tgcttctgct    60
acttctactc acactagtgg aggatgtgga tgtcaaccac caccaccagt tactcttcca   120
cctccagtta ctttgcctcc acctgtgact ttgccacctc tgttacact ccctccacca   180
gttactctcc caccacctgt gactcttcca ccaccagtga ctgttccacc tcctgttact  240
cttccacctc tccatgtca ttatccaact caaccaccta ggccacaacc acatccacaa   300
cctcatccat gtccatgtca acagccacat ccttcaccat gtcaaaggcg cgccggaggt   360
ggaggtggaa ccatggtgag caagggcgag gagctgttca cggggtggt gcccatcctg    420
gtcgagctgg acggcgacgt aaacggccac aggttcagcg tgtccggcga gggcgagggc   480
gatgccacct acggcaagct gaccctgaag ttcatctgca ccaccggcaa gctgccgtg    540
ccctggccca cctcgtgac cacccctgacc tggggcgtgc agtgcttcag ccgctacccc   600
gaccacatga agcagcacga cttcttcaag tccgccatgc ccgaaggcta cgtccaggag   660
```

```
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat caccgccgac    840
aagcagaaga cggcatcaa ggcccacttc aagatccgcc acaacatcga ggacggcagc     900
gtgcagctcg ccgaccacta ccagcagaac accccccatcg cgacggccc cgtgctgctg    960 cccgacaacc actacctgag cacccagtcc gccctgagca agacccccaa cgagaagcgc    1020
gatcacatgg tcctgctgga gttcgtgacc gccgccggga tcactctcgg catggacgag    1080
ctgtacaagt aaggatcc                                                  1098

<210> SEQ ID NO 61
<211> LENGTH: 336
<212> TYPE: DNA
<213> ORGANISM: Artificial sequence
<220> FEATURE:
<223> OTHER INFORMATION: RX3(T) DNA

<400> SEQUENCE: 61
atgagagttc ttttggtggc tcttgctctt ttggctcttg ctgcttctgc tacttctact     60
cacactagtg gaggatgtgg atgtcaacca ccaccaccag ttactcttcc acctccagtt   120
actttgcctc cacctgtgac tttgccacct cctgttacac tccctccacc agttactctc   180
ccaccacctg tgactcttcc accaccagtg actgttccac tcctgttac tcttccacct    240 cctccatgtc attatccaac tcaaccacct aggccacaac cacatccaca acctcatcca   300
tgtccatgtc aacagccaca tccttcacca tgtcaa                             336

<210> SEQ ID NO 62
<211> LENGTH: 112
<212> TYPE: PRT
<213> ORGANISM: Artificial sequence
<220> FEATURE:
<223> OTHER INFORMATION: RX3(T) PROTEIN (including 19 aa signal peptide)

<400> SEQUENCE: 62

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val Thr Leu Pro Pro Pro Val Thr Leu Pro Pro Pro Val Thr Leu
        35                  40                  45

Pro Pro Pro Val Thr Leu Pro Pro Val Thr Leu Pro Pro Pro Val
    50                  55                  60

Thr Leu Pro Pro Pro Val Thr Val Pro Pro Val Thr Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

<210> SEQ ID NO 63
<211> LENGTH: 1098
<212> TYPE: DNA
<213> ORGANISM: Artificial sequence
<220> FEATURE:
<223> OTHER INFORMATION: RX3(N)-ECFP (SalI/BamHI fragment)

<400> SEQUENCE: 63
```

```
gtcgacacca tgagagttct tttggtggct cttgctcttt tggctcttgc tgcttctgct    60
acttctactc acactagtgg aggatgtgga tgtcaaccac caccaccagt taatcttcca   120
cctccagtta atttgcctcc acctgtgaat tgccacctc ctgttaattt gcctccacca    180
gttaatctcc caccacctgt gaatcttcca ccaccagtga atgttccacc tcctgttaat   240
cttccacctc ctccatgtca ttatccaact caaccaccta ggccacaacc acatccacaa   300
cctcatccat gtccatgtca acagccacat ccttcaccat gtcaaaggcg cgccggaggt   360
ggaggtggaa ccatggtgag caagggcgag gagctgttca ccggggtggt gcccatcctg   420
gtcgagctgg acggcgacgt aaacggccac aggttcagcg tgtccggcga gggcgagggc   480
gatgccacct acggcaagct gaccctgaag ttcatctgca ccaccggcaa gctgcccgtg   540
ccctggccca ccctcgtgac caccctgacc tggggcgtgc agtgcttcag ccgctacccc   600
gaccacatga agcagcacga cttcttcaag tccgccatgc ccgaaggcta cgtccaggag   660
cgtaccatct tcttcaagga cgacggcaac tacaagaccc gcgccgaggt gaagttcgag   720
ggcgacaccc tggtgaaccg catcgagctg aagggcatcg acttcaagga ggacggcaac   780
atcctggggc acaagctgga gtacaactac atcagccaca acgtctatat caccgccgac   840
aagcagaaga acggcatcaa ggcccacttc aagatccgcc acaacatcga ggacggcagc   900
gtgcagctcg ccgaccacta ccagcagaac cccccatcg cgacggccc cgtgctgctg    960 cccgacaacc actacctgag cacccagtcc gccctgagca agaccccaa cgagaagcgc   1020 gatcacatgg tcctgctgga gttcgtgacc gccgccggga tcactctcgg catggacgag   1080
ctgtacaagt aaggatcc                                                  1098

<210> SEQ ID NO 64
<211> LENGTH: 336
<212> TYPE: DNA
<213> ORGANISM: Artificial sequence
<220> FEATURE:
<223> OTHER INFORMATION: RX3(N) DNA

<400> SEQUENCE: 64
atgagagttc ttttggtggc tcttgctctt ttggctcttg ctgcttctgc tacttctact    60
cacactagtg gaggatgtgg atgtcaacca ccaccaccag ttaatcttcc acctccagtt   120
aatttgcctc cacctgtgaa tttgccacct cctgttaatt tgcctccacc agttaatctc   180
ccaccacctg tgaatcttcc accaccagtg aatgttccac ctcctgttaa tcttccacct   240
cctccatgtc attatccaac tcaaccacct aggccacaac cacatccaca acctcatcca   300
tgtccatgtc aacagccaca tccttcacca tgtcaa                              336

<210> SEQ ID NO 65
<211> LENGTH: 112
<212> TYPE: PRT
<213> ORGANISM: Artificial sequence
<220> FEATURE:
<223> OTHER INFORMATION: RX3(N) PROTEIN (including 19 aa signal peptide)

<400> SEQUENCE: 65

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val Asn Leu Pro Pro Pro Val Asn Leu Pro Pro Pro Val Asn Leu
        35                  40                  45
```

Pro Pro Pro Val Asn Leu Pro Pro Val Asn Leu Pro Pro Val
    50              55              60

Asn Leu Pro Pro Val Asn Val Pro Pro Val Asn Leu Pro Pro
65              70              75              80

Pro Pro Cys His Tyr Pro Thr Gln Pro Pro Arg Pro Gln His Pro
            85              90              95

Gln Pro His Pro Cys Pro Cys Gln Gln Pro His Pro Ser Pro Cys Gln
        100             105             110

<210> SEQ ID NO 66
<211> LENGTH: 1098
<212> TYPE: DNA
<213> ORGANISM: Artificial sequence
<220> FEATURE:
<223> OTHER INFORMATION: RX3(Q)-ECFP (SalI/BamHI fragment)

<400> SEQUENCE: 66

| | | | | | |
|---|---|---|---|---|---|
| gtcgacacca | tgagagttct | tttggtggct | cttgctcttt | tggctcttgc | tgcttctgct | 60 |
| acttctactc | acactagtgg | aggatgtgga | tgtcaaccac | caccaccagt | tcaacttcca | 120 |
| cctccagttc | aattgcctcc | acctgtgcaa | ttgccacctc | ctgttcaact | ccctccacca | 180 |
| gttcaactcc | caccacctgt | gcaacttcca | ccaccagtgc | aagttccacc | tcctgttcaa | 240 |
| cttccacctc | ctccatgtca | ttatccaact | caaccaccta | ggccacaacc | acatccacaa | 300 |
| cctcatccat | gtccatgtca | acagccacat | ccttcaccat | gtcaaaggcg | cgccggaggt | 360 |
| ggaggtggaa | ccatggtgag | caagggcgag | gagctgttca | ccggggtggt | gcccatcctg | 420 |
| gtcgagctgg | acggcgacgt | aaacggccac | aggttcagcg | tgtccggcga | gggcgagggc | 480 |
| gatgccacct | acggcaagct | gaccctgaag | ttcatctgca | ccaccggcaa | gctgcccgtg | 540 |
| ccctggccca | cccctcgtgac | cacctgacc | tggggcgtgc | agtgcttcag | ccgctacccc | 600 |
| gaccacatga | agcagcacga | cttcttcaag | tccgccatgc | ccgaaggcta | cgtccaggag | 660 |
| cgtaccatct | tcttcaagga | cgacggcaac | tacaagaccc | gcgccgaggt | gaagttcgag | 720 |
| ggcgacaccc | tggtgaaccg | catcgagctg | aagggcatcg | acttcaagga | ggacggcaac | 780 |
| atcctggggc | acaagctgga | gtacaactac | atcagccaca | cgtctatat | caccgccgac | 840 |
| aagcagaaga | acggcatcaa | ggcccacttc | aagatccgcc | acaacatcga | ggacggcagc | 900 |
| gtgcagctcg | ccgaccacta | ccagcagaac | acccccatcg | gcgacggccc | cgtgctgctg | 960 |
| cccgacaacc | actacctgag | cacccagtcc | gccctgagca | aagaccccaa | cgagaagcgc | 1020 |
| gatcacatgg | tcctgctgga | gttcgtgacc | gccgccggga | tcactctcgg | catggacgag | 1080 |
| ctgtacaagt | aaggatcc | | | | | 1098 |

<210> SEQ ID NO 67
<211> LENGTH: 336
<212> TYPE: DNA
<213> ORGANISM: Artificial sequence
<220> FEATURE:
<223> OTHER INFORMATION: RX3(Q) DNA

<400> SEQUENCE: 67

| | | | | | |
|---|---|---|---|---|---|
| atgagagttc | ttttggtggc | tcttgctctt | ttggctcttg | ctgcttctgc | tacttctact | 60 |
| cacactagtg | gaggatgtgg | atgtcaacca | ccaccaccag | ttcaacttcc | acctccagtt | 120 |
| caattgcctc | cacctgtgca | attgccacct | cctgttcaac | tccctccacc | agttcaactc | 180 |
| ccaccacctg | tgcaacttcc | accaccagtg | caagttccac | ctcctgttca | acttccacct | 240 |
| cctccatgtc | attatccaac | tcaaccacct | aggccacaac | cacatccaca | acctcatcca | 300 |

```
tgtccatgtc aacagccaca tccttcacca tgtcaa                          336
```

<210> SEQ ID NO 68
<211> LENGTH: 112
<212> TYPE: PRT
<213> ORGANISM: Artificial sequence
<220> FEATURE:
<223> OTHER INFORMATION: RX3(Q) Prot (including 19 aa signal peptide)

<400> SEQUENCE: 68

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val Gln Leu Pro Pro Pro Val Gln Leu Pro Pro Pro Val Gln Leu
            35                  40                  45

Pro Pro Pro Val Gln Leu Pro Pro Pro Val Gln Leu Pro Pro Pro Val
        50                  55                  60

Gln Leu Pro Pro Pro Val Gln Val Pro Pro Pro Val Gln Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110
```

<210> SEQ ID NO 69
<211> LENGTH: 1098
<212> TYPE: DNA
<213> ORGANISM: Artificial sequence
<220> FEATURE:
<223> OTHER INFORMATION: RX3(A3)-ECFP (SalI/BamHI fragment)

<400> SEQUENCE: 69

```
gtcgacacca tgagagttct tttggtggct cttgctcttt tggctcttgc tgcttctgct    60
acttctactc acactagtgg tggatgtgga tgtcaaccac caccaccagc tgctgctcca   120
cctcctgctg ctgctcctcc accagctgca gcaccaccac cagcagcagc tcctccacca   180
gcagctgctc caccaccagc tgctgcacca cctccagcag ctgctccacc tccagcagca   240
gcacctcctc ctccatgtca ttatccaact caaccaccta ggccacaacc acatccacaa   300
cctcatccat gtccatgtca acagccacat ccttcaccat gtcaaaggcg cgccggaggt   360
ggaggtggaa ccatggtgag caagggcgag gagctgttca ccggggtggt gcccatcctg   420
gtcgagctgg acggcgacgt aaacggccac aggttcagcg tgtccggcga gggcgagggc   480
gatgccacct acggcaagct gaccctgaag ttcatctgca ccaccggcaa gctgcccgtg   540
ccctggccca ccctcgtgac caccctgacc tggggcgtgc agtgcttcag ccgctacccc   600
gaccacatga gcagcacga cttcttcaag tccgccatgc ccgaaggcta cgtccaggag   660
cgtaccatct tcttcaagga cgacggcaac tacaagaccc gcgccgaggt gaagttcgag   720
ggcgacaccc tggtgaaccg catcgagctg aagggcatcg acttcaagga ggacggcaac   780
atcctgggc acaagctgga gtacaactac atcagccaca acgtctatat caccgccgac   840
aagcagaaga acggcatcaa ggcccacttc aagatccgcc acaacatcga ggacggcagc   900
gtgcagctcg ccgaccacta ccagcagaac ccccatcg cgacggccc cgtgctgctg   960
cccgacaacc actacctgag cacccagtcc gccctgagca agaccccaa cgagaagcgc  1020
gatcacatgg tcctgctgga gttcgtgacc gccgccggga tcactctcgg catggacgag  1080
```
ctgtacaagt aaggatcc                                                      1098

<210> SEQ ID NO 70
<211> LENGTH: 336
<212> TYPE: DNA
<213> ORGANISM: Artificial sequence
<220> FEATURE:
<223> OTHER INFORMATION: RX3(A3) DNA

<400> SEQUENCE: 70

```
atgagagttc ttttggtggc tcttgctctt ttggctcttg ctgcttctgc tacttctact      60
cacactagtg gtggatgtgg atgtcaacca ccaccaccag ctgctgctcc acctcctgct     120
gctgctcctc caccagctgc agcaccacca ccagcagcag ctcctccacc agcagctgct     180
ccaccaccag ctgctgcacc acctccagca gctgctccac ctccagcagc agcacctcct     240
cctccatgtc attatccaac tcaaccacct aggccacaac cacatccaca acctcatcca     300
tgtccatgtc aacagccaca tccttcacca tgtcaa                               336
```

<210> SEQ ID NO 71
<211> LENGTH: 112
<212> TYPE: PRT
<213> ORGANISM: Artificial sequence
<220> FEATURE:
<223> OTHER INFORMATION: RX3(A3) Prot (including 19 aa signal peptide)

<400> SEQUENCE: 71

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Ala Ala Ala Pro Pro Ala Ala Ala Pro Pro Ala Ala Ala
        35                  40                  45

Pro Pro Pro Ala Ala Ala Pro Pro Ala Ala Ala Pro Pro Pro Ala
    50                  55                  60

Ala Ala Pro Pro Pro Ala Ala Ala Pro Pro Ala Ala Ala Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110
```

<210> SEQ ID NO 72
<211> LENGTH: 1098
<212> TYPE: DNA
<213> ORGANISM: Artificial sequence
<220> FEATURE:
<223> OTHER INFORMATION: PP2 -ECFP (SalI-BamHI DNA sequence cloned in
      pC2300)

<400> SEQUENCE: 72

```
gtcgacacca tgagagttct tttggtggct cttgctcttt tggctcttgc tgcttctgct      60
acttctactc accctcctcc tccttgtcca ccatgtccac ctcctcctcc accaccgcct     120
ccgcctccac ctcccccacc tccaccccg ccaccacccc ctccaccgcc accgccacct     180
ccgccgcctc ccccccacc ccctcctccg ccccctcctc ctcctccccc gccacctcac     240
ctgcccccac cacctgtcc tccgccgcca ccgcctcccc caccaccacc acctccccca     300
ccgcctccat gtcctccatg tccgccccca ccccgtgtc ctccaaggcg cgccggaggt     360
```

```
ggaggtggaa ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgcccgtg    540
ccctggccca ccctcgtgac cacccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca acgtctatat caccgccgac    840
aagcagaaga acggcatcaa ggcccacttc aagatccgcc acaacatcga ggacggcagc    900
gtgcagctcg ccgaccacta ccagcagaac ccccccatcg gcgacggccc cgtgctgctg    960
cccgacaacc actacctgag cacccagtcc gccctgagca agacccccaa cgagaagcgc   1020
gatcacatgg tcctgctgga gttcgtgacc gccgccggga tcactctcgg catggacgag   1080
ctgtacaagt aaggatcc                                                  1098

<210> SEQ ID NO 73
<211> LENGTH: 336
<212> TYPE: DNA
<213> ORGANISM: Artificial sequence
<220> FEATURE:
<223> OTHER INFORMATION: PP2 DNA

<400> SEQUENCE: 73
atgagagttc ttttggtggc tcttgctctt ttggctcttg ctgcttctgc tacttctact     60
caccctcctc ctccttgtcc accatgtcca cctcctcctc caccaccgcc tccgcctcca    120
cctcccccac ctccaccccc gccaccaccc ctccaccgc accgccacc tccgccgcct     180 ccccccccac cccctcctcc gcccctcct cctcctcccc gccacctca cctgccccca    240 ccacctgtc ctccgccgcc accgcctccc ccaccaccac cacctccccc accgcctcca    300
tgtcctccat gtccgccccc accccgtgt cctcca                              336

<210> SEQ ID NO 74
<211> LENGTH: 112
<212> TYPE: PRT
<213> ORGANISM: Artificial sequence
<220> FEATURE:
<223> OTHER INFORMATION: PP2 Protein (including 19 aa signal peptide)

<400> SEQUENCE: 74

Met Arg Val Leu Leu Val Ala Leu Ala Leu Leu Ala Leu Ala Ala Ser
1               5                   10                  15

Ala Thr Ser Thr His Pro Pro Pro Cys Pro Pro Cys Pro Pro Pro
                20                  25                  30

Pro Pro Pro Pro Pro Pro Pro Pro Pro Pro Pro Pro Pro
            35                  40                  45

Pro Pro Pro Pro Pro Pro Pro Pro Pro Pro Pro Pro Pro
        50                  55                  60

Pro Pro Pro Pro Pro Pro Pro Pro Pro Pro His Leu Pro Pro
65                  70                  75                  80

Pro Pro Cys Pro Pro Pro Pro Pro Pro Pro Pro Pro Pro
                85                  90                  95

Pro Pro Pro Pro Cys Pro Pro Cys Pro Pro Pro Pro Cys Pro Pro
                100                 105                 110
```

<210> SEQ ID NO 75
<211> LENGTH: 1092
<212> TYPE: DNA
<213> ORGANISM: Artificial sequence
<220> FEATURE:
<223> OTHER INFORMATION: RX3-mcherry (SalI-BamHI DNA sequence cloned in pC2300)

<400> SEQUENCE: 75

```
gtcgacacca tgagggtgtt gctcgttgcc ctcgctctcc tggctctcgc tgcgagcgcc      60
acctccacgc atacaagcgg cggctgcggc tgccagccac cgccgccggt tcatctaccg     120
ccgccggtgc atctgccacc tccggttcac ctgccacctc cggtgcatct cccaccgccg     180
gtccacctgc cgccgccggt ccacctgcca ccgccggtcc atgtgccgcc gccggttcat     240
ctgccgccgc caccatgcca ctaccctact caaccgcccc ggcctcagcc tcatccccag     300
ccacacccat gcccgtgcca acagccgcat ccaagcccgt gccaaaggcg cgccggtgga     360
ggcggaggta ccatgatggt gagcaagggc gaggaggata acatggccat catcaaggag     420
ttcatgcgct tcaaggtgca catggagggc tccgtgaacg gccacgagtt cgagatcgag     480
ggcgagggcg agggccgccc ctacgagggc acccagaccg ccaagctgaa ggtgaccaag     540
ggtggccccc tgcccttcgc ctgggacatc ctgtcccctc agttcatgta cggctccaag     600
gcctacgtga agcaccccgc cgacatcccc gactacttga gctgtccttt ccccgagggc     660
ttcaagtggg agcgcgtgat gaacttcgag gacggcggcg tggtgaccgt gacccaggac     720
tcctccctgc aggacggcga gttcatctac aaggtgaagc tgcgcggcac caacttcccc     780
tccgacggcc ccgtaatgca gaagaagacc atgggctggg aggcctcctc cgagcggatg     840
taccccgagg acggcgccct gaagggcgag atcaagcaga gctgaagct gaaggacggc     900
ggccactacg acgctgaggt caagaccacc tacaaggcca gaagcccgt gcagctgccc     960
ggcgcctaca cgtcaacat caagttggac atcacctccc acaacgagga ctacaccatc    1020
gtggaacagt acgaacgcgc cgagggccgc cactccaccg gcggcatgga cgagctgtac    1080
aagtaaggat cc                                                         1092
```

<210> SEQ ID NO 76
<211> LENGTH: 1092
<212> TYPE: DNA
<213> ORGANISM: Artificial sequence
<220> FEATURE:
<223> OTHER INFORMATION: RX3(A)-mcherry (SalI-BamHI DNA sequence cloned in pC2300)

<400> SEQUENCE: 76

```
gtcgacacca tgagggtgtt gctcgttgcc ctcgctctcc tggctctcgc tgcgagcgcc      60
actagtacgc atacatccgg aggctgcggc tgccagccac cgccgcctgt agcactaccg     120
ccgccggtgg ctctgccacc tccggtggca ctgccacctc cggtggcact cccaccgccg     180
gtcgctctgc cgccgccggt cgctctgcca ccgccggtcg cagtgccgcc gcctgtacat     240
ctaccgccgc caccatgcca ctaccctact caaccgcccc ggcctcagcc tcatccccag     300
ccacacccat gcccgtgcca acagccgcat ccaagcccgt gccaaaggcg cgccggtgga     360
ggcggaggta ccatgatggt gagcaagggc gaggaggata acatggccat catcaaggag     420
ttcatgcgct tcaaggtgca catggagggc tccgtgaacg gccacgagtt cgagatcgag     480
ggcgagggcg agggccgccc ctacgagggc acccagaccg ccaagctgaa ggtgaccaag     540
ggtggccccc tgcccttcgc ctgggacatc ctgtcccctc agttcatgta cggctccaag     600
```

```
gcctacgtga agcaccccgc cgacatcccc gactacttga agctgtcctt ccccgagggc      660
ttcaagtggg agcgcgtgat gaacttcgag gacggcggcg tggtgaccgt gacccaggac      720
tcctccctgc aggacggcga gttcatctac aaggtgaagc tgcgcggcac caacttcccc      780
tccgacggcc ccgtaatgca gaagaagacc atgggctggg aggcctcctc cgagcggatg      840
taccccgagg acggcgccct gaagggcgag atcaagcaga ggctgaagct gaaggacggc      900
ggccactacg acgctgaggt caagaccacc tacaaggcca agaagcccgt gcagctgccc      960
ggcgcctaca acgtcaacat caagttggac atcacctccc acaacgagga ctacaccatc     1020
gtggaacagt acgaacgcgc cgagggccgc cactccaccg gcggcatgga cgagctgtac     1080
aagtaaggat cc                                                         1092

<210> SEQ ID NO 77
<211> LENGTH: 1088
<212> TYPE: DNA
<213> ORGANISM: Artificial sequence
<220> FEATURE:
<223> OTHER INFORMATION: RX3(E)-mcherry (SalI-BamHI DNA sequence cloned
      in pC2300)

<400> SEQUENCE: 77
gtcgacacca tgagggtgtt gctcgttgcc ctcgctctcc tggctctcgc tgcgagcgcc       60
actagtacgc atacatccgg aggctgcggc tgccagccac cgccgcctgt agaactaccg      120
ccgccggtgg aactgccacc tccggtggaa ctgccacctc cggtggaact cccaccgccg      180
gtcgagctgc cgccgccggt cgaactgcca ccgccggtcg aagtgccgcc gcctgtagag      240
ctaccgccgc caccatgcca ctaccctact caaccgcccc ggcctcagcc tcatccccag      300
ccacacccat gccgtgccac aagccgcat ccaagcccgt gccaaaggcg cgccggtgga      360
ggcggaggta ccatgatggt gagcaagggc gaggaggata acatggccat catcaaggag      420
ttcatgcgct tcaaggtgca catggagggc tccgtgaacg gccacgagtt cgagatcgag      480
ggcgagggcg agggccgccc ctacgagggc acccagaccg ccaagctgaa ggtgaccaag      540
ggtggccccc tgcccttcgc ctgggacatc ctgtcccctc agttcatgta cggctccaag      600
gcctacgtga agcaccccgc cgacatcccc gactacttga agctgtcctt ccccgagggc      660
ttcaagtggg agcgcgtgat gaacttcgag gacggcggcg tggtgaccgt gacccaggac      720
tcctccctgc aggacggcga gttcatctac aaggtgaagc tgcgcggcac caacttcccc      780
tccgacggcc ccgtaatgca gaagaagacc atgggctggg aggcctcctc cgagcggatg      840
taccccgagg acggcgccct gaagggcgag atcaagcaga ggctgaagct gaaggacggc      900
ggccactacg acgctgaggt caagaccacc tacaaggcca agaagcccgt gcagctgccc      960
ggcgcctaca acgtcaacat caagttggac atcacctccc acaacgagga ctacaccatc     1020
gtggaacagt acgaacgcgc cgagggccgc cactccaccg gcggcatgga cgagctgtac     1080
aagtaagc                                                              1088

<210> SEQ ID NO 78
<211> LENGTH: 1101
<212> TYPE: DNA
<213> ORGANISM: Artificial sequence
<220> FEATURE:
<223> OTHER INFORMATION: RX3(R)-Gfp (SalI-BamHI DNA sequence cloned in
      pC2300)

<400> SEQUENCE: 78
```

```
gtcgacacca tgagggtgtt gctcgttgcc ctcgctctcc tggctctcgc tgcgagcgcc        60
actagtactc atacttctgg tggttgtggt tgtcaacctc ctcctcccgt acgactaccg       120
ccgccggtga gactgccacc tccggtgagg ctgccacctc cggtgagact cccaccgccg       180
gtcaggctgc cgccgccggt caggctgcca ccgccggtca gagtgccgcc gcctgtaaga       240
ctaccgccgc caccatgcca ctaccctact caaccgcccc ggcctcagcc tcatccccag       300
ccacacccat gcccgtgcca acagccgcat ccaagcccgt gccaaaggcg cgccggtgga       360
ggcggaggta ccatgagcag taaaggagaa gaacttttca ctggagttgt cccaattctt       420
gttgaattag atggtgatgt taatgggcac aaattttctg tcagtggaga gggtgaaggt       480
gatgcaacat acggaaaact tacccttaaa tttatttgca ctactggaaa actacctgtt       540
ccatggccaa cacttgtcac tactttctct tatggtgttc aatgcttttc aagatacccca      600 gatcatatga agcggcacga cttcttcaag agcgccatgc ctgagggata cgtgcaggag       660
aggaccatct tcttcaagga cgacgggaac tacaagacac gtgctgaagt caagtttgag       720
ggagacaccc tcgtcaacag gatcgagctt aagggaatcg atttcaagga ggacggaaac       780
atcctcggcc acaagttgga atacaactac aactcccaca acgtatacat catggccgac       840
aagcaaaaga acggcatcaa agccaacttc aagacccgcc acaacatcga agacggcggc       900
gtgcaactcg ctgatcatta tcaacaaaat actccaattg gcgatggccc tgtccttttt a      960 ccagacaacc attacctgtc cacacaatct gcccttttcga aagatcccaa cgaaaagaga     1020
gaccacatgg tccttcttga gtttgtaaca gctgctggga ttacacatgg catggatgaa     1080
ctatacaaat aatgaggatc c                                               1101

<210> SEQ ID NO 79
<211> LENGTH: 336
<212> TYPE: DNA
<213> ORGANISM: Artificial sequence
<220> FEATURE:
<223> OTHER INFORMATION: RX3(R) DNA

<400> SEQUENCE: 79
atgagggtgt tgctcgttgc cctcgctctc ctggctctcg ctgcgagcgc cactagtact       60
catacttctg gtggttgtgg ttgtcaacct cctcctcccg tacgactacc gccgccggtg      120
agactgccac ctccggtgag gctgccacct ccggtgagac tcccaccgcc ggtcaggctg      180
ccgccgccgg tcaggctgcc accgccggtc agagtgccgc cgcctgtaag actaccgccg      240
ccaccatgcc actaccctac tcaaccgccc cggcctcagc ctcatcccca gccacaccca      300
tgcccgtgcc aacagccgca tccaagcccg tgccaa                               336

<210> SEQ ID NO 80
<211> LENGTH: 112
<212> TYPE: PRT
<213> ORGANISM: Artificial sequence
<220> FEATURE:
<223> OTHER INFORMATION: RX3(R) Protein

<400> SEQUENCE: 80

Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Pro Pro
            20                  25                  30

Pro Val Arg Leu Pro Pro Pro Val Arg Leu Pro Pro Pro Val Arg Leu
        35                  40                  45
```

```
Pro Pro Pro Val Arg Leu Pro Pro Val Arg Leu Pro Pro Val
    50                  55                  60
Arg Leu Pro Pro Pro Val Arg Val Pro Pro Val Arg Leu Pro Pro
65                  70                  75                  80
Pro Pro Cys His Tyr Pro Thr Gln Pro Pro Arg Pro Gln Pro His Pro
                85                  90                  95
Gln Pro His Pro Cys Pro Cys Gln Gln Pro His Pro Ser Pro Cys Gln
            100                 105                 110
```

<210> SEQ ID NO 81
<211> LENGTH: 1092
<212> TYPE: DNA
<213> ORGANISM: Artificial sequence
<220> FEATURE:
<223> OTHER INFORMATION: RX3(E)-Gfp (SalI-BamHI DNA sequence cloned in pC2300)

<400> SEQUENCE: 81

```
gtcgacacca tgagggtgtt gctcgttgcc ctcgctctcc tggctctcgc tgcgagcgcc      60
actagtacgc atacatccgg aggctgcggc tgccagccac cgccgcctgt agaactaccg     120
ccgccggtgg aactgccacc tccggtggaa ctgccacctc cggtggaact cccaccgccg     180
gtcgagctgc cgccgccggt cgaactgcca ccgccggtcg aagtgccgcc gcctgtagag     240
ctaccgccgc caccatgcca ctaccctact caaccgcccc ggcctcagcc tcatccccag     300
ccacacccat gcccgtgcca acagccgcat ccaagcccgt gccaaaggcg cgccggtgga     360
ggcggaggta ccatgatggt gagcaagggc gaggaggata acatggccat catcaaggag     420
ttcatgcgct tcaaggtgca catggagggc tccgtgaacg gccacgagtt cgagatcgag     480
ggcgagggcg agggccgccc ctacgagggc acccagaccg ccaagctgaa ggtgaccaag     540
ggtggccccc tgcccttcgc ctgggacatc ctgtcccctc agttcatgta cggctccaag     600
gcctacgtga agcaccccgc cgacatcccc gactacttga agctgtcctt ccccgagggc     660
ttcaagtggg agcgcgtgat gaacttcgag gacggcggcg tggtgaccgt gacccaggac     720
tcctccctgc aggacggcga gttcatctac aaggtgaagc tgcgcggcac caacttcccc     780
tccgacggcc ccgtaatgca gaagaagacc atgggctggg aggcctcctc cgagcggatg     840
taccccgagg acggcgccct gaagggcgag atcaagcaga gcgaagct gaaggacggc     900
ggccactacg acgctgaggt caagaccacc tacaaggcca gaagcccgt gcagctgccc     960
ggcgcctaca cgtcaacat caagttggac atcacctccc acaacgagga ctacaccatc    1020
gtggaacagt acgaacgcgc cgagggccgc cactccaccg gcggcatgga cgagctgtac    1080
aagtaaggat cc                                                        1092
```

<210> SEQ ID NO 82
<211> LENGTH: 336
<212> TYPE: DNA
<213> ORGANISM: Artificial sequence
<220> FEATURE:
<223> OTHER INFORMATION: RX3(E) DNA

<400> SEQUENCE: 82

```
atgagggtgt tgctcgttgc cctcgctctc ctggctctcg ctgcgagcgc cactagtacg      60
catacatccg gaggctgcgg ctgccagcca ccgccgcctg tagaactacc gccgccggtg     120
gaactgccac ctccggtgga actgccacct ccggtggaac tcccaccgcc ggtcgagctg     180
ccgccgccgg tcgaactgcc accgccggtc gaagtgccgc cgcctgtaga gctaccgccg     240
```

```
ccaccatgcc actaccctac tcaaccgccc cggcctcagc ctcatcccca gccacaccca    300
tgcccgtgcc aacagccgca tccaagcccg tgccaa                              336
```

<210> SEQ ID NO 83
<211> LENGTH: 112
<212> TYPE: PRT
<213> ORGANISM: Artificial sequence
<220> FEATURE:
<223> OTHER INFORMATION: RX3(E) Protein (including 19 aa signal peptide)

<400> SEQUENCE: 83

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val Glu Leu Pro Pro Val Glu Leu Pro Pro Val Glu Leu
        35                  40                  45

Pro Pro Pro Val Glu Leu Pro Pro Val Glu Leu Pro Pro Val
    50                  55                  60

Glu Leu Pro Pro Val Glu Val Pro Pro Val Glu Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Pro His Pro Ser Pro Cys Gln
            100                 105                 110
```

<210> SEQ ID NO 84
<211> LENGTH: 1101
<212> TYPE: DNA
<213> ORGANISM: Artificial sequence
<220> FEATURE:
<223> OTHER INFORMATION: RX3(L)-Gfp (SalI-BamHI DNA sequence cloned in pC2300)

<400> SEQUENCE: 84

```
gtcgacacca tgagggtgtt gctcgttgcc ctcgctctcc tggctctcgc tgcgagcgcc     60
actagtacgc atacatccgg aggctgcggc tgccagccac cgccgcctgt actcctaccg    120
ccgccggtgc tactgccacc tccggtgctg ctgccacctc cggtgttgct cccaccgccg    180
gtcctcctgc cgccgccggt cctactgcca ccgccggtcc tagtgccgcc gcctgtactg    240
ctaccgccgc caccatgcca ctaccctact caaccgcccc ggcctcagcc tcatcccag     300 ccacacccat gcccgtgcca acagccgcat ccaagcccgt gccaaaggcg cgccggtgga    360
ggcggaggta ccatgagcag taaaggagaa gaacttttca ctggagttgt cccaattctt    420
gttgaattag atggtgatgt taatgggcac aaattttctg tcagtggaga gggtgaaggt    480
gatgcaacat acggaaaact tacccttaaa tttatttgca ctactggaaa actacctgtt    540
ccatggccaa cacttgtcac tactttctct tatggtgttc aatgcttttc aagataccca    600
gatcatatga agcggcacga cttcttcaag agcgccatgc ctgagggata cgtgcaggag    660
aggaccatct tcttcaagga cgacgggaac tacaagacac gtgctgaagt caagtttgag    720
ggagacaccc tcgtcaacag gatcgagctt aagggaatcg atttcaagga ggacggaaac    780
atcctcggcc acaagttgga atacaactac aactcccaca cgtatacat catggccgac    840 aagcaaaaga acggcatcaa agccaacttc aagaccgcc acaacatcga gacggcggc    900 gtgcaactcg ctgatcatta tcaacaaat actccaattg gcgatggccc tgtcctttta    960
ccagacaacc attacctgtc cacacaatct gccctttcga aagatcccaa cgaaaagaga   1020
```

```
gaccacatgg tccttcttga gtttgtaaca gctgctggga ttacacatgg catggatgaa    1080
ctatacaaat aatgaggatc c                                              1101
```

<210> SEQ ID NO 85
<211> LENGTH: 336
<212> TYPE: DNA
<213> ORGANISM: Artificial sequence
<220> FEATURE:
<223> OTHER INFORMATION: RX3(L) DNA

<400> SEQUENCE: 85

```
atgagggtgt tgctcgttgc cctcgctctc ctggctctcg ctgcgagcgc cactagtacg     60
catacatccg gaggctgcgg ctgccagcca ccgccgcctg tactcctacc gccgccggtg    120
ctactgccac ctccggtgct gctgccacct ccggtgttgc tcccaccgcc ggtcctcctg    180
ccgccgccgg tcctactgcc accgccggtc ctagtgccgc cgcctgtact gctaccgccg    240
ccaccatgcc actaccctac tcaaccgccc cggcctcagc ctcatcccca gccacaccca    300
tgcccgtgcc aacagccgca tccaagcccg tgccaa                              336
```

<210> SEQ ID NO 86
<211> LENGTH: 112
<212> TYPE: PRT
<213> ORGANISM: Artificial sequence
<220> FEATURE:
<223> OTHER INFORMATION: RX3(L) Protein (including 19 aa signal peptide)

<400> SEQUENCE: 86

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val Leu Leu Pro Pro Pro Val Leu Leu Pro Pro Pro Val Leu Leu
        35                  40                  45

Pro Pro Pro Val Leu Leu Pro Pro Pro Val Leu Leu Pro Pro Pro Val
    50                  55                  60

Leu Leu Pro Pro Pro Val Leu Val Pro Pro Val Leu Leu Pro Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110
```

<210> SEQ ID NO 87
<211> LENGTH: 1101
<212> TYPE: DNA
<213> ORGANISM: Artificial sequence
<220> FEATURE:
<223> OTHER INFORMATION: RX3(A)-Gfp (SalI-BamHI DNA sequence cloned in pC2300)

<400> SEQUENCE: 87

```
gtcgacacca tgagggtgtt gctcgttgcc ctcgctctcc tggctctcgc tgcgagcgcc     60
actagtacgc atacatccgg aggctgcggc tgccagccac cgccgcctgt agcactaccg    120
ccgccggtgg ctctgccacc tccggtggca ctgccacctc cggtggcact cccaccgccg    180
gtcgctctgc cgccgccggt cgctctgcca ccgccggtcg cagtgccgcc gcctgtacat    240
ctaccgccgc caccatgcca ctaccctact caaccgcccc ggcctcagcc tcatccccag    300
```

```
ccacacccat gcccgtgcca acagccgcat ccaagcccgt gccaaaggcg cgccggtgga    360
ggcggaggta ccatgagcag taaaggagaa gaacttttca ctggagttgt cccaattctt    420
gttgaattag atggtgatgt taatgggcac aaattttctg tcagtggaga gggtgaaggt    480
gatgcaacat acggaaaact tacccttaaa tttatttgca ctactggaaa actacctgtt    540
ccatggccaa cacttgtcac tactttctct tatggtgttc aatgcttttc aagatacccca   600 gatcatatga gcggcacga cttcttcaag agcgccatgc ctgagggata cgtgcaggag    660
aggaccatct tcttcaagga cgacgggaac tacaagacac gtgctgaagt caagtttgag    720
ggagacaccc tcgtcaacag gatcgagctt aagggaatcg atttcaagga ggacggaaac    780
atcctcggcc acaagttgga atacaactac aactcccaca cgtatacat catggccgac    840 aagcaaaaga cggcatcaa agccaacttc aagacccgcc acaacatcga agacggcggc    900
gtgcaactcg ctgatcatta tcaacaaaat actccaattg gcgatggccc tgtccttta    960 ccagacaacc attacctgtc cacacaatct gcccttcga agatcccaa cgaaaagaga    1020 gaccacatgg tccttcttga gtttgtaaca gctgctggga ttacacatgg catggatgaa    1080
ctatacaaat aatgaggatc c                                              1101

<210> SEQ ID NO 88
<211> LENGTH: 336
<212> TYPE: DNA
<213> ORGANISM: Artificial sequence
<220> FEATURE:
<223> OTHER INFORMATION: RX3(A) DNA

<400> SEQUENCE: 88
atgagggtgt tgctcgttgc cctcgctctc ctggctctcg ctgcgagcgc cactagtacg    60
catacatccg gaggctgcgg ctgccagcca ccgccgcctg tagcactacc gccgccggtg    120
gctctgccac ctccggtggc actgccacct ccggtggcac tccaccgcc ggtcgctctg    180 ccgccgccgg tcgctctgcc accgccggtc gcagtgccgc cgcctgtaca tctaccgccg    240
ccaccatgcc actaccctac tcaaccgccc cggcctcagc ctcatcccca gccacaccca    300
tgcccgtgcc aacagccgca tccaagcccg tgccaa                              336

<210> SEQ ID NO 89
<211> LENGTH: 112
<212> TYPE: PRT
<213> ORGANISM: Artificial sequence
<220> FEATURE:
<223> OTHER INFORMATION: RX3(A) Protein (including 19 aa signal peptide)

<400> SEQUENCE: 89

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val Ala Leu Pro Pro Val Ala Leu Pro Pro Val Ala Leu
        35                  40                  45

Pro Pro Pro Val Ala Leu Pro Pro Val Ala Leu Pro Pro Val
    50                  55                  60

Ala Leu Pro Pro Pro Val Ala Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
```

<210> SEQ ID NO 90
<211> LENGTH: 561
<212> TYPE: DNA
<213> ORGANISM: Artificial sequence
<220> FEATURE:
<223> OTHER INFORMATION: RX3-EGF (SalI-BamHI DNA sequence cloned in pC2300)

<400> SEQUENCE: 90

| | | | | | |
|---|---|---|---|---|---|
| gtcgacacca | tgagggtgtt | gctcgttgcc | ctcgctctcc | tggctctcgc | tgcgagcgcc | 60 |
| acctccacgc | atacaagcgg | cggctgcggc | tgccagccac | cgccgccggt | tcatctaccg | 120 |
| ccgccggtgc | atctgccacc | tccggttcac | ctgccacctc | cggtgcatct | cccaccgccg | 180 |
| gtccacctgc | cgccgccggt | ccacctgcca | ccgccggtcc | atgtgccgcc | gccggttcat | 240 |
| ctgccgccgc | caccatgcca | ctaccctact | caaccgcccc | ggcctcagcc | tcatccccag | 300 |
| ccacacccat | gccgtgcca | acagccgcat | ccaagcccgt | gccaaaggcg | cgccggtgga | 360 |
| ggcggaggta | ccatggatga | tgatgataag | aactctgatt | cagaatgccc | actcagtcac | 420 |
| gacggatatt | gtcttcacga | tggggtatgc | atgtacatcg | aggccttgga | caagtacgca | 480 |
| tgtaattgtg | tagtgggata | cattggtgaa | cgctgtcagt | atcgagactt | gaaatggtgg | 540 |
| gagcttaggt | gataaggatc | c | | | | 561 |

<210> SEQ ID NO 91
<211> LENGTH: 561
<212> TYPE: DNA
<213> ORGANISM: Artificial sequence
<220> FEATURE:
<223> OTHER INFORMATION: RX3(A)-EGF (SalI-BamHI DNA sequence cloned in pC2300)

<400> SEQUENCE: 91

| | | | | | |
|---|---|---|---|---|---|
| gtcgacacca | tgagggtgtt | gctcgttgcc | ctcgctctcc | tggctctcgc | tgcgagcgcc | 60 |
| actagtacgc | atacatccgg | aggctgcggc | tgccagccac | cgccgcctgt | agcactaccg | 120 |
| ccgccggtgg | ctctgccacc | tccggtggca | ctgccacctc | cggtggcact | cccaccgccg | 180 |
| gtcgctctgc | cgccgccggt | cgctctgcca | ccgccggtcg | cagtgccgcc | gcctgtacat | 240 |
| ctaccgccgc | caccatgcca | ctaccctact | caaccgcccc | ggcctcagcc | tcatccccag | 300 |
| ccacacccat | gccgtgcca | acagccgcat | ccaagcccgt | gccaaaggcg | cgccggtgga | 360 |
| ggcggaggta | ccatggatga | tgatgataag | aactctgatt | cagaatgccc | actcagtcac | 420 |
| gacggatatt | gtcttcacga | tggggtatgc | atgtacatcg | aggccttgga | caagtacgca | 480 |
| tgtaattgtg | tagtgggata | cattggtgaa | cgctgtcagt | atcgagactt | gaaatggtgg | 540 |
| gagcttaggt | gataaggatc | c | | | | 561 |

<210> SEQ ID NO 92
<211> LENGTH: 561
<212> TYPE: DNA
<213> ORGANISM: Artificial sequence
<220> FEATURE:
<223> OTHER INFORMATION: RX3(E)-EGF (SalI-BamHI DNA sequence cloned in pC2300)

<400> SEQUENCE: 92

| | | | | | |
|---|---|---|---|---|---|
| gtcgacacca | tgagggtgtt | gctcgttgcc | ctcgctctcc | tggctctcgc | tgcgagcgcc | 60 |
| actagtacgc | atacatccgg | aggctgcggc | tgccagccac | cgccgcctgt | agaactaccg | 120 |

```
ccgccggtgg aactgccacc tccggtggaa ctgccacctc cggtggaact cccaccgccg    180
gtcgagctgc cgccgccggt cgaactgcca ccgccggtcg aagtgccgcc gcctgtagag    240
ctaccgccgc caccatgcca ctaccctact caaccgcccc ggcctcagcc tcatcccag     300 ccacacccat gcccgtgcca acagccgcat ccaagcccgt gccaaaggcg cgccggtgga    360
ggcggaggta ccatggatga tgatgataag aactctgatt cagaatgccc actcagtcac    420
gacggatatt gtcttcacga tggggtatgc atgtacatcg aggccttgga caagtacgca    480
tgtaattgtg tagtgggata cattggtgaa cgctgtcagt atcgagactt gaaatggtgg    540
gagcttaggt gataaggatc c                                              561
```

<210> SEQ ID NO 93
<211> LENGTH: 561
<212> TYPE: DNA
<213> ORGANISM: Artificial sequence
<220> FEATURE:
<223> OTHER INFORMATION: PA -EGF (SalI-BamHI DNA sequence cloned in pC2300)

<400> SEQUENCE: 93

```
gtcgacacca tgagagttct tttggtggct cttgctcttt tggctcttgc tgcttctgct    60
acttctactc acactagtgg tggttgtggt tgtcaaccct ctcctcctgc tcctgcacct    120
cctccagctc cagctccacc accagcccct gctccacctc ctgcaccagc tcctccgcct    180
gcaccggcac caccaccagc accagcccct ccaccggctc cagcacctcc cctgctcac    240 ctgccacctc caccttgtcc tccacccgca ccagctccgc ctccagctcc tgccccgcca    300
cccgctccat gtccttgtcc tgcccctgct cctccaccat gtccaaggcg cgccggaggt    360
ggaggtggaa ccatgggaat tgagggtagg aactctgatt cagaatgccc actcagtcac    420
gacggatatt gtcttcacga tggggtatgc atgtacatcg aggccttgga caagtacgca    480
tgtaattgtg tagtgggata cattggtgaa cgctgtcagt atcgagactt gaaatggtgg    540
gagcttaggt gataaggatc c                                              561
```

<210> SEQ ID NO 94
<211> LENGTH: 561
<212> TYPE: DNA
<213> ORGANISM: Artificial
<220> FEATURE:
<223> OTHER INFORMATION: PP -EGF (SalI-BamHI DNA sequence cloned in pC2300)

<400> SEQUENCE: 94

```
gtcgacacca tgagagttct tttggtggct cttgctcttt tggctcttgc tgcttctgct    60
acttctactc acactagtgg tggttgtggt tgtcaaccac ctcctcctcc accaccgcct    120
ccgcctccac ctccccccacc tccaccccccg ccaccacccc ctccaccgcc accgccacct    180
ccgccgcctc cccccccacc ccctcctccg cccctcctc ctcctccccc gccacctcac    240
ctgccccccc ctccctgtcc tccgccgcca ccgcctcccc caccaccacc acctccccca    300
ccgcctccat gtccttgtcc accgccccca ccccgccctt gtccaaggcg cgccggaggt    360
ggaggtggaa ccatgggaat tgagggtagg aactctgatt cagaatgccc actcagtcac    420
gacggatatt gtcttcacga tggggtatgc atgtacatcg aggccttgga caagtacgca    480
tgtaattgtg tagtgggata cattggtgaa cgctgtcagt atcgagactt gaaatggtgg    540
gagcttaggt gataaggatc c                                              561
```

<210> SEQ ID NO 95
<211> LENGTH: 953
<212> TYPE: DNA
<213> ORGANISM: Artificial
<220> FEATURE:
<223> OTHER INFORMATION: RX3-Hgh (SalI-BamHI DNA sequence cloned in pC2300)

<400> SEQUENCE: 95

```
gtcgacccat gagggtgttg ctcgttgccc tcgctctcct ggctctcgct gcgagcgcca      60
cctccacgca taagcggc ggctgcggct gccagccacc gccgccggtt catctaccgc      120
cgccggtgca tctgccacct ccggttcacc tgccacctcc ggtgcatctc ccaccgccgg      180
tccacctgcc gccgccggtc cacctgccac cgccggtcca tgtgccgccg ccggttcatc      240
tgccgccgcc accatgccac taccctactc aaccgcccg gctcagcct catcccagc      300
cacacccatg cccgtgccaa cagccgcatc caagcccgtg ccagaccatg gacgatgatg      360
acaagtttcc tactattcct ttatctcgac tcttcgacaa cgctatgctt agagcgcacc      420
gcctacacca gcttgcattc gatacatacc aagagtttga agaggcctac attcctaagg      480
aacagaagta ttcatttcta cagaatcctc aaacaagtct ttgtttctct gagtccatcc      540
ctactccctc gaacagggag gaaactcaac agaagagtaa tttggagttg cttcgcatat      600
ccttgttact catacaatct tggcttgaac ccgttcaatt cttaaggtca gtgtttgcca      660
attcacttgt atatggtgca tcagattcga atgtatatga cctattgaaa gacttggaag      720
agggtattca aacacttatg ggacgtttgg aagatgggtc tccaaggacg ggacaaatct      780
tcaaacagac ttcagcaaa ttcgatacaa attcacataa cgacgatgca ttacttaaga      840
actatgggtt gctttattgt ttccggaagg atatggacaa agtcgagacc tttctgagaa      900
ttgttcaatg tagatctgta gaaggttcct gtggattctg atgatgagga tcc      953
```

<210> SEQ ID NO 96
<211> LENGTH: 953
<212> TYPE: DNA
<213> ORGANISM: Artificial
<220> FEATURE:
<223> OTHER INFORMATION: RX3(A)-hGH (SalI-BamHI DNA sequence cloned in pC2300)

<400> SEQUENCE: 96

```
gtcgacccat gagggtgttg ctcgttgccc tcgctctcct ggctctcgct gcgagcgcca      60
ctagtacgca tacatccgga ggctgcggct gccagccacc gccgcctgta gcactaccgc      120
cgccggtggc tctgccacct ccggtggcac tgccacctcc ggtggcactc ccaccgccgg      180
tcgctctgcc gccgccggtc gctctgccac cgccggtcgc agtgccgccg cctgtacatc      240
taccgccgcc accatgccac taccctactc aaccgcccg gctcagcct catcccagc      300
cacacccatg cccgtgccaa cagccgcatc caagcccgtg ccaaaccatg gacgatgatg      360
acaagtttcc tactattcct ttatctcgac tcttcgacaa cgctatgctt agagcgcacc      420
gcctacacca gcttgcattc gatacatacc aagagtttga agaggcctac attcctaagg      480
aacagaagta ttcatttcta cagaatcctc aaacaagtct ttgtttctct gagtccatcc      540
ctactccctc gaacagggag gaaactcaac agaagagtaa tttggagttg cttcgcatat      600
ccttgttact catacaatct tggcttgaac ccgttcaatt cttaaggtca gtgtttgcca      660
attcacttgt atatggtgca tcagattcga atgtatatga cctattgaaa gacttggaag      720
agggtattca aacacttatg ggacgtttgg aagatgggtc tccaaggacg ggacaaatct      780
```
tcaaacagac ttacagcaaa ttcgatacaa attcacataa cgacgatgca ttacttaaga    840
actatgggtt gctttattgt ttccggaagg atatggacaa agtcgagacc tttctgagaa    900
ttgttcaatg tagatctgta gaaggttcct gtggattctg atgatgagga tcc    953

<210> SEQ ID NO 97
<211> LENGTH: 1098
<212> TYPE: DNA
<213> ORGANISM: Artificial sequence
<220> FEATURE:
<223> OTHER INFORMATION: NPA-ECFP (SalI-BamHI DNA sequence cloned in
    pC2300)

<400> SEQUENCE: 97
gtcgacacca tgagagttct tttggtggct cttgctcttt tggctcttgc tgcttctgct     60
acttctactc accctcctcc tccttgtcct tgtccaccte ctcctcctgc tcctgcacct    120
cctccagctc cagctccacc accagcccct gctccacctc ctgcaccagc tcctccgcct    180
gcaccggcac caccaccagc accagcccct ccaccggctc cagcacctcc ccctgctcac    240
ctgccaccac caccttgtcc tccacccgca ccagctccgc ctccagctcc tgccccgcca    300
cccgctccat gtccttgtcc tgcccctgct cctccaccat gtccaaggcg cgccggtgga    360
ggcggaggta ccatggtgag caagggcgag gagctgttca ccggggtggt gcccatcctg    420
gtcgagctgg acggcgacgt aaacggccac aggttcagcg tgtccggcga gggcgagggc    480
gatgccacct acggcaagct gaccctgaag ttcatctgca ccaccggcaa gctgccgtg    540 ccctggccca ccctcgtgac caccctgacc tggggcgtgc agtgcttcag ccgctacccc    600
gaccacatga agcagcacga cttcttcaag tccgccatgc ccgaaggcta cgtccaggag    660
cgtaccatct tcttcaagga cgacggcaac tacaagaccc gcgccgaggt gaagttcgag    720
ggcgacaccc tggtgaaccg catcgagctg aagggcatcg acttcaagga ggacggcaac    780
atcctggggc acaagctgga gtacaactac atcagccaca cgtctatat caccgccgac    840 aagcagaaga acggcatcaa ggcccacttc aagatccgcc acaacatcga ggacggcagc    900
gtgcagctcg ccgaccacta ccagcagaac ccccccatcg cgacggccc cgtgctgctg    960 cccgacaacc actacctgag cacccagtcc gccctgagca agaccccaa cgagaagcgc   1020 gatcacatgg tcctgctgga gttcgtgacc gccgccggga tcactctcgg catggacgag   1080
ctgtacaagt aaggatcc                                                 1098

<210> SEQ ID NO 98
<211> LENGTH: 336
<212> TYPE: DNA
<213> ORGANISM: Artificial sequence
<220> FEATURE:
<223> OTHER INFORMATION: NPA DNA

<400> SEQUENCE: 98
atgagagttc ttttggtggc tcttgctctt ttggctcttg ctgcttctgc tacttctact     60
caccctcctc ctccttgtcc ttgtccacct cctcctcctg ctcctgcacc tcctccagct    120
ccagctccac caccagcccc tgctccacct cctgcaccag ctcctccgcc tgcaccggca    180
ccaccaccag caccagcccc tccaccggct ccagcacctc ccctgctca cctgccacca    240 ccaccttgtc ctccacccgc accagctccg cctccagctc ctgccccgcc acccgctcca    300
tgtccttgtc ctgcccctgc tcctccacca tgtcca                              336

<210> SEQ ID NO 99

```
<211> LENGTH: 112
<212> TYPE: PRT
<213> ORGANISM: Artificial sequence
<220> FEATURE:
<223> OTHER INFORMATION: NPA Protein

<400> SEQUENCE: 99
```

Met Arg Val Leu Leu Val Ala Leu Ala Leu Leu Ala Leu Ala Ala Ser
1               5                   10                  15

Ala Thr Ser Thr His Pro Pro Pro Cys Pro Cys Pro Pro Pro
            20                  25                  30

Pro Ala Pro Ala Pro Pro Ala Pro Ala Pro Pro Ala Pro Ala
        35                  40                  45

Pro Pro Pro Ala Pro Ala Pro Pro Ala Pro Ala Pro Pro Ala
50                  55                  60

Pro Ala Pro Pro Ala Pro Ala Pro Pro Ala His Leu Pro Pro
65                  70                  75                  80

Pro Pro Cys Pro Pro Ala Pro Ala Pro Pro Ala Pro Ala Pro
            85                  90                  95

Pro Pro Ala Pro Cys Pro Cys Pro Ala Pro Pro Pro Cys Pro
            100                 105                 110

```
<210> SEQ ID NO 100
<211> LENGTH: 57
<212> TYPE: DNA
<213> ORGANISM: Artificial sequence
<220> FEATURE:
<223> OTHER INFORMATION: Signal peptide gamma-zein DNA

<400> SEQUENCE: 100
atgagggtgt tgctcgttgc cctcgctctc ctggctctcg ctgcgagcgc cacctcc      57

<210> SEQ ID NO 101
<211> LENGTH: 19
<212> TYPE: PRT
<213> ORGANISM: Artificial sequence
<220> FEATURE:
<223> OTHER INFORMATION: Signal peptide gamma-zein Protein

<400> SEQUENCE: 101
```

Met Arg Val Leu Leu Val Ala Leu Ala Leu Leu Ala Leu Ala Ala Ser
1               5                   10                  15

Ala Thr Ser

```
<210> SEQ ID NO 102
<211> LENGTH: 75
<212> TYPE: DNA
<213> ORGANISM: Artificial sequence
<220> FEATURE:
<223> OTHER INFORMATION: Signal peptide PR10 (=PR-S) DNA

<400> SEQUENCE: 102
atgaatttcc tcaaaagttt cccctttat gccttccttt gttttggcca atactttgta      60
gctgttactc atgct                                                       75

<210> SEQ ID NO 103
<211> LENGTH: 25
<212> TYPE: PRT
<213> ORGANISM: Artificial sequence
<220> FEATURE:
<223> OTHER INFORMATION: Signal peptide PR10 (=PR-S) Protein

<400> SEQUENCE: 103
```

Met Asn Phe Leu Lys Ser Phe Pro Phe Tyr Ala Phe Leu Cys Phe Gly
1               5                   10                  15

Gln Tyr Phe Val Ala Val Thr His Ala
            20                  25

<210> SEQ ID NO 104
<211> LENGTH: 720
<212> TYPE: DNA
<213> ORGANISM: Artificial sequence
<220> FEATURE:
<223> OTHER INFORMATION: Green fluorescent protein (Gfp) DNA

<400> SEQUENCE: 104

```
atgagcagta aaggagaaga acttttcact ggagttgtcc caattcttgt tgaattagat      60
ggtgatgtta atgggcacaa attttctgtc agtggagagg gtgaaggtga tgcaacatac     120
ggaaaactta cccttaaatt tatttgcact actggaaaac tacctgttcc atggccaaca     180
cttgtcacta ctttctctta tggtgttcaa tgcttttcaa gatacccaga tcatatgaag     240
cggcacgact tcttcaagag cgccatgcct gagggatacg tgcaggagag gaccatcttc     300
ttcaaggacg acgggaacta caagacacgt gctgaagtca agtttgaggg agacaccctc     360
gtcaacagga tcgagcttaa gggaatcgat ttcaaggagg acggaaacat cctcggccac     420
aagttggaat acaactacaa ctcccacaac gtatacatca tggccgacaa gcaaaagaac     480
ggcatcaaag ccaacttcaa gacccgccac aacatcgaag acggcggcgt gcaactcgct     540
gatcattatc aacaaaatac tccaattggc gatggccctg tccttttacc agacaaccat     600
tacctgtcca cacaatctgc cctttcgaaa gatcccaacg aaaagagaga ccacatggtc     660
cttcttgagt ttgtaacagc tgctgggatt acacatggca tggatgaact atacaaataa     720
```

<210> SEQ ID NO 105
<211> LENGTH: 239
<212> TYPE: PRT
<213> ORGANISM: Artificial sequence
<220> FEATURE:
<223> OTHER INFORMATION: Green fluorescent protein (Gfp) Protein

<400> SEQUENCE: 105

Met Ser Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn

```
145                 150                 155                 160
Gly Ile Lys Ala Asn Phe Lys Thr Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr His Gly Met Asp Glu Leu Tyr Lys
225                 230                 235
```

<210> SEQ ID NO 106
<211> LENGTH: 720
<212> TYPE: DNA
<213> ORGANISM: Artificial sequence
<220> FEATURE:
<223> OTHER INFORMATION: Enhanced Cyan fluorescent protein (ECFP) DNA

<400> SEQUENCE: 106

```
atggtgagca agggcgagga gctgttcacc ggggtggtgc ccatcctggt cgagctggac      60
ggcgacgtaa acggccacag gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccty gggcgtgcag tgcttcagcc gctaccccga ccacatgaag     240
cagcacgact tcttcaagtc cgccatgccc gaaggctacg tccaggagcg taccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg cccacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 107
<211> LENGTH: 239
<212> TYPE: PRT
<213> ORGANISM: Artificial sequence
<220> FEATURE:
<223> OTHER INFORMATION: Enhanced Cyan fluorescent protein (ECFP)
      Protein

<400> SEQUENCE: 107

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 108
<211> LENGTH: 711
<212> TYPE: DNA
<213> ORGANISM: Artificial sequence
<220> FEATURE:
<223> OTHER INFORMATION: mCherry DNA

<400> SEQUENCE: 108
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420 atgcagaaga gaccatgggc ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg ccgccactc caccggcggc atggacgagc tgtacaagta a              711

<210> SEQ ID NO 109
<211> LENGTH: 236
<212> TYPE: PRT
<213> ORGANISM: Artificial
<220> FEATURE:
<223> OTHER INFORMATION: mCherry fluorescent protein

<400> SEQUENCE: 109

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr

```
            35                  40                  45
Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 110
<211> LENGTH: 162
<212> TYPE: DNA
<213> ORGANISM: Artificial sequence
<220> FEATURE:
<223> OTHER INFORMATION: EGF DNA

<400> SEQUENCE: 110
aactctgatt cagaatgccc actcagtcac gacggatatt gtcttcacga tggggtatgc     60
atgtacatcg aggccttgga caagtacgca tgtaattgtg tagtgggata cattggtgaa    120
cgctgtcagt atcgagactt gaaatggtgg gagcttaggt ga                       162

<210> SEQ ID NO 111
<211> LENGTH: 53
<212> TYPE: PRT
<213> ORGANISM: Artificial sequence
<220> FEATURE:
<223> OTHER INFORMATION: EGF Protein

<400> SEQUENCE: 111

Asn Ser Asp Ser Glu Cys Pro Leu Ser His Asp Gly Tyr Cys Leu His
  1               5                  10                  15

Asp Gly Val Cys Met Tyr Ile Glu Ala Leu Asp Lys Tyr Ala Cys Asn
             20                  25                  30

Cys Val Val Gly Tyr Ile Gly Glu Arg Cys Gln Tyr Arg Asp Leu Lys
         35                  40                  45

Trp Trp Glu Leu Arg
     50

<210> SEQ ID NO 112
<211> LENGTH: 576
```

<212> TYPE: DNA
<213> ORGANISM: Artificial sequence
<220> FEATURE:
<223> OTHER INFORMATION: hGH DNA

<400> SEQUENCE: 112

```
tttcctacta ttcctttatc tcgactcttc gacaacgcta tgcttagagc gcaccgccta    60
caccagcttg cattcgatac ataccaagag tttgaagagg cctacattcc taaggaacag   120
aagtattcat ttctacagaa tcctcaaaca agtctttgtt tctctgagtc catccctact   180
ccctcgaaca gggaggaaac tcaacagaag agtaatttgg agttgcttcg catatccttg   240
ttactcatac aatcttggct tgaacccgtt caattcttaa ggtcagtgtt tgccaattca   300
cttgtatatg gtgcatcaga ttcgaatgta tatgacctat tgaaagactt ggaagagggt   360
attcaaacac ttatgggacg tttggaagat gggtctccaa ggacgggaca aatcttcaaa   420
cagacttaca gcaaattcga tacaaattca cataacgacg atgcattact taagaactat   480
gggttgcttt attgtttccg gaaggatatg gacaaagtcg agacctttct gagaattgtt   540
caatgtagat ctgtagaagg ttcctgtgga ttctga                             576
```

<210> SEQ ID NO 113
<211> LENGTH: 191
<212> TYPE: PRT
<213> ORGANISM: Artificial sequence
<220> FEATURE:
<223> OTHER INFORMATION: hGH Protein

<400> SEQUENCE: 113

```
Phe Pro Thr Ile Pro Leu Ser Arg Leu Phe Asp Asn Ala Met Leu Arg
1               5                  10                  15
Ala His Arg Leu His Gln Leu Ala Phe Asp Thr Tyr Gln Glu Phe Glu
            20                  25                  30
Glu Ala Tyr Ile Pro Lys Glu Gln Lys Tyr Ser Phe Leu Gln Asn Pro
        35                  40                  45
Gln Thr Ser Leu Cys Phe Ser Glu Ser Ile Pro Thr Pro Ser Asn Arg
    50                  55                  60
Glu Glu Thr Gln Gln Lys Ser Asn Leu Glu Leu Leu Arg Ile Ser Leu
65                  70                  75                  80
Leu Leu Ile Gln Ser Trp Leu Glu Pro Val Gln Phe Leu Arg Ser Val
                85                  90                  95
Phe Ala Asn Ser Leu Val Tyr Gly Ala Ser Asp Ser Asn Val Tyr Asp
            100                 105                 110
Leu Leu Lys Asp Leu Glu Glu Gly Ile Gln Thr Leu Met Gly Arg Leu
        115                 120                 125
Glu Asp Gly Ser Pro Arg Thr Gly Gln Ile Phe Lys Gln Thr Tyr Ser
    130                 135                 140
Lys Phe Asp Thr Asn Ser His Asn Asp Asp Ala Leu Leu Lys Asn Tyr
145                 150                 155                 160
Gly Leu Leu Tyr Cys Phe Arg Lys Asp Met Asp Lys Val Glu Thr Phe
                165                 170                 175
Leu Arg Ile Val Gln Cys Arg Ser Val Glu Gly Ser Cys Gly Phe
            180                 185                 190
```

<210> SEQ ID NO 114
<211> LENGTH: 9866
<212> TYPE: DNA
<213> ORGANISM: Artificial sequence
<220> FEATURE:

<223> OTHER INFORMATION: pC2300

<400> SEQUENCE: 114

```
gatcctctag agtccgcaaa atcaccagtc tctctctac aaatctatct ctctctattt    60
ttctccagaa taatgtgtga gtagttccca gataagggaa ttagggttct tatagggttt   120
cgctcatgtg ttgagcatat aagaaaccct tagtatgtat ttgtatttgt aaaatacttc   180
tatcaataaa atttctaatt cctaaaacca aatccagtg acctgcaggc atgcaagctg    240
ggtacccgag ctcgaattcg taatcatggt catagctgtt tcctgtgtga aattgttatc   300
cgctcacaat tccacacaac atacgagccg aagcataaa gtgtaaagcc tggggtgcct    360
aatgagtgag ctaactcaca ttaattgcgt tgcgctcact gcccgctttc cagtcgggaa   420
acctgtcgtg ccagctgcat taatgaatcg gccaacgcgc ggggagaggc ggtttgcgta   480
ttggctagag cagcttgcca acatggtgga gcacgacact ctcgtctact ccaagaatat   540
caaagataca gtctcagaag accaaagggc tattgagact tttcaacaaa gggtaatatc   600
gggaaacctc ctcggattcc attgcccagc tatctgtcac ttcatcaaaa ggacagtaga   660
aaaggaaggt ggcacctaca aatgccatca ttgcgataaa ggaaaggcta tcgttcaaga   720
tgcctctgcc gacagtggtc ccaaagatgg acccccaccc acgaggagca tcgtggaaaa   780
agaagacgtt ccaaccacgt cttcaaagca agtggattga tgtgataaca tggtggagca   840
cgacactctc gtctactcca agaatatcaa agatacagtc tcagaagacc aaagggctat   900
tgagactttt caacaaaggg taatatcggg aaacctcctc ggattccatt gcccagctat   960
ctgtcacttc atcaaaagga cagtagaaaa ggaaggtggc acctacaaat gccatcattg  1020
cgataaagga aggctatcg ttcaagatgc ctctgccgac agtggtccca agatggacc    1080
cccacccacg aggagcatcg tggaaaaaga agacgttcca accacgtctt caaagcaagt  1140
ggattgatgt gatatctcca ctgacgtaag ggatgacgca caatcccact atccttcgca  1200
agaccttcct ctatataagg aagttcattt catttggaga ggacacgctg aaatcaccag  1260
tctctctcta caaatctatc tctctcgagc tttcgcagat ctgtcgatcg accatgggga  1320
ttgaacaaga tggattgcac gcaggttctc cggccgcttg ggtggagagg ctattcggct  1380
atgactgggc acaacagaca atcggctgct ctgatgccgc cgtgttccgg ctgtcagcgc  1440
agggcgcccg gttctttttt gtcaagaccg acctgtccgg tgccctgaat gaactccagg  1500
acgaggcagc gcggctatcg tggctggcca cgacgggcgt tccttgcgca gctgtgctcg  1560
acgttgtcac tgaagcggga agggactggc tgctattggg cgaagtgccg gggcaggatc  1620
tcctgtcatc tcaccttgct cctgccgaga agtatccat catggctgat gcaatgcggc   1680
ggctgcatac gcttgatccg gctacctgcc cattcgacca ccaagcgaaa catcgcatcg  1740
agcgagcacg tactcggatg aagccggtc ttgtcgatca ggatgatctg gacgaagagc    1800
atcaggggct cgcgccagcc gaactgttcg ccaggctcaa ggcgcgcatg cccgacggcg  1860
aggatctcgt cgtgacacat ggcgatgcct gcttgccgaa tatcatggtg gaaaatggcc  1920
gcttttctgg attcatcgac tgtggccggc tgggtgtggc ggaccgctat caggacatag  1980
cgttggctac ccgtgatatt gctgaagagc ttggcggcga atgggctgac cgcttcctcg  2040
tgctttacgg tatcgccgct cccgattcgc agcgcatcgc cttctatcgc cttcttgacg  2100
agttcttctg agcgggactc tggggttcgg atcgatcctc tagctagagt cgatcgacaa  2160
gctcgagttt ctccataata atgtgtgagt agttcccaga taagggaatt agggttccta  2220
tagggtttcg ctcatgtgtt gagcatataa gaaacccta gtatgtattt gtatttgtaa   2280
```

```
aatacttcta tcaataaaat ttctaattcc taaaaccaaa atccagtact aaaatccaga    2340
tcccccgaat taattcggcg ttaattcagt acattaaaaa cgtccgcaat gtgttattaa    2400
gttgtctaag cgtcaatttg tttacaccac aatatatcct gccaccagcc agccaacagc    2460
tccccgaccg gcagctcggc acaaaatcac cactcgatac aggcagccca tcagtccggg    2520
acggcgtcag cgggagagcc gttgtaaggc ggcagacttt gctcatgtta ccgatgctat    2580
tcggaagaac ggcaactaag ctgccgggtt tgaaacacgg atgatctcgc ggagggtagc    2640
atgttgattg taacgatgac agagcgttgc tgcctgtgat caccgcggtt tcaaaatcgg    2700
ctccgtcgat actatgttat acgccaactt tgaaaacaac tttgaaaaag ctgttttctg    2760
gtatttaagg ttttagaatg caaggaacag tgaattggag ttcgtcttgt tataattagc    2820
ttcttggggt atctttaaat actgtagaaa agaggaagga aataataaat ggctaaaatg    2880
agaatatcac cggaattgaa aaaactgatc gaaaaatacc gctgcgtaaa agatacggaa    2940
ggaatgtctc ctgctaaggt atataagctg gtgggagaaa atgaaaacct atatttaaaa    3000
atgacggaca gccggtataa agggaccacc tatgatgtgg aacgggaaaa ggacatgatg    3060
ctatggctgg aaggaaagct gcctgttcca aaggtcctgc actttgaacg gcatgatggc    3120
tggagcaatc tgctcatgag tgaggccgat ggcgtccttt gctcggaaga gtatgaagat    3180
gaacaaagcc ctgaaaagat tatcgagctg tatgcggagt gcatcaggct ctttcactcc    3240
atcgacatat cggattgtcc ctatacgaat agcttagaca gccgcttagc cgaattggat    3300
tacttactga ataacgatct ggccgatgtg gattgcgaaa actgggaaga agacactcca    3360
tttaaagatc gcgcgagct gtatgatttt ttaaagacgg aaaagcccga gaggaactt    3420 gtcttttccc acggcgacct gggagacagc aacatctttg tgaaagatgg caaagtaagt    3480
ggctttattg atcttgggag aagcggcagg gcggacaagt ggtatgacat tgccttctgc    3540
gtccggtcga tcagggagga tatcggggaa gaacagtatg tcgagctatt ttttgactta    3600
ctggggatca agcctgattg ggagaaaata aaatattata ttttactgga tgaattgttt    3660
tagtacctag aatgcatgac caaaatccct taacgtgagt tttcgttcca ctgagcgtca    3720
gaccccgtag aaaagatcaa aggatcttct tgagatcctt ttttctgcg cgtaatctgc    3780 tgcttgcaaa caaaaaaacc accgctacca gcggtggttt gtttgccgga tcaagagcta    3840
ccaactcttt ttccgaaggt aactggcttc agcagagcgc agataccaaa tactgtcctt    3900
ctagtgtagc cgtagttagg ccaccacttc aagaactctg tagcaccgcc tacatacctc    3960
gctctgctaa tcctgttacc agtggctgct gccagtggcg ataagtcgtg tcttaccggg    4020
ttggactcaa gacgatagtt accggataag gcgcagcggt cgggctgaac ggggggttcg    4080
tgcacacagc ccagcttgga gcgaacgacc tacaccgaac tgagatacct acagcgtgag    4140
ctatgagaaa gcgccacgct tcccgaaggg agaaaggcgg acaggtatcc ggtaagcggc    4200
agggtcggaa caggagagcg cacgagggag cttccagggg gaaacgcctg gtatctttat    4260
agtcctgtcg ggtttcgcca cctctgactt gagcgtcgat ttttgtgatg ctcgtcaggg    4320
gggcggagcc tatggaaaaa cgccagcaac gcggcctttt tacggttcct ggccttttgc    4380
tggccttttg ctcacatgtt ctttcctgcg ttatccctg attctgtgga taaccgtatt    4440
accgcctttg agtgagctga taccgctcgc cgcagccgaa cgaccgagcg cagcgagtca    4500
gtgagcgagg aagcggaaga gcgcctgatg cggtattttc tccttacgca tctgtgcggt    4560
atttcacacc gcatatggtg cactctcagt acaatctgct ctgatgccgc atagttaagc    4620
```

```
cagtatacac tccgctatcg ctacgtgact gggtcatggc tgcgccccga cacccgccaa    4680
cacccgctga cgcgccctga cgggcttgtc tgctcccggc atccgcttac agacaagctg    4740
tgaccgtctc cgggagctgc atgtgtcaga ggttttcacc gtcatcaccg aaacgcgcga    4800
ggcagggtgc cttgatgtgg gcgccggcgg tcgagtggcg acggcgcggc ttgtccgcgc    4860
cctggtagat tgcctggccg taggccagcc attttttgagc ggccagcggc cgcgataggc    4920
cgacgcgaag cggcggggcg tagggagcgc agcgaccgaa gggtaggcgc ttttttgcagc    4980 tcttcggctg tgcgctggcc agacagttat gcacaggcca ggcgggtttt aagagtttta    5040
ataagtttta aagagtttta ggcggaaaaa tcgccttttt tctcttttat atcagtcact    5100
tacatgtgtg accggttccc aatgtacggc tttgggttcc caatgtacgg gttccggttc    5160
ccaatgtacg gctttgggtt cccaatgtac gtgctatcca caggaaagag acctttttcga    5220 cctttttccc ctgctagggc aatttgccct agcatctgct ccgtacatta ggaaccggcg    5280
gatgcttcgc cctcgatcag gttgcggtag cgcatgacta ggatcgggcc agcctgcccc    5340
gcctcctcct tcaaatcgta ctccggcagg tcatttgacc cgatcagctt gcgcacggtg    5400
aaacagaact tcttgaactc tccggcgctg ccactgcgtt cgtagatcgt cttgaacaac    5460
catctggctt ctgccttgcc tgcggcgcgg cgtgccaggc ggtagagaaa acggccgatg    5520
ccgggatcga tcaaaaagta atcggggtga accgtcagca cgtccgggtt cttgccttct    5580
gtgatctcgc ggtacatcca atcagctagc tcgatctcga tgtactccgg ccgcccggtt    5640 tcgctctttta cgatcttgta gcggctaatc aaggcttcac cctcggatac cgtcaccagg    5700
cggccgttct tggccttctt cgtacgctgc atggcaacgt gcgtggtgtt taaccgaatg    5760
caggtttcta ccaggtcgtc tttctgcttt ccgccatcgg ctcgccggca gaacttgagt    5820
acgtccgcaa cgtgtggacg gaacacgcgg ccgggcttgt ctcccttccc ttcccggtat    5880
cggttcatgg attcggttag atgggaaacc gccatcagta ccaggtcgta atcccacaca    5940
ctggccatgc cggccggccc tgcggaaacc tctacgtgcc cgtctggaag ctcgtagcgg    6000
atcacctcgc cagctcgtcg gtcacgcttc gacagacgga aaacggccac gtccatgatg    6060
ctgcgactat cgcgggtgcc cacgtcatag agcatcggaa cgaaaaaatc tggttgctcg    6120
tcgcccttgg gcggcttcct aatcgacggc gcaccggctg ccggcggttg ccgggattct    6180
ttgcggattc gatcagcggc cgcttgccac gattccaccgg ggcgtgcttc tgcctcgatg    6240
cgttgccgct gggcggcctg cgcggccttc aacttctcca ccaggtcatc acccagcgcc    6300
gcgccgattt gtaccgggcc ggatggtttg cgaccgtcac gccgattcct cgggcttggg    6360
ggttccagtg ccattgcagg gccggcagac aacccagccg cttacgcctg ccaaccgcc    6420 cgttcctcca cacatggggc attccacggc gtcggtgcct ggttgttctt gattttccat    6480
gccgcctcct ttagccgcta aaattcatct actcatttat tcatttgctc atttactctg    6540
gtagctgcgc gatgtattca gatagcagct cggtaatggt cttgccttgg cgtaccgcgt    6600
acatcttcag cttggtgtga tcctccgccg gcaactgaaa gttgacccgc ttcatggctg    6660
gcgtgtctgc caggctggcc aacgttgcag ccttgctgct gcgtgcgctc ggacggccgg    6720
cacttagcgt gtttgtgctt ttgctcattt tctctttacc tcattaactc aaatgagttt    6780
tgatttaatt tcagcggcca cgcctggac ctcgcgggca gcgtcgccct cgggttctga    6840
ttcaagaacg gttgtgccgg cggcggcagt gcctgggtag ctcacgcgct gcgtgatacg    6900
ggactcaaga atgggcagct cgtacccggc cagcgcctcg gcaacctcac cgccgatgcg    6960
cgtgcctttg atcgcccgcg acacgacaaa ggccgcttgt agccttccat ccgtgacctc    7020
```

```
aatgcgctgc ttaaccagct ccaccaggtc ggcggtggcc catatgtcgt aagggcttgg    7080
ctgcaccgga atcagcacga agtcggctgc cttgatcgcg acacagcca agtccgccgc     7140 ctggggcgct ccgtcgatca ctacgaagtc gcgccggccg atggccttca cgtcgcggtc    7200
aatcgtcggg cggtcgatgc cgacaacggt tagcggttga tcttcccgca cggccgccca   7260
atcgcgggca ctgccctggg gatcggaatc gactaacaga acatcggccc cggcgagttg    7320
cagggcgcgg gctagatggg ttgcgatggt cgtcttgcct gacccgcctt tctggttaag   7380
tacagcgata accttcatgc gttccccttg cgtatttgtt tatttactca tcgcatcata   7440
tacgcagcga ccgcatgacg caagctgttt tactcaaata cacatcacct ttttagacgg   7500
cggcgctcgg tttcttcagc ggccaagctg gccggccagg ccgccagctt ggcatcagac   7560
aaaccggcca ggatttcatg cagccgcacg gttgagacgt gcgcgggcgg ctcgaacacg   7620
tacccggccg cgatcatctc cgcctcgatc tcttcggtaa tgaaaaacgg ttcgtcctgg   7680
ccgtcctggt gcggtttcat gcttgttcct cttggcgttc attctcggcg gccgccaggg   7740
cgtcggcctc ggtcaatgcg tcctcacgga aggcaccgcg ccgcctggcc tcggtgggcg   7800
tcacttcctc gctgcgctca agtgcgcggt acagggtcga gcgatgcacg ccaagcagtg   7860
cagccgcctc tttcacggtg cggccttcct ggtcgatcag ctcgcgggcg tgcgcgatct   7920 gtgccgggt gagggtaggg cggggccaa acttcacgcc tcgggccttg gcggcctcgc    7980
gcccgctccg ggtgcggtcg atgattaggg aacgctcgaa ctcggcaatg ccggcgaaca   8040
cggtcaacac catgcggccg gccggcgtgg tggtgtcggc ccacggctct gccaggctac   8100
gcaggcccgc gccggcctcc tggatgcgct cggcaatgtc cagtaggtcg cgggtgctgc   8160
gggccaggcg gtctagcctg gtcactgtca caacgtcgcc agggcgtagg tggtcaagca   8220
tcctggccag ctccgggcgg tcgcgcctgg tgccggtgat cttctcggaa aacagcttgg   8280
tgcagccggc cgcgtgcagt tcggcccgtt ggttggtcaa gtcctggtcg tcggtgctga   8340
cgcgggcata gcccagcagg ccagcggcgg cgctcttgtt catggcgtaa tgtctccggt    8400
tctagtcgca agtattctac tttatgcgac taaaacacgc gacaagaaaa cgccaggaaa   8460
agggcagggc ggcagcctgt cgcgtaactt aggacttgtg cgacatgtcg ttttcagaag   8520
acggctgcac tgaacgtcag aagccgactg cactatagca gcggaggggt tggatcaaag   8580
tactttgatc ccgaggggaa ccctgtggtt ggcatgcaca tacaaatgga cgaacggata   8640
aaccttttca cgcccttta aatatccgtt attctaataa acgctctttt ctcttaggtt    8700
tacccgccaa tatatcctgt caaacactga tagtttaaac tgaaggcggg aaacgacaat   8760
ctgatccaag ctcaagctgc tctagcattc gccattcagg ctgcgcaact gttgggaagg   8820
gcgatcggtg cgggcctctt cgctattacg ccagctggcg aaaggggat gtgctgcaag    8880 gcgattaagt tgggtaacgc cagggttttc ccagtcacga cgttgtaaaa cgacggccag   8940
tgccaagctt gcatgcctgc aggtcaacat ggtggagcac gacacacttg tctactccaa   9000
aaatatcaaa gatacagtct cagaagacca aagggcaatt gagactttc aacaaagggt    9060 aatatccgga aacctcctcg gattccattg cccagctatc tgtcacttta ttgtgaagat   9120
agtggaaaag gaaggtggct cctacaaatg ccatcattgc gataaaggaa aggccatcgt   9180
tgaagatgcc tctgccgaca gtggtcccaa agatggaccc ccacccacga ggagcatcgt   9240
ggaaaaagaa gacgttccaa ccacgtcttc aaagcaagtg gattgatgtg ataacatggt   9300
ggagcacgac acacttgtct actccaaaaa tatcaaagat acagtctcag aagaccaaag   9360
```

```
ggcaattgag acttttcaac aaagggtaat atccggaaac ctcctcggat tccattgccc    9420
agctatctgt cactttattg tgaagatagt ggaaaaggaa ggtggctcct acaaatgcca    9480
tcattgcgat aaaggaaagg ccatcgttga agatgcctct gccgacagtg gtcccaaaga    9540
tggaccccca cccacgagga gcatcgtgga aaagaagca gttccaacca cgtcttcaaa    9600
gcaagtggat tgatgtgata tctccactga cgtaagggat gacgcacaat cccactatcc    9660
ttcgcaagac ccttcctcta tataaggaag ttcatttcat ttggagagga cctcgagtct    9720
caacacaaca tatacaaaac aaacgaatct caagcaatca agcattctac ttctattgca    9780
gcaatttaaa tcatttcttt taaagcaaaa gcaattttct gaaaattttc accatttacg    9840
aacgatagca gtcgacacct gataag                                        9866
```

<210> SEQ ID NO 115
<211> LENGTH: 36
<212> TYPE: PRT
<213> ORGANISM: Artificial
<220> FEATURE:
<223> OTHER INFORMATION: proline rich repeat

<400> SEQUENCE: 115

```
Pro Pro Pro Val His Leu Pro Pro Pro Val His Leu Pro Pro Pro Val
1               5                   10                  15

His Leu Pro Pro Pro Val His Leu Pro Pro Pro Val His Leu Pro Pro
            20                  25                  30

Pro Val His Leu
        35
```

<210> SEQ ID NO 116
<211> LENGTH: 6
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (4)..(6)
<223> OTHER INFORMATION: Xaa can be any naturally occurring amino acid

<400> SEQUENCE: 116

```
Pro Pro Pro Xaa Xaa Xaa
1               5
```

<210> SEQ ID NO 117
<211> LENGTH: 4
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (3)..(4)
<223> OTHER INFORMATION: Xaa can be any naturally occurring amino acid

<400> SEQUENCE: 117

```
Pro Pro Xaa Xaa
1
```

<210> SEQ ID NO 118
<211> LENGTH: 5
<212> TYPE: PRT
<213> ORGANISM: Artificial
<220> FEATURE:
<223> OTHER INFORMATION: proline rich repeat
<220> FEATURE:

```
<221> NAME/KEY: misc_feature
<222> LOCATION: (4)..(5)
<223> OTHER INFORMATION: Xaa can be any naturally occurring amino acid

<400> SEQUENCE: 118

Pro Pro Pro Xaa Xaa
1               5

<210> SEQ ID NO 119
<211> LENGTH: 4
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (4)..(4)
<223> OTHER INFORMATION: Xaa can be any naturally occurring amino acid

<400> SEQUENCE: 119

Pro Pro Pro Xaa
1

<210> SEQ ID NO 120
<211> LENGTH: 6
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 120

Pro Pro Pro Xaa Pro Xaa
1               5

<210> SEQ ID NO 121
<211> LENGTH: 6
<212> TYPE: PRT
<213> ORGANISM: Artificial
<220> FEATURE:
<223> OTHER INFORMATION: non amphipathic

<400> SEQUENCE: 121

Pro Pro Pro Val Ala Leu
1               5

<210> SEQ ID NO 122
<211> LENGTH: 6
<212> TYPE: PRT
<213> ORGANISM: Artificial
<220> FEATURE:
<223> OTHER INFORMATION: non amphipathic

<400> SEQUENCE: 122

Pro Pro Pro Val Leu Leu
1               5

<210> SEQ ID NO 123
<211> LENGTH: 6
<212> TYPE: PRT
<213> ORGANISM: Artificial
<220> FEATURE:
```

<223> OTHER INFORMATION: non amphipathic

<400> SEQUENCE: 123

Pro Pro Pro Ala Ala Ala
1               5

<210> SEQ ID NO 124
<211> LENGTH: 6
<212> TYPE: PRT
<213> ORGANISM: Artificial
<220> FEATURE:
<223> OTHER INFORMATION: amphipathic and negative

<400> SEQUENCE: 124

Pro Pro Pro Val Asp Leu
1               5

<210> SEQ ID NO 125
<211> LENGTH: 6
<212> TYPE: PRT
<213> ORGANISM: Artificial
<220> FEATURE:
<223> OTHER INFORMATION: amphipathic negative

<400> SEQUENCE: 125

Pro Pro Pro Val Glu Leu
1               5

<210> SEQ ID NO 126
<211> LENGTH: 6
<212> TYPE: PRT
<213> ORGANISM: Artificial
<220> FEATURE:
<223> OTHER INFORMATION: amphipathic non charged

<400> SEQUENCE: 126

Pro Pro Pro Val Thr Leu
1               5

<210> SEQ ID NO 127
<211> LENGTH: 6
<212> TYPE: PRT
<213> ORGANISM: Artificial
<220> FEATURE:
<223> OTHER INFORMATION: amphipathic non charged

<400> SEQUENCE: 127

Pro Pro Pro Val Asn Leu
1               5

<210> SEQ ID NO 128
<211> LENGTH: 6
<212> TYPE: PRT
<213> ORGANISM: Artificial
<220> FEATURE:
<223> OTHER INFORMATION: amphipathic non charged

<400> SEQUENCE: 128

Pro Pro Pro Val Gln Leu
1               5

<210> SEQ ID NO 129
<211> LENGTH: 6
<212> TYPE: PRT
<213> ORGANISM: Artificial
<220> FEATURE:
<223> OTHER INFORMATION: proline rich -continued

```
<400> SEQUENCE: 129

Pro Pro Pro Ala Pro Ala
1               5

<210> SEQ ID NO 130
<211> LENGTH: 93
<212> TYPE: PRT
<213> ORGANISM: Artificial
<220> FEATURE:
<223> OTHER INFORMATION: PP2

<400> SEQUENCE: 130

Thr His Pro Pro Pro Pro Cys Pro Pro Cys Pro Pro Pro Pro Pro Pro
1               5                   10                  15

Pro Pro Pro Pro Pro Pro Pro Pro Pro Pro Pro Pro Pro Pro
            20                  25                  30

Pro Pro Pro Pro Pro Pro Pro Pro Pro Pro Pro Pro Pro Pro
        35                  40                  45

Pro Pro Pro Pro Pro Pro Pro Pro His Leu Pro Pro Pro Cys
    50                  55                  60

Pro Pro Pro Pro Pro Pro Pro Pro Pro Pro Pro Pro Pro Pro
65                  70                  75                  80

Pro Cys Pro Pro Cys Pro Pro Pro Pro Cys Pro Pro
                85                  90

<210> SEQ ID NO 131
<211> LENGTH: 93
<212> TYPE: PRT
<213> ORGANISM: Artificial
<220> FEATURE:
<223> OTHER INFORMATION: mature RX3

<400> SEQUENCE: 131

Thr His Thr Ser Gly Gly Cys Gly Cys Gln Pro Pro Pro Pro Val His
1               5                   10                  15

Leu Pro Pro Pro Val His Leu Pro Pro Pro Val His Leu Pro Pro Pro
            20                  25                  30

Val His Leu Pro Pro Pro Val His Leu Pro Pro Pro Val His Leu Pro
        35                  40                  45

Pro Pro Val His Val Pro Pro Val His Leu Pro Pro Pro Cys
    50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90

<210> SEQ ID NO 132
<211> LENGTH: 93
<212> TYPE: PRT
<213> ORGANISM: Artificial
<220> FEATURE:
<223> OTHER INFORMATION: PP

<400> SEQUENCE: 132

Thr His Thr Ser Gly Gly Cys Gly Cys Gln Pro Pro Pro Pro Pro
1               5                   10                  15

Pro Pro Pro Pro Pro Pro Pro Pro Pro Pro Pro Pro Pro Pro
            20                  25                  30

Pro Pro Pro Pro Pro Pro Pro Pro Pro Pro Pro Pro Pro Pro
```

```
                35                  40                  45
Pro Pro Pro Pro Pro Pro Pro His Leu Pro Pro Pro Cys
        50                  55                  60
Pro Pro Pro Pro Pro Pro Pro Pro Pro Pro Pro Pro Pro Pro Pro
65                  70                  75                  80
Pro Cys Pro Cys Pro Pro Pro Pro Pro Pro Cys Pro
                85                  90
```

```
<210> SEQ ID NO 133
<211> LENGTH: 93
<212> TYPE: PRT
<213> ORGANISM: Artificial
<220> FEATURE:
<223> OTHER INFORMATION: PA

<400> SEQUENCE: 133

Thr His Thr Ser Gly Gly Cys Gly Cys Gln Pro Pro Pro Ala Pro
1               5                   10                  15
Ala Pro Pro Ala Pro Ala Pro Pro Ala Pro Ala Pro Pro Pro
                20                  25                  30
Ala Pro Ala Pro Pro Ala Pro Ala Pro Pro Ala Pro Ala Pro
            35                  40                  45
Pro Pro Ala Pro Ala Pro Pro Pro Ala His Leu Pro Pro Pro Cys
        50                  55                  60
Pro Pro Pro Ala Pro Ala Pro Pro Pro Ala Pro Ala Pro Pro Pro Ala
65                  70                  75                  80
Pro Cys Pro Cys Pro Ala Pro Ala Pro Pro Pro Cys Pro
                85                  90
```

```
<210> SEQ ID NO 134
<211> LENGTH: 4
<212> TYPE: PRT
<213> ORGANISM: Artificial
<220> FEATURE:
<223> OTHER INFORMATION: cysteine sequence

<400> SEQUENCE: 134

Cys Pro Pro Cys
1
```

```
<210> SEQ ID NO 135
<211> LENGTH: 5
<212> TYPE: PRT
<213> ORGANISM: Artificial
<220> FEATURE:
<223> OTHER INFORMATION: 5 Gly linker

<400> SEQUENCE: 135

Gly Gly Gly Gly Gly
1               5
```

```
<210> SEQ ID NO 136
<211> LENGTH: 6
<212> TYPE: PRT
<213> ORGANISM: Artificial
<220> FEATURE:
<223> OTHER INFORMATION: proline rich sequence

<400> SEQUENCE: 136

Pro Pro Pro Val His Leu
1               5
```

```
<210> SEQ ID NO 137
<211> LENGTH: 4
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (2)..(4)
<223> OTHER INFORMATION: Xaa can be any naturally occurring amino acid

<400> SEQUENCE: 137

Pro Xaa Xaa Xaa
1

<210> SEQ ID NO 138
<211> LENGTH: 4
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (3)..(3)
<223> OTHER INFORMATION: Xaa can be any naturally occurring amino acid

<400> SEQUENCE: 138

Pro Pro Xaa Pro
1

<210> SEQ ID NO 139
<211> LENGTH: 4
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (2)..(2)
<223> OTHER INFORMATION: Xaa can be any naturally occurring amino acid

<400> SEQUENCE: 139

Pro Xaa Pro Pro
1

<210> SEQ ID NO 140
<211> LENGTH: 5
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (4)..(5)
<223> OTHER INFORMATION: Xaa can be any naturally occurring amino acid

<400> SEQUENCE: 140

Pro Pro Pro Xaa Xaa
1               5

<210> SEQ ID NO 141
<211> LENGTH: 6
<212> TYPE: PRT
<213> ORGANISM: Artificial
<220> FEATURE:
<223> OTHER INFORMATION: proline rich repeat
<220> FEATURE:
<221> NAME/KEY: misc_feature
<222> LOCATION: (4)..(4)
<223> OTHER INFORMATION: Xaa can be any naturally occurring amino acid
<220> FEATURE:
```

```
<221> NAME/KEY: misc_feature
<222> LOCATION: (6)..(6)
<223> OTHER INFORMATION: Xaa can be any naturally occurring amino acid

<400> SEQUENCE: 141

Pro Pro Pro Xaa Pro Xaa
1               5

<210> SEQ ID NO 142
<211> LENGTH: 18
<212> TYPE: PRT
<213> ORGANISM: Artificial
<220> FEATURE:
<223> OTHER INFORMATION: homomeric proline-rich repeat

<400> SEQUENCE: 142

Pro Pro Pro Ala Ala Ala Pro Pro Pro Ala Ala Ala Pro Pro Pro Ala
1               5                   10                  15

Ala Ala

<210> SEQ ID NO 143
<211> LENGTH: 24
<212> TYPE: PRT
<213> ORGANISM: Artificial
<220> FEATURE:
<223> OTHER INFORMATION: heteromeric proline-rich repeat

<400> SEQUENCE: 143

Pro Pro Pro Ala Ala Ala Pro Pro Ala Ala Ala Pro Pro Ala Pro
1               5                   10                  15

Pro Pro Pro Ala Pro Pro Pro
            20

<210> SEQ ID NO 144
<211> LENGTH: 6
<212> TYPE: PRT
<213> ORGANISM: Artificial
<220> FEATURE:
<223> OTHER INFORMATION: proline rich repeat

<400> SEQUENCE: 144

Pro Pro Ala Pro Pro Pro
1               5

<210> SEQ ID NO 145
<211> LENGTH: 4
<212> TYPE: PRT
<213> ORGANISM: Artificial
<220> FEATURE:
<223> OTHER INFORMATION: cysteine sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 145

Cys Xaa Xaa Cys
1

<210> SEQ ID NO 146
<211> LENGTH: 48
<212> TYPE: PRT
<213> ORGANISM: Artificial
<220> FEATURE:
<223> OTHER INFORMATION: RX3 variants arginine sub

<400> SEQUENCE: 146
```

Pro Pro Pro Val Arg Leu Pro Pro Val Arg Leu Pro Pro Val
1               5                   10                  15

Arg Leu Pro Pro Pro Val Arg Leu Pro Pro Val Arg Leu Pro Pro
            20                  25                  30

Pro Val Arg Leu Pro Pro Val Arg Leu Pro Pro Val Arg Leu
        35                  40                  45

<210> SEQ ID NO 147
<211> LENGTH: 48
<212> TYPE: PRT
<213> ORGANISM: Artificial
<220> FEATURE:
<223> OTHER INFORMATION: RX3 variant lysine sub

<400> SEQUENCE: 147

Pro Pro Pro Val Lys Leu Pro Pro Val Lys Leu Pro Pro Val
1               5                   10                  15

Lys Leu Pro Pro Pro Val Lys Leu Pro Pro Val Lys Leu Pro Pro
            20                  25                  30

Pro Val Lys Leu Pro Pro Val Lys Leu Pro Pro Val Lys Leu
        35                  40                  45

<210> SEQ ID NO 148
<211> LENGTH: 48
<212> TYPE: PRT
<213> ORGANISM: Artificial
<220> FEATURE:
<223> OTHER INFORMATION: RX3 variant, alanine sub

<400> SEQUENCE: 148

Pro Pro Pro Val Ala Leu Pro Pro Val Ala Leu Pro Pro Val
1               5                   10                  15

Ala Leu Pro Pro Pro Val Ala Leu Pro Pro Val Ala Leu Pro Pro
            20                  25                  30

Pro Val Ala Leu Pro Pro Val Ala Leu Pro Pro Val Ala Leu
        35                  40                  45

<210> SEQ ID NO 149
<211> LENGTH: 48
<212> TYPE: PRT
<213> ORGANISM: Artificial
<220> FEATURE:
<223> OTHER INFORMATION: RX3 variant, leucine sub

<400> SEQUENCE: 149

Pro Pro Pro Val Leu Leu Pro Pro Val Leu Leu Pro Pro Val
1               5                   10                  15

Leu Leu Pro Pro Pro Val Leu Leu Pro Pro Val Leu Leu Pro Pro
            20                  25                  30

Pro Val Leu Leu Pro Pro Val Leu Leu Pro Pro Val Leu Leu
        35                  40                  45

<210> SEQ ID NO 150
<211> LENGTH: 10
<212> TYPE: PRT
<213> ORGANISM: Artificial
<220> FEATURE:
<223> OTHER INFORMATION: signal peptide

<400> SEQUENCE: 150

Thr His Thr Ser Gly Gly Cys Gly Cys Gln
1               5                   10

```
<210> SEQ ID NO 151
<211> LENGTH: 10
<212> TYPE: PRT
<213> ORGANISM: Artificial
<220> FEATURE:
<223> OTHER INFORMATION: signal peptide, pro sub

<400> SEQUENCE: 151

Thr His Pro Pro Pro Pro Cys Pro Cys Pro
1               5                   10

<210> SEQ ID NO 152
<211> LENGTH: 67
<212> TYPE: PRT
<213> ORGANISM: Artificial
<220> FEATURE:
<223> OTHER INFORMATION: Z(adh)

<400> SEQUENCE: 152

Thr His Thr Ser Gly Gly Cys Gly Cys Gln Pro Pro Thr Pro Pro Thr
1               5                   10                  15

Tyr Glu Thr Glu Lys Pro Leu Glu Pro Ala Pro Val Glu Pro Ser Tyr
            20                  25                  30

Glu Ala Glu Pro Thr Pro Pro Thr Arg Ala Pro Asp Gln Ala Glu Pro
        35                  40                  45

Asn Lys Pro Thr Pro Pro Thr Pro Val His Leu Pro Pro Pro Pro Cys
    50                  55                  60

Pro Pro Cys
65

<210> SEQ ID NO 153
<211> LENGTH: 93
<212> TYPE: PRT
<213> ORGANISM: Artificial
<220> FEATURE:
<223> OTHER INFORMATION: Z(adh)Px

<400> SEQUENCE: 153

Thr His Thr Ser Gly Gly Cys Gly Cys Gln Pro Pro Thr Pro Pro Thr
1               5                   10                  15

Tyr Glu Thr Glu Lys Pro Leu Glu Pro Ala Pro Val Glu Pro Ser Tyr
            20                  25                  30

Glu Ala Glu Pro Thr Pro Pro Thr Arg Ala Pro Asp Gln Ala Glu Pro
        35                  40                  45

Asn Lys Pro Thr Pro Pro Thr Pro Val His Leu Pro Pro Pro Pro Cys
    50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90

<210> SEQ ID NO 154
<211> LENGTH: 64
<212> TYPE: PRT
<213> ORGANISM: Artificial
<220> FEATURE:
<223> OTHER INFORMATION: Z(Col)

<400> SEQUENCE: 154

Thr His Thr Ser Gly Gly Cys Gly Cys Gln Pro Gly Pro Met Gly Pro
1               5                   10                  15
```

Arg Gly Pro Pro Gly Pro Ala Gly Ala Pro Gly Pro Gln Gly Phe Gln
            20                  25                  30

Gly Asn Pro Gly Glu Pro Gly Glu Pro Gly Val Ser Gly Pro Met Gly
            35                  40                  45

Pro Arg Gly Pro Pro Gly Pro Pro Val His Leu Cys Pro Pro Cys
        50                  55                  60

<210> SEQ ID NO 155
<211> LENGTH: 94
<212> TYPE: PRT
<213> ORGANISM: Artificial
<220> FEATURE:
<223> OTHER INFORMATION: Z(Col)Px

<400> SEQUENCE: 155

Thr His Thr Ser Gly Gly Cys Gly Cys Gln Pro Gly Pro Met Gly Pro
1               5                   10                  15

Arg Gly Pro Pro Gly Pro Ala Gly Ala Pro Gly Pro Gln Gly Phe Gln
            20                  25                  30

Gly Asn Pro Gly Glu Pro Gly Glu Pro Gly Val Ser Gly Pro Met Gly
            35                  40                  45

Pro Arg Gly Pro Pro Gly Pro Pro Val His Leu Pro Pro Pro
        50                  55                  60

Cys His Tyr Pro Thr Gln Pro Arg Pro Gln Pro His Pro Gln Pro
65                  70                  75                  80

His Pro Cys Pro Cys Gln Gln Pro His Pro Ser Pro Cys Gln
                85                  90

<210> SEQ ID NO 156
<211> LENGTH: 46
<212> TYPE: PRT
<213> ORGANISM: Artificial
<220> FEATURE:
<223> OTHER INFORMATION: Adh

<400> SEQUENCE: 156

Pro Pro Thr Pro Pro Thr Tyr Glu Thr Glu Lys Pro Leu Glu Pro Ala
1               5                   10                  15

Pro Val Glu Pro Ser Tyr Glu Ala Glu Pro Thr Pro Thr Arg Ala
            20                  25                  30

Pro Asp Gln Ala Glu Pro Asn Lys Pro Thr Pro Thr Pro
            35                  40                  45

<210> SEQ ID NO 157
<211> LENGTH: 47
<212> TYPE: PRT
<213> ORGANISM: Artificial
<220> FEATURE:
<223> OTHER INFORMATION: Col

<400> SEQUENCE: 157

Pro Gly Pro Met Gly Pro Arg Gly Pro Pro Gly Pro Ala Gly Ala Pro
1               5                   10                  15

Gly Pro Gln Gly Phe Gln Gly Asn Pro Gly Glu Pro Gly Glu Pro Gly
            20                  25                  30

Val Ser Gly Pro Met Gly Pro Arg Gly Pro Pro Gly Pro Pro
            35                  40                  45

<210> SEQ ID NO 158
<211> LENGTH: 48

<212> TYPE: PRT
<213> ORGANISM: Artificial
<220> FEATURE:
<223> OTHER INFORMATION: gamma zein highly repetitive seq

<400> SEQUENCE: 158

Pro Pro Pro Val His Leu Pro Pro Val His Leu Pro Pro Val
1               5                   10                  15

His Leu Pro Pro Pro Val His Leu Pro Pro Val His Leu Pro Pro
            20                  25                  30

Pro Val His Leu Pro Pro Pro Val His Val Pro Pro Val His Leu
            35                  40                  45

<210> SEQ ID NO 159
<211> LENGTH: 18
<212> TYPE: PRT
<213> ORGANISM: Artificial
<220> FEATURE:
<223> OTHER INFORMATION: synthetic peptide

<400> SEQUENCE: 159

Val His Leu Pro Pro Pro Val His Leu Pro Pro Pro Val His Leu Pro
1               5                   10                  15

Pro Pro

<210> SEQ ID NO 160
<211> LENGTH: 30
<212> TYPE: PRT
<213> ORGANISM: Artificial
<220> FEATURE:
<223> OTHER INFORMATION: synthetic peptide

<400> SEQUENCE: 160

Val His Leu Pro Pro Pro Val His Leu Pro Pro Pro Val His Leu Pro
1               5                   10                  15

Pro Pro Val His Leu Pro Pro Pro Val His Leu Pro Pro Pro
            20                  25                  30

<210> SEQ ID NO 161
<211> LENGTH: 48
<212> TYPE: PRT
<213> ORGANISM: Artificial
<220> FEATURE:
<223> OTHER INFORMATION: synthetic peptide

<400> SEQUENCE: 161

Val His Leu Pro Pro Pro Val His Leu Pro Pro Pro Val His Leu Pro
1               5                   10                  15

Pro Pro Val His Leu Pro Pro Pro Val His Leu Pro Pro Val His
            20                  25                  30

Leu Pro Pro Pro Val His Leu Pro Pro Pro Val His Leu Pro Pro Pro
            35                  40                  45

<210> SEQ ID NO 162
<211> LENGTH: 4
<212> TYPE: PRT
<213> ORGANISM: Artificial
<220> FEATURE:
<223> OTHER INFORMATION: KDEL sequence

<400> SEQUENCE: 162

Lys Asp Glu Leu
1

<210> SEQ ID NO 163
<211> LENGTH: 112
<212> TYPE: PRT
<213> ORGANISM: Artificial
<220> FEATURE:
<223> OTHER INFORMATION: RX3-LA1 Protein

<400> SEQUENCE: 163

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Ala Pro Pro Pro
            20                  25                  30

Pro Ala Ala Ala Pro Pro Ala Ala Ala Pro Pro Ala Ala Ala
        35                  40                  45

Pro Pro Pro Ala Ala Ala Pro Pro Ala Ala Ala Pro Pro Ala
    50                  55                  60

Ala Ala Pro Pro Pro Ala Ala Ala Pro Pro Ala Ala Ala Pro Pro
65                  70                  75                  80

Pro Pro Cys His Tyr Pro Thr Ala Pro Ala Arg Pro Ala Pro Ala Pro
                85                  90                  95

Ala Pro Ala Pro Cys Pro Cys Ala Ala Pro Ala Pro Ser Pro Cys Gln
                100                 105                 110

<210> SEQ ID NO 164
<211> LENGTH: 112
<212> TYPE: PRT
<213> ORGANISM: Artificial
<220> FEATURE:
<223> OTHER INFORMATION: RX3-LA2 Protein

<400> SEQUENCE: 164

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Ala Pro Pro Pro
            20                  25                  30

Pro Ala Ala Ala Pro Pro Ala Ala Ala Pro Pro Ala Ala Ala
        35                  40                  45

Pro Pro Pro Ala Ala Ala Pro Pro Ala Ala Ala Pro Pro Ala
    50                  55                  60

Ala Ala Pro Pro Pro Ala Ala Ala Pro Pro Ala Ala Ala Pro Pro
65                  70                  75                  80

Pro Pro Cys His Tyr Pro Pro Ala Pro Ala Pro Ala Pro Ala Pro
                85                  90                  95

Pro Ala Pro Ala Cys Pro Cys Ala Ala Pro Ala Pro Ser Pro Cys Gln
                100                 105                 110

<210> SEQ ID NO 165
<211> LENGTH: 86
<212> TYPE: PRT
<213> ORGANISM: Artificial
<220> FEATURE:
<223> OTHER INFORMATION: Z(Adh2)Px

<400> SEQUENCE: 165

Thr His Thr Ser Gly Gly Cys Gly Cys Gln Pro Pro Thr Pro Pro Thr
1               5                   10                  15

Tyr Glu Thr Glu Lys Pro Leu Glu Pro Ala Val Glu Pro Ser Tyr
            20                  25                  30

Glu Ala Glu Pro Thr Pro Pro Thr Arg Ala Pro Asp Gln Ala Glu Pro

```
                    35                  40                  45

Asn Lys Pro Thr Pro Pro Thr Pro Cys His Tyr Pro Thr Gln Pro Pro
 50                  55                  60

Arg Pro Gln Pro His Pro Gln Pro His Pro Cys Pro Cys Gln Gln Pro
65                  70                  75                  80

His Pro Ser Pro Cys Gln
                85

<210> SEQ ID NO 166
<211> LENGTH: 86
<212> TYPE: PRT
<213> ORGANISM: Artificial
<220> FEATURE:
<223> OTHER INFORMATION: Z(Col2)Px

<400> SEQUENCE: 166

Thr His Thr Ser Gly Gly Cys Gly Cys Gln Pro Gly Pro Met Gly Pro
1               5                  10                  15

Arg Gly Pro Pro Gly Pro Ala Gly Ala Pro Gly Pro Gln Gly Phe Gln
                20                  25                  30

Gly Asn Pro Gly Glu Pro Gly Glu Pro Gly Val Ser Gly Pro Met Gly
            35                  40                  45

Pro Arg Gly Pro Pro Gly Pro Pro Cys His Tyr Pro Thr Gln Pro Pro
 50                  55                  60

Arg Pro Gln Pro His Pro Gln Pro His Pro Cys Pro Cys Gln Gln Pro
65                  70                  75                  80

His Pro Ser Pro Cys Gln
                85

<210> SEQ ID NO 167
<211> LENGTH: 60
<212> TYPE: PRT
<213> ORGANISM: Artificial
<220> FEATURE:
<223> OTHER INFORMATION: Z(Adh2)

<400> SEQUENCE: 167

Thr His Thr Ser Gly Gly Cys Gly Cys Gln Pro Pro Thr Pro Pro Thr
1               5                  10                  15

Tyr Glu Thr Glu Lys Pro Leu Glu Pro Ala Pro Val Glu Pro Ser Tyr
                20                  25                  30

Glu Ala Glu Pro Thr Pro Pro Thr Arg Ala Pro Asp Gln Ala Glu Pro
            35                  40                  45

Asn Lys Pro Thr Pro Pro Thr Pro Cys Pro Pro Cys
 50                  55                  60

<210> SEQ ID NO 168
<211> LENGTH: 60
<212> TYPE: PRT
<213> ORGANISM: Artificial
<220> FEATURE:
<223> OTHER INFORMATION: Z(Col2)

<400> SEQUENCE: 168

Thr His Thr Ser Gly Gly Cys Gly Cys Gln Pro Gly Pro Met Gly Pro
1               5                  10                  15

Arg Gly Pro Pro Gly Pro Ala Gly Ala Pro Gly Pro Gln Gly Phe Gln
                20                  25                  30

Gly Asn Pro Gly Glu Pro Gly Glu Pro Gly Val Ser Gly Pro Met Gly
            35                  40                  45
```

```
Pro Arg Gly Pro Pro Gly Pro Pro Cys Pro Pro Cys
        50                  55                  60
```

<210> SEQ ID NO 169
<211> LENGTH: 93
<212> TYPE: PRT
<213> ORGANISM: Artificial
<220> FEATURE:
<223> OTHER INFORMATION: RX3(A)2

<400> SEQUENCE: 169

```
Thr His Thr Ser Gly Gly Cys Gly Cys Gln Pro Pro Pro Val Ala
1               5                   10                  15

Leu Pro Pro Pro Val Ala Leu Pro Pro Val Ala Leu Pro Pro Pro
                20                  25                  30

Val Ala Leu Pro Pro Val Ala Leu Pro Pro Val Ala Leu Pro
            35                  40                  45

Pro Pro Val Ala Val Pro Pro Val His Leu Pro Pro Pro Cys
        50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90
```

<210> SEQ ID NO 170
<211> LENGTH: 93
<212> TYPE: PRT
<213> ORGANISM: Artificial
<220> FEATURE:
<223> OTHER INFORMATION: RX3(A)

<400> SEQUENCE: 170

```
Thr His Thr Ser Gly Gly Cys Gly Cys Gln Pro Pro Pro Val Ala
1               5                   10                  15

Leu Pro Pro Pro Val Ala Leu Pro Pro Val Ala Leu Pro Pro Pro
                20                  25                  30

Val Ala Leu Pro Pro Pro Val Ala Leu Pro Pro Val Ala Leu Pro
            35                  40                  45

Pro Pro Val Ala Val Pro Pro Pro Val Ala Leu Pro Pro Pro Cys
        50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90
```

<210> SEQ ID NO 171
<211> LENGTH: 93
<212> TYPE: PRT
<213> ORGANISM: Artificial
<220> FEATURE:
<223> OTHER INFORMATION: PP3

<400> SEQUENCE: 171

```
Thr His Thr Ser Gly Gly Cys Gly Cys Gln Pro Pro Pro Pro Pro
1               5                   10                  15

Pro Pro Pro Pro Pro Pro Pro Pro Pro Pro Pro Pro Pro Pro Pro
                20                  25                  30

Pro Pro Pro Pro Pro Pro Pro Pro Pro Pro Pro Pro Pro Pro Pro
            35                  40                  45
```

```
Pro Pro Pro Pro Pro Pro Pro Pro Pro Pro Pro Cys
    50              55              60

Pro Pro Pro Pro Pro Pro Pro Pro Pro Pro Pro Pro
65              70              75              80

Pro Cys Pro Cys Pro Pro Pro Pro Pro Cys Pro
                85              90
```

<210> SEQ ID NO 172
<211> LENGTH: 93
<212> TYPE: PRT
<213> ORGANISM: Artificial
<220> FEATURE:
<223> OTHER INFORMATION: PA2

<400> SEQUENCE: 172

```
Thr His Thr Ser Gly Gly Cys Gly Cys Gln Pro Pro Pro Ala Pro
1               5                   10                  15

Ala Pro Pro Pro Ala Pro Ala Pro Pro Pro Ala Pro Ala Pro Pro Pro
            20                  25                  30

Ala Pro Ala Pro Pro Pro Ala Pro Ala Pro Pro Pro Ala Pro Ala Pro
            35                  40                  45

Pro Pro Ala Pro Ala Pro Pro Pro Ala Pro Ala Pro Pro Pro Cys
    50              55              60

Pro Pro Pro Ala Pro Ala Pro Pro Pro Ala Pro Ala Pro Pro Pro Ala
65              70              75              80

Pro Cys Pro Cys Pro Ala Pro Ala Pro Pro Pro Cys Pro
                85              90
```

<210> SEQ ID NO 173
<211> LENGTH: 279
<212> TYPE: DNA
<213> ORGANISM: Artificial
<220> FEATURE:
<223> OTHER INFORMATION: iRX3 DNA

<400> SEQUENCE: 173

```
caatgtccta gtccacatcc tcaacagtgt ccatgccctc atccacaacc tcacccacag      60
cctaggcctc ctcagacacc atatcactgc ccacctccac ctgttcatct tccacctcca    120
gtgcacttgc ctccacctgt gcatcttcca cctccagttc acttgcctcc acctgtccat    180
cttccacctc cagtccactt gcctccacct gtacatcttc cacctccagt acacttgcct    240
ccacctccac aatgtggatg cggaggttct actcataca                           279
```

<210> SEQ ID NO 174
<211> LENGTH: 93
<212> TYPE: PRT
<213> ORGANISM: Artificial
<220> FEATURE:
<223> OTHER INFORMATION: iRX3 PROTEIN

<400> SEQUENCE: 174

```
Gln Cys Pro Ser Pro His Pro Gln Gln Cys Pro Cys Pro His Pro Gln
1               5                   10                  15

Pro His Pro Gln Pro Arg Pro Pro Gln Thr Pro Tyr His Cys Pro Pro
            20                  25                  30

Pro Pro Val His Leu Pro Pro Val His Leu Pro Pro Val His
        35                  40                  45

Leu Pro Pro Pro Val His Leu Pro Pro Val His Leu Pro Pro Pro
    50              55              60
```

Val His Leu Pro Pro Pro Val His Leu Pro Pro Val His Leu Pro
65                  70                  75                  80

Pro Pro Pro Gln Cys Gly Cys Gly Gly Ser Thr His Thr
                85                  90

<210> SEQ ID NO 175
<211> LENGTH: 594
<212> TYPE: DNA
<213> ORGANISM: Artificial
<220> FEATURE:
<223> OTHER INFORMATION: Intein (I) DNA

<400> SEQUENCE: 175

```
tgcattactg gtgatgcact agttgctttg ccagagggtg aaagtgttag gattgctgat      60
attgtgccag gtgctaggcc aaattctgat aacgctatcg atctcaaggt tttggatagg     120
catggaaacc cagttcttgc tgataggctt ttccattctg gtgaacaccc agtttacact     180
gttagaactg tggaaggact tagagttact ggaactgcta accatccact tttgtgcctt     240
gttgatgttg ctggtgttcc aactcttttg tggaagctca tagatgagat taagcctggt     300
gattacgctg ttattcagag atctgctttc tctgttgatt gtgctggatt tgctagagga     360
aagccagaat tcgctccaac tacttacact gttggagttc caggacttgt tagattcctc     420
gaggctcatc acagagatcc agatgctcaa gctattgctg atgagcttac tgatggaagg     480
ttctactacg ctaaggttgc atctgttact gatgctggtg ttcagccagt ttactctctc     540
agagtggata ctgctgatca cgcgttcatc actaacggat tcgtttctca tgct           594
```

<210> SEQ ID NO 176
<211> LENGTH: 198
<212> TYPE: PRT
<213> ORGANISM: Artificial
<220> FEATURE:
<223> OTHER INFORMATION: Intein (I) Protein

<400> SEQUENCE: 176

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

```
Val Tyr Ser Leu Arg Val Asp Thr Ala Asp His Ala Phe Ile Thr Asn
            180                 185                 190

Gly Phe Val Ser His Ala
        195
```

<210> SEQ ID NO 177
<211> LENGTH: 726
<212> TYPE: DNA
<213> ORGANISM: Artificial
<220> FEATURE:
<223> OTHER INFORMATION: ECFP-KDEL DNA

<400> SEQUENCE: 177

```
gtgagcaagg gcgaggagct gttcaccggg gtggtgccca tcctggtcga gctggacggc    60
gacgtaaacg gccacaggtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgtac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag ccacaacgtc tatatcaccg ccgacaagca gaagaacggc   480
atcaaggccc acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660 ctggagttcg tgaccgccgc cgggatcact ctcggcatgg acgagctgta caagaaggac   720
gagctc                                                              726
```

<210> SEQ ID NO 178
<211> LENGTH: 242
<212> TYPE: PRT
<213> ORGANISM: Artificial
<220> FEATURE:
<223> OTHER INFORMATION: ECFP-KDEL PROTEIN

<400> SEQUENCE: 178

```
Val Ser Lys Gly Glu Glu Leu Phe Thr Gly Val Val Pro Ile Leu Val
 1               5                  10                  15

Glu Leu Asp Gly Asp Val Asn Gly His Arg Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140
```

Tyr Ile Ser His Asn Val Tyr Ile Thr Ala Asp Lys Gln Lys Asn Gly
145                 150                 155                 160

Ile Lys Ala His Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys Lys Asp
225                 230                 235                 240

Glu Leu

<210> SEQ ID NO 179
<211> LENGTH: 48
<212> TYPE: DNA
<213> ORGANISM: Artificial
<220> FEATURE:
<223> OTHER INFORMATION: Gly Five Domain DNA

<400> SEQUENCE: 179
aggcgcgcct gttgcccagg atgttgcggt ggaggtggag gtaccatg            48

<210> SEQ ID NO 180
<211> LENGTH: 10
<212> TYPE: PRT
<213> ORGANISM: Artificial
<220> FEATURE:
<223> OTHER INFORMATION: Gly Five Domain Protein

<400> SEQUENCE: 180

Arg Arg Ala Gly Gly Gly Gly Gly Thr Met
1               5                   10

<210> SEQ ID NO 181
<211> LENGTH: 6
<212> TYPE: PRT
<213> ORGANISM: Artificial
<220> FEATURE:
<223> OTHER INFORMATION: proline rich sequence

<400> SEQUENCE: 181

Pro Pro Pro Val Ser Leu
1               5

<210> SEQ ID NO 182
<211> LENGTH: 18
<212> TYPE: PRT
<213> ORGANISM: Artificial
<220> FEATURE:
<223> OTHER INFORMATION: proline rich sequence

<400> SEQUENCE: 182

Cys His Tyr Pro Tyr Gln Pro Pro Arg Pro Gln Pro His Pro Gln Pro
1               5                   10                  15

His Pro

<210> SEQ ID NO 183
<211> LENGTH: 93
<212> TYPE: PRT
<213> ORGANISM: Artificial
<220> FEATURE:

<223> OTHER INFORMATION: RX3(A)2

<400> SEQUENCE: 183

Thr His Thr Ser Gly Gly Cys Gly Cys Gln Pro Pro Pro Val Ala
1               5                   10                  15

Leu Pro Pro Pro Val Ala Leu Pro Pro Val Ala Leu Pro Pro Pro
            20                  25                  30

Val Ala Leu Pro Pro Pro Val Ala Leu Pro Pro Val Ala Leu Pro
        35                  40                  45

Pro Pro Val Ala Val Pro Pro Val Ala Leu Pro Pro Pro Cys
    50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90

<210> SEQ ID NO 184
<211> LENGTH: 93
<212> TYPE: PRT
<213> ORGANISM: Artificial
<220> FEATURE:
<223> OTHER INFORMATION: RX3(S)

<400> SEQUENCE: 184

Thr His Thr Ser Gly Gly Cys Gly Cys Gln Pro Pro Pro Val Ser
1               5                   10                  15

Leu Pro Pro Pro Val Ser Leu Pro Pro Val Ser Leu Pro Pro Pro
            20                  25                  30

Val Ser Leu Pro Pro Pro Val Ser Leu Pro Pro Val Ser Leu Pro
        35                  40                  45

Pro Pro Val Ser Val Pro Pro Val Ser Leu Pro Pro Pro Cys
    50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90

<210> SEQ ID NO 185
<211> LENGTH: 93
<212> TYPE: PRT
<213> ORGANISM: Artificial
<220> FEATURE:
<223> OTHER INFORMATION: RX3(V)

<400> SEQUENCE: 185

Thr His Thr Ser Gly Gly Cys Gly Cys Gln Pro Pro Pro Val Val
1               5                   10                  15

Leu Pro Pro Pro Val Val Leu Pro Pro Val Val Leu Pro Pro Pro
            20                  25                  30

Val Val Leu Pro Pro Pro Val Val Leu Pro Pro Val Val Leu Pro
        35                  40                  45

Pro Pro Val Val Val Pro Pro Val Val Leu Pro Pro Pro Cys
    50                  55                  60

His Tyr Pro Thr Gln Pro Pro Arg Pro Gln Pro His Pro Gln Pro His
65                  70                  75                  80

Pro Cys Pro Cys Gln Gln Pro His Pro Ser Pro Cys Gln
                85                  90

```
<210> SEQ ID NO 186
<211> LENGTH: 93
<212> TYPE: PRT
<213> ORGANISM: Artificial
<220> FEATURE:
<223> OTHER INFORMATION: NPP

<400> SEQUENCE: 186

Thr His Pro Pro Pro Pro Cys Pro Cys Pro Pro Pro Pro Pro Pro
1               5                   10                  15

Pro Pro Pro Pro Pro Pro Pro Pro Pro Pro Pro Pro Pro Pro Pro
                20                  25                  30

Pro Pro Pro Pro Pro Pro Pro Pro Pro Pro Pro Pro Pro Pro Pro
            35                  40                  45

Pro Pro Pro Pro Pro Pro Pro Pro His Leu Pro Pro Pro Pro Cys
        50                  55              60

Pro Pro Pro Pro Pro Pro Pro Pro Pro Pro Pro Pro Pro Pro Pro
65                  70                  75                  80

Pro Cys Pro Cys Pro Pro Pro Pro Pro Pro Cys Pro
                85                  90

<210> SEQ ID NO 187
<211> LENGTH: 93
<212> TYPE: PRT
<213> ORGANISM: Artificial
<220> FEATURE:
<223> OTHER INFORMATION: NPA

<400> SEQUENCE: 187

Thr His Pro Pro Pro Pro Cys Pro Cys Pro Pro Pro Pro Ala Pro
1               5                   10                  15

Ala Pro Pro Pro Ala Pro Ala Pro Pro Pro Ala Pro Ala Pro Pro
                20                  25                  30

Ala Pro Ala Pro Pro Pro Ala Pro Ala Pro Pro Pro Ala Pro Ala
            35                  40                  45

Pro Pro Ala Pro Ala Pro Pro Pro Ala His Leu Pro Pro Pro Cys
        50                  55              60

Pro Pro Pro Ala Pro Ala Pro Pro Pro Ala Pro Ala Pro Pro Ala
65                  70                  75                  80

Pro Cys Pro Cys Pro Ala Pro Ala Pro Pro Cys Pro
                85                  90
```